United States Patent
Buckman et al.

(10) Patent No.: US 6,306,884 B1
(45) Date of Patent: *Oct. 23, 2001

(54) BENZAMIDINE DERIVATIVES AND THEIR USE AS ANTI-COAGULANTS

(75) Inventors: Brad O. Buckman, Oakland; David D. Davey, El Sobrante; William J. Guilford, San Leandro; Michael M. Morrissey, Danville; Howard P. Ng, El Sobrante; Gary B. Phillips, Pleasant Hill; Shung C. Wu, El Cerrito; Wei Xu, Richmond, all of CA (US)

(73) Assignee: Berlex Laboratories, Inc., Richmond, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/436,399

(22) Filed: Nov. 8, 1999

Related U.S. Application Data

(60) Division of application No. 08/913,241, filed as application No. PCT/US96/02641 on Mar. 8, 1996, now Pat. No. 6,004,981, which is a continuation-in-part of application No. 08/473,385, filed on Jun. 7, 1995, now Pat. No. 5,691,364, which is a continuation-in-part of application No. 08/401,829, filed on Mar. 10, 1995, now abandoned.

(51) Int. Cl.$^7$ .......................... A61K 31/54; A61K 31/44; C07D 413/00; C07D 211/72; C07D 211/84

(52) U.S. Cl. ...................... 514/345; 514/235.5; 514/349; 514/352; 544/14; 546/296; 546/297; 546/301; 546/305

(58) Field of Search ..................... 546/296, 297; 546/301, 305; 514/235.5, 349, 345, 352; 544/111

(56) References Cited

U.S. PATENT DOCUMENTS

| | | |
|---|---|---|
| 4,064,169 | 12/1977 | Hamano et al. . |
| 5,332,822 | 7/1994 | Misra . |
| 5,444,083 * | 8/1995 | Yamanaka et al. ................ 514/429 |
| 5,451,700 | 9/1995 | Morrissey et al. . |
| 5,612,363 | 3/1997 | Mohan et al. . |
| 5,633,381 | 5/1997 | Dallas et al. . |
| 5,665,754 | 9/1997 | Feldman et al. ................ 514/397 |
| 5,691,364 * | 11/1997 | Buckman ........................ 514/341 |
| 5,693,641 | 12/1997 | Buckman et al. . |
| 5,726,173 | 3/1998 | Mohan et al. . |
| 5,726,198 | 3/1998 | Mohan et al. . |
| 5,728,697 | 3/1998 | Mohan et al. . |
| 5,731,308 | 3/1998 | Mohan et al. . |
| 5,731,311 | 3/1998 | Mohan et al. . |
| 5,753,635 | 5/1998 | Buckman et al. . |
| 5,846,970 | 12/1998 | Buckman et al. . |
| 5,846,972 | 12/1998 | Buckman et al. . |
| 5,849,759 | 12/1998 | Arnaiz et al. . |
| 5,859,005 | 1/1999 | Mohan et al. . |
| 5,863,914 | 1/1999 | Mohan et al. . |
| 5,877,181 | 3/1999 | Buckman et al. . |
| 5,883,100 | 3/1999 | Buckman et al. . |
| 5,889,005 | 3/1999 | Buckman et al. . |
| 5,998,428 | 12/1999 | Barnette et al. ................ 514/285 |
| 6,034,103 * | 3/2000 | Buckman ........................ 514/318 |

FOREIGN PATENT DOCUMENTS

| | | |
|---|---|---|
| 0518818A2 | 6/1992 | (EP) . |
| 0540051A1 | 10/1992 | (EP) . |
| 0567966A1 | 4/1993 | (EP) . |
| 0601459A2 | 12/1993 | (EP) . |
| 824908 | 12/1959 | (GB) . |
| WO93/15756 | 8/1993 | (WO) . |
| WO94/02470 | 2/1994 | (WO) . |
| WO94/13693 | 6/1994 | (WO) . |
| WO94/17817 | 8/1994 | (WO) . |
| WO96/10022 | 4/1996 | (WO) . |
| WO97/29067 | 8/1997 | (WO) . |
| WO98/11094 | 3/1998 | (WO) . |
| WO98/15547 | 4/1998 | (WO) . |
| WO99/32477 | 7/1999 | (WO) . |

OTHER PUBLICATIONS

Spillert, CA 107:211855, 1987.*
Delia, Bio. & Med Chem Lett, vol. 6, No. 19, pp 2367–2370, 1996.*
Chemical Abstracts 81:105045, abstact of Kono, JP 49036650, 1974.*
K.L. Molnar–Kimer et al., *Mediators of Inflammation*, 1, pp. 411–417 (1992).
M.W. Verghese et al., *J. Mol. Cell. Cardiiol.*, 21 (Suppl. 2), S61 (1989).
C.P. Nielson et al., *J. Allergy Immunol.*, 86, pp. 801–808 (1990).
P.T. Peachell et al., *J. Immunol.*, 148, pp. 2503–2510 (1992).
G. Dent et al., *J. Pharmacol.*, 103, pp. 1339–1346 (1991).
S.A. Robicsek et al., *Biochem. Pharmacol.*, 42, pp. 869–877 (1991).
H.S. Dhillon et al., *J. Neurotrauma*, 12, pp. 1035–1043 (1995).
N. Suttorp et al., *J. Clin. Invest.*, 91, pp. 1421–1428 (1993).
M.R. Bristow et al., *Circulation*, 97, pp. 1340–1341 (1998).
G. Poli et al., *Proc. Natl. Acad. Sci. USA*, 87, pp. 782–785 (1990).
P. Orosz et al., *J. Exp. Med.*, 177, pp. 1391–1398 (1993).
M. Mentz et al., *Blood*, 88, pp. 2172–2182 (1996).
S. Takeda et al., *Kidney Int.*, 37, p. 362 (1990).
D. Chabardea et al., *Kidney Int.*, 35, p. 494 (1989).
C.D. Nicholson, *Psychopharmacology*, 101, p. 147 (1990).
F. Eckmann et al., *Curr. Ther. Res.*, 43, p 291 (1988).
A. Klodzinska et al., *Neuropharmacology*, 38, p. 1831 (1991).

(List continued on next page.)

*Primary Examiner*—D. Margaret Seaman
(74) *Attorney, Agent, or Firm*—Carol J. Roth

(57) ABSTRACT

This invention is directed to benzamidine derivatives which are useful as anti-coagulants. This invention is also directed to pharmaceutical compositions containing the compounds of the invention, and methods of using the compounds to treat disease-states characterized by thrombotic activity.

14 Claims, No Drawings

OTHER PUBLICATIONS

H. Kato et al., *Eur. J. Pharmacol.*, 272, p. 107 (1995).
G. Gardos et al., *J. Clin. Pharmocol.*, 16, p. 304 (1976).
I. Shoulson et al., *Neurology*, 25, p. 722 (1975).
T. Hayakawa et al., *Clin. Exp. Pharmacol. Physiol.*, 26, p. 421 (1999).
R.D. Porsolt et al., *Eur. J. Pharmacol.*, 47, p. 379 (1978).
R.D. Porsolt et al., *Eur. J. Pharmacol.*, 57, p. 431 (1979).
L. Steru, *Psychopharmacology*, 85, p. 376 (1985).
M. Takahashi, *J. Neuroscience*, 19, p. 610 (1999).
D. Pinsky et al., *J. Clin. Invest.*, 92, pp. 2994–3002 (1993).
*Antidepressants: neurochemical, behavioral and clinical prospectives*, Enna, Malick, and Richelson, eds., Raven Press, pp. 121–139 (1981).
J.E. Schultz et al., *Naunyn–Schmiedeberg's Arch Pharmacol*, 333, pp. 23–30 (1986).
Z. Ma et al., *Tetrahedron: Asymmetry*, vol. 8, No. 6, pp. 883–887 (1997).
A. Robichaud et al., *Neuropharmacology*, 38, pp. 289–297 (1999).
R.A. Allen et al., *Biochemical Pharmacology*, vol. 57, pp. 1375–1382 (1999).
J. Beavo et al., "Cyclic nucleotide phosphodiesterases: Structure, regulation and drug action," Wiley and Sons, Chichester, pp. 3–14 (1990).
T.J. Torphy et al., *Drug News and Perspectives*, 6, pp. 203–214 (1993).
M.A. Giembycz et al., *Clin. Exp. Allergy*, 22, pp. 337–344 (1992).
J. Semmler et al., *Int. J. Immunopharmacol.*, 15, pp. 409–413 (1993).
Tidwell, R. et al., "Strategies for Anticoagulation with Synthetic Protease Inhibitors, Xa Inhibitors Versus Thrombin Inhibitors," *Thrombosis Research*, (1980) 19:339—349.
Wagner, G. et al., "Synthese von a–a'–Bis[amidinobenzyliden]–und a–a' Bis–[amidinobenzyl]–cycloalkanonen," *Pharmazie*, (1977) 32, 141–145.
Stürzebecher, J. et al., "Cyclic Amides of Nα–arysulfonylaminoacylated 4–amidinophenylalanine—Tight Binding Inhibitors of Thrombin," *Thrombosis Research*, (1983) 29:635–642.
Kikumoto, R. et al., "Selective inhibition of Thrombin by (2R,4R)–4–Methyl–1–[N$^2$–[(3–methyl–1,2,3, 4–tetrahydro–8–quinolinyl)–sulfonyl]–L–arginyl)]–2piperidinecarboxylic Acid," *Biochemistry*, (1984) 23:85–90.

Stürzebecher, J. et al., "Synthetic Inhibitors of Serine Proteinases XXIII, Inhibition of Factor Xa by Diamidines", *Thrombosis Research*, (1980) 17:545:548.
Chauhan, P. et al., "Effect of new diamidines against *Leishmania donovani* infection," *Indian Journal of Experimental Biology*, (1993) 31:196–198.
Ashley, J. et al., "The Search for Chemotherapeutic Amidines. Part XVI. Amidinoanilino–1,3,5–triazines and Related Compounds", *J. of the Chemical Society*, (1960) 4525:4532.
Geratz, J. et al., "The Inhibition of Urokinase by Aromatic Diamidines" *Thrombos. Diathes haemorrh. (Stuttg.)*, (1975)33:230–243.
Geratz, J. et al. "Novel Bis (benzamidino) Compounds with an Aromatic Central Link. Inhibitors of Thrombin, Pancreatic Kallikrein, Trypsin, and Complement" *J. of Medicinal Chemistry*, (1976) 19(5):634–639.
Chauhan, P. et al., "Antiparasitic Agents: Part VI—Synthesis of 1,2–,1,3–&1,4–Bis(4–substituted aryloxy)benzenes & Their Biological Activities", *Indian Journal of Chemistry*, (1988) 27B:38–42.
U.S. Patent application Ser. No. 09/205,498, filed Dec. 4, 1998, entitled: *Aryl Substituted N–Heterocyclic Derivatives and Anti–Coagulants*.
U.S. Patent application Ser. No. 09/187,459 filed Nov. 5, 1998, entitled: Ortho–*Anthranilamide Derivatives as Anti–Coagulants*.
U.S. Patent application Ser. No. 09/196,921, filed Nov. 19, 1998, entitled: *Polyhydroxylated Monocyclic N–Heterocyclic Derivatives as Anti–Coagulants*.
U.S. Patent application Ser. No. 08/920,319, filed Aug. 27, 1997, entitled: Benzamidine Derivatives Substituted by Cyclic Amino Acid and Cyclic Hydroxy Acid Derivatives and Their Use as Anti–Coagulants.
U.S. Patent application Ser. No. 08/599,834, filed Feb. 12, 1996, entitled: Benzamidine Derivatives Substituted by Amino Acid and Hydroxy Acid Derivatives and Their Use as Anti–Coagulants.
U.S. Patent application Ser. No. 08/731,128, filed Oct. 9, 1996, entitled: Thio Acid Derived Monocyclics N–Heterocyclics as Anticoagulants.
Delia, T. et al., "Ring–Based Analogues of Pentamidine Versus *P.Carinii* Pneumonia In Culture", *Bioorganic & Medicinal Chemistry Letters*, (1996) 6(19):2267–2370.

* cited by examiner

BENZAMIDINE DERIVATIVES AND THEIR USE AS ANTI-COAGULANTS

This application is a divisional application of U.S. Ser. No. 08/913,241, filed Dec. 8, 1997, which is the national phase application of PCT patent application No. PCT/US96/02641, filed Mar. 8, 1996, which is a continuation U.S. patent application, Ser. No. 08/473,385, filed Jun. 7, 1995, now U.S. Pat. No. 5,691,364, issue date Nov. 25, 1997, which is a continuation-in-part application of U.S. patent application, Ser. No. 08/401,829, filed Mar. 10, 1995, now abandoned. The disclosures of these applications are incorporated by reference in full herein.

FIELD OF THE INVENTION

The present invention is directed to benzamidine derivatives and their pharmaceutically acceptable salts, which inhibit the enzyme, factor Xa, thereby being useful as anti-coagulants. It also relates to pharmaceutical compositions containing the derivatives or their pharmaceutically acceptable salts, and methods of their use.

BACKGROUND OF THE INVENTION

Factor Xa is a member of the trypsin-like serine protease class of enzymes. A one-to-one binding of factors Xa and Va with calcium ions and phospholipid forms the prothrombinase complex which converts prothrombin to thrombin. Thrombin, in turn, converts fibrinogen to fibrin which polymerizes to form insoluble fibrin.

In the coagulation cascade, the prothrombinase complex is the convergent point of the intrinsic (surface activated) and extrinsic (vessel injury-tissue factor) pathways (*Biochemistry* (1991), Vol. 30, p. 10363; and *Cell* (1988), Vol. 53, pp. 505–518). The model of the coagulation cascade has been refined further with the discovery of the mode of action of tissue factor pathway inhibitor (TFPI) (*Seminars in Hematology* (1992), Vol. 29, pp. 159–161). TFPI is a circulating multi-domain serine protease inhibitor with three Kunitz-like domains which competes with factor Va for free factor Xa. Once formed, the binary complex of factor Xa and TFPI becomes a potent inhibitor of the. factor VIIa and tissue factor complex.

Factor Xa can be activated by two distinct complexes, by tissue factor-VIIa complex on the "Xa burst" pathway and by the factor IXa-VIIIA complex (TENase) of the "sustained Xa" pathway in the coagulation cascade. After vessel injury, the "Xa burst" pathway is activated via tissue factor (TF). Up regulation of the coagulation cascade occurs via increased factor Xa production via the "sutained Xa" pathway. Down regulation of the coagulation cascade occurs with the formation of the factor XA-TFPI complex, which not only removes factor Xa but also inhibits further factor formation via the "Xa burst" pathway. Therefore, the coagulation cascade is naturally regulated by factor Xa.

The primary advantage of inhibiting factor Xa over thrombin in order to prevent coagulation is the focal role of factor Xa versus the multiple functions of thrombin. Thrombin not only catalyzes the conversion of fibrinogen to fibrin, factor VIII to VIIIA, factor V to Va, and factor XI to XIa, but also activates platelets, is a monocyte chemotactic factor, and mitogen for lymphocytes and smooth muscle cells. Thrombin activates protein C, the in vivo anti-coagulant inactivator of factors Va and VIIIa, when bound to thrombomodulin. In circulation, thrombin is rapidly inactivated by antithrombin III IATIII) and heparin cofactor II (HCII) in a reaction which is catalyzed by heparin or other proteolycan-associated glycosaminoglycans, whereas thrombin in tissues is inactivated by the protease, nexin. Thrombin carries out its multple cellular activation functions through a unique "tethered ligand" thrombin receptor (*Cell* (1991), Vol. 64, p. 1057), which requires the same anionic binding site and active site used in fibrinogen binding and cleavage and by thrombomodulin binding and protein C activation. Thus, a diverse group of in vivao molecular targets compete to bind thrombin and the subsequent proteolytic events will have very different physiological consequences depending upon which cell type and which receptor, modulator, substrate or inhibitor binds thrombin.

Published data with the proteins antistasin and tick anti-coagulant peptide (TAP) demonstrate that factor Xa inhibitors are efficacious anti-coagulants (*Thrombosis and Haemostasis* (1992), Vol. 67, pp. 371–376; and *Science* (1990), Vol. 248, pp. 593–596).

The active site of factor Xa can be blocked by either a mechanism-based or a tight binding inhibitor (a tight binding inhibitor differs from a mechanism-based inhibitor by the lack of a covalent link between the enzyme and the inhibitor). Two types of mechanism-based inhibitors are known, reversible and irreversible, which are distinguished by ease of hydrolysis of the enzyme-inhibitor link (*Thrombosis Res* (1992), Vol. 67, pp. 221–231; and *Trends Pharmacol. Sci*, (1987), Vol. 8, pp. 303–307). A series of guanidino compounds are examples of tight-binding inhibitors (*Thrombosis Res.* (1980), Vol. 19, pp. 339–349). Arylsulfonyl-arginine-piperidinecarboxylic acid derivatives have also been shown to be tight-binding inhibitors of thrombin (*Biochem.* (1984), Vol. 23, pp. 85–90), as well as a series of arylamidine-containing compounds, including 3-amidinophenylaryl derivatives (*Thrombosis Res.* (1983), Vol. 29, pp. 635–642) and bis(amidino)benzyl cycloketones (*Thrombosis Res.* (1980), Vol. 17, pp. 545–548). However, these compounds demonstrate poor selectivity for factor Xa.

RELATED DISCLOSURES

European Published Patent Application 0 540 051 (Nagahara et al) describes aromatic amidine derivatives which are stated to be capable of showing a strong anticoagulant effect through reversible inhibition of factor Xa.

The synthesis of α,α'-bis(amidinobenzylidene) cycloalkanones and α,α'-bis(amidinobenzyl)cycloalkanones is described in *Pharmazie* (1977), Vol. 32, No. 3, pp. 141–145. These compounds are disclosed as being serine protease inhibitors.

SUMMARY OF THE INVENTION

This invention is directed to compounds or their pharmaceutically acceptable salts which inhibit human factor Xa and are therefore useful as pharmacological agents for the treatment of disease-states characterized by thrombotic activity.

Accordingly, in one aspect, this invention provides compounds selected from the group consisting of the following formulae:

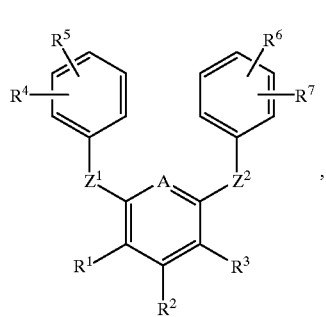

(I)

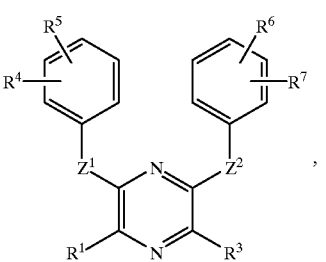

(II)

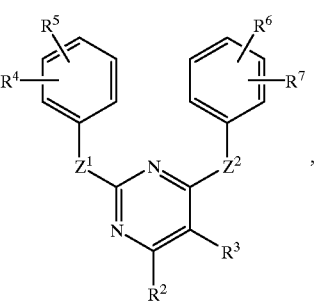

(III)

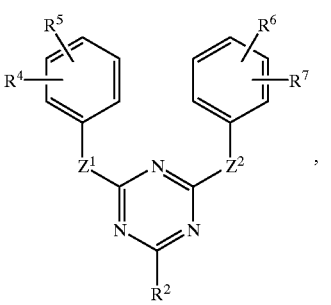

(IV)

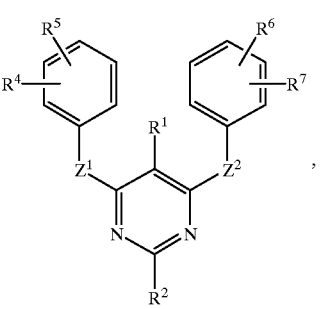

(V)

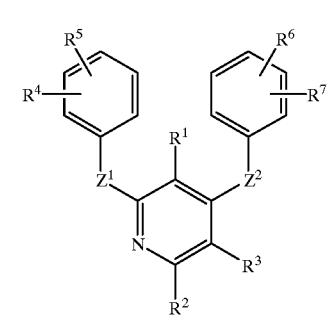

(VI)

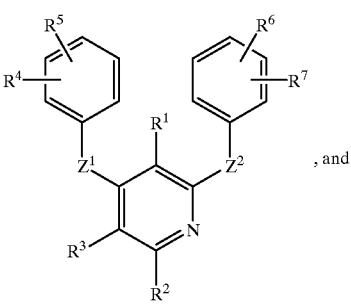

(VII)

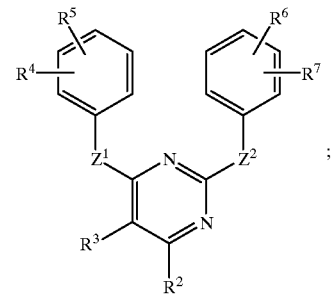

(VIII)

wherein

A is —C($R^{11}$)= or —N=;

$Z^1$ and $Z^2$ are independently —O—, —N($R^8$)—, —S—, or —OCH$_2$—;

$R^1$ and $R^3$ are independently hydrogen, halo, alkyl, haloalkyl, alkoxy, haloalkoxy, nitro, —N($R^8$)$R^9$, —C(O)$R^8$, —C(O)N($R^8$)$R^9$, —C(O)N($R^8$)CH$_2$C(O)N($R^8$)$R^9$, —N($R^8$)C(O)N($R^8$)$R^9$, —N($R^8$)C(O)$R^8$, —N($R^8$)S(O)$_2R^{12}$, or —N($R^8$)C(O)N($R^8$)CH$_2$C(O)N($R^8$)$R^9$;

$R^2$ is hydrogen; halo; alkyl; haloalkoxy; —O$R^8$; —C(O)O$R^8$; —C(O)N($R^8$)$R^9$; —N($R^8$)$R^9$; —C(O)N($R^8$)(CH$_2$)$_m$C(O)O$R^8$ (where m is 0 to 3); —N($R^8$)(CH$_2$)$_n$C(O)O$R^8$ (where n is 1 to 3); —N((CH$_2$)$_n$N($R^8$)$R^9$)(CH$_2$)$_n$C(O)O$R^8$ (where each n is 1 to 3); —O(CH$_2$)$_n$C(O)N($R^8$)$R^9$, (where n is 1 to 3); —O(CH$_2$)PC(O)O$R^8$ (where p is 1 to 6); —N($R^8$)(CH$_2$)$_n$C(O)N($R^8$)(CH$_2$)$_n$C(O)O$R^8$ (where each n is independently 1 to 3); morpholin-4-yl; 3-tetrahydrofuranoxy;

or $R^2$ is aryloxy (optionally substituted by one or more substituents independently selected from the group consisting of —O$R^8$, —C(O)N($R^8$)$R^9$, halo, alkyl, carboxy, alkoxycarbonyl, haloalkoxy, haloalkoxycarbonyl, alkoxycarbonylalkyl, carboxyalkyl, aminocarbonylalkyl, (alkylamino) carbonylalkyl, (dialkylamino)carbonylalkyl, (arylamino)carbonylalkyl, (aralkylamino) carbonylalkyl, alkoxycarbonylalkenyl, carboxyalkenyl, aminocarbonylalkenyl, (alkylamino)carbonylaikenyl, (dialkylamino)carbonylaikenyl, (arylamino) carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy) alkoxycarbonyl, tetrazolyl, morpholin-4-ylalkyl, and (1,2)-imidazolinyl (optionally substituted by alkyl));

or $R^2$ is piperazin-1-yl (optionally substituted by one or more substituents independently selected from the group consisting of alkyl, carboxy, —C(O)N($R^8$)$R^9$, carboxyalkyl, alkoxycarbonyl, and alkoxycarbonylalkyl);

or $R^2$ is 1-piperazinoyl (optionally substituted by one or more substituents selected from the group consisting of alkyl, carboxy, —C(O)N($R^8$)$R^9$, carboxyalkyl, alkoxycarbonyl, and alkoxycarbonylalkyl);

or $R^2$ is piperidin-1-yl (optionally substituted by one or more substituents selected from the group consisting of carboxy, —C(O)N($R^8$)$R^9$, carboxyalkyl, alkoxycarbonyl, and alkoxycarbonylalkyl);

or $R^2$ is (3,4)-piperidinyloxy (optionally substituted by one or more substituents selected from the group consisting of alkylcarbonyl, carboxy, —C(O)N($R^8$)$R^9$, alkoxycarbonyl, carboxyalkyl, alkoxycarbonylalkyl, and tetrazolylalkyl);

or $R^2$ is piperidin-4-ylamino (wherein the amino is optionally substituted by alkyl and the piperidinyl-group is optionally substituted by one or more substituents selected from the group consisting of alkyl, alkoxycarbonyl, —C(O)N($R^8$)$R^9$, carboxyalkyl, alkoxycarbonylalkyl and aralklyl);

or $R^2$ is 3-pyrrolidinyloxy (optionally substituted by one or more substituents selected from the group consisting of alkyl, aralkyl, amidino, 1-iminoethyl, carboxy, —C(O)N($R^8$)$R^9$, carboxyalkyl, alkoxycarbonyl and alkoxycarbonylalkyl);

$R^4$ and $R^7$ are independently hydrogen, halo, alkyl, nitro, —$OR^8$, —C(O)$OR^8$, —C(O)N($R^8$)$R^9$, —N($R^8$)$R^9$, —N(H)C(O)$R^8$, or —N(H)S(O)$_2R^{12}$;

$R^5$ is —C(NH)NH$_2$, —C(NH)N(H)$OR^8$, —C(NH)N(H) C(O)$OR^{12}$, —C(NH)N(H)S(O)$_2R^{12}$, —C(NH)N(H)C (O)N($R^8$)$R^9$, or —C(NH)N(H)C(O)$R^8$;

$R^6$ is halo, alkyl, haloalkyl, haloalkoxy, nitro, amino, ureido, guanidino, —$OR^8$, —C(NH)NH$_2$, —C(NH) NHOH, —C(O)$R^{10}$, —(CH$_2$)$_m$C(O)N($R^8$)$R^9$ (where m is 0 to 3), —CH(OH)C(O)N($R^8$)$R^9$, —(CH$_2$)$_m$N($R^8$)$R^9$ (where m is 0 to 3), —(CH$_2$)$_m$C(O)$OR^8$ (where m is 0 to 3), —N(H)C(O)$R^8$, (1,2)-tetrahydropyrimidinyl (optionally substituted by alkyl), (1,2)-imidazolyl (optionally substituted by alkyl), or (1,2)-imidazolinyl (optionally substituted by alkyl);

each $R^8$ and $R^9$ is independently hydrogen, alkyl, aryl, or aralkyl;

$R^{10}$ is hydrogen, alkyl, aryl, aralkyl, 1-pyrrolidinyl, 4-morpholinyl, 4-piperazinyl, 4-(N-methyl)piperazinyl, or piperidin-1-yl;

$R^{11}$ is hydrogen, alkyl or halo; and $R^{12}$ is alkyl, aryl or aralkyl;

or a pharmaceutically acceptable salt thereof.

In another aspect, this invention provides compositions useful in treating a human having a disease-state character- ized by thrombotic activity, which composition comprises a therapeutically effective amount of a compound of the invention as described above, or a pharmaceutically accept- able salt thereof, and a pharmaceutically acceptable excipi- ent.

In another aspect, this invention provides a method of treating a human having a disease-state characterized by thrombotic activity, which method comprises administering to a human in need thereof a therapeutically effective amount of a compound of the invention as described above.

In another aspect, this invention provides a method of treating a human having a disease-state alleviated by the inhibition of factor Xa, which method comprises adminis- tering to a human in need thereof a therapeutically effective amount of a compound of the invention as described above.

In another aspect, this invention provides a method of inhibiting human factor Xa in vitro or in vivo by the administration of a compound of the invention.

DETAILED DESCRIPTION OF THE INVENTION

Definitions

As used in the specification and appended claims, unless specified to the contrary, the following terms have the meaning indicated:

"Halo" refers to bromo, chloro or fluoro.

"Aminocarbonyl" refers to the radical —C(O)NH$_2$.

"Amidino" refers to the radical —C(NH)NH$_2$.

"Benzamidine" refers to a phenyl radical substituted by an amidino radical.

"Carboxy" refers to the radical —C(O)OH.

"Dimethylaminocarbonyl" refers to the radical —C(O)N (CH$_3$)$_2$.

"Alkyl" refers to a straight or branched chain monovalent or divalent radical consisting solely of carbon and hydrogen, containing no unsaturation and having from one to six carbon atoms, e.g., methyl, ethyl, n-propyl, 1-methylethyl (iso-propyl), n-butyl, n-pentyl, 1,1- dimethylethyl (t-butyl), and the like.

"Alkenyl" refers to a straight or branched chain monova- lent or divalent radical consisting solely of carbon and hydrogen, containing at least one double bond and having from one to six carbon atoms, e.g., ethenyl, prop-1-enyl, but-1-enyl, pent-1-enyl, pent-1,4-dienyl, and the like.

"Haloalkyl" refers to an alkyl radical, as defined above, that is substituted by one or more halo radicals, as defined above, e.g., trifluoromethyl, difluoromethyl, trichloromethyl, 2-trifluoroethyl, 1-fluoromethyl-2- fluoroethyl, 3-bromo-2-fluoropropyl, 1-bromomethyl-2- bromoethyl, and the like.

"Haloalkoxy" refers to a radical of the formula —$OR_b$ wherein $R_b$ is haloalkyl as defined above, e.g., trifluoromethoxy, difluoromethoxy, trichloromethoxy, 2-trifluoroethoxy, 1-fluoromethyl-2-fluoroethoxy, 3-bromo- 2-fluoropropoxy, 1-bromomethyl-2-bromoethoxy, and the like.

"Aryl" refers to a phenyl or naphthyl radical optionally substituted by halo, alkyl, alkoxy, amino, nitro or carboxy.

"Aralkyl" refers to a radical of the formula —$R_aR_c$ where $R_a$ is alkyl as defined above and $R_c$ is aryl as defined above, e.g., benzyl.

"Aryloxy" refers to a radical of the formula —$OR_a$ where $R_a$ is phenyl or naphthyl, e.g., phenoxy and naphthoxy.

"Alkoxy" refers to a radical of the formula —$OR_a$ where $R_a$ is alkyl as defined above, e.g., methoxy, ethoxy, n-propoxy, 1-methylethoxy (iso-propoxy), n-butoxy, n-pentoxy, 1,1-dimethylethoxy (t-butoxy), and the like.

"Alkanol" refers to a branched or unbranched aliphatic hydrocarbon of 1 to 6 carbons wherein one hydroxyl radical is attached thereto, e.g., methanol, ethanol, isopropanol, and the like.

"Aminocarbonylalkyl" refers to a radical of the formula —$R_aC(O)NH_2$ wherein $R_a$ is alkyl as defined above, e.g., aminocarbonylmethyl, 2-aminocarbonylethyl, 3-aminocarbonylpropyl, 1,1-dimethyl-2-aminocarbonylethyl, and the like.

"(Alkylamino)carbonylalkyl" refers to a radical of the formula —$R_aC(O)N(H)R_a$ wherein each $R_a$ is the same or different and is alkyl as defined above, e.g., (methylamino)carbonylmethyl, 2-(ethylamino)carbonylethyl, 3-(methylamino)-carbonylpropyl, 1,1-dimethyl-2-(ethylamino)carbonylethyl, and the like.

"(Dialkylamino)carbonylalkyl" refers to a radical of the formula —$R_aC(O)N(R_a)_2$ wherein each $R_a$ is the same or different and is alkyl as defined above, e.g., (dimethylamino)carbonylmethyl, 2-(diethylamino)carbonylethyl, 3-(dimethylamino)carbonylpropyl, 1,1-dimethyl-2-(diethylamino)carbonylethyl, and the like.

"(Arylamino)carbonylalkyl" refers to a radical of the formula —$R_aC(O)N(H)R_c$ wherein $R_a$ is ailkyl as defined above and $R_c$ is aryl as defined above, e.g., phenylaminocarbonylmethyl, 2-phenylaminocarbonylethyl, 3phenylaminocarbonylpropyl, 1,1 imethyl-2-phenylaminocarbonylethyl, and the like.

"(Aralkylamino)carbonylalkyl" refers to a radical of the formula —$R_aC(O)N(H)R_c$ wherein $R_a$ is alkyl as defined above and $R_d$ is aralkyl as defined above, e.g., benzylaminocarbonylmethyl, 2-benzylaminocarbonylethyl; 3-benzylaminocarbonylpropyl, 1,1-dimethyl-2-benzylaminocarbonylethyl, and the like.

"Alkoxycarbonylalkenyl" refers to a radical of the formula —$R_eC(O)OR_a$ wherein $R_a$ is lower alkyl as defined above and $R_e$ is alkenyl as defined above, e.g., 2-methoxycarbonylethenyl, 3-methoxycarbonyprop-1-enyl, 2-ethoxycarbonylethenyl, and the like.

"Carboxyalkenyl" refers to a radical of the formula —$R_eC(O)OH$ where $R_e$ is alkenyl as defined above, e.g., 2-carboxyethenyl, 3-carboxyprop-1-enyl, 4-carboxybut-1-enyl, and the like.

"Aminocarbonylalkenyl" refers to a radical of the formula —$R_eC(O)NH_2$ wherein $R_e$ is alkenyl as defined above, eg., 2-aminocarbonylethenyl, 3-aminocarbonylprop-1-enyl, 1-methyl-2-aminocarbonylethenyl, and the like.

"(Alkylamino)carbonylalkenyl" refers to a radical of the formula —$R_eC(O)N(H)R_a$ wherein $R_a$ is alkyl as defined above and $R_e$ is alkenyl as defined above, e.g., 2-(ethylamino)carbonylethenyl, 3-(methylamino)carbonylprop-1-enyl, 1-methyl-2-(ethylamino)carbonylethenyl, and the like.

"(Dialkylamino)carbonylalkenyl" refers to a radical of the formula —$R_eC(O)N(R_a)_2$ wherein each $R_a$ is the same or different and is as defined above and $R_e$ is alkenyl as defined above, e.g., 2-(diethylamino)carbonylethenyl, 3-(dimethylamino)carbonylprop-1-enyl, 1-methyl-2-(diethylamino)carbonylethenyl, and the like.

"(Arylamino)carbonylalkenyl" refers to a radical of the formula —$R_eC(O)N(H)R_c$ wherein $R_c$ is aryl as defined above and $R_e$ is alkenyl as defined above, e.g., 2-(phenylamino)carbonylethenyl, 3-(phenylamino)carbonylprop-1-enyl, 1-methyl-2-(phenylamino)carbonylethenyl, and the like.

"(Aralkylamino)carbonylaikenyl" refers to a radical of the formula —$R_eC(O)N(H)R_d$ wherein $R_d$ is aralkyl as defined above and $R_e$ is alkenyl as defined above, e.g., 2-(benzylamino)carbonylethenyl, 3-(benzylamino)carbonylprop-1-enyl, 1-methyl-2-(benzylamino)carbonylethenyl, and the like.

"(Hydroxyalkoxy)carbonyl" refers to a radical of the formula —$C(O)OR_a$ wherein $R_a$ is alkyl as defined above substituted by a hydroxy radical, e.g., 2-(hydroxy)ethoxycarbonyl, 3-(hydroxy)propoxycarbonyl, 5-(hydroxy)pentoxycarbonyl, and the like.

"(Alkoxy)alkoxycarbonyl" refers to a radical of the formula —$C(O)OR_aOR_a$ wherein each $R_a$ is the same or different and is alkyl as defined above, e.g., 2-(methoxy)ethoxycarbonyl, 3-(methoxy)propoxycarbonyl, 5-(ethoxy)pentoxycarbonyl, and the like.

"(Hydroxyalkoxy)alkoxycarbonyl" refers to a radical of the formula —$C(O)OR_aOR_a$, wherein each $R_a$ is the same or different and is alkyl as defined above, and the terminal $R_a$ radical is substituted by a hydroxy radical, e.g., 2-(2-hydroxyethoxy)ethoxycarbonyl, 2-(3-hydroxypropoxy)ethoxycarbonyl, and the like.

"((Alkoxy)alkoxy)alkoxycarbonyl" refers to a radical of the formula —$C(O)OR_aOR_aOR_a$ where each $R_a$ is the same or different and is alkyl as defined above, e.g., 2-(2-(methoxy)ethoxy)ethoxycarbonyl, 3-(2-(methoxy)ethoxy)propoxycarbonyl, 4-(3-ethoxy)propoxy)butoxycarbonyl, and the like.

"Haloalkoxycarbonyl" refers to a radical of the formula —$C(O)OR_b$ wherein $R_b$ is haloalkyl as defined above, e.g., trifluoromethoxycarbonyl, difluoromethoxycarbonyl, trichloromethoxycarbonyl, 2-trifluoroethoxycarbonyl; 1-fluoromethyl-2-fluoro-ethoxycarbonyl, 3-bromo-2-fluoropropoxycarbonyl, 1-bromomethyl-2-bromoethoxy-carbonyl, and the like.

"Carboxyalkyl" refers to a radical of the formula —$R_aC(O)OH$ where $R_a$ is alkyl as defined above, e.g., carboxymethyl, 2-carboxyethyl, 3-carboxypropyl, and the like.

"Alkoxycarbonyl" refers to a radical of the formula —$C(O)OR_a$ wherein $R_a$ is alkyl as defined above, e.g., methoxycarbonyl, ethoxycarbonyl, n-propoxycarbonyl, and the like.

"Alkoxycarbonylalkyl" refers to a radical of the formula —$R_aC(O)OR_a$ wherein each $R_a$ is the same or different and is alkyl as defined above, e.g., methoxycarbonylethyl, ethoxycarbonylethyl, t-butoxycarbonylethyl, and the like.

"Morpholin-4-ylalkyl" refers to a radical of the formula —$R_aR_f$ where $R_a$ is alkyl as defined above and $R_f$ is a morpholin-4-yl radical, eg., morpholin-4-ylmethyl, morpholin-4-ylethyl, and the like.

"4-morpholinoyl" refers to a radical of the formula —C(O)Rf where $R_f$ is a morpholin-4-yl radical.

"(3,4)-Piperidinyloxy" refers to a radical of the formula —$OR_g$ where $R_g$ is a piperidinyl radical attached to the oxygen atom at either the 3- or 4-position.

"3-Tetrahydrofuranyloxy" refers to the radical of the formula —$OR_h$ where $R_h$ is a tetrahydrofuranyl radical attached to the oxygen atom at the 3-position.

"3-Pyrrolidinyloxy" refers to the radical of the formula —$C(O)R_i$ where $R_i$ is a pyrrolidinyl radical attached to the oxygen atom at the 3-position.

"Piperazinoyl" refers to the radical of the formula —$C(O)R_j$; where $R_j$ is piperazin-1-yl.

"Piperidinoyl" refers to the radical of the formula —$C(O)R_k$ where $R_k$ is piperidin-1-yl.

"1-Pyrrolidinoyl" refers to the radical of the formula —$C(O)R_m$ where $R_m$ is pyrrolidin-1-yl.

"(1,2)-Imidazolyl" refers to an imidazolyl radical attached at either the 1- or 2-position.

"(1,2)-Imidazolinyl" refers to a 4,5-dihydroimidazolyl radical attached at either the 1- or the 2-position.

"DMSO" refers to dimethyl sulfoxide.

"HPLC" refers to high performance liquid chromatography.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethamine, dicyclohexylamine, choline and caffeine.

"Therapeutically effective amount" refers to that amount of a compound of formula (I) which, when administered to a human in need thereof, is sufficient to effect treatment, as defined below, for disease-states characterized by thrombotic activity. The amount of a compound of formula (I) which constitutes a "therapeutically effective amount" will vary depending on the compound, the disease-state and its severity, and the age of the human to be treated, but can be determined routinely by one of ordinary skill in the art having regard to his own knowledge and to this disclosure.

"Treating" or "treatment" as used herein cover the treatment of a disease-state in a human, which disease-state is characterized by thrombotic activity; and include:

(i) preventing the disease-state from occurring in a human, in particular, when such human is predisposed to the disease-state but has not yet been diagnosed as having it;

(ii) inhibiting the disease-state, i.e., arresting its development; or (iii) relieving the disease-state, i.e., causing regression of the disease-state.

The yield of each of the reactions described herein is expressed as a percentage of the theoretical yield.

The compounds of the invention, or their pharmaceutically acceptable salts, may have asymmetric carbon atoms in their structure. The compounds of the invention and their pharmaceutically acceptable salts may therefore exist as single stereoisomers, racemates, and as mixtures of enantiomers and diastereomers. All such single stereoisomers, racemates and mixtures thereof are intended to be within the scope of this invention.

The nomenclature used herein is a modified form of the I.U.P.A.C. system wherein the compounds of the invention are named as derivatives of benzamidine. For example, a compound of the invention selected from formula (I), i.e.,

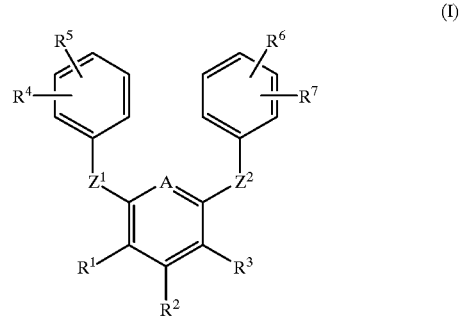

(I)

wherein A is —N═, $Z^1$ and $Z^2$ are both —O—, $R^1$ and $R^3$ are both fluoro, $R^2$ is methyl, $R^4$ is methoxy, $R^5$ is —C(NH)NH$_2$, $R^6$ is dimethylamino, and $R^7$ is hydrogen, that is, a compound of the following formula:

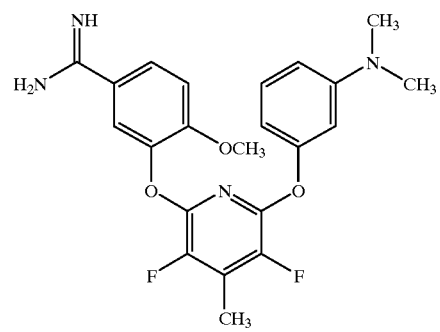

is named herein as 4-methoxy-3-[(3,5-difluoro-6-(3-dimethylaminophenoxy)-4-methylpyridin-2-yl)oxylbenzamidine.

Utility and Administration

A. Utility

The compounds of the invention are inhibitors of factor Xa and therefore useful in disease-states characterized by thrombotic activity based on factor Xa's role in the coagulation cascade (see Background of the Invention above). A primary indication for the compounds is prophylaxis for long term risk following myocardial infarction. Additional indications are prophylaxis of deep vein thrombosis (DVT) following orthopedic surgery or prophylaxis of selected patients following a transient ischemic attack. The compounds of the invention may also be useful for indications in which coumadin is currently used, such as for DVT or other types of surgical intervention such as coronary artery bypass graft and percutaneous transluminal coronary angioplasty. The compounds are also useful for the treatment of thrombotic complications associated with acute promyelocytic leukemia, diabetes, multiple myelomas, disseminated intravascular coagulation associated with septic shock, purpura fulminanas associated infection, adult respiratory distress syndrome, unstable angina, and thrombotic complications associated with aortic valve or vascular prosthesis. The compounds are also useful for prophylaxis for thrombotic diseases, in particular in patients who have a high risk of developing such disease.

In addition, the compounds of the invention are useful as in vitro diagnostic reagents for selectively inhibiting factor Xa without inhibiting other components of the coagulation cascade.

B. Testing

The primary bioassays used to demonstrate the inhibitory effect of the compounds of the invention on factor Xa are simple chromogenic assays involving only serine protease, the compound of the invention to be tested, substrate and buffer (see, e.g., *Thrombosis Res.* (1979), Vol. 16, pp. 245–254). For example, four tissue human serine proteases can be used in the primary bioassay, free factor Xa, prothrombinase, thrombin (IIa) and tissue plasminogen activator (tPA). The assay for tPA has been successfully used before to demonstrate undesired side effects in the inhibition of the fibrinolytic process (see, e.g., *J. Med. Chem.* (1993), Vol. 36, pp. 314–319). Another bioassay useful in demonstrating the utility of the compounds of the invention in inhibiting factor Xa demonstrates the potency of the compounds against free factor Xa in citrated plasma. For example, the anticoagulant efficacy of the compounds of the invention will be tested using either the prothrombin time (PT), or activated partial thromboplastin time (aPTT) while selectivity of the compounds is checked with the thrombin clotting time (TCT) assay. Correlation of the K; in the primary enzyme assay with the Ki for free factor Xa in citrated plasma will screen against compounds which interact with or are inactivated by other plasma components. Correlation of the K; with the extension of the PT is a necessary in vitro demonstration that potency in the free factor Xa inhibition assay translates into potency in a clinical coagulation assay. In addition, extension of the PT ine citrated plasma can be used to measure duration of action in subsequent pharmacodynamic studies For further information on assays to demonstrate the activity of the compounds of the invention, see R. Lottenberg et al., *Methods in Enzymology* (1981), Vol. 80, pp. 341–361, and H. Ohno et al., *Thrombosis Research* (1980), Vol. 19, pp. 579–588.

C. General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. Preferably, the composition will be about 5% to 75% by weight of a compound(s) of the invention, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of the invention (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state alleviated by the inhibition of factor Xa in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

Preferred Embodiments

Of the compounds of the invention as set forth above in the Summary of the Invention, several groups of compounds are preferred.

One preferred group are those compounds selected from formula (I):

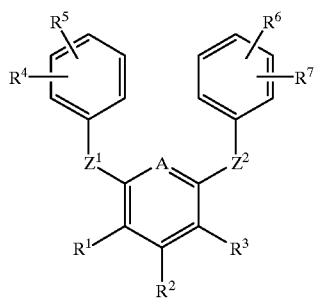

(I)

wherein

A is —N=;

$Z^1$ and $Z^2$ are independently —O—, —N($R^8$)— or —OCH$_2$—;

$R^1$ and $R^3$ are independently hydrogen, fluoro, chloro, haloalkyl, —N($R^8$)$R^9$, —C(O)O$R^8$, —C(O)N($R^8$)$R^9$, —N($R^8$)C(O)N($R^8$)$R^9$, —N($R^8$)C(O)$R^8$, or —N($R^8$)S(O)$_2R^{12}$;

$R^2$ is hydrogen; halo; alkyl; haloalkoxy; —O$R^8$; —C(O)O$R^8$; —C(O)N($R^8$)$R^9$; —N($R^8$)$R^9$; —C(O)N($R^8$)(CH$_2$)$_m$C(O)O$R^8$ (where m is 0 to 3); —N($R^8$)(CH$_2$)$_n$C(O)O$R^8$ (where n is 1 to 3); —N((CH$_2$)$_n$N($R^8$)$R^9$)(CH$_2$)$_n$C(O)O$R_a$ (where each n is 1 to 3); —O(CH$_2$)$_n$C(O)N($R^8$)$R^9$ (where n is 1 to 3); —O(CH$_2$)$_p$C(O)O$R^8$ (where p is 1 to 6); —N($R^8$)(CH$_2$)$_n$C(O)N($R^8$)(CH$_2$)$_n$C(O)O$R^8$ (where each n is independently 1 to 3); morpholin-4-yl; 3-tetrahydrofuranoxy;

or $R^2$ is aryloxy (optionally substituted by one or more substituents independently selected from the group consisting of —O$R^8$, —C(O)N($R^8$)$R^9$, halo, alkyl, carboxy, alkoxycarbonyl, haloalkoxy, haloalkoxycarbonyl, alkoxycarbonylalkyl, carboxyalkyl, aminocarbonylalkyl, (alkylamino) carbonylalkyl, (dialkylamino)carbonylalkyl, (arylamino)carbonylalkyl, (aralkylamino) carbonylalkyl, alkoxycarbonylalkenyl, carboxyalkenyl, aminocarbo nylalkenyl, (alkylamino)carbonylal kenyl, (dialkylamino) carbonylalkenyl, (arylamino) carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy) alkoxycarbonyl, tetrazolyl, morpholin-4-ylalkyl, and (1,2)-imidazolinyl (optionally substituted by alkyl));

or $R^2$ is piperazin-1-yl (optionally substituted by one or more substituents independently selected from the group consisting of alkyl, carboxy, —C(O)N($R^8$)$R^9$, carboxyalkyl, alkoxycarbonyl, and alkoxycarbonylalkyl);

or $R^2$ is 1-piperazinoyl (optionally substituted by one or more substituents selected from the group consisting of alkyl, carboxy, —C(O)N($R^8$)$R^9$, carboxyalkyl, alkoxycarbonyl, and alkoxycarbonylalkyl);

or $R^2$ is piperidin-1-yl (optionally substituted by one or more substituents selected from the group consisting of carboxy, —C(O)N($R^8$)$R^9$, carboxyalkyl, alkoxycarbonyl, or alkoxycarbonylalkyl);

or $R^2$ is (3,4)-piperidinyloxy (optionally substituted by one or more substituents selected from the group consisting of alkylcarbonyl, carboxy, —C(O)N($R^8$)$R^9$, alkoxycarbonyl, carboxyalkyl, alkoxycarbonylalkyl, or tetrazolylalkyl);

or $R^2$ is piperidin-4-ylamino (wherein the amino is optionally substituted by alkyl and the piperidinyl group is optionally substituted by one or more substituents selected from the group consisting of alkyl, alkoxycarbonyl, carboxyalkyl, —C(O)N($R^8$)$R^9$, alkoxycarbonylalkyl or aralklyl);

or $R^2$ is 3-pyrrolidinyloxy (optionally substituted by one or more substituents selected from the group consisting of alkyl, aralkyl, amidino, 1-iminoethyl, carboxy, carboxyalkyl, alkoxycarbonyl, —C(O)N($R^8$)$R^9$, or alkoxycarbonylalkyl);

$R^4$ is hydrogen, —O$R^8$ or —N($R^8$)$R^9$;

$R^5$ is —C(NH)NH$_2$;

$R^6$ is guanidino, —C(NH)NH$_2$, —C(O)N($R^8$)$R^9$, —CH(OH)C(O)N($R^8$)$R^9$, —(CH$_2$)$_m$N($R^8$)$R^9$ (where m is 0 to 3), 1-piperidinoyl, 1-pyrrolidinoyl, (1,2)-imidazolyl (optionally substituted by alkyl), or (1,2)-imidazolinyl (optionally substituted by alkyl);

$R^7$ is hydrogen, halo, alkyl, —O$R^8$, —C(O)N($R^8$)$R^9$;

$R^8$ and $R^9$ are independently hydrogen, methyl, ethyl or phenyl; and $R^{12}$ is methyl, ethyl, phenyl or benzyl.

Of this group of compounds, a preferred subgroup of compounds is that subgroup wherein $Z^1$ and $Z^2$ are independently —O— or —NCH$_3$—;

$R^1$ and $R^3$ are independently hydrogen, fluoro, chloro, trifluoromethyl, amino, —C(O)N($R^8$)$R^9$, or —NHC(O)NH$R^9$;

$R^2$ is hydrogen; alkyl; haloalkoxy; —O$R^8$; —C(O)O$R^8$; —N($R^8$)$R^9$; —N($R^8$)(CH$_2$)$_n$C(O)O$R^8$ (where n is 1 to 3); —N((CH$_2$)$_n$N($R^8$)$R^9$)(CH$_2$)$_n$C(O)O$R^8$ (where each n is 1 to 3); —O(CH$_2$)$_n$C(O)NI$R^8$)$R^9$ (where n is 1 to 3); —O(CH$_2$)$_p$C(O)O$R^8$ (where p is 1 to 6); —N($R^8$)(CH$_2$)$_n$C(O)N(RS)(CH$_2$)$_n$C(O)O$R^8$ (where each n is independently 1 to 3); morpholin-4-yl; 3-tetrahydrofuranoxy;

or $R^2$ is aryloxy (optionally substituted by one or more substituents independently selected from the group consisting of —O$R^8$, —C(O)N($R^8$)$R^9$, halo, alkyl, carboxy, alkoxycarbonyl, alkoxycarbonylalkyl, carboxyalkyl, alkoxycarbonylalkenyl, carboxyalkenyl, tetrazolyl, morpholin-4-ylalkyl, and (1,2)-imidazolinyl (optionally substituted by alkyl));

or $R^2$ is piperazin-1-yl (optionally substituted by one or more substituents independently selected from the group consisting of alkyl, carboxyalkyl, and alkoxycarbonylalkyl);

or $R^2$ is piperidin-1-yl (optionally substituted by one or more substituents selected from the group consisting of carboxy and alkoxycarbonyl);

or $R^2$ is (3,4)-piperidinyloxy (optionally substituted by one or more substituents selected from the group consisting of carboxyalkyl and alkoxycarbonylalkyl);

or $R^2$ is piperidin-4-ylamino (wherein the amino is optionally substituted by alkyl and the piperidinyl group is optionally substituted by one or more substituents selected from the group consisting of carboxyalkyl, alkoxycarbonylalkyl and aralklyl);

or $R^2$ is 3-pyrrolidinyloxy (optionally substituted by one or more substituents selected from the group consisting of 1-iminoethyl, carboxy, carboxyalkyl, alkoxycarbonyl and alkoxycarbonylalkyl);

$R^4$ is hydrogen, amino, hydroxy, or methoxy;

$R^5$ is —C(NH)NH$_2$;

$R^6$ is guanidino, —C(NH)NH$_2$, —C(O)N(R$^8$)R$^9$, —(CH$_2$)$_m$N(R$^8$)R$^9$ (where m is 0 to 1), (1,2)-imidazolyl substituted by alkyl, or 2-imidazolinyl substituted by alkyl;

$R^7$ is hydrogen, methoxy, or hydroxy; and $R^8$ and $R^9$ are independently hydrogen, methyl, ethyl, or phenyl.

Of this subgroup of compounds, a preferred class of compounds is that class wherein $Z^1$ and $Z^2$ are both —O—; $R^1$ and $R^3$ are independently hydrogen, fluoro, or chloro; $R^4$ is amino, hydrogen, hydroxy or methoxy; $R^6$ is guanidino, —C(NH)NH$_2$, —C(O)N(R$^8$)R$^9$, —(CH$_2$)$_m$N(R$^8$)R$^9$ (where m is 0 or 1), (1,2)-imidazolyl substituted by methyl, or 2-imidazolinyl optionally substituted by methyl; and $R^7$ is hydrogen or hydroxy.

Of this class of compounds, a preferred subclass of compounds is that subclass wherein $R^4$ is hydroxy; $R^6$ is dimethylamino or dimethylaminocarbonyl; and $R^7$ is hydrogen.

Of this subclass of compounds, preferred compounds are selected from the following:

4-hydroxy-3-[(3,5-difluoro-6-(3-dimethylaminocarbonylphenoxy)-4-(2-methoxy-4-carboxyphenoxy)pyridin-2-yl)oxylbenzamidine;

4-hydroxy-3-[(3,5-difluoro-6-(3dimethylaminocarbonylphenoxy)-4-(1-ethoxycarbonyl-methylpyrrolidin-3-yloxy)pyridin-2-yl)oxy]benzamidine;

4-hydroxy-3-[(3,5-difluoro-6-(3-dimethylaminocarbonylphenoxy)-4-propoxypyridin-2-yl)oxy]benzamidine;

4-hydroxy-3-[(3,5-difluoro-6-(3-dimethylaminocarbonylphenoxy)-pyridin-2-yl)oxy]benzamidine;

4-hydroxy-3-[(3,5-dimethylaminocarbonylphenoxy)-4-4-carboxypiperidin-1-yl)pyridin-2-yl)oxy]benzamidine;

4-hydroxy-3-[(3,5-difluoro-6-(3-dimethylaminocarbonylphenoxy)-4-dimethylamino-pyridin-2-yl)oxy]benzamidine;

4-hydroxy-3-[(3,5-difluoro-6-(3-dimethylaminocarbonylphenoxy)-4-(2,2,2-trifluoroethoxy)pyridin-2-yl)oxy]benzamidine;

4-hydroxy-3-[(3,5-difluoro-6-(3-dimethylaminocarbonylphenoxy)-4-(1,3-difluoroprop-2-oxy)pyridin-2-yl)oxy]benzamidine;

4-hydroxy-3-[(3,5-difluoro-6-(3-dimethylaminocarbonylphenoxy)-4-(1-bromo-3-fluoro-prop-2-oxy)pyridin-2-yl)oxy]benzamidine;

4-hydroxy-3-[(3,5-difluoro-6-(3-dimethylaminocarbonylphenoxy)-4-methylpyridin-2-yl)oxy]benzamidine;

4-hydroxy-3-[(3,5-difluoro-6-(3-dimethylaminocarbonylphenoxy)-4-((methyl)-(carboxymethyl)amino)pyridin-2-yl)oxy]benzamidine;

4-hydroxy-3-[(3,5-difluoro-6-(3-dimethylaminocarbonylphenoxy)-4-methoxy-pyridin-2-yl)oxy]benzamidine;

4-hydroxy-3-[(3,5 difluoro-6-(3-dimethylaminocarbonylphenoxy)-4-(3-carboxypiperidin-1-yl)pyridin-2-yl)oxy]benzamidine;

4-hydroxy-3-[(3,5-difluoro-6-(3-dimethylaminocarbonylphenoxy)-4-(4-carboxymethyl-piperazin-1-yl)pyridin-2-yl)oxy]benzamidine;

4-hydroxy-3-[(3,5-difluoro-6-(3-dimethylaminocarbonylphenoxy)-4-(pipefidin-1-yl)-pyridin-2-yl)oxy]benzamidine;

4-hydroxy-3-[(3,5-difluoro-6-(3-dimethylaminocarbonylphenoxy)-4-(4-methylpiperazin-1-yl)pyridin-2-yl)oxy]benzamidine;

4-hydroxy-3-[(3,5-difluoro-6-(3-dimethylaminocarbonylphenoxy)-4-(morpholin-4-yl)-pyridin-2-yl)oxy]benzamidine;

4-hydroxy-3-[(3,5-difluoro-6-(3-dimethylaminophenoxy)-4-(4-carboxymethyl-piperazinyl)pyridin-2-yl)oxy]benzamidine;

4-hydroxy-3-[(3,5-difluoro-6-(3-dimethylaminophenoxy)-4-(4-ethoxycarbonyl-methylpiperazinyl)pyridin-2-yl)oxy]benzamidine;

4-hydroxy-3-[(3,5-difluoro-6-(3-dimethylaminophenoxy)-4-(4-carboxy-2-methoxyphenoxy)pyridin-2-yl)oxy]benzamidine;

4-hydroxy-3-[(3,5-difluoro-6-(3-dimethylaminophenoxy)-4-(4-carboxy-2-(morpholin-4-ylmethyl)phenoxy)pyridin-2-yl)oxy]benzamidine;

4-hydroxy-3-[(3,5-difluoro-6-(3-dimethylaminophenoxy)-4-((methyl)-(carboxymethyl)amino)pyridin-2-yl)oxy]benzamidine;

4-hydroxy-3-[(3,5-difluoro-6-(3-dimethylaminocarbonylphenoxy)-4-(aminocarbonylmethoxy)pyridin-2-yl)oxy]benzamidine;

4-hydroxy-3-[(3,5-difluoro-6-(3-dimethylaminocarbonylphenoxy)-pyridin-2-yl)oxy]benzamidine;

4-hydroxy-3-[(3,5-difluoro-6-(3-dimethylaminophenoxy)-4-(1-carboxy-methylpiperidin-4-yloxy)pyridin-2-yl)oxy]benzamidine;

4-hydroxy-3-[(3,5-difluoro-6-(3-dimethylaminophenoxy)-4-carboxymethoxypyridin-2-yl)oxy]benzamidine;

4-hydroxy-3-[(3,5-difluoro-6-(3-dimethylaminocarbonylphenoxy)-4-(12-dimethyl-aminoethyl)carboxymethyl)amino)pyridin-2-yl)oxy]benzamidine;

4-hydroxy-3-[(3,5-difluoro-6-(3-dimethylaminophenoxy)-4-(1-(1-iminoethyl)pyrrolidin-3-yloxy)pyridin-2-yl)oxy]benzamidine;

4-hydroxy-3-((3,5-difluoro-6-43-dimethylaminocarbonylphenoxy)-4-(pyrrolidin-3-yloxy)pyridin-2-yl)oxy]benzamidine;

4-hydroxy-3-[(3,5-difluoro-6-(3-dimethylaminocarbonylphenoxy)-4-(1-ethoxycarbonyl-methylpyrrolidin-3-yloxy)pyridin-2-yl)oxy]benzamidine;

4-hydroxy-3-((3,5-difluoro-6-(3-dimethylaminocarbonylphenoxy)-4-(1-(1-iminoethyl)pyrrolidin-3-yloxy)pyridin-2-yl)oxy]benzamidine;

4-hydroxy-3-[(3,52difluoro-6-(3-dimethylaminocarbonylphenoxy)-4-((1-carboxymethyl)pyrrolidin-3-yloxy)pyridin-2-yl)oxy]benzamidine; and 4-hydroxy-3-[(3,5-difluoro-6-(3-dimethylaminophenoxy)-4-((methyl)-((carboxymethyl)aminocarbonylmethyl)amino)pyridin-2-yl)oxy]benzamidine.

Of this class of compounds, another preferred subclass of compounds is that subclass wherein wherein $R^4$ is hydroxy; $R^6$ is (1,2)-imidazolyl substituted by methyl or 2-imidazolinyl substituted by methyl; and $R^7$ is hydrogen.

Of this subclass, preferred compounds are selected from the following:

4-hydroxy-3-[(3,5-difluoro-6-(3-(1-methylimidazolin-2-yl)phenoxy)-4-(2-methoxycarbonylpiperidin-1-yl)pyridin-2-yl)oxy]benzamidine;

4-hydroxy-3-[(3,5-difluoro-6-(3-(1-methylimidazolin-2-yl)phenoxy)-4-(2-methoxphenoxy)pyridin-2-yl)oxy]benzamidine;

4-hydroxy-3-[(3,5-difluoro-6-(3-(1-methylimidazolin-2-yl)phenoxy)-4-((methyl)-(carboxymethyl)amino)pyridin-2-yl)oxy]benzamidine;

4-hydroxy-3-[(3,5-difluoro-6-(3-(1-methylimidazolin-2-yl)phenoxy)-4-((methyl)(ethoxycarbonylmethyl)amino)pyridin-2-yl)oxy]benzamidine;

4-hydroxy-3-[(3,5-difluoro-6-(3-(1-methylimidazolin-2-yl)phenoxy)-4-((1-(1-carbonyl)ethyl)piperidin-4-yl)aminopyridin-2-yl)oxy]benzamidine;

4-hydroxy-3-[(3,5-difluoro-6-(3-(1-methylimidazolin-2-yl)phenoxy)-4-(2,6-dimethoxy-(2-(ethoxycarbonyl)ethenyl)phenoxy)pyridin-2-yl)oxy]benzamidine;

4-hydroxy-3-[(3,5-difluoro-6-(3-(1-methylimidazolin-2-yl)phenoxy)-4-(2,6-dimethoxy-4-(2-carboxyethenyl)phenoxy)pyridin-2-yl)oxy]benzamidine;

4-hydroxy-3-[(3,5-difiuoro-6-(3-(1-methylimidazolin-2-yl)phenoxy)-4-(5-carboxypyrrolidin-3-yloxy)pyridin-2-yl)oxy]benzamidine;

4-hydroxy-3-[(3,5-difluoro-6-(3-(1-methylimidazolin-2-yl)phenoxy)-4-(4-(1-(ethoxycarbonyl)ethyl)piperazin-1-yl)pyridin-2-yl)oxy]benzamidine;

4-hydroxy-3-[(3,5-difluoro-6-(3-(1-methylimidazolin-2-yl)phenoxy)-4-(2-methoxy-4-ethoxycarbonylphenoxy)pyridin-2-yl)oxy]benzamidine;

4-hydroxy-3-[(3,5-difluoro-6-(3-(1-methylimidazolin-2-yl)phenoxy)-4-(2-methoxy-4-carboxyphenoxy)pyridin-2-yl)oxy]benzamidine;

4-hydroxy-3-[(3,5-difluoro-6-(3-(1-methylimidazolin-2-yl)phenoxy)-4-(4-ethoxycarbonylphenoxy)pyridin-2-yl)oxy]benzamidine;

4-hydroxy-3-[(3,5-difluoro-6-(3-(1-methylimidazolin-2-yl)phenoxy)-4-(2-hydroxy-4-carboxyphenoxy)pyridin-2-yl)oxy]benzamidine;

4-hydroxy-3-[(3,5-difluoro-6-(3-(1-methylimidazolin-2-yl)phenoxy)-4-(4-carboxyphenoxy)pyridin-2-yl)oxy]benzamidine;

4-hydroxy-3-[(3,5-difluoro-6-(3-(1-methylimidazolin-2-yl)phenoxy)-4-(2-methoxy-5-ethoxycarbonylphenoxy)pyridin-2-yl)oxy]benzamidine;

4-hydroxy-3-[(3,5-difluoro-6-(3-(1-methylimidazolin-2-yl)phenoxy)-4-(2-methoxy-5-carboxyphenoxy)pyridin-2-yl)oxy]benzemidine;

4-hydroxy-3-[(3,5-difluoro-6-(3-(1-methylimidazolin-2-yl)phenoxy)-4-(2,3-dimethoxy-5-ethoxycarbonylphenoxy)pyridin-2-yl)oxy]benzamidine;

4-hydroxy-3-[(3,5-difluoro-6-(3-(1-methylimidazolin-2-yl)phenoxy)-4-(2,3-dimethoxy-5-carboxyphenoxy)pyfidin-2-yl)oxy]benzamidine;

4-hydroxy-3-[(3,5-difluoro-6-(3-(1-methylimidazolin-2-yl)phenoxy)-4-3-aminocarbonyt-5-ethoxycarbonylphenoxy)pyridin-2-yl)oxy]benzamidine;

4-hydroxy-3-[(3,5-difluoro-6-(3-(1-methylimidazolin-2-yl)phenoxy)-4-(3-(1-methylimidazolin-2-yl)phenoxy)pyridin-2-yl)oxy]benzamidine;

4-hydroxy-3-[(3,5-difluoro-6-(3-(1-methylimidazolin-2-yl)phenoxy)-4-(3-ethoxycarbonylphenoxy)pyridin-2-yl)oxy]benzamidine;

4-hydroxy-3-[(3,5-difluoro-6-(3-(1-methylimidazolin-2-yl)phenoxy)-4-(2,6-dimethoxy-4-methoxycarbonylphenoxy)pyridin-2-yl)oxy]benzamidine;

4-hydroxy-3-[(3,5-difluoro-6-(3-(1-methylimidazolin-2-yl)phenoxy)-4-(2,6-dimethoxy-4-ethoxycarbonylphenoxy)pyridin-2-yl)oxy]benzamidine;

4-hydroxy-3-[(3,5-difluoro-6-(3-(1-methylimidazolin-2-yl)phenoxy)-4-(3-carboxyphenoxy)pyridin-2-yl)oxy]benzamidine;

4-hydroxy-3-[(3,5-difluoro-6(3-(1-methylimidazolin-2-yl)phenoxy)-4-(3,5-dicarboxyphenoxy)pyridin-2-yl)oxy]benzamidine;

4-hydroxy-3-[(3,5-difluoro-4-(3-(1-methylimidazolin-2-yl)phenoxy)-6-(3,5-dicarboxyphenoxy)pyridin-2-yl)oxy]benzamidine;

4-hydroxy-3-[(3,5-difluoro-6-(3-(1-methylimidazolin-2-yl)phenoxy)-4-(3-carboxy-5-ethoxycarbonylphenoxy)pyridin-2-yl)oxy]benzamidine;

4-hydroxy-3-[(3,5-difluoro-6-(3-(1-methylimidazolin-2-yl)phenoxy)-4-(2,6-dimethoxy-4-carboxyphenoxy)pyridin-2-yl)oxy]benzamidine;

4-hydroxy-3-[(3,5-difluoro-6-(3-(1-methylimidazolin-2-yl)phenoxy)-4-(2-hydroxy-4-methoxycarbonylphenoxy)pyridin-2-yl)oxy]benzamidine;

4-hydroxy-3-[(3,5-difluoro-6-(3-amidinophenoxy)-4-(2-methoxy-4-carboxy-phenoxy)pyridin-2-yl)oxy]benzamidine;

4-hydroxy-3-[(3,5-difluoro-6-(3-(1-methylimidazolin-2-yl)phenoxy)-4-(3-aminocarbonyl-5-carboxyphenoxy)pyridin-2-yl)oxy]benzamidine;

4-hydroxy-3-[(3,5-difluoro-6-(3-(1-methylimidazolin-2-yl)phenoxy)-4-(2-chloro-4-carboxyphenoxy)pyridin-2-yl)oxy]benzamidine;

4-hydroxy-3-[(3,5-difluoro-6-(3-(1-methylimidazolin-2-yl)phenoxy)-4-(2,6-dimethyl-4-carboxyphenoxy)pyridin-2-yl)oxy]benzamidine;

4-hydroxy-3-[(3,5-difluoro-6-(3-(1-methylimidazolin-2-yl)phenoxy)-4-((1-ethoxycarbonylmethyl)piperidin-4-yloxy)pyridin-2-yl)oxy]benzamidine;

4-hydroxy-3-[(3,5!difluoro-6-(3-(1-methylimidazolin-2-yl)phenoxy)-4-(4-(ethoxycarbonylmethyl)piperazin-1-yl)pyridin-2-yl)oxy]benzamidine;

4-hydroxy-3-[(3,5-difluoro-6-(3-(1-methylimidazolin-2-yl)phenoxy)-4-(5-ethoxycarbonylpyrrolidin-3-yloxy)pyridin-2-yl3oxy]benzamidine;

4hydroxy-3-[(3,5-difluoro-6-(3-(1-methylimidazolin-2-yl)phenoxy)-4-(1-carboxymethylpiperidin-4-yloxy)pyridin-2-yl)oxy]benzamidine;

4-hydroxy-3-[(3,5-difluoro-6-(3-(1-methylimidazolin-2-yl)phenoxy)-4-(1-(1-carboxy-1-methylethyl)piperidin-4-yl)oxy)pyridin-2-yl)oxy]benzamidine; 4-hydroxy-3-[(3,5-difluoro-6-(3-(1-methylimidazolin-2-yl)phenoxy)-4-(4-ethoxycarbonylpiperidin-1-yl)pyridin-2-yl)oxy]benzamidine;

4-hydroxy-3-[(3,5-difluoro-6-(3-(1-methylimidazolin-2-yl)phenoxy)-4-(3-ethoxycarbonylpiperidin-1-yl)pyridin-2-yl)oxy]benzamidine;

4-hydroxy-3-[(3,5-difluoro-6-(3-(1-methylimidazolin-2-yl)phenoxy)-4-(3-carboxypiperidin-1-yl)pyridin-2-yl)oxy]benzamidine;

4-hydroxy-3-[(3,5-difluoro-6-(3-(1-methylimidazolin-2-yl)phenoxy)-4-(4-carboxypiperidin-1-yl)pyridin-2-yl)oxy]benzamidine;

4-hydroxy-3-[(3,5-difluoro-6-(3-(1-methylimidazolin-2-yl)phenoxy)-4-(3-(2-ethoxycarbonylethyl)phenoxy)pyridin-2-yl)oxy]benzamidine;

4-hydroxy-3-[(3,5-difluoro-6-(3-(1-methylimidazolin-2-yl)phenoxy)-4-(2-methoxy-4-ethoxycarbonylmethylphenoxy)pyridin-2-yl)oxy]benzamidine;

4-hydroxy-3-[(3,5-difluoro-6-(3-(1-methylimidazolin-2-yl)phenoxy)-4-(2-methoxy-4-carboxymethylphenoxy)pyridin-2-yl)oxy]benzamidine;

4-hydroxy-3-[(3,5-difluoro-6-(3-(1-methylimidazolin-2-yl)phenoxy)-4-(2-methoxy-5-(tetrazol-5-yl)phenoxy)pyridin-2-yl)oxy]benzamidine;

4-hydroxy-3-[(3,5-difluoro-6-(3-(1-methylimidazol-2-yl)phenoxy)-4-((2-dimethylaminoethyl)(carboxymethyl)amino)pyridin-2-yl)oxy]benzamidine;

4-hydroxy-3-[(3,5-difluoro-6-(3-(1-methylimidazolin-2-yl)phenoxy)-4-((1-carboxymethylpiperidin-4-yl)(methylamino)pyridin-2-yl)oxy]benzamidine;

4-hydroxy-3-[(3,5-difluoro-6-(3-(1-methylimidazolin-2-yl)phenoxy)-4-((1-carboxymethylpiperidin-4-yl)amino)pyridin-2-yl)oxy]benzamidine;

4-hydroxy-3-[(3,5-difluoro-6-(3-(1-methylimidazolin-2-yl)phenoxy)-4-((1-ethoxycarbonylmethylpiperidin-4-yl)(methyl)amino)pyridin-2-yl)oxy]benzamidine;

4-hydroxy-3-[(3,5-difluoro-6-(3-(1-methylimidazolin-2-yl)phenoxy)-4-((1-(ethoxycarbonylmethyl)piperidin-4-yl)amino)pyridin-2-yl)oxy]benzamidine;

4-hydroxy-3-[(3,5-difluoro-6-(3-(1-methylimidazolin-2-yl)phenoxy)-4-t(piperidin-4-yl)amino)pyridin-2-yl)oxy]benzamidine;

4-hydroxy-3-[(3,5-difluoro-6-(3-(1-methylimidazolin-2-yl)phenoxy)-4-((1-benzylpiperidin-4-yl)amino)pyridin-2-yl)oxy]benzamidine;

4-hydroxy-3-[(3,5-difluoro-6-(3-(1-methylimidazolin-2-yl)phenoxy)-4-((piperidin-4-yl)amino)pyridin-2-yl)oxy]benzamidine;

4-hydroxy-3-[(3,5-difluoro-6-(3-(1-methylimidazolin-2-yl)phenoxy)-4-((1-benzylpiperidin-4-yl)(methyl)amino)pyridin-2-yl)oxy]benzamidine;

4-hydroxy-3-[(3,5-difluoro-6-(3-(1-methylimidazolin-2-yl)phenoxy)-4-(5-carboxypent-1-oxy)pyridin-2-yl)oxy]benzamidine; and 4-hydroxy-3-[(3,5-difluoro-6-(3-(1-methylimidazolin-2-yl)phenoxy)-4-(4-carboxymethylpiperazin-1-yl)pyridin-2-yl)oxy]benzamidine.

Of this class of compound, another preferred subclass of compounds is that subclass wherein $R^4$ is hydroxy; $R^6$ is guanidino; and $R^7$ is hydrogen.

Of this subclass of compounds, preferred compounds are selected from the following:

4-hydroxy-3-[(3,5-difluoro-6-(3-(guanidino)phenoxy)-4-((1-ethoxycarbonylmethyl)piperidine- 4-yloxy)pyridin-2-yl)oxy]benzamidine;

4-hydroxy-3-[(3,5-difluoro-6-(3-(guanidino)phenoxy)-4-(1-carboxymethylpiperidin-4-yloxy)pyridin-2-yl)oxy]benzamidine;

4-hydroxy-3-[(3,5-difluoro-6-(3-(guanidino)phenoxy)-4-(5-ethoxycarbonylpyrrolidin-3-yl-oxy)pyridin-2-yl)oxy]benzamidine;

4-hydroxy-3-[(3,5-difluoro-6-(3-(guanidino)phenoxy)-4(2,6dimethoxy-4-methoxy-carbonylphenoxy)pyridin-2-yl)oxy]benzamidine;

4-hydroxy-3-[(3,5-difluoro-6(3-guanidino)phenoxy)-4-(2,6-dimethoxy-4-ethoxycarbonylphenoxy)pyridin-2-yl)oxy]benzamidine;

4-hydroxy-3-[(3,5-difluoro-6-(3-(guanidino)phenoxy)-4-(2,6-dimethoxy-4-carboxyphenoxy)pyridin-2-yl)oxy]benzamidine;

4-hydroxy-3-[(3,5-difluoro-6-(3-(guanidino)phenoxy)-4-(2,6-dimethoxy-4-aminocarbonylphenoxy)pyridin-2-yl)oxy]benzamidine;

4-hydroxy-3-[(3,5-difluoro-6-(3-(guanidino)phenoxy)-4-(2-methoxy-4-carboxyphenoxy)-pyridin-2-yl)oxy]benzamidine;

4-hydroxy-3-[(3,5-difluoro-6-(3-(guanidino)phenoxy)-4-(methyl)(phenyl)aminocarbonylpyridin-2-yl)oxy]benzamidine; and 4-hydroxy-3-[(3,5-difluoro-6-(3-(guanidino)phenoxy)-4(4carboxy-methylpiperazin-1-yl)pyridin-2-yl)oxy]benzamidine.

Another preferred group of compounds are selected from formula (VII):

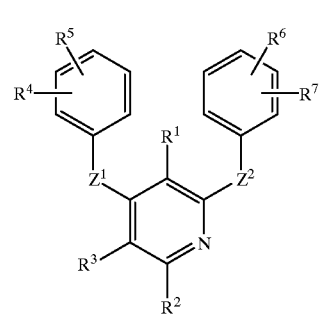

(VII)

wherein $Z^1$ and $Z^2$ are independently —O—, —N($R^8$)— or —OCH$_2$—;

$R^1$ and $R^3$ are independently hydrogen, fluoro, chloro, haloalkyl, —N($R^8$)$R^9$, —C(O)O$R^8$, —C(O)N($R^8$)$R^9$, —N($R^8$)C(O)N$R^8$)$R^9$, —N($R^8$)C(O)$R^8$, or —N($R^8$)S(O)$_2R^{12}$;

$R^2$ is hydrogen; halo; alkyl; haloalkoxy; —O$R^8$; —C(O)O$R^8$; —C(O)N($R^8$)$R^9$; —N($R^8$)$R^9$; —C(O)N($R^8$)(CH$_2$).C(O)O$R^8$ (where m is 0 to 3); —N($R^8$)(CH$_2$)$_n$C (O)OR⁸ (where n is 1 to 3); —N((CH₂)ₙN(R⁸)R⁹)(CH₂)ₙC(O)OR⁸ (where each n is 1 to 3); —O(CH₂)ₙC(O)N(R⁸)R⁹ (where n is 1 to 3); —O(CH₂)ₚC(O)OR⁸ (where p is 1 to 6); —N(R⁸)(CH₂)ₙC(O)N(R⁸)(CH₂)ₙC(O)OR⁸ (where each n is independently 1 to 3); morpholin-4-yl; 3-tetrahydrofuranoxy;

or R² is aryloxy (optionally substituted by one or more substituents independently selected from the group consisting of —OR⁸, —C(O)N(R⁸)R⁹, halo, alkyl, carboxy, alkoxycarbonyl, haloalkoxy, haloalkoxycarbonyl, alkoxycarbonylalkyl, carboxyalkyl, aminocarbonylalkyl, (alkylamino)carbonylalkyl, idialkylamino)carbonylalkyl, (arylamino)carbonylalkyl, (aralkylamino)carbonylalkyl, alkoxycarbonylalkenyl, carboxyalkenyl, aminocarbonylalkenyl, (alkylamino)carbonylalkenyl, (dialkylamino)carbonylalkenyl, (arylamino)carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy)alkoxycarbonyl, tetrazolyl, morpholin-4-ylalkyl, and (1,2)-imidazolinyl (optionally substituted by alkyl));

or R² is piperazin-1-yl (optionally substituted by one or more substituents independently selected from the group consisting of alkyl, carboxy, —C(O)N(R⁸)R⁹, carboxyalkyl, alkoxycarbonyl, and alkoxycarbonylalkyl);

or R² is 1-piperazinoyl (optionally substituted by one or more substituents selected from the group consisting of alkyl, carboxy, —C(O)N(R⁸)R⁹, carboxyalkyl, alkoxycarbonyl, and alkoxycarbonylalkyl);

or R² is piperidin-1-yl (optionally substituted by one or more substituents selected from the group consisting of carboxy, —C(O)N(R⁸)R⁹, carboxyalkyl, alkoxycarbonyl, or alkoxycarbonylalkyl);

or R² is (3,4)-piperidinyloxy (optionally substituted by one or more substituents selected from the group consisting of alkylcarbonyl, carboxy, —C(O)N(R⁸)R⁹, alkoxycarbonyl, carboxyalkyl, alkoxycarbonylalkyl, or tetrazolylalkyl);

or R² is piperidin-4-ylamino (wherein the amino is optionally substituted by alkyl and the piperidinyl group is optionally substituted by one or more substituents selected from the group consisting of alkyl, alkoxycarbonyl, carboxyalkyl, —C(O)N(R⁸)R⁹, alkoxycarbonylalkyl or aralklyl);

or R² is 3-pyrrolidinyloxy (optionally substituted by one or more substituents selected from the group consisting of alkyl, aralkyl, amidino, 1-iminoethyl, carboxy, carboxyalkyl, —C(O)N(R⁸)R⁹, alkoxycarbonyl or alkoxycarbonylalkyl);

R⁴ is hydrogen, —OR⁸ or —N(R⁸)R⁹;
R⁵ is —C(NH)NH₂;
R⁶ is guanidino, —C(NH)NH₂, —C(O)N(R⁸)R⁹, —CH(OH)C(O)N(R⁸)R⁹, —(CH₂)ₘN(R⁸)R⁹ (where m is 0 to 3), 1-piperidinoyl, 1-pyrrolidinoyl, (11,2)-imidazolyl (optionally substituted by alkyl), or (1,2)-imidazolinyl (optionally substituted by alkyl);
R⁷ is hydrogen, halo, alkyl, —OR⁸, C(O)N(R⁸)R⁹;
R⁸ and R⁹ are independently hydrogen, methyl, ethyl or phenyl;
R¹² is methyl, ethyl, phenyl or benzyl.

Of this group of compounds, a preferred subgroup of compounds is that subgroup wherein Z¹ and Z² are independently —O— or —NCH₃—;

R¹ and R³ are independently hydrogen, fluoro, chloro, trifluoromethyl, amino, —C(O)N(Rₐ)R⁹, or —NHC(O)NHR⁹;

R² is hydrogen; alkyl; haloalkoxy; —OR⁸; —C(O)OR⁸; —N(R⁸)R⁹; —N(R⁸)(CH₂)ₙC(O)OR⁸ (where n is 1 to 3); —N((CH₂)ₙN(R⁸)R⁹)(CH₂)ₙC(O)OR⁸ (where each n is 1 to 3); —O(CH₂)ₙC(O)N(R⁸)R⁹ (where n is 1 to 3); —O(CH₂)ₚC(O)OR⁸ (where p is 1 to 6); —N(R⁸)(CH₂)ₙC(O)N(R⁸)(CH₂)ₙC(O)OR⁸ (where each n is independently 1 to 3); morpholin-4-yl; 3-tetrahydrofuranoxy;

or R² is aryloxy (optionally substituted by one or more substituents independently selected from the group consisting of —OR⁸, —C(O)N(R⁸)R⁹, halo, alkyl, carboxy, alkoxycarbonyl, alkoxycarbonylalkyl, carboxyalkyl, alkoxycarbonylalkenyl, carboxyalkenyl, tetrazolyl, morpholin-4-ylalkyl, and (1,2)-imidazolinyl (optionally substituted by alkyl));

or R² is piperazin-1-yl (optionally substituted by one or more substituents independently selected from the group consisting of alkyl, carboxyalkyl, and alkoxycarbonylalkyl);

or R² is piperidin-1-yl (optionally substituted by one or more substituents selected from the group consisting of carboxy and alkoxycarbonyl);

or R² is (3,4)-piperidinyloxy (optionally substituted by one or more substituents selected from the group consisting of carboxyalkyl and alkoxycarbonylalkyl);

or R² is piperidin-4-ylamino (wherein the amino is optionally substituted by alkyl and the piperidinyl group is optionally substituted by one or more substituents selected from the group consisting of carboxyalkyl, alkoxycarbonylalkyl and aralklyl);

or R² is 3-pyrrolidinyloxy (optionally substituted by one or more substituents selected from the group consisting of 1-iminoethyl, carboxy, carboxyalkyl, alkoxycarbonyl and alkoxycarbonylalkyl);

R⁴ is hydrogen, amino, hydroxy, or methoxy;
R⁵ is —C(NH)NH₂;
R⁶ is guanidino, —C(NH)NH₂, —C(O)N(R⁸)R⁹, —(CH₂)ₘN(R⁸)R⁹ (where m is 0 to 1), (1,2)-imidazolyl substituted by alkyl, or 2-imidazolinyl substituted by alkyl;
R⁷ is hydrogen, methoxy, or hydroxy; and
R⁸ and R⁹ are independently hydrogen, methyl, ethyl, or phenyl.

Of this subgroup of compounds, a preferred class of compounds is that class wherein Z¹ and Z² are both —O—; R¹ and R³ are independently hydrogen, fluoro, or chloro; R⁴ is amino, hydrogen, hydroxy or methoxy; R⁶ is guanidino, —C(NH)NH₂, —C(O)N(R⁸)R⁹, —(CH₂)ₘN(R⁸)R⁹ (where m is 0 or 1), (1,2)-imidazolyl substituted by methyl, or 2-imidazolinyl optionally substituted by methyl; and R⁷ is hydrogen or hydroxy Of this class of compounds, a preferred subclass of compounds is that subclass wherein R⁴ is hydroxy; R⁶ is dimethylamino or dimethylaminocarbonyl; and R⁷ is hydrogen.

Of this subclass of compounds, preferred compounds are 4-hydroxy-3-[(3,5-difluoro-6-(3-dimethylaminocarbonylphenoxy)-2-methoxypyridin-4-yl)-oxy]benzamidine; and 4-hydroxy-3-[(3,5-difluoro-6-(3-dimethylaminocarbonyl-phenoxy)-2-(2-methoxy-5-ethoxycarbonylphenoxy)pyridin-4-yl)oxy]benzamidine.

Preparation of Compounds of the Invention

As a matter of convenience, the following description of the preparation of the compounds of the invention is directed to the preparation of compounds of formula (1). It is understood, however, that similar synthetic processes may be used to prepare the compounds of formula (II), (III), (IV), (V), (VI), (VII) and (VIII). It is also understood that in the following description, combinations of substituents and/or variables (e.g., $R^4$ and $R^5$) on the depicted formulae are permissible only if such combinations result in stable compounds.

A. Preparation of Intermediates

1. Compounds of Formula (C)

Compounds of formula (C), as shown below, are intermediates in the preparation of the compounds of the invention. As illustrated below in Reaction Scheme 1, compounds of formula (C) are prepared from compounds of formulae (A) and (B) wherein X is chloro or fluoro and $R^{2a}$ is —N($R^8$)$R^9$, —N($R^8$)(CH$_2$)$_m$C(O)OR$^8$ (where m is 0 to 3) or piperazinyl (optionally substituted by alkyl, carboxy, carboxyalkyl, alkoxycarbonyl or alkoxycarbonylalkyl); and each $R^8$ and $R^9$ is independently hydrogen, alkyl, aryl or aralkyl:

REACTION SCHEME 1

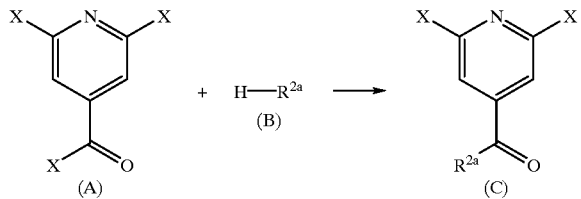

Compounds of formula (A) and (B) can be prepared according to methods known to those of ordinary skill in the art or are commercially available, for example, from Aldrich Chemical Company, Inc. or from Maybridge Co.

In general, compounds of formula (C) are prepared by reacting a compound of formula (A) with an equimolar amount of a compound of formula (B) at 0° C. to 40° C., preferably at ambient temperature, in the presence of a base, e.g., triethylamine, or in the presence of a second equivalent of the compounds of formula (B). The compounds of formula (C) are isolated from the resulting reaction mixture by conventional methods.

2. Compounds of Formula (F)

Compounds of formula (F), as shown below, are also intermediates in the preparation of the compounds of the invention. As illustrated below in Reaction Scheme 2, compounds of formula (F) are prepared from compounds of formulae (D) and (E) where each X is independently chloro or fluoro; and $R^2$ is alkoxy, haloalkoxy, —O(CH)$_p$C(O)OR$^8$ (where p is 1 to 6), —N($R^8$)$R^9$, —N($R^8$)(CH$_2$)$_n$C(O)OR$^8$ (where n is 1 to 3), —N($R^8$)(CH$_2$)$_n$C(O)N($R^8$)(CH$_2$)$_n$C(O)OR$^8$ (where each n is independently 1 to 3), morpholin-4-yl, 3-tetrahydrofuranyloxy; or $R^2$ is aryloxy (optionally substituted by one or more substituents independently selected from the group consisting of —OR$^8$, —C(O)N($R^8$)$R^9$, halo, alkyl, alkoxycarbonyl, haloalkoxy, haloalkoxycarbonyl, alkoxycarbonylalkyl, aminocarbonylalkyl, (alkylamino)carbonylalkyl, (dialkylamino)carbonylalkyl, (arylamino)carbonylalkyl, (aralkylamino)carbonylalkyl, alkoxycarbonylalkenyl, aminocarbonylalkenyl, (alkylamino)carbonylalkenyl, (dialkylamino)carbonylalkenyl, (arylamino)carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy)alkoxycarbonyl, tetrazolyl, morpholin-4-ylalkyl, and (1,2)-imidazolinyl (optionally substituted by alkyl)); or $R^2$ is 1-piperidinyl (optionally substituted by alkoxycarbonyl or alkoxycarbonylalkyl); or $R^2$ is 1-piperazinyl (optionally substituted by alkyl, alkoxycarbonyl or alkoxycarbonylalkyl); or $R^2$ is (3,4)-piperidinyloxy (optionally substituted by alkylcarbonyl, alkoxycarbonyl, alkoxycarbonylalkyl or tetrazolylalkyl); or $R^2$ is piperidin-4-ylamino (wherein the amino is optionally substituted by alkyl and the piperidinyl group is optionally substituted by alkyl, alkoxycarbonyl, alkoxycarbonylalkyl or aralklyl); or $R^2$ is 3-pyrrolidinyloxy (optionally substituted by alkyl, aralkyl or alkoxycarbonylalkyl); and each $R^8$ and $R^9$ is independently hydrogen, alkyl, aryl or aralkyl:

REACTION SCHEME 2

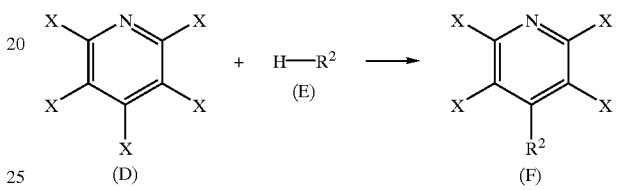

Compounds of formulae (D) and (E) are commercially available, for example, from Aldrich Chemical Company, Inc., or may be prepared according to methods known to those skilled in the art.

In general, compounds of formula (F) are prepared by treating a compound of formula (D) with a compound of formula (E) in an aprotic solvent, for example, methylene chloride, at between about 0° C. and 50° C., preferably at ambient temperature, and, if the hydrogen in the compound of formula (E) is an hydroxyl hydrogen, in the presence of a base, for example, cesium carbonate. The compound of formula IF) is isolated from the reaction mixture by standard techniques.

3. Compounds of Formulae (J) and (K)

Compounds of formulae (J) and (K), as shown below, are also intermediates in the preparation of the compounds of the invention. As illustrated below in Reaction Scheme 3, compounds of formula (J) and (K) are prepared from compounds of formula (G) and formula (H) where A is —N= or —C($R^{11}$)= (where $R^{11}$ is hydrogen, alkyl or halo); X is fluoro of chloro; $R^1$ and $R^3$ are independently hydrogen, halo, alkyl, haloalkyl, alkoxy, haloalkoxy, nitro, —N($R^8$)$R^9$, —C(O)OR$^8$, —C(O)N($R^8$)$R^9$, —C(O)N($R^8$)CH$_2$C(O)N($R^8$)$R^9$, —N($R^8$)C(O)N($R^8$)$R^9$, —N($R^8$)C(O)R$^8$, —N($R^8$)S(O)$_2$R$^{12}$, or —N($R^8$)C(O)N($R^8$)CH$_2$—C(O)N($R^8$)$R^9$; $R^2$ is hydrogen, alkyl, haloalkoxy, —OR$^{12}$, —C(O)OR$^8$, —C(O)N($R^8$)$R^9$, —N($R^8$)$R^9$, —C(O)N($R^8$)(CH$_2$)$_m$C(O)OR$^8$ (where m is 0 to 3), —N($R^8$)(CH$_2$)$_n$C(O)OR$^8$ (where n is 1 to 3), —N((CH$_2$)$_n$N($R^8$)$R^9$)(CH$_2$)$_n$C(O)OR$^8$ (where each n is 1 to 3), —O(CH$_2$)$_n$C(o)N($R^8$)$R^9$ (where n is 1 to 3), —O(CH$_2$)$_p$C(O)OR$^8$ (where p is 1 to 6), —N($R^8$)(CH$_2$)$_n$C(O)N($R^8$)(CH$_2$)$_n$C(O)OR$^8$ (where each n is independently 1 to 3), morpholin-4-yl, 3-tetrahydrofuranoxy; or $R^2$ is aryloxy (optionally substituted by one or more substituents independently selected from the group consisting of —OR$^{12}$, —C(O)N($R^8$)$R^9$, halo, alkyl, alkoxycarbonyl, haloalkoxy, haloalkoxycarbonyl, alkoxycarbonylalkyl, aminocarbonylalkyl, (alkylamino)carbonylalkyl, (dialkylamino)carbonylalkyl, (arylamino)carbonylalkyl, (aralkylamino)carbonylalkyl, alkoxycarbonylalkenyl, aminocarbonylalkenyl, (alkylamino)carbonylalkenyl, (dialkylamino)carbonylalkenyl, (arylamino)

carbonylalkenyl, (aralkylamino)carbonylalkenyl, (hydroxyalkoxy)carbonyl, (alkoxy)alkoxycarbonyl, (hydroxyalkoxy) alkoxycarbonyl, ((alkoxy)alkoxy) alkoxycarbonyl, tetrazolyl, morpholi n-4-ylalkyl, and (1,2)-imidazolinyl (optionally substituted by alkyl)); or $R^2$ is piperazin-1-yl (optionally substituted by one or more substituents independently selected from the group consisting of alkyl, alkoxycarbonyl, and alkoxycarbonylalkyl); or $R^2$ is 1-piperazinoyl (optionally substituted by one or more substituents selected from the group consisting of alkyl, alkoxycarbonyl, and alkoxycarbonylalkyl); or $R^2$ is piperidin-1-yl (optionally substituted by one or more substituents selected from the group consisting of alkoxycarbonyl, and alkoxycarbonylalkyl); or $R^2$ is (3,4)-piperidinyloxy (optionally substituted by one or more substituents selected from the group consisting of alkylcarbonyl, alkoxycarbonyl, alkoxycarbonylalkyl, and tetrazolylalkyl); or $R^2$ is piperidin-4-ylamino (wherein the amino is optionally substituted by alkyl and the piperidinyl group is optionally substituted by one or more substituents selected from the group consisting of alkyl, alkoxycarbonyl, alkoxycarbonylalkyl and aralklyl); or $R^2$ is 3-pyrrolidinyloxy (optionally substituted by one or more substituents selected from the group consisting of alkyl, aralkyl, alkoxycarbonyl and alkoxycarbonylalkyl); $R^4$ is independently hydrogen, halo, alkyl, nitro; —$OR^{12}$, —C(O)$OR^8$, —C(O)N($R^8$)$R^9$, —N($R^8$)$R^9$, or —N(H)C(O)$R^8$; each $R^8$ and $R^9$ is independently hydrogen, alkyl, aryl or aralkyl; and $R^{12}$ is alkyl, aryl or aralkyl:

REACTION SCHEME 3

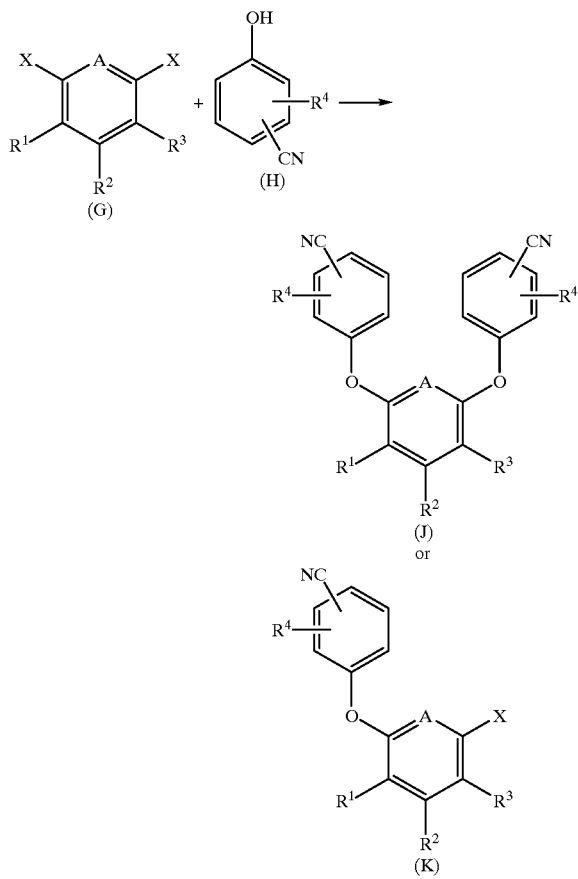

Compounds of formula (G) include compounds of formulae (C) and (F) as described above, or may be prepared by methods described herein or by methods known to one of ordinary skill in the art. They may also be commercially available, for example, from Aldrich Chemical Co., Inc. or from Maybridge Co. Compounds of formula (H) may be prepared by methods known to one of ordinary skill in the art or may be commercially available, for example, from Aldrich Chemical Co., Inc.

In general; the compounds of formulae IJ) and (K) are prepared by reacting a compound of formula (G) with a compound of formula (H) (in an equimolar amount for a compound of formula (K) and with two or more equivalents of a compound of formula (H) for a compound of formula (J)) in the presence of a base, e.g., sodium hydride or cesium carbonate, at temperatures between about 20° C. and 120° C., preferably, for compounds of formula (J), at temperatures of around 50° C., in an aprotic solvent, for example, dimethylformamide, DMSO or acetonitrile, for a period of time sufficient to complete the desired reaction as monitored by thin layer chromatography (TLC). Compounds of formulae (J) and (K) are then isolated from the reaction mixture by standard isolation techniques.

In a similar manner, compounds of formula (G) may be treated with compounds of formula (H) wherein the hydroxy group is replaced by an amino group to produce compounds of formulae (J) and (K) wherein the ether connecting group is replaced by an amino connecting group. The amina group can then be alkylated by standard procedures.

Compounds of formulae (J) and (K) wherein $R^4$ is an amino group may be further treated with an alkylsulfonyl halide, e.g., methylsulfonylchloride, under basic conditions at ambient temperature to produce compounds of formulae (J) and (K) wherein $R^4$ is —N(H)S(O)$_2R^{12}$.

4. Compounds of Formula (M)

Compounds of formula (M), as shown below, are also intermediates in the preparation of the compounds of the invention. As illustrated below in Reaction Scheme 4, compounds of formula (M) are prepared from compounds of formula (K) and formula (L) where A is —N= or —C($R^{11}$)= (where $R^{11}$ is hydrogen, alkyl or halo); X is fluoro of chloro; $R^1$ and $R^3$ are independently hydrogen, halo, alkyl, haloalkyl, alkoxy, haloalkoxy, nitro, —N($R^8$)$R^9$, —C(O)$OR^8$, —C(O)N($R^8$)$R^9$, —C(O)N($R^8$)$CH_2$C(O)N($R^8$)$R^9$, or —N($R^8$)C(O)N($R^8$)$CH_2$C(O)N($R^8$)$R^9$; $R^2$ is hydrogen, alkyl, haloalkoxy, —$OR^{12}$, —C(O)$OR^8$, —C(O)N($R^8$)$R^9$, —N($R^8$)$R^9$, —C(O)N($R^8$)(CH$_2$)$_m$C(O)$OR^8$ (where m is 0 to 3), —N($R^8$)(CH$_2$)C(O)$OR^8$ (where n is 1 to 3), —N((CH$_2$)$_n$N($R^8$)$R^9$)(CH$_2$)$_n$C(O)$OR^8$ (where each n is 1 to 3), —O(CH$_2$)$_n$C(O)N($R^{8)R9}$ (where n is 1 to 3), —O(CH$_2$)$_p$C(O)$OR^8$ (where p is 1 to 6), —N($R^8$)(CH$_2$)$_n$C(O)N($R^8$)(CH$_2$)$_n$C(O)$OR^8$ (where each n is independently 1 to 3), morpholin-4-yl, 3-tetrahydrofuranoxy; or $R^2$ is aryloxy (optionally substituted by one or more substituents independently selected from the group consisting of —OR$^1$2, —C(O)N($R^8$)$R^9$, halo, alkyl, alkoxycarbonyl, haloalkoxy, haloalkoxycarbonyl, alkoxycarbonylalkyl, aminocarbonylalkyl, (alkylamino)carbonylalkyl, (dialkylamino)carbonylalkyl, (arylamino)carbonylalkyl, (aralkylamino)carbonylalkyl, alkoxycarbonylalkenyl, aminocarbonylalkenyl, (alkylamino)carbonylalkenyl, (dialkylamino)carbonylalkenyl, (arylamino) carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy) alkoxycarbonyl, tetrazolyl, morpholin-4-ylalkyl, and (1,2)-imidazolinyl (optionally substituted by alkyl)); or $R^2$ is piperazin-1-yl (optionally substituted by one or more substituents independently selected from the group consisting of alkyl, alkoxycarbonyl, and alkoxycarbonylalkyl); or $R^2$ is 1-piperazinoyl (optionally substituted by one or more substituents selected from the group consisting of alkyl, alkoxycarbonyl, and alkoxycarbonylalkyl); or $R^2$ is piperidin-1-yl (optionally substituted by one or more substituents selected from the group consisting of alkoxycarbonyl, and alkoxycarbonylalkyl); or $R^2$ is (3,4)-piperidinyloxy (optionally substituted by one or more substituents selected from the group consisting of alkylcarbonyl, alkoxycarbonyl, alkoxycarbonylalkyl, and tetrazolylalkyl); or $R^2$ is piperidin-4-ylamino (wherein the amino is optionally substituted by alkyl and the piperidinyl group is optionally substituted by one or more substituents selected from the group consisting of alkyl, alkoxycarbonyl, alkoxycarbonylalkyl and aralklyl); or $R^2$ is 3-pyrrolidinyloxy (optionally substituted by one or more substituents selected from the group consisting of alkyl, aralkyl, alkoxycarbonyl and alkoxycarbonylalkyl); $R^4$ and $R^7$ are independently hydrogen, halo, alkyl, nitro, $-OR^{12}$, $-C(O)OR^8$, $-C(O)N(R^8)R^9$, $-N(R^8)R^9$, or $-N(H)C(O)R^8$; $R^6$ is halo, alkyl, haloalkyl, haloalkoxy, nitro, amino, ureido, guanidino, $-OR^{12}$, $-C(NH)NH_2$, $-C(NH)NHOH$, $-C(O)R^{10}$, $-(CH_2)_mC(O)N(R^8)R^9$ (where m is 0 to 3), $-CH(OH)C(O)N(R^8)R^9$, $-(CH_2)_mN(R^8)R^9$ (where m is 0 to 3), $-(CH_2)_mC(O)OR^8$ (where m is 0 to 3), $-N(H)C(O)R^8$, (1,2)-tetrahydropyrimidinyl (optionally substituted by alkyl), (1,2)-imidazolyl (optionally substituted by alkyl), or (1,2)-imidazolinyl (optionally substituted by alkyl); each $R^8$ and $R^9$ is independently hydrogen, alkyl, aryl, or aralkyl; and $R^{12}$ is alkyl, aryl or aralkyl:

REACTION SCHEME 4

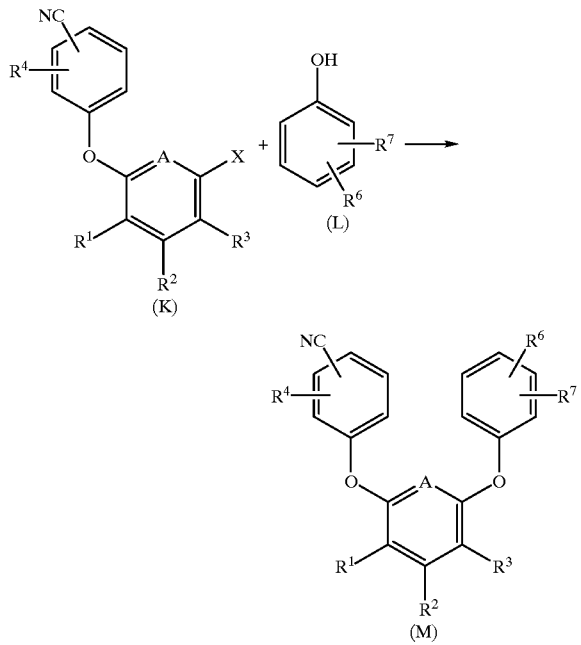

Compounds of formula (K) are prepared according to the methods described herein (see Reaction Scheme 3 above) Compounds of formula (L) are commercially available, for example, from Aldrich Chemical Co., or from Maybridge Co., or may be prepared according to methods known to those of ordinary skill in the art.

In general, the compounds of formula (M) are prepared in a manner similar to that described above for compounds of formula (J) and (K).

Compounds of formula (M) where $R^4$ or $R^7$ is hydroxy may be reacted with a haloalkane, such as iodomethane, under standard conditions to produce the corresponding compounds of formula (M) where $R^4$ or $R^7$ is alkoxy.

Compounds of formula (M) where $R^6$ or $R^7$ contains $-C(OOR^8$ where $R^8$ is alkyl or aryl may be hydrolyzed under basic conditions (for example, in the presence of sodium hydroxide) to produce compounds of formula (M) where $R^6$ or $R^7$ contains $-C(O)OR^8$ where $R^8$ is hydrogen.

Compounds of formula (M) where the ether connecting group has been replaced by an unsubstituted amino connecting group may be treated with an alkylating agent, such as iodomethane, in the presence of a base, to produce compounds of formula (M) wherein the amino connecting group is substituted by alkyl, aryl, or aralkyl. In addition, compounds of formula (K) can be treated with a compound of formula (L) wherein the hydroxy group is replaced by a hydroxymethyl ($-CH_2OH$) group to produce the corresponding compounds of formula (M).

Compounds of formula (M) where each $R^6$ and $R^7$ independently contains $-C(O)OR^8$ where $R^8$ is hydrogen may be amidated or esterified under standard conditions to produce compounds of formula (M) where $R^6$ or $R^7$ contains $-C(O)OR^8$ where $R^8$ is alkyl, aryl or aralkyl, or compounds of formula (M) where $R^6$ or $R^7$ contains $-C(O)N(R^8)R^9$ where $R_8$ and $R^9$ are independently hydrogen, alkyl, aryl or aralkyl.

Compounds of formula (M) where $R^3$ is nitro may be reduced under standard conditions to produce compounds of formula (M) where $R^3$ is amino; which can then be reacted with the appropriate acid halide or aryl- or alkylsulfonyl halide to produce compounds of formula (M) where $R^3$ is $-N(R^8)C(O)R^8$ or $-N(R^8)S(O)_2R^{12}$ where $R^8$ and $R^{12}$ are as defined above. In addition, compounds of formula (M) where $R^3$ is amino can be reacted with an isocyanate or chloroformate to produce compounds of formula (M) where $R^3$ is $-N(R^8)C(O)N(R^8)R^9$ or $-N(R^8)C(O)OR^8$.

5. Compounds of Formula (P)

Compounds of formula (P), as shown below, are also intermediates in the preparation of the compounds of the invention, particularly those compounds of formula (l) wherein A is $-C(R^{11})=$. As illustrated below in Reaction Scheme 5, compounds of formula (P) are prepared from compounds of formulae (N) and (O) where X is fluoro or chloro; $R^1$ and $R^3$ are independently hydrogen, halo, alkyl, haloalkyl, alkoxy, haloalkoxy, $-N(R^8)R^9$, $-C(O)OR^8$, $-C(O)N(R^8)R^9$, $-C(O)N(R^8)CH_2C(O)N(R^8)R^9$, $-N(R^8)C(N(R^8)R^9$, $-N(R^8)C(O)R^8$, $-N(R^8)S(O)_2R^{12}$, or $-N(R^8)C(O)N(R^8)CH_2-C(O)N(R^8)R^9$; $R^2$ is hydrogen, alkyl, haloalkoxy, $-OR^{12}$, $-C(O)OR^8$, $-C(O)N(R^8)R^9$, $-N(R^8)R^9$, $-C(O)N(R^8)(CH_2)_mC(O)OR^8$ (where m is 0 to 3), $N(R^8)(CH_2)$ $C(O)OR^8$ (where n is 1 to 3), $-N((CH_2)_nN(R^8)R^9)(CH_2)_nC(O)OR^8$ (where each n is 1 to 3), $-O(CH_2)_pC(8)N(R^8)R^9$ (where n is 1 to 3), $-O(CH_2)_pC(O)OR^8$ (where p is 1 to 6), $-N(R^8)(CH_2)_nC(O)N(R^8)(CH_2)_nC(O)OR^8$ (where each n is independently 1 to 3), morpholin-4-yl, 3-tetrahydrofuranoxy; or $R^2$ is aryloxy (optionally substituted by one or more substituents independently selected from the group consisting of $-OR^{12}$, $-C(O)N(R^8)R^9$, halo, alkyl, carboxy, alkoxycarbonyl, haloalkoxy, haloalkoxycarbonyl, alkoxycarbonylalkyl, carboxyalkyl, aminocarbonylalkyl, (alkylamino)carbonylalkyl, (dialkylamino)carbonylalkyl, (arylamino)carbonylalkyl, (aralkylamino)carbonylalkyl, alkoxycarbonylalkenyl, carboxyalkenyl, aminocarbonylalkenyl, (alkylamino)carbonylalkenyl, (dialkylamino)carbonylalkenyl, (arylamino)carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy) alkoxycarbonyl, tetrazolyl, morpholin-4-ylalkyl, and (1,2)-imidazolinyl (optionally substituted by alkyl)); or $R^2$ is piperazin-1-yl (optionally substituted by one or more substituents independently selected from the group consisting of alkyl, carboxy, carboxyalkyl, alkoxycarbonyl, and alkoxycarbonylalkyl); or $R^2$ is 1-piperazinoyl (optionally substituted by one or more substituents selected from the group consisting of alkyl, carboxy, carboxyalkyl, alkoxycarbonyl, and alkoxycarbonylalkyl); or $R^2$ is piperidin-1-yl (optionally substituted by one or more substituents selected from the group consisting of carboxy, carboxyalkyl, alkoxycarbonyl, and alkoxycarbonylalkyl); or $R^2$ is (3,4)-piperidinyloxy (optionally substituted by one or more substituents selected from the group consisting of alkylcarbonyl, carboxy, alkoxycarbonyl, carboxyalkyl, alkoxycarbonylalkyl, and tetrazolylalkyl); or $R^2$ is piperidin-4-ylamino (wherein the amino is optionally substituted by alkyl and the piperidinyl group is optionally substituted by one or more substituents selected from the group consisting of alkyl, alkoxycarbonyl, carboxyalkyl, alkoxycarbonylalkyl and aralklyl); or $R^2$ is 3-pyrrolidinyloxy (optionally substituted by one or more substituents selected from the group consisting of alkyl, aralkyl, amidino, 1-iminoethyl, carboxy, carboxyalkyl, alkoxycarbonyl and alkoxycarbonylalkyl); each $R^8$ and $R^9$ is independently hydrogen, alkyl, aryl, or aralkyl; $R^{11}$ is hydrogen, alkyl or halo; and $R^{12}$ is alkyl, aryl or aralkyl:

REACTION SCHEME 5

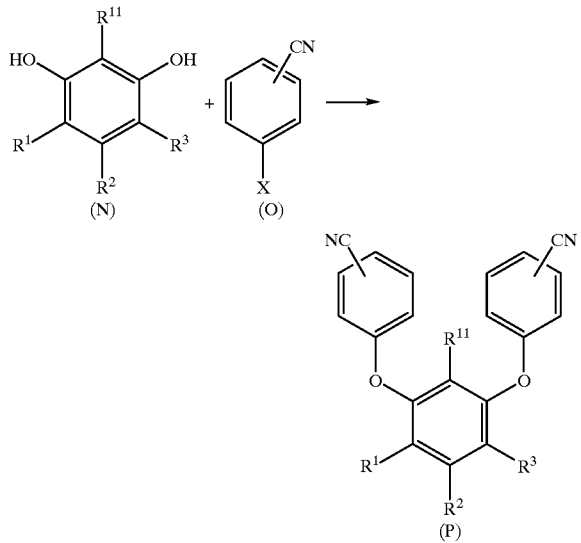

Compounds of formulae (N) and (O) may be prepared according to ordinary skill in the art, or by methods described herein, or may be commercially available, for example, from Aldrich Chemical Co., Inc.

In general, compounds of formula (P) are prepared in the same manner as described above for compounds of formula (J), except the temperatures at which the reaction is run are elevated to between about 50° C. and 130° C. The compounds of formula (P) are isolated from the reaction mixture by conventional techniques.

B. Preparation of the Compounds of the Invention

In the following Reaction Scheme 6, compounds of formula (Ia) are compounds of formula (I) as described above in the Summary of the Invention wherein $Z^1$ and $Z^2$ are —O—. As illustrated below in Reaction. Scheme 6, wherein A is —N= or —C($R^{11}$)= (where $R^{11}$ is hydrogen, alkyl or halo); $R^1$ and $R^3$ is hydrogen, halo, alkyl, haloalkyl, alkoxy, haloalkoxy, nitro, —N($R^8$)$R^9$, —C(O)O$R^{13}$, —C(O)N($R^8$)$R^9$, —C(O)N(Fe)CH$_2$C(O)N($R^8$)$R^9$, —N($R^8$)C(O)N($R^8$)$R^9$, —N($R^8$)C(O)$R^8$, —N($R^8$)S(O)$_2$$R^{12}$, or —N($R^8$)C(O)N($R^8$)CH$_2$—C(O)N($R^8$)$R^9$; $R^2$ is hydrogen, alkyl, haloalkoxy, —O$R^8$, —C(O)O$R^{13}$, —C(O)N($R^8$)$R^9$, —N($R^8$)$R^9$, —C(O)N($R^8$)(CH$_2$)$_m$C(O)O$R^{13}$ (where m is 0 to 3), —N($R^8$)(CH$_2$)$_n$C(O)O$R^{13}$, (where n is 1 to 3), —N((CH$_2$)$_n$N($R^8$)$R^9$)(CH$_2$)$_n$C(O)O$R^{13}$ (where each n is 1 to 3), —O(CH$_2$)$_n$C(O)N($R^8$)$R^9$ (where n is 1 to 3), —O(CH$_2$)$_p$C(O)O$R^{13}$ (where p is 1 to 6), —N($R^8$)(CH$_2$)$_n$C(O)N($R^8$)(CH$_2$)$_n$C(O)O$R^{13}$ (where each n is independently 1 to 3), morpholin-4-yl, 3-tetrahydrofuranoxy; or $R^2$ is aryloxy (optionally substituted by one or more substituents independently selected from the group consisting of —O$R^8$, —C(O)N($R^8$)$R^9$, halo, alkyl, carboxy, alkoxycarbonyl, haloalkoxy, haloalkoxycarbonyl, alkoxycarbonylalkyl, carboxyalkyl, aminocarbonylalkyl, (alkylamino)carbonylalkyl, (dialkylamino)carbonylalkyl, (arylamino)carbonylalkyl, (aralkylamino)carbonylalkyl, alkoxycarbonylalkenyl, carboxyalkenyl, aminocarbonylalkenyl, (alkylamino)carbonylalkenyl, (dialkylamino)carbonylalkenyl, (arylamino)carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy) alkoxycarbonyl, tetrazolyl, morpholin-4-ylalkyl, and (1,2)-imidazolinyl (optionally substituted by alkyl)); or $R^2$ is piperazin-1-yl (optionally substituted by one or more substituents independently selected from the group consisting of alkyl, carboxy, carboxyalkyl, alkoxycarbonyl, and alkoxycarbonylalkyl); or $R^2$ is 1-piperazinoyl (optionally substituted by one or more substituents selected from the group consisting of alkyl, carboxy, carboxyalkyl, alkoxycarbonyl, and alkoxycarbonylalkyl); or $R^2$ is piperidin-1-yl (optionally substituted by one or more substituents selected from the group consisting of carboxy, carboxyalkyl, alkoxycarbonyl, and alkoxycarbonylalkyl); or $R^2$ is (3,4)-piperidinyloxy (optionally substituted by one or more substituents selected from the group consisting of alkylcarbonyl, carboxy, alkoxycarbonyl, carboxyalkyl, alkoxycarbonylalkyl, and tetrazolylalkyl); or $R^2$ is piperidin-4-ylamino (wherein the amino is optionally substituted by alkyl and the piperidinyl group is optionally substituted by one or more substituents selected from the group consisting of alkyl, alkoxycarbonyl, carboxyalkyl, alkoxycarbonylalkyl and aralklyl); or $R^2$ is 3-pyrrolidinyloxy (optionally substituted by one or more substituents selected from the group consisting of alkyl, aralkyl, amidino, 1-iminoethyl, carboxy, carboxyalkyl, alkoxycarbonyl and alkoxycarbonylalkyl); $R^4$ and $R^7$ are independently hydrogen, halo, alkyl, nitro, —O$R^5$, —C(O)$R^{13}$, —C(O)N($R^8$)$R^9$, —N($R^8$)$R^9$, or —N(H)C(O)$R^8$; $R^6$ is haloalkoxy, nitro, amino, ureido, guanidino, —O$R^8$, —C(NH)NH$_2$, —C(NH)NHOH, —C(O)$R^{10}$, —(CH$_2$)$_m$C(O)N($R^8$)$R^9$ (where m is 0 to 3), —CH(OH)CJO)N($R^8$)$R^9$, —(CH$_2$)$_m$N($R^8$)$R^9$ (where m is 0 to 3), —(CH$_2$)$_m$C(O)O$R^{13}$ (where m is 0 to 3), —N(H)C(O) $R^8$, (1,2)-tetrahydropyrimidinyl (optionally substituted by alkyl), (1,2)-imidazolyl (optionally substituted by alkyl), or (1,2)-imidazolinyl (optionally substituted by alkyl); each $R^8$ and $R^9$ is independently hydrogen, alkyl, aryl, or aralkyl; $R^{10}$ is hydrogen, alkyl, aryl, aralkyl, 1-pyrrolidinyl, 4-morpholinyl, 4-piperazinyl, 4-(N-methyl)piperazinyl, or 1-piperidinyl; $R^{12}$ is alkyl, aryl or aralkyl; and $R^{13}$ is hydrogen, alkyl or aralkyl; compounds of formula (Ia) are prepared from compounds of formula (Q) as follows:

REACTION SCHEME 6

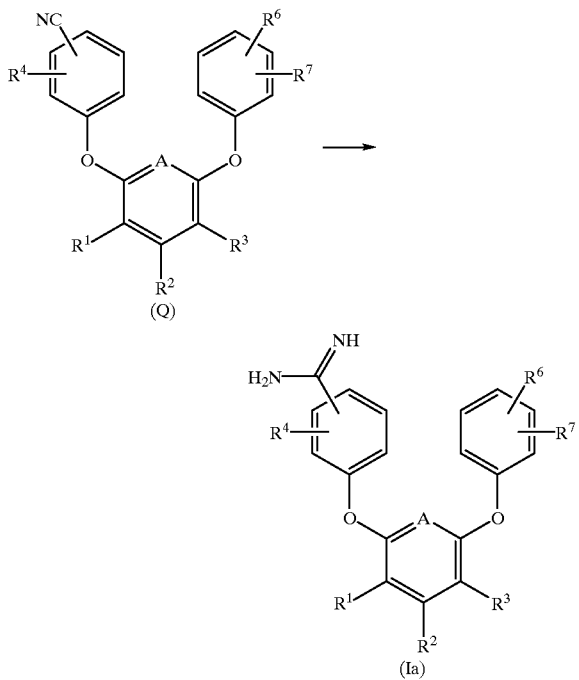

Compounds of formula (Q) are prepared as described herein above for compounds of formulae (J), (M), and (P).

In general, compounds of formula (Ia) are prepared from compounds of formula (Q) by dissolving the compound of formula (Q) in an anhydrous alkanol, preferably ethanol and then treating the solution with an anhydrous mineral acid, preferably HCl, while maintaining the reaction temperatures between about −78° C. and ambient temperature for between 2 hours and 24 hours, allowing the temperature to rise to ambient temperature while monitoring for reaction completion, for example, through thin layer chromatography. The solvent is then removed and the resulting residue dissolved in fresh anhydrous alkanol, preferably ethanol. The resulting solution was then treated with anhydrous ammonia at ambient pressure or in a sealed flask, at temperatures from between ambient temperature and 100° C. for about 1 to about 5 hours. The compounds of formula (Ia) are then isolated from the reaction mixture by standard techniques.

Compounds of formula (Ia) wherein $R^6$ is —C(NH)NH$_2$ or —C(NH)NHOH are produced from the corresponding cyano compounds.

Alternatively, instead of treating the resulting residue above with anhydrous ammonia, the resulting residue may be treated with a compound of the formula NH$_2$OR$^8$ to afford the corresponding compound of formula (Ia) wherein $R^5$ is —C(NH)N(H)OR$^8$.

In addition, compounds of formula (Ia) which contain a —C(O)OR$^{13}$ group may be treated under standard transesterification conditions with an phenol or a naphthol (either optionally substituted by halo, alkyl, alkoxy, amino, nitro or carboxy) to produce compounds of the invention which contain a —C(O)OR$^8$ group where $R^8$ is aryl.

Compounds of formula (Ia) wherein $R^6$ is —C(NH)NH$_2$ or —C(NH)N(H)OR$^{13}$ are produced from the corresponding cyano compounds in a similar manner as that described above for the compounds of formula (Ia).

In addition, compounds of formula (Ia) where $R^1$, $R^2$, $R^3$, $R^4$, and $R^7$ contains a —N(R$^8$)R$^9$ group where $R^8$ and $R^9$ are hydrogen, can be treated with the appropriate alkylating agents to afford the corresponding compounds of formula (Ia) where $R^1$, $R^2$, $R^3$, $R^4$, and $R^7$ contains —N(R$^8$)R$^9$, —N(R$^8$)S(O)$_2$R$^{12}$, —N(R$^8$)C(O)N(R$^8$)R$^9$, —N(R$^8$)C(O)N(R$^8$)CH$_2$—C(O)N(R$^8$)R$^9$, or —N(R$^8$)C(O)R$^8$ where each $R^8$ and $R^9$ is independently hydrogen, alkyl, aryl or aralkyl, and $R^{12}$ is alkyl, aryl or aralkyl.

Compounds of formula IIa) may be further treated with the appropriate acid halide, preferably acid chloride, or with the appropriate acid anhydride or an equivalent, to yield compounds of the invention wherein $R^5$ is —C(NH)N(H)C(O)R$^8$ where $R^8$ is hydrogen, alkyl, aryl or aralkyl.

Alternatively, compounds of formula (Ia) may further be treated with carbamoyl chlorides or their equivalents to yield compounds of the invention where $R^5$ is —C(NH)N(H)C(O)OR$^{12}$ where $R^{12}$ is alkyl, aryl or aralkyl.

Alternatively, compounds of formula (Ia) may be further treated with compounds of the formula $R^{12}$—S(O)$_2$-imidazole where $R^{16}$ is described in the Summary of the Invention in a polar solvent, such as methylene choride, at ambient temperature to afford compounds of the invention where $R^5$ is —C(NH)N(H)S(O)$_2$R$^{12}$.

Alternatively, compounds of formula (Ia) may be further treated with an appropriatly N—R$^9$-substituted phenylcarbamate in a polar solvent, preferably methylene chloride, at ambient temperature, for about 6 to 24 hours, preferably for about 12 hours, to afford compounds of the invention where $R^5$ is —C(NH)N(H)C(O)N(R$^8$)R$^9$.

Compounds of formula (Ia) wherein $R^1$, $R^2$ or $R^3$ contains —C(O)N(R$^8$)R$^9$ or —C(O)OR$^{13}$ where each $R^8$ and $R^9$ are independently alkyl, haloalkyl, aryl or aralkyl, and $R^{13}$ is alkyl or aralkyl may be hydrolyzed under acidic conditions to prepare compounds of formula (Ia) where $R^1$, $R^2$ or $R^3$ contains —C(O)OR$^8$ where $R^8$ is hydrogen.

Under the same conditions as previously described, compounds of formula (Ia) where $R^1$, $R^2$ or $R^3$ contains —C(O)OR$^{13}$ where $R^{13}$ is hydrogen, alkyl, or aralkyl, may be amidated to form compounds of formula (Ia) where $R^1$, $R^2$ or $R^3$ contains —C(O)N(R$^8$)R$^9$ where $R^8$ and $R^9$ are independently hydrogen, alkyl, aryl or aralkyl.

Compounds of formula (Ia) where $R^4$ is —OR$^8$ where $R^8$ is alkyl, aryl or aralkyl, may be converted to compounds of formula (Ia) where $R^4$ is —OR$^8$ where $R^8$ is hydrogen by treatment with boron tribromide in an aprotic solvent, for example, methylene chloride, at temperatures at first between −80° C. and 0° C., then at ambient temperature, for about 4 hours to about 16 hours.

Alternatively, compounds of formula (Ia) where $R^4$ is —OR$^8$ where $R^8$ is arylmethyl, preferably, benzyl, may be treated with hydrogen and the appropriate catalyst, for example, palladium on carbon, to give compounds of formula (Ia) where $R^4$ is —OR$^8$ where $R^8$ is hydrogen.

Compounds of formula (Ia) where $R^2$ is 3-pyrrolidinyloxy substituted by arylmethyl on the nitrogen may be treated under standard hydrogenolysis conditions to remove the arylmethyl group to produce compounds of formula (Ia) where $R^2$ is unsubstituted 3-pyrrolidinyloxy, which can then be reacted with the appropriate imidate to produce the compounds of formula (Ia) where $R^2$ is 3-pyrrolidinyloxy substituted by 1-iminoethyl, or with the appropriate haloalkyl esters to produce the compounds of formula (Ia) where $R^2$ is 3-pyrrolidinyloxy substituted by alkoxycarbonylalkyl.

In summary, compounds of the invention, are prepared by:
1) reacting a compound of formula (A) as described above with a compound of formula (B) as described above under the conditions as described above to produce a compound of formula (C) as described above, which is an intermediate in the preparation of the compounds of the invention; or
2) reacting a compound of formula (D) as described above with a compound of formula (E) as described above under conditions as described above to produce a compound of formula (F) as described above, which is an intermediate in the preparation of the compounds of the invention; or
3) reacting a compound of formula (G) as described above, which can be a compound of formula (C) as described above or a compound of formula (F) as described above, with a compound of formula (H) as described above under conditions as described above to produce a compound of formula (J) or a compound of formula (K) as described above, which are intermediates in the preparation of the compounds of the invention; then
4) reacting a compound of formula (K) as described above with a compound of formula (L) as described above under conditions as described above to produce a compound of formula (M) as described above, which is an intermediate in the preparation of the compounds of the invention; or
5) reacting a compound of formula (N) as described above with a compound of formula (O) as described above under conditions as described above to produce a compound of formula (P) as described above, which is an intermediate in the preparation of the compounds of the invention: then
6) reacting a compound of formula IQ as described above, which can be a compound of formula (J), a compound of formula (M) or a compound of formula (P) as described above, with the appropriate reagent under the conditions as described above to form compounds of formula (Ia) as described above.

Similar reactions may be performed on similar starting materials and intermediates to produce the corresponding compounds of the inventions not depicted in the Reaction Schemes above.

In addition, all compounds of the invention that exist in free base form or free acid form may be converted to their pharmaceutically acceptable salts by treatment with the appropriate inorganic or organic acid, or by the appropriate inorganic or organic base. Salts of the compounds of the invention can also be converted to the free base form or to the free acid form or to another salt.

The following specific preparations and examples are provided as a guide to assist in the practice of the invention, and are not intended as a limitation on the scope of the invention.

PREPARATION 1

4-Methoxy-2,3,5,6-tetrafluoropyridine

A. To pentafluoropyridine (1.0 g, 5.9 mmol) in petroleum ether (60 mL) at 0° C. was added sodium methoxide (0.32 mg, 5.9 mmol). After stirring for 12 hours at ambient temperature, the reaction was washed with water, dried (MgSO$_4$), and the solvent was removed in vacuo to give 4-methoxy-2,3,5,6-tetrafluoropyridine; NMR (CDCl$_3$) 4.3 ppm.

B. In a similar manner, the following compounds were made:
2,3,5,6-tetrafluoro-4-[2,2,2-trifluoroethoxy)pyridine; and
2,3,5,6-tetrafluoro-4-(1,3-difluoroprop-2-oxy)pyridine.

PREPARATION 2

4-Dimethylamino-2,3,5,6-tetrafluoropyridine

A. To methylene chloride (50 mL) cooled in an ice bath was added pentafluoropyridine (2.0 g, 11.8 mmol) and dimethylamine (2.97 mL of a 40% solution in water, 24 mmol). After stirring for 30 minutes the solution was washed with water, and dried over basic alumina. The solvent was removed in vacuo to give 4-dimethylamino-2,3,5,6-tetrafluoropyridine; NMR (CDCl$_3$) 3.13 (m,6) ppm.

B. In a similar manner, the following compounds were made:
1-(2,3,5,6-tetrafluoropyridin-4-yl)piperidine-4-carboxylic acid, ethyl ester; NMR (CDCl$_3$) 4.15 (q,2), 3.7 (m,2), 3.25 (m,2), 2.55 (m,1), 2.05 (m,2), 1.9 (m,2), 1.15 (t,3), ppm;
1-(2,3,5,6-tetrafluoropyridin-4-yl)piperidine-3-carboxylic acid, ethyl ester; NMR (CDCl$_3$) 4.15 (q,2), 3.8 (m,1), 3.55 (m,1), 3.4 (m,1), 3.25 (m,1), 2.7 (m,1), 2.15 (m,1), 1.8 (m,3), 1.15 (t,3) ppm;
4-(piperidin-1-yl)-2,3,5,6-tetrafluoropyridine; NMR (CDCl$_3$) 3.4 (m,4), 1.7 (m,6) ppm;
4-(4-methylpiperazin-1-yl)-2,3,5,6-tetrafluoropyridine; NMR (CDCl$_3$) 3.45 (m,4), 2.5 (m,4), 2.3 (s,3) ppm;
4-(2,3,5,6-tetrafluoropyridin-4-yl)piperazine-1-acetic acid, ethyl ester; NMR (CDCl$_3$) 4.2 (q,2), 3.55 (m,4), 3.3 (s,2), 2.7 (m,4), 1.3 (t,3) ppm;
N-methyl-N-(2,3,5,6-tetrafluoropyridin-4-yl)glycine, ethyl ester; and
4-(morpholin-1-yl)-2,3,5,6-tetrafluoropyridine.

PREPARATION 3

1-[(2,6-Dichloropyridin-4-yl)carbonyl]-4-methylpiperazine, Hydrochloride

To methylene chloride (15 mL) was added 2,6-dichloropyridine-4-carbonyl chloride (1.0 g, 4.8 mmol) and 1-methylpiperazine (0.48 g, 4.8 mmol). After stirring for 1 day, the reaction was poured into ether. The resulting solid was filtered to give 1-[(2,6-dichloropyridin-4-yl)-carbonyl]-4-methylpiperazine, hydrochloride.

PREPARATION 4

3-(1-Methylimidazolin-2-yl)phenol, Hydrobromide

A. To ethanol (200 mL) was added 3-methoxybenzonitrile (10.9 g, 82 mmol). The solution was cooled in an ice bath and HCl (g) was bubbled into the solution. The reaction was warmed to ambient temperature and stirred for 2 days. The solvent was removed in vacuo and the residue was slurried in ethanol (20 mL). N-methylethylene—diamine (12 g, 160 mmol) was added and the reaction was refluxed for 7 hours. The solvent was removed in vacuo and the residue was chromatographed on silica gel with methylene chloride/methanol/ammonium hydroxide (20/1/0.1). The resulting oil was dissolved in 48% HBr (20 mL) and refluxed for 19 hours. The mixture was cooled to ambient temperature and the solvent was removed in vacuo to give 3-(1-methylimidazolin-2-yl)phenol, hydrobromide.

B. In a similar manner, the following compound is made:
3-(1-methyltetrahydropyrimidin-2-yl)phenol, hydrobromide.

PREPARATION 5

3,3'-[2,6-Pyridinediylbis(oxy)]bis(benzonitrile)

A. To sodium hydride (0.38 g, 9.5 mmol) in N,N-dimethylformamide (3 mL) was added 3-cyanophenol (1.1 g, 8.9 mmol) and 2,6-difluoropyridine -0.4 mL, 4.4 mmol). After heating in an oil bath at 100° C. for 15 hours the reaction was partitioned with ethyl acetate and water. The organic layer was separated, washed with water, dried ($Na_2SO_4$), and the solvent was removed in vacuo. The residue was chromatographed on silica gel (50 g) with methylene chloride/hexane (3/1) to give 3,3'-[2,6-pyridinediylbis(oxy)]bis(benzonitrile). Recrystallization from ethyl acetatelhexane gave pure 3,3'-[2,6-pyridinediylbis(oxy)]bis(benzonitrile); NMR ($CDCl_3$) 7.79 (t,1), 7.45 (m,4), (m,4), 6.72 (d,2) ppm.

B. In a similar manner, the following compounds were made:

- 4,4'-[2,6-pyridinediylbis(oxy)]bis(benzonitrile); NMR ($CDCl_3$) 7.8 (t,1), 7.6 (d,4), 7.2 (d,4), 6.8 (d,2) ppm;
- 3,3'-[3,5-dichloro-2,6-pyridinediylbis(oxy)]bis(benzonitrile); NMR ($CDCl_3$) 7.9 (s,1), 7.45 (m,4), 7.2 (m,4) ppm;
- 4,4'-[3,5-dichloro-2,6-pyridinediylbis(oxy)]bis(benzonitrile); NMR ($CDCl_3$) 7.95 (s,1), 7.6 (d,4), 7.1 (d,4) ppm;
- 2,6-bis(3-cyanophenoxy)pyridine-4-carboxylic acid, ethyl ester; NMR ($CDCl_3$), 7.45 (m,4), 7.35 (m,6), 4.45 (q,2), 1.45 (t,3) ppm;
- 2,6-bis(3-cyanophenoxy)pyridine-3-carboxylic acid, ethyl ester; NMR ($CDCl_3$), 8.4 (d,1), 7.45 (m,4), 7.25 (m,4), 6.75 (d,1), 4.4 (q,2), 1.45 (t,3) ppm;
- 3,3'-(3,5-difluoro-2,6-pyridinediylbis(oxy)]bis(benzonitrile); NMR ($CDCl_3$), 7.55 (t,1), 7.45 (m,4), 7.29 (m,4) ppm;
- 3,3'-[2,6-pyrazinediylbis(oxy)]bis(benzonitrile); NMR ($CDCl_3$) 8.2 (s,2), 7.5 (m,4), 7.3 (m,4) ppm;
- 3,3'-[2,6-pyrimidinediylbis(oxy))]bis(benzonitrile); NMR ($CDCl_3$) 8.4 (d,1), 7.5 (m,4), 7.4 (m,4), 6.8 (d,1) ppm;
- 3,3'-[3,5-difluoro-4-methyl-26-pyridinediylbis3oxy)]bis3benzonitrile); NMR ($CDC_3$) 7.44 (m,4), 7.27 (m,4), 2.4 (s,3) ppm;
- 3,3'-[4-nitro-1,3-phenylenebis(oxy)]bis(benzonitrile); NMR ($CDCl_3$) 8.13 (d,1), 7.5 (m,4), 7.3 (m,4), 6.84 (dd,1), 6.69 (d,1) ppm; and
- 3,3'-[3-trifluoromethyl-2,6-pyridinediylbis(oxy)]bis(benzonitrile); NMR ($CDCl_3$) 8.05 (t,1), 7.5 (m,4), 7.3 (m,4), 6.8 (d,1) ppm.

PREPARATION 6

3-[(3,5,6-Trifluoro-4-methylpyridin-2-yl)oxy]benzonitrile

A. To 2,3,5,6-tetrafluoro-4-methylpyridine (0.71 g, 4.3 mmol) dissolved in acetonitrile (5 mL) was added 3-cyanophenol (0.5 g, 4.2 mmol) and cesium carbonate (1.44 g, 4.4 mmol). The reaction was heated in an oil bath at 45° C. for 16 hours and partitioned with ether and water. The organic layer was separated, washed with brine, dried ($Na_2SO_4$), and the solvent removed in vacuo. Chromatography on silica gel with methylene chloride/hexane (7/3) gave 3-[(3,5,6-trifluoro-4-methylpyridin-2-yl)-oxy]benzonitrile; NMR ($CDCl_3$) 7.55 (m,2), 7.45 (m,2), 2.24 (s,3) ppm.

B. In a similar manner, the following compounds were made:

- 4-[(2,3,5,6-tetrafluoropyridin-4-yl)oxy]-3-methoxybenzoic acid, ethyl ester;
- 3-14-dimethylamino-3,5,6-trifluoropyridin-2-yl)-4-methoxybenzonitrile; NMR ($CDCl_3$) 7.55 (d,1), 7.4 (s,1), 7.05 (d,3), 3.85 (s,3), 3.15 (s,6) ppm;
- 1-(2-(5-cyano-2-methoxyphenoxy)-3,5,6-trifuoropyridin-4-yl)piperidine-4-carboxylic acid, ethyl ester; NMR ($CDCl_3$) 7.5 (d,1), 7.4 (s,1), 7.05 (d,1), 4.15 (q,2), 3.8 (s,3), 3.7 (m,2), 3.25 (m,2), 2.55 (m,1), 2.1 (m,2), 1.9 (m,2), 1.15 (t,3) ppm;
- 1-(2-(5-cyano-2-methoxyphenoxy)-3,5,6-trifluoropyridin-4-yl)piperidine-3-carboxylic acid, ethyl ester; NMR ($CDCl_3$) 7.5 (d,1), 7.4 (s,1), 7.05 (d,1), 4.15 (q,2), 3.8 (s,3), 3.8 (m,1), 3.55 (m,1), 3.4 (m,1), 3.25 (m,1), 2.7 (m,1l), 2.15 (m,1), 1.8 (m,3), 1.15 (t,3), ppm;
- 2-chloro-6-(5-cyano-2-methoxyphenoxy)pyridine-4-carboxylic acid, ethyl ester; NMR ($CDCl_3$) 7.6 (m,2), 7.4 (m,2), 7.0 (d,2), 4.4 (q,2), 3.8 (s,3), 1.4 (t,3), ppm;
- 2-chloro-6-(3-dimethylaminophenoxy)pyridine-4-carboxylic acid, ethyl ester; NMR ($CDCl_3$) 7.6 (s,1), 7.2 (m,2), 6.6 (d,1), 6.5 (m,2), 4.4 (q,2), 3.0 (s,6), 1.4 (t,3) ppm;
- 4-benzyloxy-3-(4-(piperidin-1-yl)-3,5,6-trifluoropyridin-2-yl)benzonitrile; NMR ($CDCl_3$) 7.5 (m,2), 7.35 (m,3), 7.2 (m,2), 7.05 (d,1), 5.1 (s,2), 3.4 (m,4), 1.75 (m,6) ppm;
- 4-benzyloxy-3-(4-(4-methylpiperazin-1-yl)-3,5,6-trifluoropyridin-2-yl)benzonitrile; NMR ($CDCl_3$) 7.5 (m,2), 7.35 (m,3), 7.2 (m,2), 7.05 (d,1), 5.1 (s,2), 3.4 (m,4), 2.5 (m,4), 2.35 (s,3) ppm;
- 1-[(2-(5-cyano-2-methoxyphenoxy)-6-chloropyridin-4-yl)carbonyl)-4-methylpiperazine; NMR ($CDCl_3$) 7.44 (dd,1), 7.3 (d,1), 6.95 (d,1), 6.9 (s,1), 6.74 (s,1), 3.7 (s,3), 3.7 (m,2), 3.3 (m,2), 2.4 (m,2), 2.3 (m,2), 2.2 (s,3) ppm;
- 4-[(2-(5-cyano-2-benzyloxyphenoxy)-3,5,6-trifluoropyridinyl)piperazine-1-acetic acid, ethyl ester; NMR ($CDCl_3$) 7.5 (m,2), 7.35 (m,3), 7.2 (m,2), 7.05 (d,1), 5.1 (s,2), 4.2 (q,2), 3.5 (m,4), 3.3 (s,2), 2.75 (m,4), 1.3 (t,3) ppm;
- 3-[(3,5,6-trifluoro-4-methylpyridin-2-yl)oxy]-4-methoxybenzonitrile; NMR ($CDCl_3$) 7.6 (d,1), 7.4 (s,1), 7.0 (d,1), 3.8 (s,3), 2.4 (s,3) ppm;
- 3-[(3,5, 6-trifluoro-4-(2,2,2-trifluoroethoxy)pyridin-2-yl)oxy-N,N-dimethylbenzamide; NMR ($CDCl_3$)7.4 (m,1), 7.2 (d,1), 7.3 (m,1), 7.1–7.2 (m,2), 4.7 (q,2), 3.1 (s,3), 3.0 (s,3) ppm;
- 3-[(4-(11,3-difluoroprop-2-oxy)-35,6-trifluoropyridin-2-yl,oxy]-N,N-dimethylbenzamide;
- N-(2-(5-cyano-2-methoxyphenoxy(-3,5,6-trifluoropyridin-4-yl)-N-methylglycine, ethyl ester;
- N-(2-(3-cyanophenoxy)-3,5,6-trifluoropyridin-4-yl)-N-methylglycine, ethyl ester;
- 3-(4-(morpholin-1-yl)-3,5,6-trifluoropyridin-2-yl)oxy)-4-(benzyloxy)benzonitrile;
- 2-chloro-6-(3-dimethylaminocarbonylphenoxy)pyridine-4-carboxylic acid, ethyl ester; NMR ($CDCl_3$) 7.59 (s,1), 7.46 (t,1), 7.38 (s,1), 7.32 (d,1), 7.21 (s,1), 7.2 (d,1), 4.42 (q,2), 3.05 (s,3), 2.88 (s,3), 1.20 (t,3) ppm;
- 3-[(6-fluoropyridin-2-yl)oxy]-N,N-dimethylbenzamide; NMR ($CDCl_3$) 7.75 ($q_{1}$), 7.43 (m,1), 7.27 (m,l), 7.2 (m,2), 6.75 (m,l), 6.62 (d,1), 3.1 (s,3), 3.0 (s,3) ppm;
- 4-[(2-(5-cyano-2-benzyloxyphenoxy)-3,5,6-trifluoropyridin-4-yl)oxy]-3-methoxybenzoic acid, ethyl ester; and
- 4-[(2-(5-cyano-2-benzyloxyphenoxy)-3,5-difluoro-6-(3-(1-methylimidazolin-2-yl)phenoxy)pyridin-4-yl)oxy]-3-methoxybenzoic acid, ethyl ester.

PREPARATION 7

3-[(3,5-Difluoro-6-(5-dimethylamino-2-methylphenoxy)-4-methyl-pyridin-2-yl)oxy]benzonitrile A. In a manner similar to preparation 6, reaction of 3-(3,5,6-trifluoro-4-methylpyridin-2-yl)benzonitrile (1.1 g, 4.4 mmol), 5-dimethylamino-2-methylphenol (0.66 g, 4.4 mmol), and cesium carbonate (1.7 g, 5.2 mmol) in acetonitrile (10 mL) gave 3-[(3,5-difluoro-6-(5-dimethylamino-2-methylphenoxy)-4-methylpyridin-2-ylsoxy]-benzonitrile; NMR (CDCl$_3$) 7.3 (m,4), 7.0 (d,1), 6.5 (d,1), 6.3 (s,1), 2.8 (s,6), 2.4 (s,3), 2.0 (s,3) ppm.

B. In a similar manner, the following compounds were made:

3-[(3,5-difluoro-6-(3-dimethylamino-2-methylphenoxy)-4-methylpyridin-2-yl)oxy]benzonitrile; NMR (CDCl$_3$) 7.1–7.5 (m,5), 6.9 (d,1), 6.65 (d,1), 6.3 (s,1), 2.6 (s,6), 2.4 (s,3), 2.0 (s,3) ppm;

3,3'-[3,5-difluoro-4-methoxy-2,6-pyridinediylbis(oxy)]bis(benzonitrile); NMR CDCl$_3$) 7.45 (m,4), 7.3 (m,4), 4.3 (s,3) ppm;

3-[(6-(3-cyanophenoxy)-3,5-difluoro-4-methylpyridin-2-yl)oxy]-4-methoxybenzenecarboxylic acid; NMR (CDCl$_3$) 7.9 (d,1), 7.7 (s,1), 7.2 (m,4), 6.95 (d,1), 3.85 (s,3), 2.4 (s,3)pmm;

3-[(6-(3-cyanophenoxy)-3,5-difluoro-4-methylpyridin-2-yl)oxy]-4,5-dimethoxybenzenecarboxylic acid, ethyl ester; NMR (CDCl$_3$) 7.4 (s,1), 7.2–7.4 (m,5), 4.35 (q,2), 3.9 (s,3), 3.8 (s,3), 2.4 (s,3) ppm;

3-[a6-(3-cyanophenoxy)-3,5-difluoro-4-methylpyridin-2-yl)oxy]-4-methylbenzoic acid; NMR (CDCl$_3$) 7.75 (d,1), 7.55 (s,1), 7.1–7.3 (m,5), 2.4 (s,3), 2.2 (s,3) ppm;

5-[6-(3-cyanophenoxy)-3,5-difluoro-4-methylpyridin-2-yl)oxy]benzene-1,3-dicarboxylic acid, diethyl ester; NMR (CDCl$_3$) 8.45 (s,1), 7.85 (s,2), 7.25 (m,4), 4.4 (q,4), 2.4 (s,3), 1.4 (t,6) ppm;

4-[(6-(3-cyanophenoxyc-3,5-difluoro-4-methylpyridin-2-yl)oxy]-3-methoxybenzoic add; NMR (CDCl$_3$) 7.65 (dd,1), 7.62 (d,1), 7.33 (dt,1), 7.27 (dt,1), 7.18 (m,2), 7.05 (d,1), 3.8 (s,3), 2.4 (s,3) ppm;

3,3'-[3-nitro-2,6-pyridinediylbis(oxy)]bis(benzonitrile); NMR (CDCl$_3$) 8.6 (d,1), 7.5 (m,4), 7.2 (m,4), 6.8 (d,1) ppm;

3-[N3,5-difluoro-6-(4-dimethylaminomethylphenoxy)-4-methylpyridin-2-yl)oxy]benzonitrile; NMR (CDCl$_3$) 7.3 (m,5), 7.15 (m,1), 6.9 (m,2), 3.35 (s,2), 2.4 (s,3), 2.15 (s,6) ppm;

3-[(3,5-difluoro-4-methyl-6-(3-(morpholin-4-yl)phenoxy)pyridin-2-yl)oxy]benzonitrile;
NMR (CDCl$_3$) 7.1–7.4 (m,5), 6.7 (m,1), 6.5 (s,1), 3.8 (m,4), 3.1 (m,4), 2.4 (s,3) ppm;

3-[(3,5-difluoro-6-(3-(2-(1H-imidazol-1-yl)-1-oxoethyl)phenoxy)-4-methylpyridin-2-yl)oxy]benzonitrile; NMR (CDCl$_3$) 7.8 (d,1), 7.7 (s,1), 7.5 (m,2), 7.3 (m,5), 7.1 (s,1), 7.0 (s,1), 5.45 (s,2), 2.4 (s,3) ppm;

4-[(6-(3-cyanophenoxy)-3,5-difluoro-4-methylpyridin-2-yl)oxy]benzoic acid; NMR (CDCl$_3$) 8.05 (d,2), 7.2–7.5 (m,4), 7.1 (d,2), 2.4 (s,3) ppm;

3-[(3,5-difluoro-4-methyl-6-(3-((phenyl)oxomethyl)phenoxy)pyridin-2-yl)oxy]benzonitrile; NMR (CDCl$_3$) 7.75 (d,2), 7.4–7.6 (m,6), 7.3 (m,5), 2.4 (s,3) ppm;

3-[(3,5-difluoro-6-(3-hydroxyphenoxy)-4-methylpyridin-2-yl)oxybenzonitrile; NMR (CDCl$_3$) 7.35 (m,4), 7.2 (t,1), 6.65 (dd,1), 6.6 (m,2), 5.65 (s,1), 2.4 (s,3) ppm;

5-[(3,5-difluoro-6-(3-dimethylaminophenoxy)-4-methylpyridin-2-yl)oxy]-2-methoxybenzonitrile; NMR (CDCl$_3$) 7.4 (d,1), 7.3 is,1), 7.03 (t,1), 6.8 (d,1), 6.43 (d,1), 6.25 (s,1), 6.18 (d,1), 3.68 (s,3), 2.85 (s,6), 2.45 (s,3) ppm;

3-[(6-(3-cyanophenoxy)-3,5-difluoro-4-methylpyridin-2-yl)oxy]benzeneacetic acid, ethyl ester; NMR (CDCl$_3$) 7.3 (m,5), 7.05 (d,1), 6.9 (m,2), 3.65 (s,3), 3.6 (s,2), 2.4 (s,3) ppm;

3-[(6-c3-cyanophenoxy)-3,5-difluoro-4-methylpyridin-2-yl)oxy]benzenepropionic acid; NMR (CDCl$_3$) 7.3 (m,5), 7.05 (d,1), 6.85 (m,2), 2.9 (t,2), 2.6 (t,2), 2.4 (s,3) ppm;

3-[(3,5-difluoro-6-3-dimethylaminophenoxy)-4-methylpyridin-2-yl)oxy]-2,6-dimethoxybenzonitrile; NMR (CDCl$_3$) 7.3 (d,1), 7.0 (t,1), 6.55 (d,1), 6.4 (d,1), 6.2 (m,2), 3.9 (s,3), 3.7 (s,3), 2.9 ls,6), 2.4 (s,3) ppm;

3-[(3,5-difluoro-6-(3-(2-hydroxyethyl)phenoxy)-4-methylpyridin-2-yl)oxy]benzonitrile; NMR (CDCl$_3$) 7.2–7.4 (m,5), 7.0 (d,1), 6.85 (m,2), 3.75 (t,2), 2.8 (t,2), 2.4 (s,3) ppm;

3-[(6-(3-cyanophenoxy)-3,5-difluoro-4-methylpyridin-2-yl)oxy]-N,N-dimethylbenzenepropionamide; NMR (CDCl$_3$) 7.45 (d,1), 7.1–7.4 (t,4), 7.0 (d,1), 6.85 (m,1), 6.8 (d,1), 3.9 (s,3), 3.85 (s,3), 3.85 (m,2), 2.5 (t,2), 2.35 (s,3) ppm;

3-[(3,5-difluoro-6-(3-(hydroxymethyl)phenoxy)-4-methylpyridin-2-yl)oxy]benzonitrile; NMR (CDCl$_3$) 7.3–7.5 (m,5), 7.2 (d,1), 7.1 (s,1), 6.95 (d,1), 4.7 (s,2), 2.4 (s,3) ppm;

3-[(6-(3-cyanophenoxy)-3,5-difluoro-4-methylpyridin-2-yl)oxy]-N,N-dimethylbenzamide; NMR (CDCl$_3$) 7.2–7.4 (m,5), 7.0 (m,1), 6.9 (m,2), 3.65 (s,2), 2.95 (s,6), 2.35 (s,3) ppm;

3-[(6-(3-cyanophenoxy)-3,5-difluoro-4-methylpyridin-2-yl)oxy]benzonitrile; NMR (CDCl$_3$) 7.35 (m,2), 7.25 (m,2), 7.2 (t,1), 7.0 (d,1), 6.85 (m,2), 2.9 (t,2), 2.45 (t,2), 2.4 (s,3) ppm;

4-[(6-(3-cyanophenoxy)-3,5-difluoro-4-methylpyridin-2-yl)oxy]-α-hydroxybenzeneacetic acid; NMR (CDCl$_3$) 7.25 (m,6), 7.15 (s,1), 6.95 (m,1), 5.2 (s,1), 2.4 (s,3) ppm;

3-[(3,5-difluoro-4-methyl-6-(3-(1-oxoethyl)phenoxy)pyridin-2-yl)oxy]benzonitrile; NMR (CDCl$_3$) 7.75 (dt, 1), 7.59 (m,$_1$), 7.44 (t,1), 7.2–7.4 (m,5), 2.57 (s,3), 2.40 (s,3) ppm;

3-[(3,5-difluoro-4-methyl-6-(3-(2-methyl-1-oxopropyl)phenoxy)pyridin-2-yl)oxy]-benzonitrile; NMR (CDCl$_3$) 7.75 (d,1), 7.6 (m,1), 7.45 (t,1), 7.2–7.4 (m,5), 3.45 (m,1), 2.4 (s,3), 1.25 (m,6) ppm;

3-[(3,5-difluoro-4-methyl-6-(3-(1-methylethoxy)phenoxy)pyridin-2-yl)oxy]benzonitrile; NMR (CDCl$_3$) 7.2–7.5 (m,5), 6.7 (d,1), 6.55 (m,2), 4.45 (m,1), 2.4 (s,3), 1.3 (m,6) ppm;

α-acetoxy-4-[(6-(3-cyanophenoxy)-3,5-difluoro-4-methylpyridin-2-yl)oxy]-N,N-dimethylbenzeneacetamide; NMR (CDCl$_3$) 7.3 (m,6), 7.15 (m,1), 7.0 (m,1), 6.1 (s,1), 2.9 (s,3), 2.85 (s,3), 2.40 (s,3), 2.1 (s,3) ppm;

4-[(6-(3-cyanophenoxy)-3,5-difluoro-4-methylpyridin-2-yl)oxy]-α-ethoxybenzeneacetic acid, methyl ester; NMR (CDCl$_3$) 7.0–7.5 (m,8), 4.75 (s,1), 3.75 (s,3), 3.35 (s,3), 2.4 (s,3) ppm;

3-[(6-(5-cyano-2-methoxyphenoxy)-3,5-difluoro-4-dimethylaminopyridin-2-yl)oxy]-N,N- dimethylbenzamide; NMR (CDCl$_3$) 7.4 (m,2), 7.1 (d,1), 6.95 (m,3), 3.8 (s,3), 3.1 (s,6), 3.05 (s,3), 2.9 (s,3) ppm;

1-[(2-(5-cyano-2-methoxyphenoxy)-3,5-difluoro-6-(3-dimethylaminocarbonylphenoxy)pyridin-4-yl] piperidine-4-carboxylic acid, ethyl ester; NMR (CDCl$_3$) 7.4 (d,1), 7.2 (m,2), 7.1 (d,1), 6.9 (m,3), 4.15 (q,2), 3.75 (s,3), 3.7 (m,2), 3.25 (m,2), 3.1 (s,3), 2.95 (s,3), 2.55 (m,1), 2.0 (m,4), 1.15 (t,3) ppm;

1-[(2-(5-cyano-2-methoxyphenoxy)-3,5-difluoro-6-(3-dimethylaminocarbonyl-phenoxy)pyridin-4-yl) piperidine3-carboxylic acid, ethyl ester; NMR (CDCl$_3$) 7.4 (d,1), 7.3 (m,2), 7.1 (d,1), 6.9 (m,3), 4.15 (q,2), 3.8 (m,1), 3.75 (s,3), 3.6 (m,1), 3.4 (m,1), 3.25 (m,1), 3.1 (s,3), 2.9 (s,3), 2.7 (m,1), 2.15 (m,1), 1.8 (m,3), 1.15 (t,3) ppm;

3-[(6-(5-cyano-2-benzyloxyphenoxy)-3,5-difluoro-4-(piperidin-1-yl)pyridin-2-yl)oxy]-N,N-dimethylbenzamide; NMR (CDCl$_3$) 7.4 (m,5), 7.2 (m,3), 7.1 (m,1), 6.95 (m,3), 5.1 (s,2), 3.4 (m,4), 3.1 (s,3), 2.9 (s,3), 1.75 (m,6) ppm;

3-[(6-(5-cyano-2-benzyloxyphenoxy)-3,5-difluoro-4-(4-methylpiperazin-1-yl)pyridin-2-yl)oxy]-N,N-dimethylbenzamide; NMR (CDCl$_3$) 7.2 (m,9), 6.95 (m,3), 5.1 (s,2), 3.5 (m,4), 3.1 (s,3), 2.9 (s,3), 2.6 (m,4), 2.4 (s,3) ppm;

4-[(2-(5-cyano-2-benzyloxyphenoxy)-3,5-difluoro-6-(3-dimethylaminocarbonylphenoxy)pyridin-4-yl) piperazine-1-acetic acid, ethyl ester; NMR (CDCl$_3$) 7.3 (m,5), 7.1 5 (m,4), 6.95 (m,3), 5.1 (s,2), 4.2 (q,2), 3.5 (m,4), 3.3 (s,2), 3.1 (s,3), 2.75 (m,4), 3.1 (t,3) ppm;

1-[(2-(5-cyano-2-methoxyphenoxy)-6-(3-dimethylaminocarbonylphenoxy)pyridin-4-yl) carbonyl]-4-methylpiperazine; NMR (CDCl$_3$) 7.4 (dd, 1), 7.27 (m,2), 7.16 (m,1), 7.0 (m,2), 6.9 (d,1), 6.63 (s,1), 6.55 (s,1), 3.8 (m,2), 3.8 (s,3), 3.5 (m,2), 2.9 (s,3), 2.5 (m,2), 2.4 (m,2), 2.4 (s,3) ppm;

1-[(2-(5-cyano-2-methoxyphenoxy)-6-chloropyridin-4-yl)carbonyl]-4-methylpiperazine; NMR (CDCl$_3$) 7.44 (dd,1), 7.3 (d,1), 6.95 (d,1), 6.9 (s,1), 6.74 (s,1), 3.7 (s,3), 3.7 (m,2), 3.3 (m,2), 2.4 (m,2), 2.3 (m,2), 2.2 (s,3) ppm;

2-(5-cyano-2-methoxyphenoxy)-6-(3-(imidazol-1-yl) phenoxy)pyridine-4-carboxylic acid, ethyl ester; NMR (CDCl$_3$) 7.8 (s,1), 7.3 (m,3), 7.2 (m,5), 7.0 (m,2), 6.7 (d,1), 4.4 (q,2), 3.7 (s,3), 1.4 (t,3) ppm;

2-(5-cyano-2-methoxyphenoxy)-6-(3-dimethylaminophenoxy)pyridine-4-carboxylic acid, ethyl ester; NMR (CDCl$_3$) 7.4 (d,1), 7.3 (s,1), 7.2 (s,1), 7.1 (t,1), 7.0 (s,1), 6.8 ($^d$,1), 6.5 (d,1), 6.3 (m,2), 4.4 (q,2), 3.7 (s,3), 2.8 (s,6), 1.4 (t,3) ppm;

3-[(6-(5-cyano-2-methoxyphenoxy)-3,5-difluoro-4-methylpyridin-2-yl)oxy]-N,N-dimethylbenzamide; NMR (CDCl$_3$) 8.00 (bs,1), 7.40 (dt,1), 7.25 (t,1), 7.21 (dt,1), 7.08 (bd,1), 6.91 (bs,1), 6.87 ttd,1), 3.74 (s,3), 2.92 (1,3), 2.85 (s,3), 2.39 (s,3), ppm;

3-[(6-(2-amino-5-cyanophenoxy3-3,5-difluoro-4-methylpyridin-2-yl)oxy]-N,N-dimethylbenzamide; NMR (CDCl$_3$) 7.5 (t,1), 7.2–7.0 (m,5), 6.6 (d,1), 4.6 (s,2), 3.1 (s,3), 2.9 (s,3), 2.0 (s,3) ppm;

3-[(6-(2-amino-5-cyanophenoxy)-3,5-difluoro-4-(2,2,2-trifluoroethoxy)pyridin-2-yl)oxy]-N,N-dimethylbenzamide; NMR (CDCl$_3$) 7.3 (dd,1), 7.2 (d,1), 7.1 (m,2), 7.0–7.1 (m,2), 6.6 (d,1), 4.8 (q,2), 4.6 (s,2), 3.1 (s,3), 2.9 (s,3) ppm;

3-[(6-(5-cyano-2-methoxyphenoxy)-3,5-difluoro-4-(2,2,2-trifluoroethoxy)pyridin-2-yl)oxy]-N,N-dimethylbenzamide; NMR (CDCl$_3$) 7.4 (dd,1), 7.3 (d,1), 7.2 (t,1), 7.1 (d,1), 6.9–7.0 (m,2), 6.9 (d,1), 4.7 (q,2), 3.7 (s,3), 3.1 (s,3), 2.9 (s,3) ppm; and 3-[(6-(5-cyano-2-methoxyphenoxy)-4-(1,3-difluoroprop-2-oxy)-3,5-difluoropyridin-2-yl)oxy]-N,N-dimethylbenzamide; NMR (CDCl$_3$) 7.4 (dd,1), 7.3 (d,1), 7.2 (t,1), 7.1 (d,1), 6.9–7.0 (m,2), 6.9 (d,1), 5.0 (m,1), 4.9 (d,2), 4.7 td,2), 3.7 (s,3), ppm.

PREPARATION 8

4-(6-Fluoropyridin-2-yl)oxy-3-methoxybenzonitrile

A. To 4-hydroxy-3-methoxybenzonitrile (2.6 g, 17 mmol) in DMSO (15 mL) was added sodium hydride (0.44 g, 18 mmol) and 2,6-difluoropyridine (1.0 g, 8.7 mmol). After heating at: 100° C. for 18 hours the reaction was partitioned with ethyl acetate and water. The organic layer was separated, washed with water, dried (Na$_2$SO$_4$), and the solvent was removed in vacuo to give 4-(6-fluoropyridin-2-yl)oxy-3-methoxybenzonitrile (1.3 g); NMR (CDCl$_3$) 7.8 (q,1), 7.35 (m,1), 7.25 (m,2), 6.85 (d,1), 6.65 (m,1), 3.85 (s,3) ppm.

B. In a similar manner, the following compounds were made:

3-[(4-methyl-3,5,6-trifluoropyridin-2-yl)amino] benzonitrile; NMR (CDCl$_3$) 8.05 (s,1), 8.95 (d,1), 7.6 (d,1), 7.45 (t,1), 7.25 (s,1), 2.3 (s,3) ppm; 2-chloro-6-(3-cyanophenoxy)pyridine-4-carboxylic acid, ethyl ester, NMR (CDCl$_3$) 7.80–7.38 (m,6), 4.41 (q,2), 1.92 (t,3) ppm;

2-chioro-6-t5-cyano-2-methoxyphenoxy)-N,N-dimethylpyridine-4-carboxamide; NMR (CDCl$_3$) 7.2 (m,5), 3.84 (s,3), 3.13 (s,3), 2.95 (s,3) ppm; and 2-chloro-6-(5-cyanophenoxy)-N,N-dimethylpyridine-4-carboxamide; NMR (CDCl$_3$) 7.45 (m,3), 7.08 (s,1), 6.87 (s,1), 6.67 (s,1), 3.14 (s,3), 3.00 (s,3) ppm.

PREPARATION 9

2-Methoxy-3',4-[2,6-pyridinediylbis(oxy)] benzonitrile

A. To 4-(6-fluoropyridin-2-yl)oxy-3-methoxybenzonitrile (0.65 g, 2.7 mmol) in DMSO (15 mL) was added 3-cyanophenol (0.32 9, 0.91 mmol) and sodium hydride (0.070 g, 2.9 mmol). After heating at 140° C. for 2 days, the reaction was poured into water and the precipitate was filtered off. The solid was chromatographed to give 2-methoxy-3',4-[2,6-pyridinediylbis(oxy)]benzonitrile; NMR (CDCl$_3$) 7.75 (t,1), 7.2–7.5 (m,6), 7.1 (d,$_1$), 6.7 (d,1), 6.65 (d,1), 6.65 (d,1), 3.8 (s,3) ppm.

B. In a similar manner, the following compounds were made:

3,3'-bis(methoxy)-4,4'-[2,6-pyridinediylbis(oxy)]bis (benzonitrile); NMR (CDCl$_3$) 7.75 (t,1), 7.2 (d,2), 7.1 (m,4), 6.65 (d,2), 3.75 (s,6) ppm;

3-[(3,5-difluoro-6-(3-ethylamino-4-methylphenoxy)-4-methylpyridin-2-yl)oxy]benzonitrile; NMR (CDCl$_3$) 7.3 (m,4), 6.95 (d,1), 6.25 (m,2), 3.45 (br s,1), 3.1 (q,2), 1.3 (t,3) ppm;

3,4'-[2,6-pyridinediylbis(oxy)]bis(benzonitrile); NMR (CDCl$_3$) 7.8 (t,1), 7.6 (d,2), 7.2–7.5 (m,4), 7.14 (d,2), 6.7 (d,2) ppm;

3-[(6-[(3-cyanophenyl)aminol-3,5-difluoro-4-methylpyridin-2-yl)oxy]benzonitrile; NMR (CDCl$_3$) 7.65 (m,2), 7.5 (m,2), 7.2–7.4 (m,4), 2.4 (s,3) ppm;

3-[6-(3-cyanophenyl)amino-3,5-difluoro-4-methylpyridin-2-yl(methylamino)]-benzonitrile; NMR (CDCl$_3$) 7.1–7.5 (m,9), 3.4 (s,3), 2.3 (s,3) ppm;

3-[(3,5-difluoro-4-methyl-6-(pyridin-3-yloxy3pyridin-2-yl)oxy]benzonitrile; NMR (CDCl$_3$) 8.4 (m,2), 7.35 (m,4), 7.25 (m,4), 2.4 (s,3) ppm;

3-[(3,5-difluoro4-methyl-6-phenoxypyridin-2-yl)oxy]benzonitrile; NMR (CDCl$_3$) 7.25–7.5 (m,6), 7.2 (t,1), 7.0 (d,2), 2.4 (s,3) ppm;

3-[(3,5-difluoro-6(4-dimethylaminophenoxy)-4-methylpyridin-2-yl)oxy]benzonitrile; NMR (CDCl$_3$) 7.25–7.5 (m,4), 6.95 (d,2), 6.65 (d,2), 2.95 (s,6), 2.4 (s,3) ppm;

3-[(6-(3,5-difluoro-6-(3-(1H-imidazol-1-yl)phenoxy)-4-methylpyridin-2-yl)oxy]-benzonitrile; NMR (CDCl$_3$) 7.75 (s,1), 7.4 (t,1), 7.1–7.3 (m,7), 7.03 (m,2), 2.4 (s,3), ppm;

3-[(3,5-difluoro-4-methyl-6-(3-nitrophenoxy)pyridin-2-yl)oxy]benzonitrile; NMR (CDCl$_3$) 8.03 (d,1), 7.85 (s,1), 7.5 (t,1), 7.4 (m,3), 7.3 (m,2), 2.4 (s,3) ppm;

3-[(6-(3-aminophenoxy)-3,5-difluoro-4-methylpyridin-2-yl)oxy]benzonitrile; NMR (CDCl$_3$) 7.35 (m,4), 7.05 (t,1), 6.45 (d,$_1$), 6.35 (m,2), 2.4 (s,3) ppm;

N-[3-((6-(3-cyanophenoxy)-3,5-difluoro4-methylpyridin-2-yl)oxy)phenoxy]acetamide; NMR (CDCl$_3$) 7.55 (m,2), 7.2–7.4 (m,5), 7.0 (d,1), 6.75 (d,1), 2.4 (s,3), ppm;

3-[(3,5-difluoro-6-(3-dimethyleminophenoxy)-4-methylpyridin-2-ylsoxy]benzonitrile;

3-[(3,5-difluoro-6-(3-(2-(dimethylamino)ethyl)phenoxy)-4-methylpyridin-2-ylsoxy]benzonitrile;

1-[3-((6-(3-cyanophenoxy)-3,5-difluoro-4-methylpyridin-2-yl)oxy)phenyl]urea;

3-[(6-(3-cyanophenoxy)-3,5-difluoro-4-methylpyridin-2-yl)oxy]benzoic acid, ethyl ester;

3-[(6-(3-cyanophenoxy)-3,5-difluoro-4-methylpyridin-2-yl)oxy]-N,N-dimethylbenzenecarboxamide;

3-[(3,5-difluoro-6-(3-ethylaminophenoxy)-4-methylpyridin-2-yl)oxy]benzonitrile;

3-[(6-(3-diethylaminophenoxy)-3,5difluoro-4-methylpyridin-2-yl)oxy]benzonitrile;

3-[13,6-difluoro-4-methyl-6-(3-phenylaminophenoxy)pyridin-2-yl)oxy]benzonitrile;

3-[16-(3-chlorophenoxy)-3,5-difluora-4-methylpyridin-2-yl)oxy]benzonitrile; NMR (CDCl$_3$) 7.4 (m,2), 7.2–7.33 (m,3), 7.13 (ddd,1), 7.0 (t,1), 6.91 (ddd,1), 2.4 (s,3) ppm;

3-[(3,5-difluoro-4-methyl-6-(3-trifluoromethylphenoxy)pyridin-2-yl)oxy]benzonitrile; NMR (CDCl$_3$) 7.42 (m,3), 7.33 (t,1), 7.15–7.3 (m,4), 2.4 (s,3) ppm;

3-1N3,5-difluoro-6-(3-methoxyphenoxy)-4-methylpyridin-2-ylsoxy]benzonitrile; NMR (CDCl$_3$) 7.25–7.42 (m,5), 6.72 (ddd,1), 6.6 (m,1), 6.58 (m,l), 3.8 (s,3), 2.4 (s,3), ppm;

3-[(3,5-difluoro-6-(3-fluorophenoxy)-4-methylpyridin-2-yl)oxy]benzonitrile; NMR (CDCl$_3$) 7.35–7.45 (m,2), 7.2–7.33, (m,3), 6.85 (m,2), 6.73 (dt,1), 2.4 (s,3) ppm;

3-[(3,5-difluoro-6-(3-dimethylaminophenoxy)-4-methylpyridin-2-yl)oxy]-4-methylbenzonitrile; NMR (CDCl$_3$) 7.28 (m,1), 7.26 (s,1), 7.2 (m,2), 7.12 (t,1), 6.48 (dd,1), 6.28 (m,2), 2.88 (s,6), 2.38 (s,3), 2.21 (s,3) ppm;

4-amino-3-[(3,5-difluoro-6-(3-dimethylaminophenoxy)-4-methylpyridin-2-yl)-oxy]benzonitrile; NMR (CDCl$_3$) 7.2 (m,3), 6.66 (d,1), 6.54 (d,1), 6.35 (m,2), 4.28 (s,2), 2.91 (s,6), 2.37 (s,3) ppm;

3-[(6-(5-cyano-2-methoxyphenoxy)pyridin-2-yl)oxy]-N,N-dimethylbenzamide; NMR (CDCl$_3$) 7.7 (t,1), 7.4 (dd,1), 7.3 (d,1), 7.27 (d,1), 7.15 (dt,1), 7.0 (m,2), 6.9 (d,1), 6.66 (d,1), 6.57 (d,1), 3.8 (s,3), 3.1 (s,3), 2.9 (s,3) ppm;

3-[(6-(3-cyanophenoxy)-3,5-difluoro-4-methylpyridin-2-yl)oxy]-5-hydroxybenzoic acid, ethyl ester; NMR (CDCl$_3$) 7.3 (m,6), 6.7 (s,1), 4.3 (q,2), 2.4 (s,3), 1.5 (t,3), ppm;

3-[(6-(5-cyano-2-methoxyphenoxy)-3,5-difluoro-4-methylpyridin-2-yl)oxy]-5-hydroxybenzoic acid; NMR (CDCl$_3$) 7.4 (d,1), 7.3 (m,2), 7.1 (s,1), 6.8 (d,1), 6.6 (s,1), 5.6 (s,1), 4.4 (q,2), 3.8 (s,3), 2.4 (s,3), 1.4 (t,3) ppm;

2-(3-cyanophenoxy)-6-(5-cyano-2-(benzyloxy)phenoxy)pyridine-4-carboxylic acid, ethyl ester; NMR (CDCl$_3$) 7.62–7.02 (m,12), 5.16 (s,2H), 4.42 (q,2), 1.41 (t,3) ppm;

N-[2-(5-cyano-2-methoxyphenoxy)-6-(3-dimethylaminocarbonylphenoxy)-3,5difluoropyridin-4-yl]-N-methylglycine, ethyl ester;

N-[2-(5-cyanophenoxy)-6-(3-dimethylaminophenoxy)-3,5-difluoropyridin-4-yl]-N-methylglycine, ethyl ester;

3-[(6-(5-cyano-2-benzyloxyphenoxy)-3,5 difluoro-4-(morpholin-1-yl)pyridin-2-yl)oxy]-N,N-dimethylbenzamide;

2-(5-cyano-2-methoxyphenoxy)-6-(3-dimethylaminocarbonylphenoxy)pyridine-4-carboxylic acid, methyl ester; NMR (CDCl$_3$) 7.2 (m,9), 3.92 (s,3), 3.70 (s,3), 3.10 (s,3), 2.88 (s,3) ppm;

2-(5-cyano-2-methoxyphenoxy)-6-(3-dimethylaminocarbonylphenoxy)-N,N-dimethylpyridine-4-carboxamide; NMR (CDCl3) 7.1 (m,7), 6.55 (s,1), 6.48 (s,1), 3.65 (s,3), 2.95 (m,12) ppm;

2-(3-cyanophenoxy)-6-(3-dimethylaminocarbonylphenoxy)-N,N-dimethylpyridine-4-carboxamide; NMR (CDCl$_3$) 7.16 (m,8), 6.57 (s,1), 6.53 (s,1), 2.95 (m,12) ppm; and 4-[(2-(3-aminophenoxy)-6-(5-cyano-2-phenylmethoxyphenoxy)-3,5-difluoropyridin-4-yl)oxy]-3-methoxybenzoic acid, ethyl ester.

PREPARATION 10

2,6-Bis(3-cyanophenoxy)-N-methylpyridine-4-carboxamide

A. To 2,6-bis(3-cyanophenoxy)pyridine-4-carboxylic acid, ethyl ester (1.6 g, 4.0 mmol) in tetrahydrofuran/water (50 mL, 1/1) was added lithium hydroxide (0.85 g, 20 mmol). After stirring for 1.5 hours the reaction was partitioned with 1 M HCl and ethyl acetate. The organic layer was separated, dried (MgSO$_4$), and the solvent was removed in vacuo. The residue was dissolved in methylene chloride (50 mL) and thionyl chloride (2.4 g, 20 mmol) was added. After stirring for 2 hours the solvent was removed in vacuo. The residue was dissolved in methylene chloride/water (30/10 mL) and methylamine hydrochloride (0.090 g, 1.3 mmol) and potassium carbonate (0.46 g, 3.3 mmol) were added. The organic layer was separated, washed with brine, dried (MgSO$_4$), and the solvent removed in vacuo to give 2,6-bis(3-cyanophenoxy)-N-methylpyridine-4-carboxamide; NMR (CDCl$_3$) 7.5 (m,4), 7.3 (m,4), 7.0 (s,2), 6.25 (br s,1), 3.1 (d,3) ppm.

B. In a similar manner, the following compounds were made:

2,6-bis(3-cyanophenoxy)-N-methylpyridine-3-carboxamide; NMR (CDCl$_3$) 7.8 (d,1), 7.4–7.6 (m,5), 7.1–7.3 (m,4), 6.8 (d,1), 3.1 (d,3) ppm;

N-[t2,6-bis(3-cyanophenoxy)pyridin-3-yl)oxomethyl] glycine, ethyl ester; NMR (CDCl$_3$) 8.65 (d,1), 8.1 (t,1), 7.2–7.6 (m,8), 6.8 (d,1), 4.3 (m,4), 1.3 (t,3) ppm; and 2,6-bis (3-cyanophenoxy)-N,N-dimethylpyridine-4-carboxamide; NMR (CDCl$_3$) 7.85 (d,1), 7.45 (m,4), 7.25 (m,4), 6.75 (d,1), 3.2 (s,3), 3.1 (s,3) ppm.

PREPARATION 11

3-[(6-(3-Cyanophenyl)methylamino-3,5-difluoro-4-methylpyridin-2-yl)oxy]benzonitrile A. To 3-[(6-(3-cyanophenyl)amino-3,5-difluoro-4-methylpyridin-2-yl)oxy]-benzonitrile (0.10 g, 0.28 mmol) in acetonitrile (10 mL) was added iodomethane (0.20 g, 1.4 mmol) and sodium hydride (0.055 g, 1.4 mmol). After stirring for 18 hours the reaction was partitioned with water and ethyl acetate. The organic layer was separated, dried (Na$_2$SO$_4$), and the solvent was removed in vacuo. Chromatography of the residue on silica gel with ethyl acetate/hexane (1/3) as eluent gave 3-[(6-(3-cyanophenyl)-methylamino-3,6-difluoro-4-methylpyfidin-2-yl)oxy]-benzonitrile; NMR (CDCl$_3$) 7.4 (m,5), 7.25 (m,1), 7.1 (m,2), 3.25 (s,3), 2.3 (s,3) ppm.

B. In a similar manner, the following compounds were made:

3-(4-methyl-3,5,6-trifluoropyridin-2-yl) methylaminobenzonitrile; NMR (CDCl$_3$) 7.35 (t,1), 7.3 (m,1), 7.2 (m,2), 3.4 (s,3), 2.3 (s,3) ppm; and 3,3'-[3,5-difluoro-4-methyl-2,6-pyridinediylbis (methylamino)]bis)benzonitrile); NMR (CDCl$_3$) 7.1–7.5 (m,8), 3.4 (s,6), 2.3 (s,3) ppm.

PREPARATION 12

3-[(6-(3-Cyanophenoxy)-3,5-difluoro-4-methylpyridin-2-yl)oxy]-5-methoxybenzoic Acid, Ethyl Ester A. To acetonitrile (5 mL) was added 3-[(6-(3-cyanophenoxy)-3,5-difluoro-4-methylpyridin-2-yl)oxy]-5-hydroxybenzoic acid, ethyl ester (0.20 g, 0.47 mmol), cesium carbonate (0.31 g, 0.94 mmol), and iodomethane (0.13 g, 0.94 mmol). After stirring for 15 hours the mixture was partitioned with ethyl acetate and water. The organic layer was dried (MgSO$_4$) and the solvent was removed in vacuo to give 3-[(6-(3-cyanophenoxy)-3,5-difluoro-4-methyl-pyridin-2-yl)oxy]-5-methoxybenzoic acid, ethyl ester; NMR (CDCl$_3$) 7.3 (m,6), 6.8 (s,1), 4.4 (q,2), 3.8 (s,3), 2.4 (s,3), 1.4 (t,3) ppm.

B. In a similar manner, the following compound was made:

3-[(6-(5-cyano-2-methoxyphenoxy)-3,5-difluoro-4-methylpyridin-2-yl)oxy]-5-methoxybenzoic acid, ethyl ester; NMR (CDCl$_3$) 7.4 (d,1), 7.3 (m,2), 7.1 (s,1), 6.8 (d,1), 6.6 (s,1), 4.4 (q,2), 3.8 (s,3), 3.7 (s,3), 2.4 (s,3), 1.4 (t,3) ppm.

PREPARATION 13

5-[(6-(3-Cyanophenoxy)-3,5-difluoro4-methylpyridin-2-yl)oxy]benzene-1,3-dicarboxylic acid A. To 5-[(6-(3-cyanophenoxy)-3,5-difluoro-4-methylpyridin-2-yl)oxy]benzene-1,3-dicarboxylic acid, diethyl ester (0.97 g, 2.0 mmol) in tetrahydrofuran/water (20 mL, 1/1) was added lithium hydroxide (0.42 g, 10 mmol). After heating at 60° C. for 90 minutes, the material was partitioned between ethyl acetate and 2 N HCl. The organic layer was separated, dried (MgSO$_4$), and the solvent removed in vacuo to give 5-[(6-(3-cyanophenoxy)-3,5-difluoro-4-methylpyridin-2-yl)oxy]benzene-1,3-dicarboxylic acid; NMR (DMSO) 8.25 (s,1), 7.85 (s,2), 7.4–7.7 (m,3), 7.3 (m,3), 2.4 (s,3) ppm.

B. In a similar manner, the following compounds were made:

3-[(6-(3-cyanophenoxy)-3,5-difluoro-4-methylpyridin-2-yl)oxy]-2,3-dimethoxybenzenecarboxylic acid; NMR (DMSO-d$_6$) 7.95 (s,1), 7.1–7.7 (m,5), 3.85 (s,3), 3.6 (s,3), 2.4 (s,3), ppm;

3-[a6-(3-cyanophenoxy)-3,5-difluoro-4-methylpyridin-2-ylsoxy]-5-methoxybenzoic acid; and 3-[(6-(5-cyano-2-methoxyphenoxy)-3,5-difluoro-4-methylpyridin-2-yl)oxy]-5-methoxybenzoic acid

PREPARATION 14

3-[(6-(3-Cyanophenoxy)-3,5-difluoro-4-methylpyridin-2-yl)oxy]-N,N-dimethyl-4-methoxybenzamide A. To 3-16-(3-cyanophenoxy)-3,5-difluoro4-methylpyridin-2-yl)oxy]-4-methoxybenzoic acid (0.47 g, 1.1 mmol) in tetrahydrofuran (12 mL) was added 1,1'-carbonyldimidazole (0.22 g, 1.4 mmol) and stirred at ambient temperature for 3 hours. Then dimethylamine (aq, 0.077 g, 1.7 mmol) was added. After stirring for 12 hours the solution was partitioned between water and ethyl acetate. The organic layer was separated, dried (MgSO$_4$), and the solvent was removed in vacuo. Chromatography on silica gel with ethyl acetatelhexane 11/8) as eluent gave 3-[(6-(3-cyanophenoxy)-3,5-difluoro-4-methylpyridin-2-yl)oxy]-NN-dimethyl-4-methoxybenzamide; NMR (CDCl$_3$) 6.9–7.4 (m,7), 3.8 (s,3), 3.0 (br,6), 2.4 (s,3) ppm.

B. In a similar manner, the following compounds were made:

3-[(6-(3-cyanophenoxy)-3,5-difluoro-4-methylpyridin-2-yl)oxy]-N,N-dimethyl-4-methoxybenzamide; NMR (CDCl$_3$) 7.3 (m,2), 7.2 (m,3), 7.15 (d,1), 6.95 (s,1), 3.05 (br,3), 2.85 (br,3), 2.4 (s,3), 2.15 (s,3) ppm;

5-[(6-(3-cyanophenoxy)-3,5-difluoro-4-methylpyridin-2-yl)oxy3-N,N,N', N'-tetraethylbenzene-1,3-dicarboxamide; NMR (CDCl$_3$) 7.9 (s,1), 7.65 (s,2), 7.1–7.5 (m,4), 3.45 (br,4), 3.15 (br,4), 2.4 (s,3), 1.25 (br,6), 1.05 (br,6) ppm;

5-[(6-(3-cyanophenoxy)-3,5-difluoro-4-methylpyridin-2-yl)oxy]-2,3-dimethoxy-N,N-dimethylbenzamide; NMR (DMSO-d$_6$) 7.95 (m,1), 7.1–7.7 (m,5), 3.9 (s,3), 3.65 (s,3), 3.4 (s,3), 3.15 (s,3), 2.4 (s,3) ppm;

5-[(6-(3-cyanophenoxy)-3,5-difluoro-4-methylpyridin-2-ylsoxy]-N,NN',N'-tetramethylbenzene-1,3-dicarboxamide; NMR (CDCl$_3$) 7.7 (s,2), 7.1–7.5 (m,5), 3.1 (m,6), 2.9 (s,3), 2.85 (s,3), 2.4 (s,3) ppm;

4-[(6-(3-cyanophenoxy)-3,5-difluoro-4-methylpyfidin-2-yl)oxy]-3-methoxy-N,N-dimethylbenzamide; NMR (CDCl$_3$) 7.7 (s,1), 7.2–7.4 (m,3), 7.1 (s,1), 7.05 (m,1), 6.95 (d,1), 3.8 (s,3), 3.1 (s,3), 3.0 (s,3), 2.4 (s,3) ppm;

1-(3-[(6-(3-cyanophenoxy)-3,5-difluoro-4-methylpyridin-2-yl)oxy]benzoyl)pyrrolidine; NMR (CDCl$_3$) 7.2–7.5 (m,6), 7.2 (s,1), 7.1 (d,1), 3.65 (m,2), 3.3 (m,2), 2.4 (s,3), 1.8–2.1 (m,4) ppm;

1-[3-[(6-(3-cyanophenoxy)-3,5-difluoro-4-methylpyridin-2-yl)oxy]benzoyl]morpholine;

4-[(6-(3-cyanophenoxy)-3,5-difluoro4-methylpyridin-2-yl)oxy]-N,N-dimethylbenzamide; NMR (CDCl$_3$) 7.2–7.6 (m,6), 7.05 (d,2), 3.2 (br,3), 3.0 (br,3), 2.4 (s,3) ppm;

3-[(6-(3-cyanophenoxy)-3,5-difluoro-4-methylpyridin-2-yl)oxy]-N-methylbenzenecarboxamide;

1-[3-[(6-(3-cyanophenoxy)-3,5-difluoro-4-methylpyridin-2-yl)oxybenzoyl]-4-ethylpiperazine;

1-[3-[(6-(3-cyanophenoxy)-3,5-difluoro-4-methylpyridin-2-yl)oxy]benzoyl]piperidine;

3-[(6-(3-cyanophenoxy)-3,5-difluoro-4-methylpyridin-2-yl)oxy]-N-methyl-N-(phenylmethyl) benzamide;

3-[(6-(3-cyanophenoxy)-3,5-difluoro-4-methylpyridin-2-yl)oxy]-N-methyl-N-[2-(pyridin- 2-yl)ethyl) benzamide;

3-[(6-(3-cyanophenoxy)-3,5-difluoro-4-methylpyridin-2-yl)oxy]-N-ethyl-N-methylbenzamide;

3-[(6-(3-cyanophenoxy)-3,5-difluoro-4-methylpyridin-2-yl)oxy]-N,N-diethylbenzamide;

N-[3-[(6-(3-cyanophenoxy)-3,5-difluoro-4-methylpyridin-2-yl)oxy]benzoyl]-β-alanine, ethyl ester;

3-[(6-(3-cyanophenoxy)-3,5-difluoro-4-methylpyridin-2-yl)oxy]-N,N-dimethyl-5-methoxybenzamide; NMR (CDCl$_3$) 7.4 (m,2), 7.3 (m,2), 6.7 (s,1), 6.6 (s,2), 3.8 (s,3), 3.0 (s,3), 2.8 (s,3), 2.4 (s,3) ppm; and 3-[(6-(5-cyano-2-methoxyphenoxy)-3,5-difluoro-4-methylpyridin-2-yl)oxy]-N,N-dimethyl-5-methoxybenzamide; NMR (CDCl$_3$) 7.4 (d,1), 7.3 (s,1), 6.9 (d,1), 6.6 (d,1), 6.5 (D,1), 3.8 (s,6), 3.1 (s,3), 2.9 (s,3), 2.4 (s,3) ppm.

PREPARATION 15

3,3'-(3-Amino-2,6-pyridinediylbis(oxy)]bis(benzonitrile)

A. To 3,3'-(3-nitro-2,6-pyridinediylbis(oxy)]bis(benzonitrile) (18.5 g, 50 mmol) dissolved in ethanol/ethyl acetate (500 mL, 2/3) was added 10% palladium on carbon (1.8 g). After subjecting the mixture to hydrogen at 15 psi for 2 hours, the reaction was suction filtered through celite. The solvent was removed in vacuo to give 3,3'-(3-amino-2,6-pyridinediylbis(oxy)]-bis(benzonitrile); NMR (CDCl$_3$) 7.5 (m,7), 7.2 (m,2), 6.6 (d,1), 3.8 (br,2) ppm.

PREPARATION 16

N-[2,6-Bis(3-cyanophenoxy)pyridin-3-yl]benzamide

A. To 3,3'-(3-amino-2,6-pyridinediylbistoxy)]bis(benzonitrile) (1.0g, 2.9 mmol) dissolved in acetonitrile (50 mL) was added benzoyl chloride (0.50 g, 3.5 mmol) and triethylamine (0.45 g, 0.60 mmol). After stirring for 3 hours, the reaction was partitioned between ether and water. The organic layer was separated, washed with water, saturated aqueous sodium bicarbonate, and brine, dried (MgSO$_4$), and the solvent was removed in vacuo. Chromatography on silica gel with ethyl acetate/hexane (1/3) as eluent gave N-[2,6-bist3-cyanophenoxy)-pyridin-3-yl]benzamide; NMR (CDCl$_3$) 8.95 (d,1), 8.25 (s,1), 7.9 (d,1), 7.2–7.7 (m,12), 6.8 (d,1) ppm.

B. In a similar manner, the following compounds were made:

N-[2,6-bis(3-cyanophenoxy)pyridin-3-yl]acetamide; NMR (CDCl$_3$) 8.65 (d,1), 7.6 (s,1), 7.1–7.6 (m,8), 6.7 (d,1), 2.3 (s,3) ppm;

N-[2,6-bis(3-cyanophenoxy)pyridin-3-yl) aminolcarboxylglycine, ethyl ester; NMR (CDCl$_3$) 8.5 (d,1), 7.2–7.5 (m,8), 7.15 (s,1), 6.6 (d,1), 5.7 (m,1), 4.2 (q,2), 4.1 (m,2), 1.25 (d,3) ppm;

N-[2,6-bis(3-cyanophenoxy)pyridin-3-yl]methanesulfonamide; NMR (CDCl$_3$) 8.0 (d,1), 7.45 (m,4), 7.25 (m,4), 6.75 (d,1), 6.6 (s,1), 3.1 (s,3) ppm; and N-[3-[(6-(3-cyanophenoxy)-3,5-difluoro-4-methylpyridin-2-yl)oxy]phenyl]methanesulfonamide; NMR (CDCl$_3$) 8.8 (d,1), 7.65 (m,2), 7.35 (m,4), 7.05 (m,2), 2.95 (s,3), 2.3 (s,3) ppm.

PREPARATION 17

N-[2,6-Bis(3-cyanophenoxy)pyridin-3-yl]-N'-phenylurea

A. To 3,3'-[3-amino-2,6-pyridinediylbis(oxy)]bis(benzonitrile) (3.0g, 8.7 mmol) dissolved in acetonitrile (100 mL) was added phenyl isocyanate (1.1 g, 9.5 mmol). After refluxing for 4 hours, the reaction was partitioned between ether and water. The organic layer was separated, washed with water, saturated aqueous sodium bicarbonate, and brine, dried (MgSO$_4$), and the solvent was removed in vacuo. Chromatography on silica gel with ethyl acetate/hexane (1/4) as eluent gave material which was crystallized from ethyl acetate/hexane to give N-[2,6-bis(3-cyanophenoxy) pyridin-3-yl]-N'-phenylurea; NMR (CDCl$_3$) 8.65 (d,1), 7.4 (m,8), 7.1–7.3 (m,6), 6.8 (s,1), 6.7 (d,1) ppm.

B. In a similar manner, the following compound was made:

N-[2,6-bis(3-cyanophenoxy)pyridin-3-yl]-N'-methylurea; NMR (CDCl$_3$) 8.65 (d,1), 7.5 (m,4), 7.25 (m,4), 6.8 (s,1), 6.7 (d,1), 2.9 (d,3) ppm.

PREPARATION 18

3-[(6-(3-Cyanophenoxy)-3,5-difluoro-4-methylpyridin-2-yl)oxy]-benzenepropionic Acid, Methyl Ester To 3-[(6-(3-cyanophenoxy)-3,5-difluoro-4-methylpyridin-2-yl)oxy]benzene-propionicacid(0.50 g, 1.2 mmol) in methylene chloride (20 mL) was added methyl iodide (0.26 g, 1.8 mmol) and diazabicycloundecane (2.8 g, 1.8 mmol). After stirring for 15 hours, the solution was concentrated in vacuo and chromatographed on silica gel with ethyl acetate/hexane (1/4) to give 3-[(6-(3-cyanophenoxy)-3,5-difluoro-4-methylpyridin-2-yl)oxy] benzenepropionic acid, methyl ester; NMR (CDCl$_3$) 7.3 (m,5), 7.05 (d,1), 6.85 (m,2), 3.68 (s,3), 2.9 (t,2), 2.24 (s,3) ppm.

PREPARATION 19

4,4'-[1,3-Phenylenebis(oxy)]benzonitrile

To DMSO (6 mL) was added resorcinol (1.1 g, 10 mmol), 4-fluorobenzonitrile (2.4 g, 20 mmol) and potassium carbonate (2.4 g, 17 mmol). After heating in an oil bath at 100° C. for 16 hours the reaction mixture was partitioned with water and ethyl acetate. The organic layer was separated, washed with 1 N sodium hydroxide, water, brine, dried (sodium sulfate) and concentrated in vacuo. Chromatography on silica gel with methylene chloride/hexane (20/1) as eluent gave 4,4'-[1,3-phenylenebis(oxy)]benzonitrile; NMR (CDCl$_3$) 7.64 (d,4), 7.43 (t,1), 7.06 (d,4), 6.82 (dd,2), 6.80 (t,1) ppm.

PREPARATION 20

4-[(2-(3-(Guanidino)phenoxy)-6-(5-cyano-2-benzyloxyphenoxy)-3,5-difluoropyridin-4-yl)oxy]-3-methoxybenzoic Acid, Ethyl Ester.

To ethanol (15 mL) was added 4-[[2-(3-aminophenoxy)-6-(5-cyano-2-phenylmethoxyphenoxy)-3,5-difluoropyridin-4-yl]oxy]-3-methoxybenzoic acid, ethyl ester (0.50 g, 0.80 mmol), cyanamide (0.60 g, 14 mmol), and 6 M hydrochloric acid (0.7 mL). After refluxing for 19 hours, cyanamide (0.60 9, 14 mmol) and 6 M hydrochloric acid (0.7 mL) was added and refluxing was continued for 4 hours. The reaction mixture was concentrated in vacuo and purified by HPLC to give 4-[[2-[3-(guanidino)phenoxy)-6-(5-cyano-2-benzyloxyphenoxy)-3,5-difluoro-pyridin-4-yl)oxy]-3-methoxybenzoic acid, ethyl ester.

EXAMPLE 1

3,3'-[2,6-Pyridinediylbis(oxy)]bis(benzamidine), Dihydrochloride

A. To 3,3'-[2,6-pyridinylbis(oxy)]bis(benzonitrile) (0.2 g, 0.7 mmol) slurried in ethanol (6 mL) cooled in a dry ice/isopropanol bath was bubbled HCl (g). After the solution was saturated the reaction flask was sealed and allowed to warm to ambient temperature and stir for 18 hours. The solvent was removed in vacuo and the residue was triturated with ether. The ether was removed by decantation and the residue was dissolved in ethanol (6 mLl. The solution was cooled in a dry ice/isopropanol bath and ammonia 1g) was bubbled in. The reaction flask was sealed and heated to 50° C. for 2 hours. The solvent was removed in vacuo and the residue was recrystallized from 5 M HCl to give 3,3'-[2,6-pyridinediylbis(oxy)]bis(benzamidine), dihydrochloride as a solid; m.p. 160° C. (decom); NMR (DMSO-d$_6$) 9.45 (s,4), 9.3 (s,4), 8.02 (t,1), 7.4–7.8 (m,8), 6.90 (d,2) ppm.

B. In a similar manner, the following compounds were made:

4,4'-[2,6-pyridinediylbis(oxy)]bis(benzamidine), dihydrochloride; NMR (DMSO-d$_6$) 9.4 (s,4), 9.2 (s,4), 8.1 (t,1), 7.95 (d,4), 7.40 (d,4), 6.96 (d,2) ppm;

3,3'-bisimethoxy)-4,4'-[2,6-pyridinediylbis(oxy)] bisibenzamidine), dihydrochloride; NMR (DMSO-d$_6$) 9.5 (br s,4), 9.2 (br s,4), 7.9 (t,1), 7.7 (s,2), 7.5 (d,2), 3.85 (s,6) ppm;

4-[(6-(3-amidinophenoxy)pyfidin-2-yl)oxy]-3-methoxybenzamidine, dihydrochloride; NMR (DMSO-d$_6$) 9.7 (s,2), 9.55 (s,2), 9.4 (br s,4), 7.95 (t,$_1$), 7.75 (s,1), 7.3–7.7 (m,6), 6.85 (d, 1), 6.75 (d,1), 3.9 (s,3) ppm;

3-[(3,5-difluoro-6-(3-ethylamino-4-methylphenoxy)-4-methylpyridin-2-yl)oxy]-benzamidine, dihydrochloride; NMR (DMSO-d$_6$) 9.4 (s,2), 9.2 1s,2), 7.6 (m,2), 7.55 (t,1), 7.45 (m,1), 7.3 (m,2), 7.15 (dd,1), 3.2 (q,2), 2.4 (s,3), 2.35 (s,3), 1.2 (t,3) ppm;

3,3'-[3-trifluoromethyl-2,6-pyridinediylbis(oxy)]bis (benzamidine), dihydrochloride; NMR (DMSO-d$_6$) 9.4 (s,4), 9.2 (s,4), 8.3 (d,1), 7.7 (m,4), 7.6 (d,4), 7.0 (m,1) ppm;

3,4'-[2,6-pyridinediylbis(oxy)]bis(benzamidine), dihydrochloride; NMR (DMSO-d$_6$) 9.4 (br s,8), 8.1 (t,l), 7.9 (d,2), 7.5–7.8 (m,4), 7.40 (d,2), 6.95 (m,2) ppm;

3,3'-[3-methylaminocarbonylamnino-2,6-pyridinediylbis (oxy)]bisibenzamidine), dihydrochloride; m.p. 205–206° C.;

4-methoxy-3-[(3,5-difluoro-6-(3-dimethylaminocarbonylphenoxy)-4-carboxy-pyridin-2-yl)oxy]benzamidine, hydrochloride; NMR (DMSO-d$_6$) 9.2 (s,2), 9.0 (s,2), 7.9 (t,1), 7.78 (dd,1), 7.68 (m,1), 7.36 (t,1), 7.26 (d,1), 7.15 (d,1), 7.05 (m,1), 7.02 (m,1), 6.75 (d,1), 6.7 (d,1), 3.8(s,3), 2.95(s,3), 2.8 (s,3) ppm;

4-methoxy-3-[(3,5-difluoro-6-(3-dimethylaminocarbonylphenoxy)-4-(4-methylpiperazinoyl)pyridin-2-yl)oxy]benzamidine, dihydrochloride;

3-[(3,5-difluoro-6-(3-dimethylaminophenoxy)-4-((methyl)(ethoxycarbonylmethyl)amino) pyridin-2-yl) oxy]benzamidine, ethyl ester, hydrochloride; NMR (DMSO-d$_6$) 9.3 (s,2), 9.2 (s,2), 7.5 (m,4), 7.2 (1,1), 6.7 (m,2), 6.5 (d,1), 4.2 (s,2), 3.2 (s,3), 2.9 (s,2), 4-methoxy-3-[(6-(3-dimethylaminocarbonylphenoxy)-4-(dimethylaminocarbonyl)pyridin-2-yl)oxy] benzamidine, hydrochloride;

4-methoxy-3-[(6-(3-dimethylaminocarbonylphenoxy)-4-(aminocarbonyl)-pyridin-2-yl)oxy]benzamidine, hydrochloride; and 4-methoxy-3-[(6-(3-dimethylaminocarbonylphenoxy)-4-(ethoxycarbonyl)pyridin-2-yl)oxy]benzamidine, hydrochloride.

C. In a similar manner, reaction of 3,3'-(3,5-difluoro-4-methyl-2,6-pyridinediyl-bis(oxy)]bis(benzonitrile) gave 3,3'-[3,5-difluoro-4-methyl-2,6-pyridinediylbis(oxy)]bis (benzamidine); which was purified by HPLC on a Cl 8 Dynamax column with a 20–80% acetonitrile in water gradient with 0.1% trifluoroacetic acid to give the compound as a pure trifluoroacetic acid salt; m.p. >210° C.; NMR (DMSO-d$_6$) 9.3 (br s,8), 7.6 (m,4), 7.54 (m,4), 2.4 (m,3) ppm.

D. In a similar manner, the following compounds were made:

3,3'-(3,5-dichloro-2,6-pyridinediylbis(oxy))bis (benzamidine), trifluoroacetic acid salt; NMR (DMSO-d$_6$) 9.2 (br s,8), 8.6 (s,1), 7.4–7.7 (m,8) ppm;

4,4'-(3,5-dichloro-2,6-pyridinediylbis(oxy))bis (benzamidine), trifluoroacetic acid salt; NMR (DMSO-d$_6$) 9.25 (s,4), 9.0 (s,4), 8.58 (s,1), 7.8 (d,4) 7.4 (d,4) ppm;

3,3'-(4-ethoxycarbonyl-2,6-pyridinediylbis(oxy))bis (benzamidine), trifluoroacetic acid salt; NMR (DMSO-d$_6$) 9.55 (br s,4), 9.4 (br s,4), 7.65 (m,4), 7.6 (m,4), 7.2 (s,2), 4.4 (q,2), 1.4 (t,3) ppm;

3,3'-(3-ethoxycarbonyl-2,6-pyridinediylbis(oxy))bis (benzamidine), trifluoroacetic acid salt; NMR (DMSO-d6) 9.35 (br s,4), 9.1 (br s,4), 8.4 (d,1), 7.6 (m,4), (m,4), 6.9 (d,1), 4.3 (q,2), 1.3 (t,3) ppm;

3,3'-(3,5-difluoro-2,6-pyridinediylbis(oxy)) bistbenzamidine), trifluoroacetic acid salt; NMR (DMSO-d$_6$) 9.55 (br s,4), 9.4 (br s,4), 8.5 (t,1), 7.7 (m,4), 7.55 (m,4) ppm;

3,3'-(4-methylaminocarbonyl-2,6-pyridinediylbisloxy)) bis(benzamidine), trifluoroacetic acid salt; NMR (DMSO-d$_6$) 9.35 (br s,4), 9.2 (br s,4), 8.85 (m,1), 7.5–7.7 (m,8), 7.2 (s,2), 2.9 (d,3) ppm;

3,3'-3-methylaminocarbonyl-2,6-pyridinediylbis(oxy)) bis]benzamidine), trifluoroacetic acid salt; NMR (DMSO-d₆) 9.6 (m,4), 9.4 (br s,4), 8.65 (d,1), 8.5 (m,1), 7.7–8.0 (m,8), 7.2 (d,1), 2.85 (d,3) ppm.

3,3'-(3-dimethylaminocarbonyl-2,6-pyridinediylbis(oxy)) bis(benzamidine), trifluoroacetic acid salt; m.p. 180–183° C.;

3,3'-(3-((aminocarbonyl)methylamin(carbonyl)-2,6-pyridinediylbisloxy))bis(benzamidine), trifluoroacetic acid salt; NMR (DMSO-d₆) 9.3 (s,2),-9.25 (s,2), 9.05 (s,4), 8.5 (d,1), 7.4–7.7 (m,11), 6.85 (d,1), 4.0 (d,2) ppm;

3-[(3,5-difluoro-6-(5-dimethylamino-2-methylphenoxy)-4-methylpyridin-2-yl)oxy]-benzamidine, trifluoroacetic acid salt; NMR (DMSO-d6) 9.25 (s,2), 9.1 (s,2), 7.4–7.6 (m,3), 7.2–7.4 (m,4), 3.1 (s,6), 2.4 (s,3), 2.1 (s,3) ppm;

3-(3,5-difluoro-6-(3dimethylamino-2-methylphenoxy)-4-methylpyridin-2-yl(oxy)-benzamidine, trifluoroacetic acid salt; NMR (DMSO-d₆) 9.25 (s,2), 9.1 (s,2), 7.5–7.7 (m,4), 7.4 (m,1). 7.3 (m,1), 7.2 (d,1), 3.1 (s,6), 2.4 (s,3), 2.3 (s,3) ppm;

3-[(3,5-difluoro-6-((3-amidinophenyl)methylamino)-4-methylpyridin-2-yl)oxy]benzamidine, trifluoroacetic acid salt; NMR (DMSO-d₆) 9.35 (s,2), 9.3 (s,2), 9.15 (s,2), 9.05 (s,2), 7.6 (m,4), 7.4 (m,3), 7.25 (m,1), 7.2 (d,1), 3.25 (s,3), 2.3 (s,3) ppm;

3-[(3,5-difluoro-6-[(3-amidinophenyl)aminol-4-methylpyridin-2-yl)oxy]-benzamidine; trifluoroacetic acid salt; NMR (DMSO-d₆) 9.35 (s,2), 9.2 (s,4), 8.95 (s,2), 7.5–7.8 (m,6), 7.25 (m,2), 2.35 (s,3) ppm;

3,3'-(3,5-difluoro-4-methoxy-2,6-pyridinediylbis(oxy)) bis(benzamidine), trifluoroacetic acid salt; NMR (DMSO-d6) 9.3 (br s,4), 9.2 (br s,4), 7.6 (m,4), 7.5 (m,4), (s,3), 2.3 (m,3) ppm;

3,3'-(3,5-difluoro-4-methyl-2,6-pyridinediylbis (methylamino))bis)benzamidine), trifluoroacetic acid salt; m.p. 115–120° C.;

3-[(6-(2-methoxy-5-dimethylaminocarbonylphenoxy)-3,5-difluoro-4-methylpyridin-2-yl)-oxy]benzamidine, trifluoroacetic acid salt; NMR (DMSO-d₆) 9.3 (s,2), 9.1 (s,2), 7.5 (m,3), 7.3 (d,1), 7.2 (m,2), 7.1 (d,1), 3.75 (s,3), 2.9 (br,6), 2.4 (s,3) ppm;

3-[(6-(2,3-dimethoxy-5-ethoxycarbonylphenoxy)-3,5-difluoro-4-methylpyridin-2-yl)-oxy]benzamidine, trifluoroacetic acid salt; m.p. 200–202° C.;

3-[(6-(2-methyl-5-dimethylaminocarbonylphenoxy)-3,5-difluoro-4-methylpyridin-2-yl)-oxy]benzamidine, trifluoroacetic acid salt; NMR (DMSO-d₆) 9.3 (s,2), 9.15 (s,2), 7.5 (m,3), 7.45 (d,1), 7.3 (d,1), 7.1 (m,2), 2.95 (s,3), 2.75 (s,3), 2.4 (s,3), 2.15 (s,3) ppm;

3-[(6-(3,5-di(diethylaminocarbonyl)phenoxy)-3,5-difluoro-4-methylpyridin-2-yl)oxy]benzamidine, trifluoroacetic acid salt; NMR (DMSO-d₆) 9.35 (s,2), 9.05 (s,2), 7.6 (m,3), 7.45 (m,1), (s,2), 7.1 (s,1), 3.45 (br,4), 3.15 (br,4), 2.4 (s,3) 1.2 (br,6), 1.05 (br,6) ppm;

3-[(6-(2,3-dimethoxy-5-dimethylaminocarbonylphenoxy)-3,5-difluoro-2-methylpyridin-2-yl)oxy]benzamidine, trifluoroacetic acid salt; NMR (DMSO-d₆) 9.25 (s,2), 9.1 (s,2), 7.95 (s,1), 7.4–7.6 (m,4), 7.3 (s,1), 3.9 (s,3), 3.7 (s,3), 2.5 (s,6), 2.4 (s,3) ppm;

3-[(6-(3,5-dildimethylaminocarbonyl)phenoxy)-3,5-difluoro-4-methylpyridin-2-yl)-oxy]benzamidine, trifluoroacetic acid salt; NMR (DMSO-d₆) 9.3 (s,2), 9.05 (s,2), 7.55 (m,4), 7.25 (m,3), 7.2 (s,1), 3.0 (s,3), 2.85 ts,6), 2.4 (s,3) ppm;

3-[(6-(2-methoxy-4-dimethylaminocarbonylphenoxy)-3,5-difluoro-4-methylpyridin-2-yl)oxy]-benzamidine, trifluoroacetic acid salt; NMR (DMSO-d₆) 9.3 (s,2), 9.15 (s,2), 7.5 (m,3), 7.35 (m,1), 7.15 td,1), 7.1 (s,1), 6.9 (d,1), 3.7 (s,3), 3.05 (br,3), 2.9 (br,3), 2.4 (s,3) ppm;

3,3'-(4-phenylcarbonylamino-2,6-pyridinediylbis(oxy)) bistbenzamidine), trifluoroacetic acid salt; m.p. 269–271° C.;

3,3'-(3-phenylaminocarbonylamino-2,6-pyridinediylbis (oxy)]bis(benzamidine), trifluoroacetic acid salt; m.p. 159–160° C.;

3,3'-(3-(aminocarbonylmethyl)aminocarbonylamino-2,6-pyridinediylbis(oxy))-bis(benzamidine), trifluoroacetic acid salt; m.p. 129–130° C.;

3,3'-[3-amino-2,6-pyridinediylbis(oxy)]bis (benzamidine), trifluoroacetic acid salt; NMR (DMSO-d₆) 9.5 (br,4), 9.2 (br,4), 7.3–7.7 (m,9), 6.8 (d,1) ppm;

3,3'-(3-methylsulfonylamino-2,6-pyridinediylbistoxy)] bis(benzamidine), trifluoroacetic acid salt; NMR (DMSO-d₆) 9.6 (s,1), 9.4 (m,8), 8.4 (d,1), 7.95 (d,1), 7.5–7.7 (m,8), 6.9 (d,1), 3.1 (s,3) ppm;

3,3'-(3-methylcarbonylamino-2,6-pyridinediylbis(oxy)] bis(benzamidine), 2-trifluoroacetic acid salt; NMR (DMSO-d₆) 9.8 (s,1), 9.3 (m,4), 9.25 (m,4), 8.4 (d,1), 7.4–7.7 (m,8), 6.9 (d,1), 2.15 (s,3) ppm;

3-[(6-(3-aminophenoxy]-3,5-difluoro-4-methylpyridin-2-yl)oxy]benzamidine, trifluoroacetic acid salt; NMR (DMSO-d₆) 9.35 (s,2), 9.2 (s,2), 7.6 (m,3), 7.55 (m,1), 7.0 (t,1), 6.45 (d,1), 6.35 (m,2), 2.4 (s,3) ppm;

3-[(3,5-difluoro-6-[3-[2-(1H-imidazol-1-yl)-1-oxoethyl] phenoxy]-4-methylpyridin-2-yl)oxy]benzamidine, trifluoroacetic acid salt; NMR (DMSO-d₆) 9.4 (s,2), 9.3 (s,2), 9.0 (s,1), 7.4–7.9 (m,10), 6.0 (s,2), 2.4 (s,3) ppm;

3-[(6-(3-(2-(dimethylaminocarbonyl)ethyl)phenoxy)-3,5-difluoro-4-methylpyridin-2-ylsoxy]-benzamidine, trifluoroacetic acid salt; NMR (DMSO-d₆) 9.3 (s,2), 9.25 (s,2), 7.6 (m,4), 7.2 (t,1), 7.0 (m,2), 6.9 (d,1), 2.9 (s,3), 2.8 (s,3), 2.75 (t,2), 2.5 (m,2), 2.4 (s,3) ppm;

3-[(3,5-difluoro-6-[3-(hydroxymethyl)phenoxy]-4-methylpyridin-2-yl)oxy]-benzamidine, trifluoroacetic acid salt; NMR (DMSO-d₆) 9.4 (br,4), 7.6 (m,4), 7.25 (t,1), 7.1 (d,1), 7.05 (m,1), 7.0 (d,1), 4.45 (s,2), 2.4 (s,3) ppm;

3-[(6-(3-(dimethylaminocarbonyl)methylphenoxy)-3,5-difluoro-4-methylpyridin-2-yl)oxy]benzamidine, trifluoroacetic acid salt; NMR (DMSO-d₆) 9.3 (s,4), 7.6 (m,3), 7.55 (m,1), 7.2 (t,1), 7.0 tm,2), 3.6 (s,2), 2.95 (s,3), 2.8 (s,3), 2.4 (s,3) ppm;

3-[(6-(3-(aminocarbonyl)methylphenoxy)-3,5-difluoro-4-methylpyridin-2-yl)oxy]benzamidine, trifluoroacetic acid salt; m.p. 189–192° C.;

3-[(6-[3-(aminomethyl)phenoxy]-3,5-difluoro-4-methylpyridin-2-yl)oxy]-benzamidine, trifluoroacetic acid salt; NMR (DMSO-d₆) 9.3 (br,4), 8.2 (br,3), 7.6 (m,3), 7.55 (m,1), 7.35 (t,1), 7.2 (m,2), 7.15 (d,1), 4.0 (m,2), 2.4 (s,3) ppm;

3-[(3,5-difluoro-4-methyl-6-[3-(prop-2-oxymethyl) phenoxy]pyridin-2-yl)oxy]-benzamidine, trifluoroacetic acid salt; NMR (DMSO-d₆) 9.3 (s,2), 9.1 (s,2), 7.6 (m,4), 7.2 (t,1), 6.65 (m,3), 4.55 (m,1), 2.4 (s,3), 1.15 (m,6) ppm;

4,4'-[1,3-phenylenebis(oxy)]bis(benzamidine), trifluoroacetic acid salt; NMR (DMSO-d6) 9.4 (br,4), 9.2 (br,4), 7.96 (d,4), 7.6 (t,1), 7.3 (d,4), 7.05 (dd,2), 6.97 (m,1) ppm;

3,3'-[4-nitro-1,3-phenylenebis(oxy)]bis(benzamidine), trifluoroacetic acid salt; NMR (DMSO-d$_6$) 9.4 (s,4), 9.2 (m,4), 8.25 (d,1), 7.6 (m,8), 7.0 (dd,1), 6.9 (m,1) ppm;

3-[(6-(3-methoxy-5-dimethylaminocarbonylphenoxy)-3,5-difluoro-4-methylpyridin-2-yl)-oxy]benzamidine, trifluoroacetic acid salt; NMR (DMSO-d$_6$) 9.3 (s,2), 9.1 (s,2), 7.6 (m,4), 6.8 (s,1), 6.7 (d,2), 3.7 (s,3), 3.0 (s,3), 2.8 (s,3), 2.4 (s,3) ppm;

4-methoxy-3-[(6-(3-methoxy-5-dimethylaminocarbonylphenoxy)-3,5-difluoro-4-methylpyridin-2-yl)oxy]benzamidine, trifluoroacetic acid salt; NMR (DMSO-d$_6$) 9.1 (s,2), 9.0 (s,2), 7.8 (d,1l), 7.7 (s,1), 7.2 (d,1), 6.7 (s,1), 6.6 (s,1), 6.5 (s,1), 3.8 (s,3), 3.7 (s,3), 2.9 (s,3), 2.7 (s,3), 2.4 (s,3) ppm;

4-methoxy-3-[(6-(3-(imidazol-1-yl)phenoxy)-4-ethoxycarbonylpyridin-2-yl)oxy]-benzamidine, trifluoroacetic acid salt; NMR (DMSO-d$_6$) 9.1 (s,2), 8.9 (s,2), 8.0 (s,1), 7.6 (m,7), 7.2 (m,4), 4.4 (q,2), 3.7 (s,3), 1.3 (t,3) ppm;

4-methoxy-3-[(6-(3-dimethylaminocarbonylphenoxy)-3,5difluoro-4-methylpyridin-2-yl)oxy]benzamidine, trifluoroacetic acid salt, NMR (CDCl$_3$) 9.10 (s,2), 8.94 (s,2), 7.71 (d,1), 7.66 (s,1), 7.32 (t,1), 7.25 (d,1), 7.09 (d,1), 7.01 (d,1), 6.95 (s,1), 3.77 (s,3), 2.95 (s,3), 2.75 (s,3), 2.37 (s,3);

4-amino-3-[(6-(3-dimethylaminocarbonylphenoxy)-3,5-difluoro-4-methylpyridin-2-yl)oxy]-benzamidine, trifluoroacetic acid salt; NMR (CDCl$_3$) 8.8 (s,4), 7.71 (d,1), 7.5 (d,1), 7.4 (s,1), 7.3 (t,1), 7.1–7.2 (m,2), 7.1 ls,1), 6.6 (d,1), 6.2 (s,2), 3.0 (s,3), ppm;

4-amino-3-[(6-(3-dimethylaminocarbonylphenoxy)-3,5-difluoro-4-(2,2,2-trifluoroethoxy)-pyridin-2-yl)oxy]benzamidine, trifluoroacetic acid salt; NMR (CDCl$_3$) 8.7 (s,2), 8.5 (s,2), 7.4–7.5 (m,2), 7.3 (t,1), 7.1–7.2 (m,3), 6.7 (d,1), 6.2 (br s,2), 5.2 (q,2), 3.0 (s,3), 2.8 (s,3) ppm;

4-methoxy-3-[(6-(3-dimethylaminocarbonylphenoxy)-3,5-difluoro-4-(2,2,2-trifluoroethoxy)pyridin-2-yl)oxy]benzamidine, trifluoroacetic acid salt;

3,3'-[2,6-pyrazinediylbis(oxy)]bis(benzamidine), trifluoroacetic acid salt; NMR (DMSO-d$_6$) 9.4 (s,8), 8.4 (s,2), 7.6 (m,8) ppm;

3,3'-[2,6-pyrimidinediylbis(oxy)]bis(benzamidine), trifluoroacetic acid salt; NMR (DMSO-d$_6$) 9.4 (m,8), 8.6 (d,1), 7.7 (m,8). 7.05 (d,1) ppm;

4-hydroxy-3-[(6-(3-dimethylaminocarbonylphenoxy)-3,5-difluoro-2-methoxypyridin-4-yl)-oxy]benzamidine, trifluoroacetic acid salt; NMR (DMSO-d$_6$) 11.3 (s,1), 9.1 (m,2), 8.8 (s,2), 7.6 (m,2), 7.5 (t,1), 7.2 (m,3), 7.05 (d,1), 3.8 (s,3), 3.0 (s,3), 2.9 (s,3) ppm;

4-amino-3-[(3,5-difluoro-6-(3-dimethylaminophenoxy)-4((methyl)(aminocarbonylmethyl)amino)pyridin-2-yl)oxy]benzamidine, trifluoroacetic acid salt;

4-amino-3-[(3,5-difluoro-6-(3-dimethylaminophenoxy)-4-((methyl)(ethoxycarbonylmethyl)amino)pyridin-2-yl)oxy]benzamidine, trifluoroacetic acid salt;

4-amino-3-[(3,5-difluoro-6-(3-dimethylaminophenoxy)-4-(methyl)(phenyl)aminocarbonylpyridin-2-yl)oxy]benzamidine, trifluoroacetic acid salt;

4-methoxy-3-[(6-(3-dimethylaminocarbonylphenoxy)-3,5-difluoro-4-(1,3-difluoroprop-2-oxy)pyridin-2-yl)oxy]benzamidine, trifluoroacetic acid salt;

3-[(6-(3-dimethylaminocarbonylphenoxy)-4-dimethylaminocarbonylpyridin-2-yl)oxy]benzamidine, trifluoroacetic acid salt; NMR (DMSO-d$_6$) 9.31 (s,2), 9.24 (s,2), 7.35 (m,8), 6.81 (s,1), 6.78(s,1), 2.95 (m,12) ppm;

3-[(3,5-difluoro-6-(3-dimethylaminophenoxy)-4-(4-ethoxycarbonyl-2-methoxyphenoxy)pyridin-2-yl)oxy] benzamidine, trifluoroacetic acid salt;

3-[(3,5-difluoro-6-(3-dimethylaminophenoxy)-4-(4-ethoxycarbonyl-2-(morpholin-4-ylmethyl)phenoxy) pyridin-2-yl)oxy]benzamidine, trifluoroacetic acid salt; and 3-[(3-(3-amidinophenoxy)phen-1-yl)oxy]benzamidine, trifluoroacetic acid salt.

EXAMPLE 2

3-[(6-(3-Amidinophenoxy)-4-carboxypyridin-2-yl) oxy]benzamidine, Dihydrochloride 2,6-Bis(3-amidinophenoxy)pyridine-4-carboxamide (5 g, 11 mmol) was dissolved in 5 M HCl and heated. The solid that precipitated on cooling was collected by filtration to give 3-[(6-(3-amidinophenoxy)-4-carboxypyridin-2-yl)oxy] benzamidine, dihydrochloride; NMR (DMSO-d6) 9.4 (br s,4), 9.2 (br s,4), 7.4 (m,4), 7.3 (m,4), 7.2 (s,2) ppm.

EXAMPLE 3

3-[(3,5-Difluoro-4-methyl-6-[(pyridin-3-yl)oxy] pyridin-2-yl)oxy]benzamidine, Acetic Acid Salt A. In a manner similar to Example 1 above, 3-[(3,5-difluoro-4-methyl-6-[(pyridin-3-yl)oxy]pyridin-2-yloxy]benzonitrile was reacted with HCl and ammonia (g). The solvent was removed in vacuo and the material was partitioned with methylene chloride and 2 N aqueous potassium hydroxide. The organic layer was separated, acetic acid added, and the solvent was removed in vacuo. The residue was triturated with ether and the resulting solid was filtered to give 3-[(3,5-difluoro-4-methyl-6-[(pyridin-3-yl)-oxy]pyridin-2-yl)-oxy]benzamidine, acetic acid salt; m.p. 213–214° C.

B. In a similar manner, the following compounds were made:

3-[(3,5-difluoro-4-methyl-6-phenoxypyridin-2-yl)oxy] benzamidine, acetic acid salt; m.p. 122–123° C.;

3-[(3,5-difluoro-6-(4-dimethylaminophenoxy)-4-methylpyridin-2-yl)oxy(benzamidine, acetic acid salt; m.p. 106–107° C.;

3-[(3,5-difluoro-6-(3-(1 H-imidazol-1-yl)phenoxyl4-methylpyridin-2-yl)oxy]benzamidine, acetic acid salt; NMR (DMSO-d$_6$) 9.9 (br,4), 8.3 (s,1), 7.8 (s,1), 7.65 (m,6), 7.3 (t,1), 7.15 (m,2), 2.4 (s,3) ppm;

3-[(3,5-difluoro-4-methyl-6-(3-nitrophenoxy)pyridin-2-yl)oxy]benzamidine, acetic acid salt; NMR (DMSO-d$_6$) 10.1 (br,41, 8.05 (m,2), 7.7 (m,2), 7.6 (m,2), 7.5 (m,2), 10 2.45 (s,3) 1.8 (s,3) ppm;

3-[(3,5-difluoro-4-methyl-6-(3-[(methylsulfonyl)aminolphenoxy]pyridin-2-yl)oxy]benzamidine, acetic acid salt; NMR (DMSO-d$_6$) 10 (br,4), 7.5 (m,3), 7.4 (d,1), 7.15 (t,1), 6.85 (d,1), 6.8 (t,1), 6.66 (dd,1), 2.83 (s,3), 2.36 (s,3) 1.74 (s,3) ppm;

3-[(3,5-difluoro-6-(3-methylcarbonylaminophenoxy)-4-methylpyridin-2-yl)oxy]-benzamidine, acetic acid salt; NMR (DMSO-d$_6$) 10.3 (br,4), 10.1 (s,1), 7.4–7.7 (m,5), 7.25 (m,2), 6.8 (m,1), 2.4(s,3), 2.1 (s,3), 1.8 (s,3) ppm;

3-[(3,5-difluoro-6-(4-dimethylaminomethylphenoxy)-4-methylpyridin-2-yl)oxy]-benzamidine, acetic acid salt; m.p. 103–105° C.;

3-[(3,5-difluoro-4-methyl-6-(3-(morpholin-4-yl) phenoxy)pyridin-2-yl(oxy]benzamidine, acetic acid salt; m.p. 194–196° C.;

3-[(3,5-difluoro-4-methyl-6-(3-(1-pyrrolidinoyl) phenoxy)pyridin-2-yl)oxy]benzamidine, acetic acid salt; m.p. 162–164° C.;

3-[(3,5-difluoro-4-methyl-6-(3-(4-morpholinoyl) phenoxy)pyridin-2-yl)oxy]benzamidine, acetic acid salt; m.p. 123–126° C.;

3-[(3,5-difluoro-4-methyl-6-(3-dimethylaminocarbonylphenoxy)pyridin-2-yl)oxy]-benzamidine, acetic acid salt; m.p. 198–200° C.;

3-[(3,5-difluoro-4-methyl-6-(3-(carboxy)(hydroxy) methylphenoxy)pyridin-2-yl)oxy]-benzamidine, acetic acid salt; NMR (DMSO-d6) 10 (br,4), 7.4–7.7 (m,6), 7.25 (m,3), 7.15 (m,1), 7.05 (m,1), 4.82 (s,1), 2.4 (s,3), 1.8 (s,3) ppm;

3-[(3,5-difluoro-4-methyl-6-[3-(1-oxoethyl)]phenoxy] pyridin-2-yl)oxy]benzamidine, acetic acid salt; NMR (DMSO-$d_6$) 10.2 (br,4), 7.75 (m,1), 7.65 (m,1), 7.4–7.6 (m,6), 2.5 (s,3), 2.41 (s,3), 1.75 1s,3) ppm;

3-[(3,5-difluoro-4-methyl-6-[3-(2-methyl-1-oxopropyl)] phenoxy]pyridin-2-yl)oxy]-benzamidine, acetic acid salt; NMR (CDCl$_3$) 10.2 (br,4), 7.7 (m,1), 7.2–7.6 (m,7), 3.45 (m,1), 2.39 (s,3), 1.88 (s,3), 1.14 (m,6) ppm;

3-[(3,5-difluoro-4-methyl-6-(3-(dimethylaminocarbonyl) (hydroxy)methylphenoxy)-pyridin-2-yl)oxy] benzamidine, acetic acid salt; NMR (DMSO-$d_6$) 10 (br,4), 7.55 (m,3), 7.4 (m,1), 7.3 (t,1), 7.1 (m,3). 5.35 (s,1), 2.82 (s,6), 2.40 (s,3), 1.78 (s,3) ppm;

3-[(3,5-difluoro-4-methyl-6(3-(dimethylaminocarbonyl) (methoxy)methylphenoxy)pyridin-2-yl)oxy] benzamidine, acetic acid salt; NMR (DMSO-$d_6$) 10 (br,4), 7.5 (m,4), 7.4 (m,1), 7.3 (m,2), 7.15 (d,1), 7.05 (m,2), 4.5 (s,1), 3.3 (s,3), 2.4 (s,3), 1.78 (s,3) ppm; and 4-methoxy-3-[(3,5-difluoro-4-(ethoxycarbonylmethyl) (methyl)amino-6-(3-dimethylaminocarbonylphenoxy)- pyridin-2-yl)oxy]benzamidine, acetic acid salt.

EXAMPLE 4

3-[(3,5-Difluoro-6-(3-dimethyleminophenoxy)-4-methylpyridin-2-yl)oxy)-benzamidine, Acetic Acid Salt A. T3-[(3,5difluoro-6-(3-dimethylaminophenoxy]-4-methylpyridin-2-yl)-oxy]benzonitrile (1.4 g, 3.7 mmol) dissolved in ethanol (100 mL) and cooled to –10° C. was bubbled hydrochloric acid (g) until saturated. The mixture was allowed to warm to ambient temperature and the solvent was removed in vacuo. The residue was dissolved in ethanol (50 mL) and heated at reflux while ammonia (g) was bubbled through the reaction mixture for 2 hours. The solvent was removed in vacuo and the residue was partitioned with 2 N aqueous potassium hydroxide and methylene chloride. The organic layer was separated and dried (MgSO$_4$). Acetic acid 11 mL) was added and the solvent was removed in vacuo. Crystallization from ether gave 3-[(3,5-difluoro-6-(3-dimethylaminophenoxy)-4-methylpyridin-2-yl)oxy]benzamidine, acetic acid salt; m.p. 176–179° C.

B. In a similar manner, the following compounds were made:

3-[(3,5-difluoro-6-(3-(2-(dimethylamino)ethyl)phenoxy)-4-methylpyridin-2-yl)oxy]benzamidine, acetic acid salt; m.p. 214–216° C.;

3-[(3,5-difluoro-6-(3-aminocarbonylaminophenoxy)-4-methylpyridin-2-yl)oxy]benzamidine, hydrochloride; NMR (DMSO-$d_6$) 9.4 (s,2), 9.25 (s,2), 9.1 (s,1), 7.6 (m,2), 7.55 (m,2), 7.4 (s,1), 7.2 (t,1), 7.05 (d,1), 6.6 (d,1), 6.1 (s,3), 1.8 (s,3) ppm;

3-[(3,5-difluoro-6-(3-ethoxycarbonylphenoxy)-4-methylpyridin-2-yl)oxy)benzamidine, acetic acid salt; m.p. 198–199° C.;

3-[(3,5-difluoro-6-(3-dimethylaminocarbonylphenoxy)-4-methylpyridin-2-yl)oxy]benzamidine, acetic acid salt; m.p. 160–163° C.;

3-[(3,5-difluoro-6-(3-(ethylamino)phenoxy]-4-methylpyridin-2-yl)oxy]-benzamidine, acetic acid salt; m.p. 193–196° C.;

3-[(6-(3-diethylaminophenoxy)-3,5-difluoro-4-methylpyridin-2-yl)oxy]benzamidine, acetic acid salt; m.p. 196–197° C.;

3-[(3,5-difluoro-4-methyl-6-[3-(phenylamino)phenoxy] pyridin-2-yl(oxy]benzamidine; NMR (DMSO-$d_6$) 10.0 (br,4), 8.4 (s,1), 7.4–7.7 (m,4), 7.3 (t,2), 7.2 (t,1), 7.1 (d,2), 6.9 (m,2), 6.8 (s,1), 6.5 (d,1), 2.4 is,3), 1.8 (s,3) ppm;

3-[(3,5-difluoro-6-(3-methylaminocarbonylphenoxy)-4-methylpyridin-2-yl)oxy]benzamidine, acetic acid salt; NMR (DMSO-$d_6$) 10.3 (br,4), 8.5 (s,1), 7.6 (d,1), 7.55 (m,3), 7.4 (m,3), 2.8 (d,3), 2.4 (s,3), 1.75 (s,3) ppm;

3-[(3,5-difluoro-6-(3-(4-methylpiperazin-1-oyl) phenoxy)-4-methylpyridin-2-yl)oxy]benzamidine, acetic acid salt; NMR (DMSO-$d_6$) 10.3 (br,4). 7.6 (m,3), 7.45 (m,2), 7.25 (m,1), 7.1 tm,2), 3.6 (br,2), 3.2 (br,2), 2.4 (s,3), 2.35 (br,2), 2.2 (br,2), 2.2 (s,3), 1.8 (s,3) ppm;

3-[(3,5-difluoro-6-(3-(piperidin-1-oyl)phenoxy)-4-methylpyridin-2-yl)oxy]benzamidine, acetic acid salt; NMR (DMSO-$d_6$) 10.3 (br,4), 7.6 (m,3), 7.45 (m,2), 7.2 (d,1), 7.15 (m,2), 3.6 (br,2), 3.2 (br,2), 2.4 (s,3), 1.8 (s,3) 1.3–1.6 (m,6) ppm;

3-[(3,5-difluoro-6-(3-(methyl)(benzyl) aminocarbonylphenoxy)-4-methylpyridin-2-yl)oxy] benzamidine, acetic acid salt; m.p. 167–169° C.;

3-[(3,5-difluoro-6-(3-(methyl) (2-pyridin-1-ylethyl) aminocarbonylphenoxy)-4-methylpyridin-2-yl)oxy] benzamidine, acetic acid salt; m.p. 145–150° C.;

3-[(3,5-difluoro-6-(3-(methyl) (ethyl) aminocarbonylphenoxy)-4-methylpyridin-2-yl)oxy] benzamidine, acetic acid salt; NMR (DMSO-$d_6$) 10.2 (br,4), 8.5 (m,1), 7.1–7.7 (m,8), 3.4 (br,1), 3.05 (br,1), 1.8 (m,3), 2.4 (s,3), 1.75 (s,3) 1.1 (m,1.5), 1.0 (m,1.5) ppm;

3-[(3,5-difuoro-6-(3-diethylaminocarbonylphenoxy)-4-methylpyridin-2-yl)oxy]benzamidine, actic acid salt; NMR (DMSO-$d_6$) 10.3 (br,4), 7.5 (m,3), 7.2 (m,2), 7.2 (d,1), 7.1 (m,2), 3.4 (br,2), 3.05 (br,2), 2.4 (s,3), 1.8 (s,3) 1.15 (br,3), 1.0 (br,3) ppm;

3-[(3,5-difluoro-6-(3-(carboxyethyl) aminocarbonylphenoxy)-4-methylpyridin-2-yl)oxy] benzamidine, ethyl ester, acetic acid salt;

3-[(6-(3-chlorophenoxy)-3,5-difluoro-4-methylpyridin-2-yl)oxy]benzamidine, acetic acid salt; m.p. 200–202° C.;

3-[(3,5-difluoro-4-methyl-6-(3-trifluoromethylphenoxympyridin-2-yl)oxy] benzamidine, acetic acid salt; m.p. 192–193° C.;

3-[(3,5-difluoro-6-(3-methoxyphenoxy)-4-methylpyridin-2-yl)oxy]benzamidine, acetic acid salt; m.p. 182–185° C.;

3-[(3,5-difloro-6(3-fluorophenoxy)-4-methylpyridin-2-ylsoxy]benzamidine, acetic acid salt; m.p. 208–209° C.;

3-[(3,5-difluoro-6-(3-dimethylaminophenoxy)-4-methylpyridin-2-yl)oxy]-4-methyl benzamidine, acetic acid salt; m.p. 192–193° C.;

3-[(3,5-difluoro-4-methyl-6-[3-[(phenyl)oxamethyl]phenoxy]pyridin-2-yl)oxy]benzamidine, acetic acid salt; m.p. 162–165° C.;

3-[(3,5-difluoro-6-(3-hydroxyphenoxy)-4-methylpyridin-2-yl)oxy]benzamidine, acetic acid salt; m.p. 114–117° C.;

5-[(3,5-difluoro-6-(3-dimethylaminophenoxy)5methylpyridin-2-yl)oxy]-2-methoxy-benzamidine, acetic acid salt; NMR (DMSO-d$_6$) 9.8 (br,4), 7.75 (d,1), 7.7 (s,1), 7.3 (d,1), 7.05 (t,1), 6.45 (d,1), 6.3 (s,1), 6.15 (d,1), 3.8 (s,3), 2.85 (s,6), 2.4 (s,3), 1.8 (s,3) ppm;

3-[(6-(3-ethoxycarbonylmethylphenoxy)-3,5-difluoro-4-methylpyridin-2-yl)oxy]-benzamidine, acetic acid salt; NMR (DMSO-d$_6$) 10.0 (br,4), 7.55 (m,3), 7.45 (m,1), 7.25 (m,1), 7.05 (m,3), 4.05 (q,2), 3.65 (s,2), 2.4 (s,3), 1.8 (s,3), 1.2 (t,3) ppm;

3-[(6-(ethoxycarbonylmethylphenoxy)-3,5difluoro-4-methylpyridin-2-yl)oxy]benzamidine;

3-[(6-(3-(2-(ethoxycarbony)ethyl)phenoxy)-3,5-difluoro-4-methylpyridin-2-yl)oxy]benzenepropionic acid, ethyl ester, acetic acid salt; NMR (DMSO-d) 10.2 (br,4), 7.55 (m,3), 7.45 (m,1), 7.25 (t,1), 7.0 (m,3), 4.05 (q,4), 2.8 (t,2), 2.6 (m,2), 2.4 (s,3), 1.8 (s,3), 1.2 (t,3) ppm;

3-[(3,5-difluoro-6-(3-dimethylaminophenoxy)-4-methylpyridin-2-yl)oxy5-2,6-dimethoxybenzamidine, acetic acid salt; m.p. 109–111° C.;

3-[(3,5-difluoro-6-(3-(2-hydroxyethyl)phenoxy)-4-methylpyridin-2-yl)oxy]benzamidine, acetic acid salt; m.p. 179–182° C.;

4-methoxy-3-[(3,5-difluoro-6-(3-dimethylaminocarbanylphenoxy)-4-methylpyridin-2-yl)oxy]benzamidine, acetic acid salt; NMR (DMSO-d$_6$) 9.6 (br,4), 7.7 (d,1), 7.6 (s,1), 7.3 (t,1), 7.2 (d,$_1$), 7.05 (d,1), 7.0 (d,$_1$), 6.9 (s,1), 3.8 (s,3), 3.1 (s,6), 2.95 (s,3), 2.8 (s,3), 1.75 (s,3) ppm;

4-methoxy-3-[(3,5-difluoro-6-(3-dimethylaminocarbonylphenoxy)-4-(4-ethoxycarbonyl-piperidin-1-yl)pyridin-2-yl)oxy]benzamidine, acetic acid salt; NMR (DMSO-d$_6$) 10.0 (br,4), 7.65 (m,2), 7.3 (m,1), 7.2 (m,1), 7.0 (m,3), 4.1 (q,2), 3.8 (s,3), 3.7 (m,2), 3.3 (m,2), 3.0 (s,3), 2.8 (s,3), 2.7 (m,1), 2.0 (m,2), 1.75 (s,3), 1.25 (1,3) ppm; and 4-methoxy-3-[(3,5-difluoro-6-(3dimethylaminocarbonylphenoxy)-4-(3-ethoxycarbonylpiperidin-1-yl)pyridin-2-yl)oxy]benzamidine, acetic acid salt; NMR (DMSO-d$_6$) 9.2 (br,4), 7.8 (d,1), 7.7 (s,1), 7.3 (m,2), 7.0 (m,3), 4.1 (q,2), 3.8 (s,3), 3.7 (m,1), 3.4 (m,5), 3.0 (s,3), 2.8 (s,3), 2.7 (m,1), 2.0 (s,3), 1.8 (m,4), 1.1 (t,3) ppm.

EXAMPLE 5

4-Amino-3-[(3,5-difluoro-6-(3-dimethylaminophenoxy)-4-methylpyridin-2-yl)oxy]-benzamidine, Acetic Acid Salt A. In a manner similar to Example 1 above, 4-amino-3-[(3,5-difluoro-6-(3-dimethylaminophenoxy)-4-methylpyridin-2-y)oxy]benzenecarbonitrile was reacted with hydrogen chloride and ammonia. The resulting residue was purified by HPLC on a C18 Dynamax column with a 20–80% acetonitrile in water gradient with 0.1% trifluoroacetic acid and the material was partitioned with ethyl acetate and aqueous sodium bicarbonate. The organic layer was separated, dried (MgSO$_4$), and the solvent was removed in vacuo. The residue was dissolved in water, acidified with acetic acid, and the solvent removed to give 4-amino-3-[(3,5-difluoro-6-(3-dimethylaminophenoxy)-4-methylpyridin-2-yl)-oxy]benzamidine, acetic acid salt; NMR (DMSO-d$_6$) 10 (br,4), 7.45 (m,2), 7.03 (t,1), 6.79 (d,1), 6.44 (dd,1), 6.33 (t,1), 6.29 (d,1), 6.16 (s,1), 3.36 (s,2), 2.84 (s,6), 2.38 (s,3), 1.76 (s,3) ppm.

B. In a similar manner, the following compound was made:

4-t(3,5-difluoro-6-(3-dimethylaminophenoxy)-4-methylpyridin-2-yl)amino3-3-hydroxybenzamidine, acetic acid salt; NMR(DMSO-d$_6$) 10.94(s,1),9.01 (s,2), 8.71 (s,2), 7.86 (d,1), 7.65 (s,1), 7.26 (t,1), 7.19 (d,1), 6.89 (dd,1), 6.64 (dd,1), 6.54 (m,1), 6.44 (dd,1), 3.4 (s,1), 2.90 (s,6), 2.32 (s,3) ppm.

EXAMPLE 6

4-Hydroxy-3-[(3,5-difluoro-6-(3-dimethylaminophenoxy)-4-methylpyridin-2-yl)oxy]-benzamidine, Trifluoroacetic Acid Salt A. To 5-[(3,5-difluoro-6-(3-dimethylaminophenoxy)-4-methylpyridin-2-yl)oxy]-4-methoxybenzamidine, trifluoroacetic acid salt (0.80 9, 1.9 mmol) in methylene chloride (70 mL) at −78° C. was added boron tribromide (1 M in methylene chloride, 9 mL, 9 mmol). The reaction was warmed to ambient temperature. After stirring for 16 hours, the reaction was concentrated and purified by HPLC as described above in Example 5 to give 4-hydroxy-3-[(3,5-difluoro-6(3-dimethylaminophenoxy)-4-methylpyridin-2-yl)oxy]benzamidine, trifluoroacetic acid salt; NMR (DMSO-d$_6$) 9.06 (s,2), 8.88 (s,2), 7.67 (m,1), 7.62 (d,1), 7.1 (d,1), 7.04 (t,1), 6.45 (d,1), 6.32 (m,1), 6.23 (d,1), 2.85 (s,6), 2.4 (s,3) ppm.

B. In a similar manner, the following compounds were made:

4-hydroxy-3-[(3,5-difluoro-6-(3-dimethylaminocarbonylphenoxy)-4-dimethylaminopyridin-2-yl)oxy]benzamidine, trifluoroacetic acid salt; NMR (DMSO-d$_6$) 11.0 (s,1), 9.0 (s,2), 8.8 (s,2), 7.6 (m,2), 7.3 (t,1), 7.0 (m,4), 3.1 (s,6), 2.95 (s,3), 2.8 (s3) ppm;

4-hydroxy-3-[(3,5-difluoro-6-(3-dimethylaminocarbonylphenoxy)-4-(4-ethoxycarbonylpiperidin-1-yl)pyridin-2-yl)oxy]benzamidine, acetic acid salt; NMR (DMSO-d$_6$) 11.0 (s,1), 9.0 (s,2), 8.9 (s,2), 7.55 (m,2), 7.3 (t,1), 7.0 (m,4), 4.1 (q,2), 3.6 (m,2), 3.3 (m,2), 3.0 (s,3), 2.8 (s,3), 2.6 (m,1), 2.0 (m,2), 1.7(s,2), 1.15 (t,3) ppm;

4-hydroxy-3-[(3,5-difluoro-6-(3-dimethylaminocarbonylphenoxy)-4-(3-ethoxycarbonylpiperidin-1-yl)pyridin-2-yl)oxy]benzamidine, acetic acid salt; NMR (DMSO-d$_6$) 9.2 (br,4), 7.6 (m,2), 7.3 (t,1), 7.0 (m,4), 4.1 (q,2), 3.8 (s,3), 3.2–3.7 (m,4), 3.0 (s,3), 2.8 (s,3), 2.7 (m,1), 2.0 (s,3), 1.8 (m,4), 1.1 (t,3) ppm;

4-hydroxy-3-[(6-(3-dimethylaminocarbonylphenoxy)pyridin-2-yl)oxy]benzamidine, trifluoroacetic acid salt; NMR (DMSO-d$_6$) 11.0 (s,1), 9.1 (s,2), 8.85 (s,2), 7.9 (t,1), 7.6 (m,2), 7.4 (t,1), 7.15 (m,2), 7.05 (m,2), 6.75 (d,1), 6.7 (d,1), 2.95 (s,3), 2.8 (s,3), ppm;

4-hydroxy-3-[(6-(3-dimethylaminocarbonylphenoxy)-4-(4-methylpiperazin-1-oyl)-pyridin-2-yl)oxy]benzamidine, trifluoroacetic acid salt; NMR (DMSO-$d_6$) 11.0 (s,1), 10.1 (br,1), 9.05 (s,23, 8.85 (s,2), 7.6 (m,2), 7.4 (t,1), 7.2 (m,2), 7.05 (m,2), 6.8 (s,1), 6.7 (s,1), 3.5 (m,8), 2.95 (s,3), 2.8 (s,3) ppm;

4-hydroxy-3-[(3,5-difluoro-6-(5-hydroxy-3-dimethylaminocarbonylphenoxy)-4-methylpyridin-2-yl)oxy]benzamidine, trifluoroacetic acid salt; NMR (DMSO-$d_6$) 11.0 (s,1), 9.9 (s,1), 9.0 (s,2), 8.8 (s,2), 7.6 (m,2), 7.0 (d,1l, 6.5 (s,1), 6.4 (s,1), 6.3 (s,1), 2.9 (s,3), 2.7 (s,3), 2.4 (s,3) ppm;

4-hydroxy-3-[(3,5-difluoro-6-(3-dimethylaminocarbonylphenoxy)-4-methylpyridin-2-yl)oxy]benzamidine, trifluoroacetic acid salt; NMR JCDCl$_3$) 11.20 (bs,1), 8.98 (s,2), 8.66 (s,2), 7.59 (s,1), 7.53 (d,1), 7.29 (t,1), 7.18–6.92 (m,4), 2.96 (s,3), 1.91 (s,1.5) ppm;

4-hydroxy-3-[(3,5-difluoro-6-(3-dimethylaminocarbonylphenoxy)-4-(2,2,2-trifluoro-ethoxy)pyridin-2-yl)oxy]benzamidine, trifluoroacetic acid salt; NMR (DMSO-$d_6$) 11.1 (s,1), 9.0 (s,2), 8.8 (s,2), 7.6 (m,2), 7.3 (t,1), 7.0–7.1 (m,4), 5.2 (q,2), 3.0 (s,3), 2.8 (s,3), ppm;

4-hydroxy-3-[(3,5-difluoro-6-(3-dimethylaminocarbonylphenoxy)-4-hydroxypyridin-2-yl)oxy]benzamidine, trifluoroacetic acid salt; NMR (CD$_3$CN) 8.7 (s,2), 7.5 (s,2), 7.3–7.4 (m,4), 7.2 (dt,1), 7.1 (dd,1), 7.0 (t,1), 6.8 (d,1), 3.1 (s,3) ppm;

4-hydroxy-3-[(3,5-difluoro-6-(3-dimethylaminocarbonylphenoxy)-4-(1,3-difluoroprop-2-oxy)pyridin-2-yl)oxy]benzamidine, trifluoroacetic acid salt; NMR (CD$_3$CN) 9.8 (s,2), 7.3–7.4 (m,4), 7.2 (d,1), 7.1 (d,1), 7.0 (s,1), 6.8 (d,1), 5.1 (t,1), 4.8 (d,4), 3.1 (s,3), ppm;

4-hydroxy-3-[(3,5-difluoro-6-(3-dimethylaminocarbonylphenoxy)-4-(1-bromo-3-fluoroprop-2-oxy)pyridin-2-yl)oxy]benzamidine, trifluoroacetic acid salt; NMR (CD$_3$CN) 10.8 (s,2), 7.3–7.4 (m,4), 7.2 (d,1), 7.1 (d,1), 7.0 ts,1), 6.8 (d,1), 5.1 (m,1), 4.9 (d,1), 4.7 (d,1), 3.8 (d,1), 3.1 (s,3), 3.0 (s,3) ppm;

4-hydroxy-3-[(3,5-difluoro-6-(3-dimethylaminocarbonylphenoxy)-4-(1,3-dibromoprop-2-oxy)pyridin-2-yl)oxy]benzamidine, trifluoroacetic acid salt; NMR (DMSO-$d_6$) 11.1 (s,1), 9.0 (s,2), 8.8 (s,2), 7.5–7.6 (m,2), 7.3 (t,1), 7.1 (m,2), 7.0 (m,2), 5.1 (t,1), 3.9 (d,4), 3.0 (s,3), 2.8 (s,3) ppm;

4-hydroxy-3-[(3,5-difluoro-6-(3-dimethylaminocarbonylphenoxy)-4-((methyl)(carboxymethyl)mino)pyridin-2-yl)oxy]benzamidine, hydrochloride salt; NMR (DMSO-$d_6$) 9.0 (s,2), 8.7 (s,2), 7.6 (m,2), 7.2 (t,1), 7.0 (m,4), 4.1 (s,2), 3.2 (s,3), 2.9 (s,3), 2.8 (s,3) ppm;

4-hydroxy-3-[(6-(3-dimethylaminocarbonylphenoxy)-4-carboxypyridin-2-yl)oxy]benzamidine, trifluoroacetic acid salt; NMR (DMSO-$d_6$) 11.12 (s,2), 9.16 (s,2), 9.03 (s,2), 7.3 4m,9), 2.99 (s,3), 2.87 (s,3) ppm;

4-hydroxy-3-[(6-(3-dimethylaminocarbonylphenoxy)-4-(aminocarbonyl)pyridin-2-yl)oxy]benzamidine, trifluoroacetic acid salt; NMR (DMSO-$d_6$) 11.0 (s,1), 9.06 (s,2), 8.76 (s,2), 8.3 (s,1), 7.85 (s,1), 7.3 (m,9), 2.98(s, 3), 2.86 (s,3) ppm;

4-hydroxy-3-[(6-(3-dimethylaminocarbonylphenoxy)-4-(dimethylamino-carbonyl)pyridin-2-yl)oxy]benzamidine, trifluoroacetic acid salt; NMR (DMSO-$d_6$) 10.95 (s,1), 9.08 (s,2), 8.72 (s,2), 7.3 (m,7), 6.72 (s,1), 6.66 (s,1), 2.95 (m,12) ppm;

4-hydroxy-3-[(3,5-difluoro-6-(3-dimethylaminocarbonylphenoxy)-4-(4-ethoxycarbonylpiperidin-1-yl)pyridin-2-yl)oxy]benzamidine, trifluoroacetic acid salt;

4-hydroxy-3-[(3,5-difluoro-6-(3-dimethylaminocarbonylphenoxy)-4-(3-ethoxycarbonylpiperidin-1-yl)pyridin-2-yl)oxy]benzamidine, trifluoroacetic acid salt;

4-hydroxy-3-[(3,5-difluoro-6-(3-(1-methylimidazolin-2-yl)phenoxy)- 4-(2-hydroxy-4-carboxyphenoxy)pyridin-2-yl)oxy]benzamidine, trifluoroacetic acid salt; and 4-hydroxy-3-[(3,5-difluoro-6-(3-(1-methylimidazolin-2-yl)phenoxy)-4-(2-hydroxy-4-methoxycarbonylphenoxy)pyridin-2-yl)oxy]benzamidine, trifluoroacetic acid salt.

C. In a similar manner, the following compounds are made:

4-hydroxy-3-[(3,5-difluoro-6-(3-dimethylaminocarbonylphenoxy)-4-(2-hydroxy-4-methoxycarbonylphenoxy)pyridin-2-yl)oxy]benzamidine;

4-hydroxy-3-[(3,5difluoro-6-(3-(guanidino)phenoxy)-4-(2-hydroxy-4-methoxycarbonylphenoxy)pyridin-2-yl)oxy]benzemidine; and 4-hydroxy-3-[(3,5-difluoro-6-(3-(1-methylimidazol-2-yl)phenoxy)-4-(2-hydroxy-4-methoxycarbonylphenoxy)pyridin-2-yl)oxy]benzamidine.

EXAMPLE 7

4-Hydroxy-3-[(3,5-difluoro-6-(3-dimethylaminocarbonylphenoxy)-4-(piperidin-1-yl)-pyridin-2-yl)oxy]benzamidine, Trifluoroacetic Acid Salt A. In a manner similar to Example 1,3-[(6-(5-cyano-2-(benzyloxy)phenoxy)-3,5-difluoro-4-(piperidin-1-yl)pyridin-2-yl)oxy]-N,N-dimethylbenzamide was reacted with HCl and ammonia. The solvent was removed in vacuo. The material was dissolved in methanol and Pd(C) was added. The reaction was placed under an atmosphere of hydrogen at 50 psi for 2 hours. The reaction was filtered through celite and the solvent was removed in vacuo. The material was partially dissolved in 0.25 N aqueous potassium hydroxide and the solid was removed by filtration. The solid was purified by HPLC as described above in Example 5 to give 4-hydroxy-3-[(3,5-difluoro-6-(3-dimethylaminocarbonylphenoxy)-4-(piperidin-1-yl)pyridin-2-yl)oxy]benzamidine, trifluoroacetic acid salt, as the final product; NMR (DMSO-$d_6$) 11.0 (s,1), 9.0 (s,2), 8.7 (s,2), 7.6 (m,2), 7.3 (t,1), 7.0 (m,4), 3.4 (m,4), 2.95 (s,3), 2.8 (s,3), 1.65 (m,6) ppm;

B. In a similar manner, the following compounds were made:

4-hydroxy-3-[(3,5)-difluoro-6-(3-dimethylaminocarbonylphenoxy)-4-(4-methylpiperazin-1-yl)pyridin-2-yl)oxy]benzamidine, trifluoroacetic acid salt; NMR (DMSO-$d_6$) 11.2 (s,1), 10.3 (br,1), 9.0 (s,4), 7.6 (m,2), 7.3 (m,2), 7.0 (m,4), 3.6 (m,8), 3.0 (s,3), 2.9 (s,3), 2.8 (s,3), 1.65 (m,6) ppm;

4-hydroxy-3-[(3,5-difluoro-6-(3-dimethylaminocarbonylphenoxy)-4-(4-(ethoxycarbonylmethyl)piperazin-1-yl)pyridin-2-yl)oxy]benzamidine, acetic acid salt;

4-hydroxy-3-(3,5-difluoro-6-(3-amidinophenoxy)-4-(ethoxycarbonyl)pyridin-2-yl)oxy]benzamidine, trifluoroacetic acid salt; NMR (CDCl$_3$) 11.14 (s,1), 9.37–8.88 (m,8), 7.76–7.06 (m,9), 4.35 (q,2), 1.32 (t,3) ppm;

4-hydroxy-3-[(3,5-difluoro-6-(3-dimethylaminocarbonylphenoxy)-4-(morpholin-4-yl)-pyridin-2-yl)oxy]benzamidine, trifluoroacetic acid salt; NMR (DMSO-d$_6$) 9.0 (s,2), 8.6 (s,2), 7.5 (m,2), 7.3 (t,1), 7.0 (m,4), 3.7 (m,4), 3.4 (m,4), 2.9 (s,3), 2.8 (s,3) ppm;

4-hydroxy-3-[(3,5-difluoro-6-(3-(guanidino)phenoxy)-4-(methyl)(phenyl)amino-carbonylpyridin-2-yl)oxy]benzamidine;

4-hydroxy-3-[(3,5-difluoro-6-(3-dimethylaminocarbonylphenoxy)-4-methoxypyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxycarbonylphenoxy)pyridin-2-yl)oxy]benzamidine, trifluoroacetic acid salt;

4-hydroxy-3-[(3,5-difluoro-6-(3-dimethylaminocarbonylphenoxy)-4-(2-methoxy-4-ethoxycarbonylphenoxy)pyridin-2-yl)oxy]benzamidine;

4-hydroxy-3-[(3,5-difluoro-6-(3-(1-methylimidazol-2-yl)phenoxy)-4-(2-methoxy-4-ethoxycarbonylphenoxy)pyridin-2-yl)oxy]benzamidine;

4-hydroxy-3-[(3,5-difluoro-6-(3-dimethylaminophenoxy)-4-(4-ethoxy-carbonylphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(1-(prop-2-oxycarbonyl)methylpiperidin-4-yloxy)pyridin-2-y)oxy]benzamidindifluoroacetic acid salt;

4-hydroxy-3-[(3,5-difluoro-6-(3-(1-methylimidazolin-2-yl)phenoxy)-4-(1-(ethoxycarbonyl)methylpiperidin-4-yloxy)pyridin-2-yl)oxy]benzamidine, trifluoroacetic acid salt;

4-hydroxy-3-[(3,5-difluoro-6-(3-(1-methylimidazolin-2-yl)phenoxy)-4-(1-(ethoxycarbonyl)methylpiperidin-4-yloxy)pyridin-2-yl)oxy]benzamidine, trifluoroacetic acid salt; 4-hydroxy-3-[(3,5-difluoro-6-(3-(guanidino)phenoxy)-4-(2,6-dimethoxy-4-methoxycarbonylphenoxy)pyridin-2-yl)oxy]benzamidine;

4-hydroxy-3-[(3,5-difluoro-6-(3-(guanidino)phenoxy)-4-(2,6-dimethoxy-4-ethoxycarbonylphenoxy)pyridin-2-yl)oxy]benzamidine;

4-hydroxy-3-[(3,5-difluoro-6-(3-guanidinophenoxy)-4-(1-(ethoxycarbonyl)methylpiperidin-4-yloxy)pyridin-2-yl)oxy]benzamidine, trifluoroacetic acid salt;

4-hydroxy-3-[(3,5-difluoro-6-(3-(1-methylimidazolin-2-yl)phenoxy)-4-(4-(1-carbonyl)ethyl)piperazin-1-yl)pyridin-2-yl)oxy]benzamidine, trifluoroacetic acid salt;

4-hydroxy-3-[(3,5-difluoro-6-(3-(1-methylimidazolin-2-yl)phenoxy)-4-(ethoxycarbonylmethyl)piperazin-1-yl)pyridin-2-yl)oxy]benzamidine, trifluoroacetic acid salt;

4-hydroxy-3-[(3,5-difluoro-6-(3-(1-methylimidazolin-2-yl)phenoxy)-4-(5-ethoxycarbonylpyrrolidin-3-yloxy)pyridin-2-yl)oxy]benzamidine, trifluoroacetic acid salt; NMR (DMSO-d$_6$) 11.35 (s,1), 10.41 (s,1), 9.03 (d,4), 7.35–7.62 (m,6), 7.0 (d,1), 5.57 (s,1), 4.64 (dd,1), 4.22 (q,2), 4.05 (dd,2), 3.95 (dd,1), 3.78 (d,1), 3.65 (d,1), 2.96 (s,3), 2.75 (m,1), 2.55 (m,1), 1.23 (t,3) ppm;

4-hydroxy-3-[n3,5-difluoro-6-(3-(guanidino)phenoxy)-4-(5-ethoxycarbonylpyrrolidin-3-yloxy)-pyridin-2-yl)oxy]benzamidine, trifluoroacetic acid salt;

4-hydroxy-3-[(3,5-difluoro-6-(3-dimethylaminophenoxy)-4-(1-methoxycarbonylmethylpiperidin-4-yloxy)pyridin-2-yl)oxy]benzamidine, trifluoroacetic acid salt;

4-hydroxy-3-[(3,5-difluoro-6-(3-dimethylaminocarbonylphenoxy)-4-(pyrrolidin-3-yloxy)pyridin-2-yl)oxy]benzamidine, trifluoroacetic acid salt;

4-hydroxy-3-[(3,5-difluoro-6-(3-dimethylaminocarbonylphenoxy)-4-(1-ethoxycarbonylmethylpyrrolidin-3-yloxy)pyridin-2-yl)oxy]benzamidine, trifluoroacetic acid salt;

4-hydroxy-3-[(3,5-difluoro-6-(3-dimethylaminophenoxy)-4-(1-aminocarbonylmethylpyrrolidin-3-yloxy)pyridin-2-yl)oxy]benzamidine, trifluoroacetic acid salt;

4-hydroxy-3-[(3,5-difluoro-6-(3-dimethylaminocarbonylphenoxy)-2-(3,5-di(ethoxycarbonyl)phenoxy)pyridin-4-yl)oxy]benzamidine, trifluoroacetic acid salt;

4-hydroxy-3-[(3,5-difluoro-6-(3-(1-methylimidazolin-2-yl)phenoxy)-4-(4-ethoxycarbonylphenoxy)pyridin-2-yl)oxy]benzamidine, trifluoroacetic acid salt;

4-hydroxy-3-[(3,5-dichloro-6-(3-dimethylaminocarbonylphenoxy)-4-(1-benzylpyrrolidin-3-yloxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxy-5-ethoxycarbonylphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(4-ethoxycarbonylpiperidin-1-yl)pyridin-2-yl)oxy]benzamidine, trifluoroacetic acid salt;

4-hydroxy-3-[(3,5-difluoro-6-(3-(1-methylimidazolin-2-yl)phenoxy)-4-(3-ethoxycarbonylpiperidin-1-yl)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxycarbonylpiperidin-1-yl)pyridin-2-yl)oxy]benzamidine, trifluoroacetic acid salt;

4-hydroxy-3-[(3,5-difluoro-6-(3-(dimethylaminomethyl)phenoxy)-4-(2-methoxy-4-ethoxycarbonylphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2,3-dimethoxy-5-ethoxycarbonylphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(3-aminocarbonyl-5-ethoxycarbonylphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(3-(1-methylimidazolin-2-yl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(3-ethoxycarbonylphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2,6-dimethoxy-4- methoxycarbonylphenoxy)pyridin-2-yl)oxy]
benzamidine, trifluoroacetic acid salt;

4-hydroxy-3-[(3,5-difluoro-6-(3-(1-methylimidazolin-2-yl)phenoxy)-4-(2,6-dimethoxy-4-ethoxycarbonylphenoxy)pyridin-2-yl)oxy]benzamidine, trifluoroacetic acid salt;

4-hydroxy-3-[(3,5-difluoro-6-(3-(guanidino)phenoxy)-4-(2,6-dimethoxy-4-aminocarbonylphenoxy)pyridin-2-yl)oxy]benzamidine, trifluoroacetic acid salt;

4-hydroxy-3-[(3,5-difluoro-6-(3-amidinophenoxy)-4-(2-methoxy-4-ethoxycarbonylphenoxy)pyridin-2-yl)oxy)benzamidine, trifluoroacetic acid salt;

4-hydroxy-3-[(6-(3-amidinophenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2-chloro-4-ethoxycarbonylphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2,6-dimethyl-4-ethoxycarbonylphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(3-(2-ethoxycarbonylethyl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxy-4-ethoxycarbonylmethylphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxy-5-(tetrazol-5-yl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxy-phenoxy)pyridin-2-yl)oxy]benzamidine, trifluoroacetic acid salt;

4-hydroxy-3-[(3,5-difluoro-6-(3-dimethylaminocarbonylphenoxy)-4-methoxypyridin-2-yl)oxy]benzamidine, trifluoroacetic acid salt;

4-hydroxy-3-[(3,5-difluoro-6-(3-dimethylaminocarbonylphenoxy)-4-propoxypyridin-2-yl)oxy]benzamidine, trifluoroacetic acid salt;

4-hydroxy-3-[(3,5-difluoro-6-(3-dimethylaminocarbonylphenoxy)-4-(4-ethoxycarbonylmethylpiperazinyl)pyridin-2-yl)oxy]benzamidine, trifluoroacetic acid salt;

4-hydroxy-3-[(3,5-difluoro-6-(3-(1-methylimidazolin-2-yl)phenoxy)-4-((methyl)(ethoxycarbonylmethyl)amino)pyridin-2-yl)oxy]benzamidine, trifluoroacetic acid salt;

4-hydroxy-3-[(3,5-dichloro-6-(3-dimethylaminocarbonylphenoxy)-4-(tetrahydrofuran-3-oxy)pyridin-2-yl)oxy]benzamidine, trifluoroacetic acid salt;

4-hydroxy-3-[(3,5-dichloro-6-(3-dimethylaminocarbonylphenoxy)-4-(piperidin-4-yloxy)pyridin-2-yl)oxy]benzamidine, trifluoroacetic acid salt;

4-hydroxy-3-[(3,5-dichloro-6-(3-dimethylaminocarbonylphenoxy)-4-(piperidin-3-yloxy)pyridin-2-yl)oxy]benzamidine, trifluoroacetic acid salt;

4-hydroxy-3-[(3,5-difluoro-6-(3-dimethylaminocarbonylphenoxy)-4-(aminocarbonylmethoxy)pyridin-2-yl)oxy]benzamidine, trifluoroacetic acid salt;

4-hydroxy-3-[(3,5-dichloro-6-(3-dimethylaminocarbonylphenoxy)-4-(1-(carboxymethyl)pyrrolidin-3-yloxy)pyridin-2-yl)oxy]benzamidine, trifluoroacetic acid salt;

4-hydroxy-3-[(3,5-difluoro-6-(3-dimethylaminocarbonylphenoxy)-pyridin-2-yl)oxy]benzamidine, trifluoroacetic acid salt;

4-hydroxy-3-[(3,5-difluoro-6-(3-dimethylaminocarbonylphenoxy)-2-methoxypyridin-4-yl)oxy]benzamidine, trifluoroacetic acid salt;

4-hydroxy-3-[(3,5-difluoro-6-(3-dimethylaminocarbonylphenoxy)-2-(2-methoxy-5-ethoxycarbonylphenoxy)pyridin-4-yl)oxy]benzamidine, trifluoroacetic acid salt;

4-hydroxy-3-[3-(3-dimethylaminocarbonylphenoxy)-4-(methylamino)carbonylaminophen-1-yloxy]benzamidine, trifluoroacetic acid salt;

4-hydroxy-3-[(3-(3-dimethylaminocarbonylphenoxy)-2,4,6-trichloro-5-fluorophen-1-yl)oxy]-benzamidine, trifluoroacetic acid salt;

4-hydroxy-3-[(3,5-difluoro-6-(3-(1-methylimidazolin-2-yl)phenoxy)-4-((piperidin-4-yl)amino)pyridin-2-yl)oxy]benzamidine, trifluoroacetic acid salt;

4-hydroxy-3-[(3,5-difluoro-6-(3-(1-methylimidazolin-2-yl)phenoxy)-4-((1-benzylpiperidin-4-yl) amino)pyridin-2-yl)oxy]benzamidine;

4-hydroxy-3-[(3,5-difluoro-6-(3-(1-methylimidazolin-2-yl)phenoxy)-4-((piperidin-4-(methyl)amino)pyridin-2-yl)oxy]benzamidine;

4-hydroxy-3-[(3,5-difluoro-6-(3-(1-methylimidazolin-2-yl)phenoxy)-4-((1-benzylpiperidin-4-yl)(methyl)amino)pyridin-2-yl)oxy]benzarnidine;

4-hydroxy-3-[(3,5-difluoro-6-(3-(1-methylimidazolin-2-yl)phenoxy)-4-((1-(1-(methoxycarbonyl)ethyl)piperidin-4-yl)amino)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxy-4-aminocarbonylphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxy-4-(1-(hydroxymethyl)ethoxycarbonyl)phenoxy)pyridin-2-yl)oxy]benzamidine, trifluoroaceticacid salt;

4-hydroxy-3-[(3,5-difluoro-6-(3-(1-methylimidazolin-2-yl)phenoxy)-4-(2-methoxy-4-(prop-2-oxycarbonyl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxy-4-(2-(methoxy)ethoxycarbonyl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxy-4-n-butoxycarbonyl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxy-4-((2-(2-hydroxyethoxy)ethoxy)carbonyl)phenoxy)pyridin-2-ylsoxy]benzamidine, trifluoroacetic acid salt;

4-hydroxy-3-[(3,5-difluoro-8-(3-(1-methylimidazolin-2-yl)phenoxy)-4-(2-methoxy-4-((2-[2-methoxyethoxy2ethoxy)carbony2)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(3-(2-(aminocarbonyl)ethenyl)phenoxy)pyridin-2-yl)oxy]benzamidine, trifluoroacetic acid salt;

4-hydroxy-3-[(3,5-difluoro-83-(31-methylimidazolin-2-yl)phenoxy)-4-(3-(2-(methoxycarbonyl)ethenyl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(4-(2-(methoxycarbonyl)ethenyl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxychloro-1-methylethoxycarbonyl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(3-(2-(ethoxycarbonyl)ethenyl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(4-(2-(ethoxycarbonyl)ethenyl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2,6-dimethoxy-4-(2-(ethoxycarbonyl)ethenyl)phenoxy)pyridin-2-yl)oxy]benzamidine, trifluoroacetic acid salt; and 4-hydroxy-3-[(3,5-difluoro-6-(3-1guanidino)phenoxy)-4-(2-methoxy-4-ethoxycarbonylphenoxy)pyridin-2-yl)oxy]benzamidine, trifluoroacetic acid salt.

C. In a similar manner, the following compounds are made:

4-hydroxy-3-[(3,5-difluoro-6-(3-(1-methylimidazolin-2-yl)phenoxy)-4-(4-(1-methyl-1-(ethoxycarbonyl)ethyl)piperazin-1-yl)pyridin-2-yl)oxy]benzamidine;

4-hydroxy-3-[(3,5-difluoro-6-(3-dimethylaminocarbonylphenoxy)-4-(4-(1-methyl-1-(ethoxycarbonyl)ethyl)piperazin-1-yl)pyridin-2-yl)oxy]benzamidine;

4-hydroxy-3-[(3,5-difluoro-6-(3-(guanidino)phenoxy)-4-(4-(1-methyl-1-(ethoxycarbonyl)ethyl)piperazin-1-yl)pyridin-2-yl)oxy]benzamidine;

4-hydroxy-3-[(3,5-difluoro-6-(3-(1-methylimidazol-2-yl)phehoxy)-4-(4-(1-methyl-1-(ethoxycarbonyl)ethyl)piperazin-1-yl)pyridin-2-yl)oxy]benzamidine;

4-hydroxy-3-[(3,5-difluoro-6-(3-dimethylaminocarbonylphenoxy)-4-(2,3-dimethoxy-5-ethoxycarbonylphenoxy)pyridin-2-yl)oxy]benzamidine;

4-hydroxy-3-[(3,5-difluoro-6-(3-(1-methylimidazolin-2-yl)phenoxy)-4-(5-aminocarbonylpyrrolidin-3-yloxy)pyridin-2-yl)oxy]benzamidine;

4-hydroxy-3-[(3,5-difluoro-6-(3-(1-methylimidazolin-2-yl)phenoxy)pyrrolidin-3-yloxy)pyridin-2-yl)oxy]benzamidine;

4-hydroxy-3-[(3,5-difluoro-6-(3-(guanidino) phenoxy)-4-(5-aminocarbonylpyrrolidin-3-yloxy)pyridin-2-yl)oxy]benzamidine;

4-hydroxy-3-[(3,5-difluoro-6-(3-(1-methylimidazol-2-yl)phenoxy)-4-(5-aminocarbonylpyrrolidin-3-yloxy)pyridin-2-yl)oxy]benzamidine;

4-hydroxy-3-[(3,5-difluoro-6-(3-(1-methylimidazolin-2-yl)phenoxy)-4-(5-methylcarbonylpiperidin-4-yloxy)pyridin-2-yl)oxy]benzamidine;

4-hydroxy-3-[(3,5-difluoro-6-(3-dimethylaminocarbonylphenoxy)-4-(1-methylcarbonylpiperidin-4-yloxy)pyridin-2-yl)oxy]benzamidine;

4-hydroxy-3-!(3,5-difluoro-6-(3-(guanidino)phenoxy)-4-(1-methylcarbonylpiperidin-4-yloxy)pyridin-2-yl)oxy]benzamidine;

4-hydroxy-3-[(3,5-difluoro-6-(3-(1-methylimidazol-2-yl)phenoxy)-4-(-methylcarbonylpiperidin-4-yloxy)pyridin-2-yl)oxy]benzamidine;

4-hydroxy-3-[(3,5-difluoro-6-(3-(1-methylimidazolin-2-yl)phenoxy)-4-((ethoxycarbonyl)-methoxy)pyridin-2-yl)oxy]benzamidine;

4hydroxy-3-((3,5-difluoro-6-(3-dimethylaminocarbonylphenoxy)-4-((ethoxycarbonyl)methoxy)pyridin-2-yl)oxy]benzamidine;

4-hydroxy-3-[(3,5-difluoro-6-(3-(guanidino)phenoxy)-4-((ethoxycarbonyl)-methoxy)pyridin-2-yl)oxy]benzamidine;

4-hydroxy-3-[(3,5-difluoro-6-(3-(1-methylimidazol-2-yl)phenoxy)-4-((ethoxycarbonyl)methoxy)pyridin-2-yl)oxy]benzamidine;

4-hydroxy-3-[(3,5-difluoro-6-(3-(1-methylimidazolin-2-yl)phenoxy)-4-(1-ethyl-5-ethoxycarbonylpyrrolidin-3-yloxy)pyridin-2-yl)oxy]benzamidine;

4-hydroxy-3-[(3,5-difluoro-6-(3-dimethylaminocarbonylphenoxy)-4-(1-ethyl-5-ethoxycarbonylpyrrolidin-3-yloxy)pyridin2-yl)oxy]benzamidine;

4-hydroxy-3-[(3,5-difluoro-6-(3-(guanidino)phenoxy)-4-(1-ethyl-5-ethoxycarbonylpyrrolidin-3-yloxy)pyridin-2-yl)oxy]benzamidine;

4-hydroxy-3-[(3,5-difluoro-6-(3-1-methylimidazol-2-yl)phenoxy)-4-(1-ethyl-5-ethoxycarbonylpyrrolidin-3-yloxy)pyridin-2-yl)oxy]benzamidine;

4-hydroxy-3-[(3,5-difluoro-6-(3-(1-methylimidazolin-2-yl)phenoxy)-4-(1-(tetrazol-5-ylmethyl)piperidin-4-yloxy)pyridin-2-yl)oxy]benzamidine;

4-hydroxy-3-[(3,5-difluoro-6-(3-dimethylaminocarbonylphenoxy)-4-(1-(tetrazol-5-ylmethyl)piperidin-4-yloxy)pyridin-2-yl)oxy]benzamidine;

4-hydroxy-3-[(3,5-difluoro-6-(3-(guanidino)phenoxy)-4-(1-(tetrazol-5-ylmethyl)piperidin-4-yloxy)pyridin-2-yl)oxy]benzamidine;

4-hydroxy-3-[(3,5-difluoro-6-(3-(1-methylimidazol-2-yl)phenoxy)-4-(1-(tetrazol-5-ylmethyl)piperidin-4-yloxy)pyridin-2-yl)oxy]benzamidine;

4-hydroxy-3-[(3,5-difluoro-6-(3-(1-methylimidazolin-2-yl)phenoxy)-4-(2-methoxy-4-(tetrazol-5-yl)phenoxy)pyridin-2-yl)oxy]benzamidine;

4-hydroxy-3-[(3,5-difluoro-6-(3-dimethylaminocarbonylphenoxy)-4-(2-methoxy-5-(tetrazol-5-yl)phenoxy)pyridin-2-yl)oxy]benzamidine;

4-hydroxy-3-[(3,5-difluoro-6-(3-(guanidino)phenoxy)-4-(2-methoxy-4-(tetrazol-5-yl)phenoxy)pyfidin-2-yl)oxy]benzamidine;

4-hydroxy-3-[(3,5-difluoro-6-(3-(1-methylimidazol-2-yl)phenoxy)-4-(2-methoxy-4-(tetrazol-5-yl)phenoxy)pyridin-2-yl)oxy]benzamidine;

4-hydroxy-3-[(3,5-difluoro-6-(3-(1-methylimidazolin-2-yl)phenoxy)-4-(2-chloro-4-(tetrazol-5-yl)phenoxy)pyridin-2-yl)oxy]benzamidine;

4-hydroxy-3$_7$[(3,5-difluoro-6-(3-dimethylaminocarbonylphenoxy)-4-(2-chloro-4-(tetrazol-5-yl)phenoxy)pyridin-2-yl)oxy]benzamidine;

4-hydroxy-3-[(3,5-difluoro-6-(3-(guanidino)phenoxy)-4-(2-chloro-4-(tetrazol-5-yl)phenoxy)pyridin-2-yl)oxy]benzamidine;

4-hydroxy-3-[(3,5-difluoro-6-(3-(1-methylimidazol-2-yl) phenoxy)-4-(2-chloro-4-(tetrazol-5-yl)phenoxy) pyridin-2-yl)oxy]benzamidine;

4-hydroxy-3-[(3,5-difluoro-6-(3-(1-methylimidazolin-2-yl)phenoxy)- 4-(2-chlorophenoxy)pyridin-2-yl)oxy] benzamidine;

4-hydroxy-3-[(3,5-difluoro-6-(3-dimethylaminocarbonylphenoxy)-4-(2-chlorophenoxy)pyridin-2-yl)oxy]benzamidine;

4-hydroxy-3-[(3,5-difluoro-6-(3-(guanidino)phenoxy)-4-(2-chlorophenoxy)pyridin-2-yl)oxy]benzamidine;

4-hydroxy-3-[1(3,5-difluoro-6-(3-(1-methylimidazol-2-yl)phenoxy)-4-(2-chlorophenoxy)pyridin-2-yl)oxy] benzamidine;

4-hydroxy-3-[(3,5-difluoro-6-(3-(1-methylimidazolin-2-yl)phenoxy)-4-(1-ethoxycarbonyl-1-methylethylpiperidin-4-yloxy)pytidin-2-yl)oxy] benzamidine;

4-hydroxy-3-[(3,5-difluoro-6-(3-dimethylaminocarbonylphenoxy)-4-(1-ethoxycarbonyl-1-methylethylpiperidin-4-yloxy) pyridin-2-yl)oxy]benzamidine;

4-hydroxy-3-[(3,5-difluoro-6-(3-(guanidino)phenoxy)-4-(1-ethoxycarbonyl-1-methylethylpiperidin-4-yloxy) pyridin-2-yl)oxy]benzamidine;

4-hydroxy-3-[(3,5-difluoro-6-(3-(1-methylimidazol-2-yl) phenoxy)-4-(1-ethoxycarbonyl-1-methylethylpiperidin-4-yloxy)pyridin-2-yl)oxy] benzamidine;

4-hydroxy-3-[(3,5-difluoro-6-(3-(1-methylimidazolin-2-yl)phenoxy)-4-((2-ethoxycarbonylethyl)piperidin-4-yloxy)pyridin-2-yl)oxy]benzamidine;

4-hydroxy-3-[(3,5-difluoro-6-(3-dimethylaminocarbonylphenoxy)-4-((2-ethoxycarbonylethyl)piperidin-4-yloxy)pyridin-2-yl) oxy]benzamidine;

4-hydroxy-3-[(3,5-difluoro-6-(3-(guanidino)phenoxy)-4-((2-ethoxycarbonylethyl)piperidin-4-yloxy)pyridin-2-yl)oxy]benzamidine;

4-hydroxy-3-[(3,5-difluoro-6-(3-(1-methylimidazol-2-yl) phenoxy)-4-((2-ethoxycarbonylethyl)piperidin-4-yloxy)pyridin-2-yl)oxy]benzamidine;

4-hydroxy-3-[(3,5-difluoro-6-(3-dimethylaminocarbonylphenoxy)-4-(2-methoxycarbonylpiperidin-1-yl)pyridin-2-yl)oxy] benzamidine;

4-hydroxy-3-[(3,5-difluoro-6-(3-(guanidino)phenoxy)-4-(2-methoxycarbonylpiperidin-1-yl)pyridin-2-yl)oxy] benzamidine;

4-hydroxy-3-[(3,5-difluoro-6-(3-(1-methylimidazol-2-yl) phenoxy)-4-(2-methoxycarbonylpiperidin-1-yl) pyridin-2-yl)oxy]benzamidine;

4-hydroxy-3-[(3,5-difluoro-6-(3-(1-methylimidazolin-2-yl)phenoxy)-4-(morpholin-4-yl)-pyridin-2-yl)oxy] benzamidine;

4-hydroxy-3-[(3,5-difluoro-6-(3-(guanidino)phenoxy) (morpholin-4-yl)-pyridin-2-yl)oxy]benzamidine;

4-hydroxy-3-[(3,5-difluoro-6-(3-(1-methylimidazol-2-yl) phenoxy)-4-(morpholin-4-pyridin-2-yl)oxy] benzamidine;

4-hydroxy-3-[(3,5-difluoro-6-(3-(1-methylimidazolin-2-yl)phenoxy)-4-(piperidin-1-yl)-pyridin-2-yl)oxy] benzamidine;

4-hydroxy-3-[(3,5-difluoro-6-(3-(guanidino)phenoxy)-4-(piperidin- 1-yl)-pyridin-2-yl)oxy]benzamidine;

4-hydroxy-3-[(3,5-difluoro-6-(3-(1-methylimidazol-2-yl) phenoxy)-4-(piperidin-1-yl)-pyridin-2-yl)oxy] benzamidine;

4-hydroxy-3-[(3,5-difluoro-6-(3-(1-methylimidazolin-2-yl)phenoxy)-4-methoxypyridin-2-yl)oxy]benzamidine;

4-hydroxy-3-[(3,5-difluoro-6-(3-(guanidino)-4-methoxypyridin-2-yl)oxy]benzamidine;

4-hydroxy-3-[(3,5-difluoro-6-(3-(1 1-methylimidazol-2-yl)phenoxy)-4-methoxypyridin-2-yl)oxy]benzamidine;

4-hydroxy-3-[(3,5-difluoro-6-(3-dimethylaminocarbonylphenoxy)-4-1-(prop-2-oxycarbonyl)methylpiperidin-4-yloxy)pyridin-2-yl-oxy]benzamidine;

4-hydroxy-3-[(3,5-difluoro-6-(3-(guanidino)phenoxy)-4-(1-(prop-2-oxyycarbonyl)methylpiperidin-4-yl)oxy) pyridin-2-yl)-oxy]benzamidine;

4-hydroxy-3-[(3,5-difluoro-6-(3-(1-methylimidazol-2-yl) phenoxy)-4-(1-prop-2-oxycarbonyl)methylpiperidin-4-yl)oxy)pyridin-2-yl)oxy]benzamidine;

4-hydroxy-3-[(3,5-difluoro-6-(3-dimethylaminocarbonylphenoxy)-4-(1-(ethoxycarbonyl)ethylpiperidin-4-yloxy)pyridin-2-yl) oxy]benzamidine;

4-hydroxy-3-[(3,5-difluoro-6-(3-(guanidino)phenoxy)-4-(1-(ethoxycarbonyl)ethylpiperidin-4-yloxy)pyridin-2-yl)oxy]benzamidine;

4-hydroxy-3-[(3,5-difluoro-6-(3-(1-methylimidazol-2-yl) phenoxy)-4-(1-(ethoxycarbonyl)ethylpiperidin-4-yloxy)pyridin-2-yl)oxy]benzamidine;

4-hydroxy-3-[(3,5-difluoro-6-(3-dimethylaminocarbonylphenoxy)-4-(1-ethoxycarbonylmethylpiperidin-4-yloxy)pyridin-2-yl) oxy]benzamidine;

4-hydroxy-3-[(3,5-difluoro-6-(3-(1-methylimidazol-2-yl) phenoxy)-4-(1-ethoxycarbonylmethylpiperidin-4-yloxy)pyridin-2-yl)oxy]benzamidine;

4-hydroxy-3-[(3,5-difluoro-6-(3-dimethylaminocarbonylphenoxy)-4-(4-(1-(ethoxycarbonyl)ethyl)piperazin-1-yl)pyridin-2-yl) oxy]benzamidine;

4-hydroxy-3-[(3,5-difluoro-6-(3-(1-methylimidazol-2-yl) phenoxy)-4-(4-(1-(ethoxycarbonyl)ethyl)piperazin-1-yl)pyridin-2-yl)oxy]benzamidine;

4-hydroxy-3-[(3,5-difluoro-6-(3-(guanidino)phenoxy)-4-(4-(1-(ethoxycarbonylethyl)piperazin-1-yl)pyridin-2-yl)oxy]benzamidine;

4-hydroxy-3-[(3,5-difluoro-6(3-(guanidino)phenoxy)-4-(4-ethoxycarbonylmethylpiperazin-1-yl)pyridin-2-yl) oxy]benzamidine;

4-hydroxy-3-[(3,5-difluoro-6-(3-(1-methylimidazol-2-yl) phenoxy)-4-(4-ethoxycarbonylmethylpiperazin-1-yl) pyridin-2-yl)oxy]benzamidine;

4-hydroxy-3-[(3,5-difluoro-6-(3-dimethylaminocarbonylphenoxy)-4-(5-ethoxycarbonylpyrrolidin-3-yloxy)pyridin-2-yl)oxy] benzamidine;

4-hydroxy-3-[(3,5-difluoro-6-(3-(1-methylimidazol- 2-yl) phenoxy)-4-5-ethoxycarbonylpyrralidin-3-yloxy) pyridin-2-yl)oxy]benzamidine;

4-hydroxy-3-[(3,5-difluoro-6-(3-(1-methylimidazolin-2-yl)phenoxy)-4(pyrrolidin-3-yloxy)pyridin-2-yl)oxy] benzamidine;

4-hydroxy-3-[(3,5-difluoro-6-(3-(guanidino)-4-(pyrrolidin-3-yloxy)pyridin-2-yl)oxy]benzamidine;

4-hydroxy-3-[(3,5-difluoro-6-(3-(1-methylimidazol-2-yl)phenoxy)-4-(pyrrolidin-3-yloxy)pyridin-2-yl)oxy]benzamidine;

4-hydroxy-3-[(3,5-difluoro-6-(3-(1-methylimidazolin-2-yl)phenoxy)-4-(1-ethoxycarbonylmethylpyrrolidin-3-yloxy)pyridin-2-yl)oxy]benzamidine;

4-hydroxy-3-[(3,5-difluoro-6-(3-(guanidino)-4-(1-ethoxycarbonylmethylpyrrolidin-3-yloxy)pyridin-2-yl)oxy]benzamidine;

4-hydroxy-3-[(3,5-difluoro-6-(3-(1-methylimidazol-2-yl)phenoxy)-4-(1-ethoxycarbonylmethylpyrrolidin-3-yloxy)pyridin-2-yl)oxy]benzamidine;

4-hydroxy-3-[(3,5-difluoro-6-(3-dimethylaminocarbonylphenoxy)-4-(4-ethoxycarbonylphenoxy)pyridin-2-yl)oxy]benzamidine;

4-hydroxy-3-[(3,5-difluoro-6-(3-(guanidino)phenoxy)-4-(4-ethoxycarbonylphenoxy)-pyridin-2-yl)oxy]benzamidine;

4-hydroxy-3-[(3,5-difluoro-6-(3-(1-methylimidazol-2-yl)phenoxy)-4-(4-ethoxycarbonylphenoxy)pyridin-2-yl)oxy]benzamidine;

4-hydroxy-3-[(3,5-dichloro-6-(3-(1-methylimidazolin-2-yl)phenoxy)-4-(1-benzylpyrrolidin-3-yloxy)pyridin-2-yl)oxy]benzamidine;

4-hydroxy-3-[(3,5-dichloro-6-(3-(guanidino)phenoxy)-4-(1-benzylpyrrolidin-3-yloxy)pyridin-2-yl)oxy]benzamidine;

4-hydroxy-3-[(3,5-dichloro-6-(3-(1-methylimidazol-2-yl)phenoxy)-4-(1-benzylpyrrolidin-3-yloxy)pyridin-2-yl)oxy]benzamidine;

4-hydroxy-3-[(3,5-difluoro-6-(3-dimethylaminocarbonylphenoxy)-4-(2-methoxy-5-ethoxycabonylphenoxy)pyridin-2-yl)oxy]benzamidine;

4-hydroxy-3-[(3,5-difluoro-6-(3-(guanidino)phenoxy)-4-(2-methoxy-5-ethoxycarbonylphenoxy)pyridin-2-yl)oxy]benzamidine;

4-hydroxy-3-[(3,5-difluoro-6-(3-(1-methylimidazol-2-yl)phenoxy)-4-(2-methoxy-5-ethoxycarbonylphenoxy)pyridin-2-yl)oxy]benzamidine;

4-hydroxy-3-[(3,5-difluoro-6-(3-(guanidino)phenoxy)-4-(4-ethoxycarbonylpiperidin-1-yl)pyridin-2-yl)oxy]benzamidine;

4-hydroxy-3-[(3,5-difluoro-6-(3-(1-methylimidazol-2-yl)phenoxy)-4-(4-ethoxycarbonylpiperidin-1-yl)pyridin-2-yl)oxy]benzamidine;

4-hydroxy-3-[(3,5-difluoro-6-(3-(guanidino)phenoxy)-4-(3-ethoxycarbonylpiperidin-1-yl)pyridin-2-yl)oxy]benzamidine;

4-hydroxy-3-[(3,5-difluoro-6-(3-(1-methylimidazol-2-yl)phenoxy)-4-(3-ethoxycarbonylpiperidin-1-yl)pyridin-2-yl)oxy]benzamidine;

4-hydroxy-3-[(3,5-difluoro-6-(3-(guanidino)phenoxy)-4-(2,3-dimethoxy-5-ethoxycarbonylphenoxy)pyridin-2-yl3Oxybenzamidine;

4-hydroxy-3-[(3,5-difluoro-6-(3-(1-methylimidazol-2-yl)phenoxy)-4-(2,3-dimethoxy-5-ethoxycarbonylphenoxy)pyridin-2-yl)oxy]benzamidine;

4-hydroxy-3-[(3,5-difluoro-6-(3-dimethylaminocarbonylphenoxy)-4-(3-aminocarbonyl-5-ethoxycarbonylphenoxy)pyridin-2-yl)oxy]benzamidine;

4-hydroxy-3-[(3,5-difluoro-6-(3-(guanidino)phenoxy)-4-(3-aminocarbonyl-5-ethoxycarbonylphenoxy)pyridin-2-yl)oxy]benzamidine;

4-hydroxy-3-[(3,5-difluoro-6-(3-(1-methylimidazol-2-yl)phenoxy)-4-(3-aminocarbonyl-5-ethoxycarbonylphenoxy)pyridin-2-yl)oxy]benzamidine;

4-hydroxy-3-[(3,5-difluoro-6-(3-dimethylaminocarbonylphenoxy)-4-(3-(1-methylimidazolin-2-yl)phenoxy)pyridin-2-yl)oxy]benzamidine;

4-hydroxy-3-[(3,5-difluoro-6-(3-(guanidino)phenoxy)-4-(3-(1-methylimidazolin-2-yl)phenoxy)pyridin-2-yl)oxy]benzamidine;

4-hydroxy-3-[(3,5-difluoro-6-(3-(1-methylimidazol-2-yl)phenoxy)-4-(3-(1-methylimidazolin-2-yl)phenoxy)pyridin-2-yl)oxy]benzamidine;

4-hydroxy-3-[(3,5-difluoro-6-(3-dimethylaminocarbonylphenoxy)-4-(3-ethoxycarbonylphenoxy)pyridin-2-yl)oxy]benzamidine;

4-hydroxy-3-[(3,5-difluoro-6-(3-(guenidino)phenoxy)-4-(3-ethoxycarbonylphenoxy)pyridin-2-yl)oxy]benzamidine;

4-hydroxy-3-[(3,5-difluoro-6-(3-(1-methylimidazol-2-yl)phenoxy)-4-(3-ethoxycarbonylphenoxy)pyridin-2-yl)oxy]benzamidine;

4-hydroxy-3-[(3,5-difluoro-6-(3-dimethylaminocarbonylphenoxy)-4-(2,6-dimethoxy-4-methoxycarbonylphenoxy)pyridin-2-yl)oxy]benzamidine;

4-hydroxy-3-[(3,5-difluoro-6-(3-(1-methylimidazol-2-yl)phenoxy)-4-(2,6-dimethoxy-4-methoxycarbonylphenoxy)pyridin-2-yl)oxy]benzamidine;

4-hydroxy-3-[(3,5-difluoro-6-(3-dimethylaminocarbonylphenoxy)-4-(2,6-dimethoxy-4-ethoxycarbonylphenoxy)pyridin-2-yl)oxy]benzamidine;

4-hydroxy-3-[(3,5-difluoro-6-(3-(1-methylimidazol-2-yl)phenoxy)-4-(2,6-dimethoxy-4-ethoxycarbonylphenoxy)pyridin-2-yl)oxy]benzamidine;

4-hydroxy-3-[(3,5-difluoro-6-(3-(1-methylimidazolin-2-yl)phenoxy)-4(2,6-dimethoxy-4-aminocarbonylphenoxy)pyridin-2-yl)oxy]benzamidine;

4-hydroxy-3-[(3,5-difluoro-6-(3-dimethylaminocarbonylphenoxy)-4(2,6-dimethoxy-4-aminocarbonylphenoxy)pyridin-2-yl)oxy]benzamidine;

4-hydroxy-3-[(3,5-difluoro-6-(3-(1 1-methylimidazol-2-yl)phenoxy)-4-(2,6-dimethoxy-4-aminocarbonylphenoxy)pyridin-2-yl)oxy]benzamidine;

4-hydroxy-3-[(3,5-difluoro-6-(3-dimethylaminocarbonylphenoxy)- 4-(2-chloro-4-ethoxycarbonylphenoxy)pyridin-2-yl)oxy]benzamidine;

4-hydroxy-3-[(3,5-difluoro-6-(3-(guanidino)phenoxy)-4-(2-chloro-4-ethoxycarbonylphenoxy)pyridin-2-yl)oxy]benzamidine;

4-hydroxy-3-[(3,5-difluoro-6-(3-(1-methylimidazol-2-yl)phenoxy)-4-(2-chloro-4-ethoxycarbonylphenoxy)pyridin-2-yl)oxy]benzamidine;

4-hydroxy-3-[(3,5-difluoro-6-(3-dimethylaminocarbonylphenoxy)-4-(2,6-dimethyl-4-ethoxycarbonylphenoxy)pyridin-2-yl)oxy]benzamidine;

4-hydroxy-3-[(3,5-difluoro-6-(3-(guanidino)phenoxy)-4-(2,6-dimethyl-4-ethoxycarbonylphenoxy)pyridin-2-yl)oxy]benzamidine;

4-hydroxy-3-[(3,5-difluoro-6-(3-(1-methylimidazol-2-yl)phenoxy)-4-(2,6-dimethyl-4-ethoxycarbonylphenoxy)pyridin-2-yl)oxy]benzamidine;

4-hydroxy-3-[(3,5-difluoro-6-(3-dimethylaminocarbonylphenoxy)-4-(3-(2-ethoxycarbonylethyl)phenoxy)pyridin-2-yl)oxy]benzamidine;

4-hydroxy-3-[(3,5-difluoro-6-(3-(guanidino)phenoxy)-4-(3-(2-ethoxycarbonylethyl)phenoxy)pyridin-2-yl)oxy]benzamidine;

4-hydroxy-3-[(3,5-difluoro-6-(3-(1-methylimidazol-2-yl)phenoxy)-4-(3-(2-ethoxycarbonylethyl)phenoxy)pyridin-2-yl)oxy]benzamidine;

4-hydroxy-3-[(3,5-difluoro-6-(3-dimethylaminocarbonylphenoxy)-4-(2-methoxy-4-ethoxycarbonylmethylphenoxy)pyridin-2-yl)oxy]benzamidine;

4-hydroxy-3-[(3,5-difluoro-6-(3-(guanidino)phenoxy)-4-(2-methoxy-4-ethoxycarbonylmethylphenoxy)pyridin-2-yl)oxy]benzamidine;

4-hydroxy-3-[(3,5-difluoro-6-(3-(1-methylimidazol-2-yl)phenoxy)-4-(2-methoxy-4-ethoxycarbonylmethylphenoxy)pyridin-2-yl)oxy]benzamidine;

4-hydroxy-3-[(3,5-difluoro-6-(3-dimethylaminocarbonylphenoxy)-4-(2-methoxy-5-(tetrazol-5-yl)phenoxy)pyridin-2-yl)oxy]benzamidine;

4-hydroxy-3-[(3,5-difluoro-6-(3-(guanidino)phenoxy)-4-(2-methoxy-5-(tetrazol-5-yl)phenoxy)pyridin-2-yl)oxy]benzamidine;

4-hydroxy-3-[(3,5-difluoro-6-(3-(1-methylimidazol-2-yl)phenoxy)-4-(2-methoxy-5-(tetrazol-5-yl)phenoxy)pyridin-2-yl)oxy]benzamidine;

4-hydroxy-3-[(3,5-difluoro-6-(3-dimethylaminocarbonylphenoxy)-4-(2-methoxyphenoxy)pyridin-2-yl)oxy]benzamidine;

4-hydroxy-3-[(3,5-difluoro-6-(3-(guanidino)phenoxy)-4-(2-methoxyphenoxy) pyridin-2-yl)oxy]benzamidine;

4-hydroxy-3-[(3,5-difluoro-6-(3-(1-methylimidazol-2-yl)phenoxy)-4-(2-methoxyphenoxy)pyridin-2-yl)oxy]benzamidine;

4-hydroxy-3-[(3,5-difluoro-6-(3-(1-methylimidazolin-2-yl)phenoxy)-4-propoxypyridin-2-yl)oxy]benzamidine;

4-hydroxy-3-[(3,5-difluoro-6-(3-(guanidino)phenoxy)-4-propoxypyridin-2-yl)oxy]benzamidine;

4-hydroxy-3-[(3,5-difluoro-6-(3-(1-methylimidazol-2-yl)phenoxy)-4-propoxypyridin-2-yl)oxy]benzamidine;

4-hydroxy-3-[(3,5-difluoro-6-(3-dimethylaminocarbonylphenoxy)-4-((methyl)(ethoxycarbonylmethyl)amino)pyridin-2-yl)oxy]benzamidine;

4-hydroxy-3-[(3,5-difluoro-6-(3-(guanidino)-4-((methyl)(ethoxycarbonylmethyl)amino)pyridin-2-yl)oxy]benzamidine;

4-hydroxy-3-[(3,5-difluoro-6-(3-(1-methylimidazol-2-yl)phenoxy)-4-((methyl)(ethoxycarbonylmethyl)amino)pyridin-2-yl)oxy]benzamidine;

4-hydroxy-3-[(3,5-difluoro-6-(3-(1-methylimidazolin-2-yl)phenoxy)-4-(aminocarbonylmethoxy)pyridin-2-yl)oxy]benzamidine;

4-hydroxy-3-[(3,5-difluoro-6-(3-(guanidino)phenoxy)-4-(aminocarbonylmethoxy)pyridin-2-yl)oxy]benzamidine;

4-hydroxy-3-[(3,5-difluoro-6-(3-(1-methylimidazol-2-yl)phenoxy)-4-(aminocarbonylmethoxy)pyridin-2-yl)oxy]benzamidine;

4-hydroxy-3-[(3,5-difluoro-6-(3-(1-methylimidazolin-2-yl)phenoxy)pyridin-2-yl)oxy]benzamidine;

4-hydroxy-3-[(3,5-difluoro-6-(3-(guanidino)phenoxy)pyridin-2-yl)oxy]benzamidine;

4-hydroxy-3-[(3,5-difluoro-6-(3-(1-methylimidazol-2-yl)phenoxy)pyridin-2-yl)oxy]benzamidine;

4-hydroxy-3-[(3,5-difluoro-6-(3-dimethylaminocarbonylphenoxy)-4-((piperidin-4-yl)amino)pyridin-2-yl)oxy]benzamidine;

4-hydroxy-3-[(3,5-difluoro-6-(3-(guanidino)phenoxy)-4-((piperidin-4-yl)amino)pyridin-2-yl)oxy]benzamidine;

4-hydroxy-3-[(3,5-difluoro-6-(3-(1-methylimidazol-2-yl)phenoxy)-4-((piperldin-4-yl)amino)pyridin-2-yl)oxy]benzamidine;

4-hydroxy-3-[(3,5-difluoro-6-(3-dimethylaminocarbonylphenoxy)-4-((1-benzylpiperidin-4-yl)amino)pyridin-2-yl)oxy]benzamidine;

4-hydroxy-3-[(3,5-difluoro-6-(3-(guanidino)phenoxy)-4-((1-benzylpiperidin-4-yl)amino)pyridin-2-yl)oxy]benzamidine; 4-hydroxy-3-[(3,5-difluoro-6-(3-(1-methylimidazol-2-yl)phenoxy)-4-((1-benzylpiperidin-4-yl)amino)pyridin-2-yl)oxy]benzamidine;

4-hydroxy-3-[(3,5-difluoro-6-(3-dimethylaminocarbonylphenoxy)-4-((piperidin-4-yl)(methyl)amino)pyridin-2-yl)oxy]benzamidine;

4-hydroxy-3-[(3,5-difluoro-6-(3-(guanidino)phenoxy)-4-((piperidin-4-yl)(methyl)amino)pyridin-2-yl)oxy]benzamidine;

4-hydroxy-3-[(3,5-difluoro-6-(3-(1-methylimidazol-2-yl)phenoxy)- 4-((piperidin-4-yl)(methyl)amino)pyridin-2-yl)oxy]benzamidine;

4-hydroxy-3-[(3,5-difluoro-6-(3-dimethylaminocarbonylphenoxy)-4-((1-benzylpiperidin-4-yl)(methyl)amino)pyridin-2-yl)oxy]benzamidine;

4-hydroxy-3-[(3,5-difluoro-6-(3-(guanidino)phenoxy)-4((1-benzylpiperidin-4-yl))(methyl)amino)pyridin-2-yl)oxy]benzamidine;

4-hydroxy-3-[(3,5-difluoro-6-(3-(1-methylimidazol-2-yl)phenoxy)-4-((1-benzyl-piperidin-4-yl)(methyl)amino)pyridin-2-yl)oxy]benzamidine;

4-hydroxy-3-[(3,5-difluoro-6-(3-dimethylaminocarbonylphenoxy)-4-((1-(1-(methoxycarbonyl)ethyl)piperidin-4-yl)amino)pyridin-2-yl)oxy]benzamidine;

4-hydroxy-3-[(3,5-difluoro-6-(3-(guanidino)phenoxy)-4-((1-(1-(methoxycarbonyl)ethylpiperidin-4-yl)amino)pyridin-2-yl)oxy]benzamidine;

4-hydroxy-3-[(3,5-difluoro-6-(3-(1-methylimidazol-2-yl)phenoxy)-4-((1-(1-(methoxycarbonyl)ethylpiperidin-4-yl)amino)pyridin-2-yl)oxy]benzamidine;

4-hydroxy-3-[(3,5-difluoro-6-(3-dimethylaminocarbonylphenoxy)-4-(2-methoxy-4-aminocarbonylphenoxy)pyridin-2-yl)oxy]benzamidine;

4-hydroxy-3-[(3,5-difluoro-6-(3-(guanidino)phenoxy)-4-(2-methoxy-4-aminocarbonylphenoxy)pyridin-2-yl)oxy]benzamidine;

4-hydroxy-3-[(3,5-difluoro-6-(3-(1-methylimidazol-2-yl)phenoxy)-4-(2-methoxy-4-aminocarbonylphenoxy)pyridin-2-yl)oxy]benzamidine;

4-hydroxy-3-[(3,5-difluoro-6-(3-dimethylaminocarbonylphenoxy)-4-(2-methoxy-4-(1-(hydroxymethyl)ethoxycarbonyl)phenoxy)pyridin-2-yl)oxy]benzamidine;

4-hydroxy-3-[(3,5-difluoro-6-(3-(guanidino)phenoxy)-4-(2-methoxy-4-(1-(hydroxymethyl)ethoxycarbonyl)phenoxy)pyridin-2-yl)oxy]benzamidine;

4-hydroxy-3-[(3,5-difluoro-6-(3-(1-methylimidazol-2-yl)phenoxy)-4-(2-methoxy-4-(1-(hydroxymethyl)ethoxycarbonyl)phenoxy)pyridin-2-yl)oxy]benzamidine;

4-hydroxy-3-[(3,5difluoro-6-(3dimethylaminocarbonylphenoxy)-4-(2-methoxy-4-(prop-2-oxycarbonyl)phenoxy)pyridin-2-yl)oxy]benzamidine;

4-hydroxy-3-[(3,5-difluoro-6-(3-(guanidino)phenoxy)-4-(2-methoxy-4-(prop-2-oxycarbonyl)phenoxy)pyridin-2-yl)oxy]benzamidine;

4-hydroxy-3-[(3,5-difluoro-6-(3-(1-methylimidazol-2-yl)phenoxy)-4-(2-methoxy-4-(prop-2-oxycarbonyl)phenoxy)pyridin-2-yl)oxy]benzamidine;

4-hydroxy-3-[(3,5-difluoro-6-(3-dimethylaminocarbonylphenoxy)-4-(2-methoxy-4-(2-(methoxy)ethoxycarbonyl)phenoxy)pyridin-2-yl)oxy]benzamidine;

4-hydroxy-3-[(3,5-difluoro-6-(3-(guanidino)phenoxy)-4-(2-methoxy-4-(2-(methoxy)ethoxycarbonyl)phenoxy)pyridin-2-yl)oxy]benzamidine;

4-hydroxy-3-[(3,5-difluoro-6-(3-(1-methylimidazol-2-yl)phenoxy)-4-(2-methoxy-4-(2-(methoxy)ethoxycarbonyl)phenoxy)pyridin-2-yl)oxy]benzamidine;

4-hydroxy-3-[(3,5-difluoro-6-(3-dimethylaminocarbonylphenoxy)- 4-(2-methoxy-4-n-butoxycarbonyl)phenoxy)pyridin-2-yl)oxy]benzamidine;

4-hydroxy-3-[(3,5-difluoro-6-(3-(guanidino)phenoxy)-4-(2-methoxy-4-n-butoxycarbonyl)phenoxy)pyridin-2-yl)oxy]benzamidine;

4-hydroxy-3-[(3,5-difluoro-6-(3-(1-methylimidazol-2-yl)phenoxy)-4-(2-methoxy-4-n-butoxycarbonyl)phenoxy)pyridin-2-yl)oxy]benzamidine;

4-hydroxy-3-[(3,5-difluoro-6-(3-dimethylaminocarbonylphenoxy)-4-(2-methoxy-4-((2-(2-hydroxyethoxy)ethoxy4carbonyl)phenoxy4pyridin-2-yl-4oxy]benzamidine;

4-hydroxy-3-[(3,5-difluoro-6-(3-(guanidino)phenoxy)-4-(2-methoxy-4-((2-(2-hydroxy)ethoxy)ethoxy)carbonyl)phenoxy)pyridin-2-yl)oxy]benzamidine;

4-hydroxy-3-[(3,5-difluoro-6-(3-(1-methylimidazol-2-yl)phenoxy)-4-(2-methoxy-4-((2-(2-hydroxyethoxy)ethoxy)carbonyl)phenoxy)pyridin-2-ylsoxy]benzamidine;

4-hydroxy-3-[(3,5-difluoro-6-(3-dimethylaminocarbonylphenoxy)-4-(2-methoxy-4-((2-(2-methoxyethoxy)ethoxy)carbonyl)phenoxy)pyridin-2-yl)oxy]benzamidine;

4-hydroxy-3-[(3,5-difluoro-6-(3-(guanidino)phenoxy)-4-(2-methoxy-4-((2-(2-methoxyethoxy)ethoxy)carbonyl)phenoxy)pyridin-2-yl)oxy]benzamidine;

4-hydroxy-3-[(3,5-difluoro-6-(3-(1-methylimidazol-2-yl)phenoxy)-4-(2-methoxy-4-((2-(2-methoxyethoxy)ethoxy)carbonyl)phenoxy)pyridin-2-yl)oxy]benzamidine;

4-hydroxy-3-[(3,5-difluoro-6-(3-dimethylaminocarbonylphenoxy)-4-(3-(2-(aminocarbonyl)ethenyl)phenoxy)pyridin-2-yl)oxy]benzamidine;

4-hydroxy-3-[(3,5-difluoro-6-(3-(guanidino)phenoxy)-4-(3-(2-(aminocarbonyl)ethenyl)phenoxy)pyridin-2-yl)oxyybenzamidine;

4-hydroxy-3-[(3,5-difluoro-6-(3-(1-methylimidazol-2-yl)phenoxy)-4-(3-(2-(aminocarbonyl)ethenyl)phenoxy)pyridin-2-yl)oxy]benzamidine;

4-hydroxy-3-[(3,5-difluoro-6-(3-dimethylaminocarbonylphenoxy)-4-(3-(2-(methoxycarbonyl)ethenyl)phenoxy)pyridin-2-yl)oxy]benzamidine;

4-hydroxy-3-[(3,5-difluoro-6-(3-(guanidino)phenoxy)-4-(3-(2-(methoxycarbonyl)ethenyl)phenoxy)pyridin-2-yl)oxy]benzamidine;

4-hydroxy-3-[(3,5-difluoro-6-(3-(1-methylimidazol-2-yl)phenoxy)-4-(3-(2-(methoxycarbonyl)ethenyl)phenoxy)pyridin-2-yl)oxy]benzamidine;

4-hydroxy-3-[(3,5-difluoro-6-(3-dimethylaminocarbonylphenoxy)-4-(4-(2-(methoxycarbonyl)ethenyl)phenoxy)pyridin-2-yl)oxy]benzamidine;

4-hydroxy-3-[(3,5-difluoro-6-(3-(guanidino)phenoxy)-4-(4-2-(methoxycarbonyl)ethenyl)phenoxy)pyridin-2-yl)oxy]benzamidine; 4-hydroxy-3-[(3,5-difluoro-6-(3-(1-methylimidazol-2-yl)phenoxy)-4-(4-(2-(methoxycarbonyl)ethenyl)phenoxy)pyridin-2-yl)oxy]benzamidine;

4-hydroxy-3-[(3,5-difluoro-6-(3-dimethylaminocarbonylphenoxy)-4-(2-methoxy-4-(2-chloro-1-methylethoxycarbonyl)phenoxy)pyridin-2-yl)oxy]benzamidine;

4-hydroxy-3-[(3,5-difluoro-6-(3-(guanidino)phenoxy)-4-(2-methoxy- 4-(2-chloro-1-methylethoxycarbonyl)phenoxy)pyridin-2-yl)oxy]benzamidine;

4-hydroxy-3-[(3,5-difluoro-6-(3-(1-methylimidazol-2-yl)phenoxy)-4-(2-methoxy-4-(2-chloro-1-methylethoxycarbonyl)phenoxy)pyridin-2-yl)oxy]benzamidine;

4-hydroxy-3-[(3,5-difluoro-6-(3-dimethylaminocarbonylphenoxy)-4-(3-(2-(ethoxycarbonyl)ethenyl)phenoxy)pyridin-2-yl)oxy]benzamidine;

4-hydroxy-3-[(3,5-difluoro-6-(3-(guanidino)phenoxy)-4-(3-(2-(ethoxycarbonyl)ethenyl)phenoxy)pyridin-2-yl)oxy]benzamidine;

4-hydroxy-3-[(3,5-difluoro-6-(3-(1-methylimidazol-2-yl)phenoxy)-4-(3-(2-(ethoxycarbonyl)ethenyl)phenoxy)pyridin-2-yl)oxy]benzamidine;

4-hydroxy-3-[(3,5-difluoro-6-(3-dimethylaminocarbonylphenoxy)-4-(4-(2-(ethoxycarbonyl)ethenyl)phenoxy)pyridin-2-yl)oxy]benzamidine;

4-hydroxy-3-[(3,5-difluoro-6-(3-(guanidino)phenoxy)-4-(4-(2-(ethoxycarbonyl)ethenyl)phenoxy)pyridin-2-yl)oxy]benzamidine;

4-hydroxy-3-[(3,5-difluoro-6-(3-(1-methylimidazol-2-yl)phenoxy)-4-(4-(2-(ethoxycarbonyl)ethenyl)phenoxy)pyridin-2-yl)oxy]benzamidine;

4-hydroxy-3-[(3,5-difluoro-6-(3-dimethylaminocarbonylphenoxy)-4-(2,6-dimethoxy-4-(2-(ethoxycarbonyl)ethenyl)phenoxy)pyridin-2-yl)oxy]benzamidine;

4-hydroxy-3-[(3,5-difluoro-6-(3-(guanidino)phenoxy)-4-(2,6-dimethoxy-4-(2-(ethoxycarbonyl)ethenyl)phenoxy)pyridin-2-yl)oxy]benzamidine;

4-hydroxy-3-[(3,5-difluoro-6-(3-(1-methylimidazol-2-yl)phenoxy)-4-(2,6-dimethoxy-4-(2-(ethoxycarbonyl)ethenyl)phenoxy)pyridin-2-yl)oxy]benzamidine;

4-hydroxy-3-[(3,5-difluoro-6-(3-(1-methylimidazolin-2-yl)phenoxy)-4-(4-methylpiperazin-1-yl)pyridin-2-yl)oxy]benzamidine;

4-hydroxy-3-[(3,5-difluoro-6-(3-(guanidino)phenoxy)-4-(4-methylpiperazin-1-yl)pyridin-2-yl)oxy]benzamidine;

4-hydroxy-3-[(3,5difluoro-6-(3-(1-methylimidazol-2-yl)phenoxy)-4-(4-methylpiperazin-1-yl)pyridin-2-yl)oxy]benzamidine;

4-hydroxy-3-[(3,5-difluoro-6-(3-(1-methylimidazolin-2-yl)phenoxy)-4-dimethylaminopyridin-2-yl)oxy]benzamidine;

4-hydroxy-3-[(3,5-difluoro-6-(3-(guanidino)phenoxy)-4-dimethylaminopyridin-2-yl)oxy]benzamidine;

4-hydroxy-3-[(3,5-difluoro-6-(3-(1-methylimidazol-2-yl)phenoxy)-4-dimethylaminopyridin-2-yl)oxy]benzamidine;

4-hydroxy-3-[(3,5-difluoro-6-(3-(1-methylimidazolin-2-yl)phenoxy)-4-methylpyridin-2-yl)oxy]benzamidine;

4-hydroxy-3-[(3,5-difluoro-6-(3-(guanidino)phenoxy)-4-methylpyridin-2-yl)oxy]benzamidine;

4-hydroxy-3-[(3,5-difluoro-6-(3-(1-methylimidazol-2-yl)phenoxy)- 4-methylpyridin-2-yl)oxy]benzamidine;

4-hydroxy-3-[(3,5-difluoro-6-(3-(1-methylimidazolin-2-yl)phenoxy)-4-(2,2,2-trifluoroethoxy)pyridin-2-yl)oxy]benzamidine;

4-hydroxy-3-[(3,5-difluoro-6-(3-(guanidino)phenoxy)-4-(2,2,2-trifluoroethoxy)pyridin-2-yl)oxy]benzamidine;

4-hydroxy-3-[(3,5-difluoro-6-(3-(1-methylimidazol-2-yl)phenoxy)-4-(2,2,2-trifluoroethoxy) pyridin-2-yl)oxy]benzamidine;

4-hydroxy-3-[(3,5-difluoro-6-(3-(1-methylimidazolin-2-yl) phenoxy)-4-(1,3-difluoroprop-2-oxy) pyridin-2-yl)oxy]benzamidine;

4-hydroxy-3-[(3,5-difluoro-6-(3-(guanidino)phenoxy)-4-(1,3-difluoroprop-2-oxy)pyridin-2-yl)oxy]benzamidine; and 4-hydroxy-3-[(3,5-difluoro-6-(3-(1-methylimidazol-2-yl)phenoxy)-4-(1,3-difluoropro-2-oxy)pyridin-2-yl)oxy]benzamidine.

EXAMPLE 8

4-Hydroxy-3-[(3,5-difluoro-6-(3-(imidazol-1-yl)phenoxy)-4-(carboxy)pyridin-2-yl)oxy]benzamidine, Trifluoroacetic Acid Salt A. In a manner similar to Example 6,2-(5-amidino-2-hydroxyphenoxy]-6-(3-(imidazol-1-yl)phenoxy)pyridine-4-carboxylic acid, ethyl ester was reacted with boron tribromide. The resulting oil was dissolved in 6 N HCl and heated at reflux for 2 hours. Concentration of the mixture in vacuo and purification by HPLC as described above in Example 5 gave 4-hydroxy-3-[(3,5-difluoro-6-(3-(imidazol-1-yl)phenoxy)-4-(carboxy)pyridin-2-yl)-oxy]benzamidine, trifluoroacetic acid salt; NMR (DMSO-$d_6$, TFA) 9.7 (s,1), 9.0 (s,2), 8.8 (s,2), 8.3 (s,1), 7.9 (s,1), 7.6 (m,5), 7.3 (m,1), 7.1 (m,2), 7.0 (m,1) ppm.

B. In a similar manner, the following compound was made:

4-hydroxy-3-[(3,5-difluoro-6-(3-dimethylaminophenoxy)-4-(carboxy)pyridin-2-yl)oxy]benzamidine, trifluoroacetic acid salt; NMR (DMSO-$d_6$) 11.0 (s,1), 9.1 (s,2), 8.7 (s,2), 7.7 (m,2), 7.2 (m,2), 7.0 (s,1), 6.8 (s,1), 6.6 (d,1), 6.4 (m,2), 2.8 (s,6) ppm.

EXAMPLE 9

3,3'-[4-Aminocarbonyl-2,6-pyridinediylbis(oxy))bis(benzamidine), Trifluoroacetic Acid Salt A. In a manner similar to Example 1 above, reaction of 3,3'-[4-ethoxy-carbonyl-2,6-pyridinediylbis(oxy)]bis(benzonitrile) gave 3,3'-14-aminocarbonyl-2,6-pyridinediylbis(oxy)]bis(benzamidine), which was purified by HPLC as described above in Example 5 to give the trifluoroacetic acid salt, m.p. >210° C.; NMR (DMSO-$d_6$) 9.3 (s,4), 9.1 (s,4), 8.3 (s,1), 7.65 (m,4), 7.55 (m,4), 7.2 (s,2) ppm.

B. In a similar manner, the following compounds were made:

3,3'-[3-aminocarbonyl-2,6-pyridinediylbis(oxy)]bisibenzamidine), trifluoroacetic acid salt; NMR (DMSO) 9.45 (br s,4), 9.35 (br s,4), 8.4 (d,1), 7.4–7.9 (m,10), 6.95 (d,1) ppm;

4-methoxy-3-[(6-(3-dimethylaminophenoxy)-4aminocarbonylpyridin-2-yl)oxy]benzamidine hydrochloride, NMR (DMSO-$d_6$) 9.3 (s,2), 9.1 (s,2), 8.3 (s,1), 7.8 (m,2), 7.3 (s,1), 7.1 (m,3), 6.9 (s,1), 6.5 (d,1), 6.3 (m,2), 3.8 (s,3), 2.8 (s,6) ppm.

EXAMPLE 10

2,6-bis(3-Amidinophenoxy)pyridine-3-carboxylic acid, Dihydrochloride

A. In a manner similar to Example 2 above, 2,6-bis(3-amidinophenoxy)pyridine-3-carboxylic acid, ethyl ester (0.20 g, 0.31 mmol) was dissolved in 5 M HCl and heated for 2 hours at 80 IC. The solvent was removed in vacuo to give 2,6-bis(3-amidinophenoxy)pyridine-3-carboxylic acid, dihydrochloride; NMR (DMSO-$d_6$) 9.5 (br s,4), 9.35 (br s,4), 8.45 (d,1), 7.7 (m,2), 7.6 (m,2), 7.5 (m,4), 6.95 (d,1) ppm.

B. In a similar manner, the following compounds were made and purified by HPLC as described above in Example 5:

4-hydroxy-3-[(3,5-difluoro-6-(3-(1-methylimidazolin-2-yl)phenoxy)-4-(2-methoxy-4-carboxyphenoxy)pyridin-2-yl)oxy]benzamidine, trifluoroacetic acid salt;

4-hydroxy-3-[(3,5-difluoro-6-(3-dimethylaminophenoxy)-4-(4-carboxyphenoxy)-pyridin-2-yl)oxy]benzamidine, trifluoroacetic acid salt;

4-hydroxy-3-[(3,5-difluoro-6-(3-dimethylaminophenoxy)(ethoxycarbonylmethoxy)pyridin-2-yl)oxy]benzamidine, trifluoroacetic acid salt;

4-hydroxy-3-[(3,5-difluoro-6-(3-dimethylaminophenoxy)-4-(3,5-dicarboxyphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(4-carboxyphenoxy)pyridin-2-yl)oxy]benzamidine, trifluoroacetic acid salt;

4-hydroxy-3-[(3,5-difluoro-6-(3-(1-methylimidazol-2-yl) phenoxy)-4-(2-methoxy-4-carboxyphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2-methoxy-5-carboxyphenoxy) pyridin-2-yl)oxy]benzamidine, trifluoroacetic acid salt;

4-hydroxy-3-[(3,5-difluoro-6-(3-(1-methylimidazolin-2-yl)phenoxy)-4-(2,3-dimethoxy-5-carboxyphenoxy) pyridin-2-yl)oxy]benzamidine, trifluoroacetic acid salt;

4-hydroxy-3-[(3,5-difluoro-6-(3-(1-methylimidazolin-2-yl)phenoxy)-4-(2,6-dimethoxy-4-(2-carboxyethenyl) phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2,6-dimethoxy-4-(2-carboxyethyl) phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(3-(2-carboxyethyl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(3-(2-carboxyethenyl)phenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(4-(2-carboxyethenyl)phenoxy)pyridin-2-yl)oxy]benzamidine, trifluoroacetic acid salt;

4-hydroxy-3-[(3,5-difluoro-6-(3-(dimethylaminomethyl) phenoxy)-4-(2-methoxy-4-carboxyphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(3-carboxyphenoxy)pyridin-2-yl)oxy] benzamidine, trifluoroacetic acid salt;

4-hydroxy-3-[(3,5-dicluoro-6-(3-(1-methylimidazolin-2-yl)phenoxy)-4-(3,5-dicarboxyphenoxy)pyridin-2-yl) oxy]benzamidine, trifluoroacetic acid salt;

4-hydroxy-3-[(3,5-difluoro-6-(3-(1-methylimidazolin-2-yl)phenoxy)-4-(3-carboxy-5-ethoxycarbonylphenoxy) pyridin-2-yl)oxy]benzamidine, trifluoroacetic acid salt;

4-hydroxy-3-[(3,5-difluoro-6-(3-(1-methylimidazolin-2-yl)phenoxy)-4-(2,6-dimethoxy-4-carboxyphenoxy) pyridin-2-yl)oxy]benzamidine, trifluoroacetic acid salt;

4-hydroxy-3-[(3,5-difluoro-6-(3-(guanidino)phenoxy)-4-(2,6-dimethoxy-4-carboxyphenoxy)pyridin-2-yl)oxy] benzamidine;

4-hydroxy-3-[(3,5-difluoro-6-(3-(1-methylimidazolin-2-yl)phenoxy)-4-(2-methoxy-4-carboxymethylphenoxy) pyridin-2-yl)oxy]benzamidine, trifluoroacetic acid salt;

4-hydroxy-3-[(3,5-difluoro-6-(3-amidinophenoxy)-4-(2-methoxy-4-carboxyphenoxy)pyridin-2-yl)oxy] benzamidine, trifluoroacetic acid salt;

4-hydroxy-3-[(3,5-difluoro-6-(3-((1-methylimidazolin-2-yl)phenoxy)-4-(2-chloro-4-carboxyphenoxy)pyridin-2-yl)oxy]benzamidine, trifluoroacetic acid salt;

4-hydroxy-3-[(3,5-difluoro-6-(3-(1-methylimidazolin-2-yl)phenoxy)-4-(2,6-dimethyl-4-carboxyphenoxy) pyridin-2-yl)oxy]benzamidine, trifluoroacetic acid salt;

4-hydroxy-3-[(3,5-difluoro-6-(3-(1-methylimidazol-2-yl) phenoxy)-4-((2-dimethylaminoethyl)(carboxymethyl) amino)pyridin-2-yl)oxy]benzamidine, trifluoroacetic acid salt;

4-hydroxy-3-[(3,5-difluoro-6-(3-dimethylaminocarbonylphenoxy)-4-((2-dimethylaminoethyl)(carboxymethyl)amino)pyridin-2-yl)oxy]benzamidine, trifluoroacetic acid salt;

4-hydroxy-3-[(3,5-difluoro-6-(3-(1 1-methylimidazolin-2-yl)phenoxy)-4-((1-carboxymethylpiperidin-4-yl) (methyl)amino)pyridin-2-ylsoxy]benzamidine, trifluoroacetic acids alt; NMR (DMSO-$d_6$) 11.25 (s,1), 10.30 (s,1), 9.03 (brs,4), 7.58–7.55 (m, 2), 7.50 (t,1), 7.38–7.31 (m,3), 7.03 (d,1), 4.10 (s,2), 4.08–3.88 (m,4), 3.66 (m,2), 3.16 (m,2), 2.95 (s,6), 2.26 (m,2), 1.93(m,2) ppm;

4-hydroxy-3-[(3,5-difluoro-6-(3-(1-methylimidazolin-2-yl)phenoxy)-4-(1-carboxymethylpiperidin-4-yl)amino) pyridin-2-yl)oxy]benzamidine, trifluoroacetic acid salt;

4-hydroxy-3-[(3,5-difluoro-6-(3-(1-methylimidazolin-2-yl)phenoxy)-4-((methyl)(carboxymethyl)amino) pyridin-2-yl)oxy]benzamidine, hydrochloride salt; NMR (DMSO-$d_6$) 11.25 (s,1), 10.45 (s,1), 9.1 (d,4), 7.35 (m,7), 4.18 (s,2), 4.05 (m,4), 3.2 (s,3), 2.95 (s,3) ppm;

4-hydroxy-3-[(3,5-difluoro-6-(3-(guanidino)phenoxy)-4-(2-methoxy-4-carboxyphenoxy)pyridin-2-yl)oxy] benzamidine, trifluoroacetic acid salt.

C. In a similar manner, the following compounds are made:

4-hydroxy-3-[(3,5-difluoro-6-(3-(1-methylimidazolin-2-yl)phenoxy)-4-(4-(1-methyl-1-(carboxy)ethyl) piperazin-1-yl)pyridin-2-yl)oxy]benzamidine;

4-hydroxy-3-[(3,5-difluoro-6-(3-dimethylaminocarbonylphenoxy)-4-(4-(1-methyl-1-(carboxy)ethyl)piperazin-1-yl)pyridin-2-yl)oxy] benzamidine;

4-hydroxy-3-[(3,5-difluoro-6-(3-(guanidino)phenoxy)-4-4(1-methyl-1-(carboxy)ethyl)piperazin-1-yl)pyridin-2-yl)oxy]benzamidine;

4-hydroxy-3-[(3,5-difluoro-6-(3-(1-methylimidazol-2-yl) phenoxy)-4-(4-(1-methyl-1-(carboxy)ethyl)piperazin-1-yl)pyridin-2-yl)oxy]benzamidine;

4-hydroxy-3-[(3,5-difluoro-6-(3-(1-methylimidazolin-2-yl)phenoxy)-4-(4-(1-(carboxy)ethyl)piperazin-1-yl) pyridin-2-yl)oxy]benzamidine;

4-hydroxy-3-[(3,5-difluoro-6-(3-dimethylaminocarbonylphenoxy)-4-(4-(1-(carboxy) ethyl)piperazin-1-yl)pyridin-2-yl)oxy]benzamidine;

4-hydroxy-3-[(3,5-difluoro-6-(3-(guanidino) phenoxy)-4-(4-(1-(carboxy)ethyl)piperazin-1-yl)pyridin-2-yl)oxy] benzamidine;

4-hydroxy-3-[(3,5-difluoro-6-(3-(1-methylimidazol-2-yl) phenoxy)-4-(4-(1-(carboxy)ethyl)piperazin-1-yl) pyridin-2-yl)oxy]benzamidine;

4-hydroxy-3-[(3,5-difluoro-6-(3-(1-methylimidazolin-2-yl)phenoxy)-4-((2-carboxyethyl)phenoxy)pyridin-2-yl)oxy]benzamidine;

4-hydroxy-3-[(3,5-difluoro-6-(3-dimethylaminocarbonylphenoxy)-4-((2-carboxyethyl) phenoxy)pyridin-2-yl)oxy]benzamidine;

4-hydroxy-3-[(3,5-difluoro-6-(3-(guanidino)phenoxy)-4-((2-carboxyethyl)phenoxy)pyridin-2-yl)oxy] benzamidine;

4-hydroxy-3-[(3,5-difluoro-6-(3-(1-methylimidazol-2-yl) phenoxy)-4-((2-carboxyethyl)phenoxy)pyridin-2-yl) oxy]benzamidine;

4-hydroxy-3-[(3,5-difluoro-6-(3-(1-methylimidazolin-2-yl)phenoxy)-4-(1-(1-(carboxy)ethyl)piperidin-4-yloxy) pyridin-2-yl)oxy]benzamidine;

4-hydroxy-3-[(3,5-difluoro-6-(3-dimethylaminocarbonylphenoxy)-4-(1-(1-(carboxy) ethyl)piperidin-4-yloxy)pyridin-2-yl)oxy] benzamidine;

4-hydroxy-3-[(3,5-difluoro-6-(3-(guanidino)phenoxy)-4-(1-(1-(carboxy)ethyl)piperidin-4-yloxy)pyridin-2-yl)oxy]benzamidine;

4-hydroxy-3-[(3,5-difluoro-6-(3-(1-methylimidazol-2-yl)phenoxy)-4-(1-(1-(carboxy)ethyl)piperidin-4-yloxy)pyridin-2-yl)oxy]benzamidine;

4-hydroxy-3-[(3,5-difluoro-6-(3-(1-methylimidazolin-2-yl)phenoxy)-4-(1-(1-carboxy-1-methylethyl)piperidin-4-yloxy)pyridin-2-yl)oxy]benzamidine;

4-hydroxy-3-[(3,5-difluoro-6-(3-dimethylaminocarbonylphenoxy)-4-(1-(1-carboxy-1-methylethyl)piperidin-4-yloxy)pyridin-2-yl)oxy]benzamidine;

4-hydroxy-3-[(3,5-difluoro-6-(3-(guanidino)phenoxy)-4-(1-(1-carboxy-1-methylethyl)piperidin-4-yloxy)pyridin-2-yl)oxy]benzamidine;

4-hydroxy-3-[(3,5-difluoro-6-(3-(1-methylimidazol-2-yl)phenoxy)-4-(1-(1-carboxy-1-methylethyl)piperidin-4-yloxy)pyridin-2-yl)oxy]benzamidine;

4-hydroxy-3-[(6-(3-(1-methylimidazolin-2-yl)phenoxy)-4-(1-carboxymethylpiperidin-4-yloxy)pyridin-2-yl)oxy]benzamidine;

4-hydroxy-3-[(6-(3-dimethylaminocarbonylphenoxy)-4-(1-carboxymethylpiperidin-4-yloxy)pyridin-2-yl)oxy]benzamidine;

4-hydroxy-3-[(6-(3-(guanidino)phenoxy)-4-(1-carboxymethylpiperidin-4-yloxy)pyridin-2-yl)oxy]benzamidine;

4-hydroxy-3-[(6-(3-(1-methylimidazol-2-yl)phenoxy)-4-(1-carboxymethylpiperidin-4-yloxy)pyridin-2-yl)oxy]benzamidine;

4-hydroxy-3-[(3,5-difluoro-6-(3-(1-methylimidazolin-2-yl)phenoxy)-4-(carboxymethoxy)pyridin-2-yl)oxy]benzamidine;

4-hydroxy-3-[(3,5-difluoro-6-(3-dimethylaminocarbonylphenoxy)-4-(carboxymethoxy)pyridin-2-yl)oxy]benzamidine;

4-hydroxy-3-[(3,5-difluoro-6-(3-(guanidino)phenoxy)-4-(carboxymethoxy)pyridin-2-yl)oxy]benzamidine;

4-hydroxy-3-[(3,5-difluoro-6-(3-(1-methylimidazol-2-yl)phenoxy)-4-(carboxymethoxy)pyridin-2-yl)oxy]benzamidine;

4-hydroxy-3-[(3,5-difluoro-6-(3-tguanidino)phenoxy)-4-(4-carboxyphenoxy)pyridin-2-yl)oxy]benzamidine;

4-hydroxy-3-[(3,5-difluoro-6-(3-(1-methylimidazol-2-yl)phenoxy)-4-(4-carboxyphenoxy)pyridin-2-yl)oxy]benzamidine;

4-hydroxy-3-[(3,5difluoro-6-(3-(guanidino)phenoxy)-4-(2-methoxy-5-carboxyphenoxy)pyridin-2-yl)oxy]benzamidine;

4-hydroxy-3-[(3,5-difluoro-6-(3-(1-methylimidazol-2-yl)phenoxy)-4-(2-methoxy-5-carboxyphenoxy)pyridin-2-yl)oxy]benzamidine;

4-hydroxy-3-[(3,5-difluoro-6-(3-(guanidino)phenoxy)-4-(2,3-dimethoxy-5-carboxyphenoxy)pyridin-2-yl)oxy]benzamidine;

4-hydroxy-3-[(3,5-difluoro-6-(3-(1-methylimidazol-2-yl)phenoxy)-4-(2,3-dimethoxy-5-carboxyphenoxy)pyridin-2-yl)oxy]benzamidine;

4-hydroxy-3-[(3,5-difluoro-6-(3-(guanidino)phenoxy)-4-(3-carboxyphenoxy)pyridin-2-yl)oxy]benzamidine;

4-hydroxy-3-[(3,5-difluoro-6-(3-(1-methylimidazol-2-yl)phenoxy)-4-(3-carboxyphenoxy)pyridin-2-yl)oxy]benzamidine;

4-hydroxy-3-[(3,5-difluoro-6-(3-(guanidino)phenoxy)-4-(3,5-dicarboxyphenoxy)pyridin-2-yl)oxy]benzamidine;

4-hydroxy-3-[(3,5-difluoro-6-(3-(1-methylimidazol-2-yl)phenoxy)-4-(3,5-dicarboxyphenoxy)pyridin-2-yl)oxy]benzamidine;

4-hydroxy-3-[(3,5-difluoro-6-(3-dimethylaminocarbonylphenoxy)-4-(3-carboxy-5-ethoxycarbonylphenoxy)pyridin-2-yl)oxy]benzamidine;

4-hydroxy-3-[(3,5-difluoro-6-(3-(guanidino)phenoxy)-4-(3-carboxy-5-ethoxycarbonylphenoxy)pyridin-2-yl)oxy]benzamidine;

4-hydroxy-3-[(3,5-difluoro-6-(3-(1-methylimidazol-2-yl)phenoxy)-4-(3-carboxy-5-ethoxycarbonylphenoxy)pyridin-2-yl)oxy]benzamidine;

4-hydroxy-3-[(3,5-difluoro-6-(3-(1-methylimidazol-2-yl)phenoxy)-4-(2,6-dimethoxy-4-carboxyphenoxy)pyridin-2-yl)oxy]benzamidine;

4-hydroxy-3-[(3,5-difluoro-6-(3-(guanidino)phenoxy)-4-(2-chloro-4-carboxyphenoxy)pyridin-2-yl)oxy]benzamidine;

4-hydroxy-3-[(3,5-difluoro-6-(3-(1-methylimidazol-2-yl)phenoxy)-4-(2-chloro-4-carboxyphenoxy)pyridin-2-yl)oxy]benzamidine;

4-hydroxy-3-[(3,5-difluoro-6-(3-(guanidino)phenoxy)-4-(2,6-dimethyl-4-carboxyphenoxy)pyridin-2-yl)oxy]benzamidine;

4-hydroxy-3-[(3,5-difluoro-6-(3-t1-methylimidazol-2-yl)phenoxy)-4-(2,6-dimethyl-4-carboxyphenoxy)pyridin-2-yl)oxy]benzamidine;

4-hydroxy-3-[(3,5-difluoro-6-(3-(guanidino)phenoxy)-4-((1-carboxymethylpiperidin-4-yl)(methyl)amino)pyridin-2-yl)oxy]benzamidine;

4-hydroxy-3-[(3,5-difluoro-6-(3-(1-methylimidazol-2-yl)phenoxy)-4-((1-carboxymethylpiperidin-4-yl)(methyl)amino)pyridin-2-yl)oxy]benzamidine;

4-hydroxy-3-[(3,5-difluoro-6-(3-(guanidino)phenoxy)-4-((1-carboxymethylpiperidin-4-yl)amino)pyridin-2-yl)oxy]benzamidine;

4-hydroxy-3-[(3,5-(difluoro-6-(3-(1-methylimidazol-2-yl)phenoxy)-4((1-carboxymethylpiperidin-4-yl)amino)pyridin-2-yl)oxy]benzamidine;

4-hydroxy-3-[(3,5-difluoro-6-(3-(guanidino)phenoxy)-4-(2-methoxy-4-carboxymethylphenoxy)pyridin-2-yl)oxy]benzamidine;

4-hydroxy-3-[(3,5-difluoro-6-(3-(1-methylimidazol-2-yl)phenoxy)-4-(2-methoxy-4-carboxymethylphenoxy)pyridin-2-yl)oxy]benzamidine;

4-hydroxy-3-[(3,5-difluoro-6-(3-(guanidino)phenoxy)-4-((methyl)(carboxymethyl)amino)pyridin-2-yl)oxy]benzamidine;

4-hydroxy-3-[(3,5-difluoro-6-(3-(1-methylimidazol-2-yl)phenoxy)-4-((methyl)(carboxymethyl)amino)pyridin-2-yl)oxy]benzamidine;

4-hydroxy-3-[(3,5-difluoro-6-(3-(guanidino)phenoxy)-4-(2,6-dimethoxy-4-(2-carboxyethenyl)phenoxy)pyridin-2-yl)oxy]benzamidine;

4-hydroxy-3-[(3,5-difluoro-6-(3-(1-methylimidazol-2-yl)phenoxy)-4-(2,6-dimethoxy-4-(2-carboxyethenyl)phenoxy)pyridin-2-yl)oxy]benzamidine;

4-hydroxy-3-[(3,5-difluoro-6-(3-(guanidino)phenoxy)-4-(3-(2-carboxyethenyl)phenoxy)pyridin-2-yl)oxy]benzamidine;

4-hydroxy-3-[(3,5-difluoro-6-(3-(1-methylimidazol-2-yl)phenoxy)-4-(3-(2-carboxyethenyl)phenoxy)pyridin-2-yl)oxy]benzamidine;

4-hydroxy-3-[(3,5-difluoro-6-(3-(guanidino)phenoxy)-4-(4-(2-carboxyethenyl)phenoxy)pyridin-2-yl)oxy]benzamidine;

4-hydroxy-3-[(3,5-difluoro-6-(3-(1-methylimidazol-2-yl)phenoxy)-4-(4-(2-carboxyethenyl)phenoxy)pyridin-2-yl)oxy]benzamidine;

4-hydroxy-3-[(3,5-difluoro-6-(3-(guanidino)phenoxy)-4-(2,6-dimethoxy-4-(2-carboxyethyl)phenoxy)pyridin-2-yl)oxy]benzamidine;

4-hydroxy-3-[(3,5-difluoro-6-(3-(1-methylimidazol-2-yl)phenoxy)-4-(2,6-dimethoxy-4-(2-carboxyethyl)phenoxy)pyridin-2-yl)oxy]benzamidine;

4-hydroxy-3-[(3,5-difluoro-6-(3-(guanidino)phenoxy)-4-(3-(2-carboxyethyl)phenoxy)pyridin-2-yl)oxy]benzamidine;

4-hydroxy-3-[(3,5-difluoro-6-(3-(1-methylimidazol-2-yl)phenoxy)-4-(3-(2-carboxyethyl)phenoxy)pyridin-2-yl)oxy]benzamidine;

4-hydroxy-3-[(3,5-difluoro-6-(3-(1-methylimidazolin-2-yl)phenoxy)-4-(1-(carboxymethyl)pyrrolidin-3-yloxy)pyridin-2-yl)oxy]benzamidine;

4-hydroxy-3-[(3,5-difluoro-6-(3-(guanidino)phenoxy)-4-(1-(carboxymethyl)pyrrolidin-3-yloxy)pyridin-2-yl)oxy]benzamidine;

4-hydroxy-3-[(3,5-difluoro-6-(3-(1-methylimidazol-2-yl)phenoxy)-4-(1-(carboxymethyl)pyrrolidin-3-yloxy)pyridin-2-yl)oxy]benzamidine;

4-hydroxy-3-[(3,5-difluoro-6-(3-(1-methylimidazolin-2-yl)phenoxy)-4-((2-dimethylaminoethyl)(carboxymethyl)amino)pyridin-2-yl)oxy]benzamidine; and 4-hydroxy-3-[(3,5-difluoro-6-(3-(guanidino)phenoxy)-4((2dimethylaminoethyl)(carboxymethyl)amino)pyridin-2-yl)oxy]benzamidine.

EXAMPLE 11

4-Hydroxy-3-[(3,5-difluoro-6-(3-dimethylaminophenoxy)-4-(1-(ethoxycarbonyl-methyl)pyrrolidin-3-yloxy)pyridin-2-yloxy]benzamidine, Trifluoroacetic Acid Salt A. To ethanol (40 mL) was added 4-hydroxy-3-[(3,5-difluoro-6-(3-dimethyl-aminophenoxy)-4-(pyrrolidin-3-yloxy)pyridin-2-yloxy]-benzamidine (0.44 g, 0.90 mmol), ethyl bromoacetate (0.15 g, 0.9 mmol), and triethylamine (0.11 g, 1.1 mmol). After stirring for 19 hours, the reaction mixture was concentrated and purified by HPLC as described above in Example 5 to give 4-hydroxy-3-[(3,5-difluoro-6-(3-dimethylamino-phenoxy)-4-(1-(ethoxycarbonylmethyl)-pyrrolidin- 3-yloxy)pyridin-2-yl)-oxy]benzamidine, trifluoroacetic acid salt.

B. In a similar manner, the following compounds were made:

4-hydroxy-3-[(3,5-difluoro-6-(3-dimethylaminocarbonylphenoxy)-4-(1-ethoxycarbonylmethylpyrrolidin-3-yloxy)pyridin-2-yl)oxy]benzamidine, trifluoroacetic acid salt;

4-hydroxy-3-[(3,5-difluoro-6-(3-(1-methylimidazolin-2-yl)phenoxy)-4-((1-ethoxy-carbonylmethylpiperidin-4-yl)(methyl)amino)pyridin-2-yl)oxy]benzamidine, trifluoroacetic acid salt; and 4-hydroxy-3-[(3,5-difluoro-6-(3-(1-methylimidazolin-2-yl)phenoxy)-4-((1-(ethoxycarbonylmethyl)piperidin-4-yl)amino)pyridin-2-yl)oxy]benzamidine, trifluoroacetic acid salt.

C. In a similar manner, the following compounds are made:

4-hydroxy-3-[(3,5-difluoro-6-(3-dimethylaminocarbonylphenoxy)-4-((1-(ethoxycarbonylmethyl)piperidin-4-yl)amino)pyridin-2-yl)oxy]benzamidine;

4-hydroxy-3-[(3,5-difluoro-6-(3-(guanidino)phenoxy)-4-((1-(ethoxycarbonylmethyl)piperidin-4-yl)amino)pyridin-2-yl)oxy]benzamidine;

4-hydroxy-3-[(3,5-difluoro-6-(3-(1-methylimidazol-2-yl)phenoxy)-4-((1-(ethoxycarbonylmethyl)piperidin-4-yl)amino)pyridin-2-yl)oxy]benzamidine;

4-hydroxy-3-[(3,5-difluoro-6-(3-dimethylaminocarbonylphenoxy)-4-((1-ethoxycarbonylmethylpiperidin-4-yl)(methyl)amino)pyridin-2-yl)oxy]benzamidine;

4-hydroxy-3-[(3,5-difluoro-6-(3-(guanidino)phenoxy)-4-((1-ethoxy-carbonylmethylpiperidin-4-yl)(methyl)amino)pyridin-2-yl)oxy]benzamidine; and 4-hydroxy-3-[(3,5-difluoro-6-(3-(1-methylimidazol-2-yl)phenoxy)-4-((1-ethoxy-carbonylmethylpiperidin-4-yl)(methyl)amino)pyridin-2-yl)oxy]benzamidine.

EXAMPLE 12

3-[(3,5-Difluoro-6-(3-carboxyphenoxy)-4-methylpyridin-2-yl)oxy]benzamidine, Hydrochloride Salt A. To 3-[(3,5-difluoro-6-(3-ethoxycarbonylphenoxy)-4-methylpyridin-2-yl)-oxy]benzamidine, acetic acid salt (1.0 g, 2.0 mmol) dissolved in methanol (40 mL) was added 514 potassium hydroxide (20 mL). After stirring for 4 hours, the solvent was removed in vacuo. The residue was dissolved in water (50 mL) and acidified with 12 N HCl. The resulting solid was filtered and washed with ether to give 3-[(3,5-difluoro-6-(3-carboxyphenoxy)-4-methylpyridin-2-yl)oxy]benzamidine, hydrochloride salt; NMR (DMSO-$d_6$) 9.3 (s,2), 9.1 (s,2), 7.7 (d,1), 7.65 (s,1), 7.3–7.6 (m,6), 2.4 (s,3) ppm. If necessary the material can be further purified by HPLC as described above in Example 5.

B. In a similar manner, the following compounds were made:

3-[(3,5-difluoro-6-(3-(2-carboxyethyl)aminocarbonylphenoxy)-4-methylpyridin-2-yl)oxy]benzamidine, m.p. 145–150° C.; 3-[(3,5-difluoro-6-(3-(2-carboxyethylsphenoxy)-4-methylpyridin-2-y)oxy]benzamidine, trifluoroacetic acid salt; NMR (DMSO-$d_6$) 9.3 (s,2), 9.2 (s,2), 7.6 (m,4), 7.25 (t,1), 7.0 (m,2), 6.95 (m,l), 2.8 (t,2), 2.6 (m,2), 2.4 (s,3) ppm;

3-[(3,5-difluoro-6-(3-(carboxymethyl)phenoxy)-4-methylpyridin-2-yl)oxy]benzamidine, trifluoroacetic acid salt; NMR IDMSO-$d_6$) 9.3 (s,2), 9.2 (s,2), 7.6 (m,4), 7.25 (t,1), 7.0 (m,3), 3,.4 (s,2), 2.4 (s,3) ppm;

4-hydroxy-3-[(3,5-difluoro-6-(3-dimethylaminocarbonylphenoxy)-4-(4-carboxypiperidin-1-yl)pyridin-2-yl)oxy]benzamidine; NMR (DMSO-$d_6$) 9.75 (br,2), 8.5 (br,2), 7.5 (m,2), 7.3 (t,1), 7.0 (m,3), 6.65 (d,1), 3.6 (m,2), 3.2 (m,2), 2.95 (s,3), 2.8(s,3), 2.3 (m,1), 1.9 (m,2), 1.7 (m,2) ppm;

4-hydroxy-3-[(3,5-difluoro-6-3-dimethylaminocarbonylphenoxy)-4-(3- carboxypiperidin-1-yl)pyridin-2-yl)oxy]benzamidine; NMR (DMSO-d$_6$) 9.75 (br,2), 8.7 (br,2), 7.5 (m,2), 7.3 (t,1), 7.0 (m,3), 6.8 (d,1), 3.2–3.68 (m,4), 2.95 (s,3), 2.8 (s,3), 2.4 (m,1), 2.0 (m,1), 1.8 (m,1), 1.6 (m,2) ppm;

4-hydroxy-3-[(3,5-difluoro-6-(3-dimethylaminocarbonylphenoxy)-4-(4-carboxymethyl-piperazin-1-yl)pyridin-2-yl)oxy]benzamidine, trifluoroacetic acid salt; NMR (DMSO-d$_6$) 11.1 (s,1), 9.0 (br,2), 8.9 (br,2), 7.65 (m,2), 7.3 (m,1), 7.0 (m,4), 4.1 (s,2), 3.6 (m,8), 3.0 (s,3), 2.8 (s,3), ppm;

4-hydroxy-3-[16-(3-amidinophenoxy)-4-(carboxy)pyridin-2-ylioxy]benzamidine, trifluoroacetic acid salt; NMR (CDCl$_3$) 11.16 (s,1), 9.38–8.95 (m,8), 7.68–7.04 (m,9) ppm;

3-[(3,5-difluoro-6-(3-dimethylaminophenoxy)-4-(N-methyl-N-carboxymethylamino)pyridin-2-yl)oxy]benzamidine; NMR (DMSO-d$_6$) 9.3 (s,2), 9.2 (s,2), 7.5 (m,4), 7.2 (t,1), 6.7 (m,2), 6.5 (d,1), 4.2 (s,2), 3.2 (s,3), 2.9 (s,6) ppm; 4-hydroxy-3-[(3,5-difluoro-6-(3-dimethylaminophenoxy)-4-((methyl)(carboxymethyl)amino)pyridin-2-yl)oxy]benzamidine, trifluoroacetic acid salt;

4-hydroxy-3-[(3,5-difluoro-6-(3-(1-methylimidazolin-2-yl)phenoxy)-4-(3-carboxypiperidin-1-yl)pyridin-2-yl)oxy]benzamidine, trifluoroacetic acid salt;

4-hydroxy-3-[(3,5-difluoro-6-(3-(1-methylimidazolin-2-yl)phenoxy)-4-(5-carboxypyrrolidin-3-yloxy)pyridin-2-yl)oxy]benzamidine, trifluoroacetic acid salt; NMR (DMSO-d$_6$) 11.30 (s,1), 10.37 (s,1), 9.00 (s,2), 8.99 (s,2), 7.61 (d,1), 7.57 (dd, 1), 7.52–7.32 (m,4), 7.04 (d,1), 6.55 (s,1), 4.52 (dd,1), 4.02 (dd,2), 3.88 (dd,2), 3.72 (dd,1), 3.58 (d,1), 2.92 (s,3), 2.63 (dd,1), 2.44 (dd,1);

4-hydroxy-3-[(3,5-difluoro-6-(3-(1-methylimidazolin-2-yl)phenoxy)-4-(1-carboxymethylpiperidin-4-yloxy)pyridin-2-yl)oxy]benzamidine, trifluoroacetic acid salt; NMR (DMSO-d$_6$) 11.29 (s,1), 10.31 (s,1), 9.05 1s,2), 9.02 (s,2), 7.63–7.57 (m, 2), 7.52 (t,1), 7.42–7.37 (m,3), 7.04 (d,1), 4.92 (br s,1), 4.15 (s,2), 4.09–3.92 (m,4), 3.60–3.40 (m,4), 2.95 (s,3), 2.32–2.10 (m,4) ppm;

4-hydroxy-3-[(3,5-difluoro-6-(3-(1-methylimidazolin-2-yl)phenoxy)-4-(1-(1-carboxy-1-methylethyl)piperidinyloxy)pyridin-2-yl)oxy]benzamidine; NMR (DMSOd$_6$) 11.34 (s,1), 10.46 (s,1), 9.21 (s,2), 8.99(s,2), 7.70 (s,1), 7.63 (d, 1), 7.54 (t,1), 7.43–7.40 (m,2), 7.15 (d,1), 4.96 (br s,1), 4.12–4.09 (m,2), 3.96–3.90 (m,2), 3.40–3.20 (m,4), 2.97 (s,3), 2.40–2.30 (m,2), 2.28–2.14 (m,2), 1.54 (s,6) ppm;

4-hydroxy-3-[(3,5-difluoro-6-(3-(guanidino)phenoxy)-4-(1-carboxymethylpiperidin-4-yloxy)pyridin-2-yl)oxy]benzamidine, trifluoroacetic acid salt;

4-hydroxy-3-[(3,5-difluoro-6-(3-dimethylaminocarbonylphenoxy)-4-(2-methoxy-4-carboxyphenoxy)pyridin-2-yl)oxy]benzamidine, trifluoroacetic acid salt;

4-hydroxy-3-[3,5-difluoro-6-(3-(1-methylimidazolin-2-yl)phenoxy)-4-(carboxymethyl)(methyl)aminocarbonylpyridin-2-yl)oxy]benzamidine, trifluoroacetic acid salt;

4-hydroxy-3-[(3,5-difluoro-6-(3-dimethylaminophenoxy)-4-(1-carboxymethylpiperidin-4-yloxy)pyridin-2-yl)oxy]benzamidine, trifluoroacetic acid salt;

4-hydroxy-3-[(3,5-difluoro-6-(3-(1-methylimidazolin-2-yl)phenoxy)-4-(4-carboxypiperidin-1-yl)pyridin-2-yl)oxy]benzamidine, trifluoroacetic acid salt;

4-hydroxy-3-[(3,5-difluoro-6-(3-(1-methylimidazolin-2-yl)phenoxy)-4-(5-carboxypent-1-oxy)pyridin-2-yl)oxy]benzamidine, trifluoroacetic acid salt;

4-hydroxy-3-[(3,5-difluoro-6-(3-dimethylaminophenoxy)-4-((methyl)(carboxymethyl)aminocarbonylmethyl)amino)pyridin-2-yl)oxy]benzamidine, trifluoroacetic acid salt;

4-hydroxy-3-[(3,5-difluoro-6-(3-(1-methylimidazolin-2-yl)phenoxy)-4-(4-carboxymethylpiperazin-1-yl)pyridin-2-yl)oxy]benzamidine, trifluoroacetic acid salt;

4-hydroxy-3-[(3,5-difluoro-6-(3-dimethylaminophenoxy)-4-carboxymethoxypyridin-2-yl)oxy]benzamidine, trifluoroacetic acid salt;

4-hydroxy-3-[(3,5-difluoro-6-(3-dimethylaminophenoxy)-4-(1-(carboxymethyl)pyrrolidin-3-yloxy)pyridin-2-yl)oxy]benzamidine, trifluoroacetic acid salt;

4-hydroxy-3-[(3,5-difluoro-6-(3-dimethylaminocarbonylphenoxy)-4-(1-(carboxymethyl)pyrrolidin-3-yloxy)pyridin-2-yl)oxy]benzamidine, trifluoroacetic acid salt;

4-hydroxy-3-[(6-(3-(2,4-dimethylimidazol-1-yl)phenoxy)-4-(carboxy)pyridin-2-yl)oxy]benzamidine, trifluoroacetic acid salt;

4-hydroxy-3-[(6-(3-(2-methylimidazol-1-yl)phenoxy)-4-(carboxy)pyridin-2-yl)oxy]benzamidine, trifluoroacetic acid salt;

4-hydroxy-3-[(6-(3-(4-methylimidazol-1-yl)phenoxy)-4-(carboxy)pyridin-2-yl)oxy]benzamidin, trifluoroacetic acid salt;

4-hydroxy-3-[(3,5-difluoro-6-(3-dimethylaminophenoxy)-4-(4-carboxymethyl-piperazin-1-yl)pyridin-2-yl)oxy]benzamidine, trifluoroacetic acid salt;

4-hydroxy-3-[(3,5-difluoro-6-(3-dimethylaminophenoxy)-4-(4-carboxy-2-methoxyphenoxy)pyridin-2-yl)oxy]benzamidine, trifluoroacetic acid salt;

4-hydroxy-3-[(3,5-difluoro-6-(3-dimethylaminophenoxy)-4-(4-carboxy-2-(morpholin-4-ylmethyl)phenoxy)pyridin-2-yl)oxy]benzamidine, trifluoroacetic acid salt;

4-hydroxy-3-[(6-(3-(1-methylimidazolin-2-yl)phenoxy)-4-(carboxy)pyridin-2-yl)oxy]benzamidine, trifluoroacetic acid salt;

4-hydroxy-3-[(6-(3-(1-methylimidazol-2-yl)phenoxy)-4-(carboxy)pyridin-2-yl)oxy]benzamidine, trifluoroacetic acid salt;

4-amino-3-[(3,5-difluoro-6-(3-dimethylaminophenoxy)-4-((methyl)(carboxymethyl)amino)pyridin-2-yl)oxy]benzamidine, trifluoroacetic acid salt;

3-hydroxy-4-[(6-(3-(1-methylimidazolin-2-yl)phenoxy)-4-(carboxy)pyridin-2-yl)oxy]benzamidine, trifluoroacetic acid salt;

3-hydroxy-4-[(6-(3-(1-methylimidazol-2-yl)phenoxy)-4-(carboxy)pyridin-2-yl)oxy]benzamidine, trifluoroacetic acid salt;

4-hydroxy-3-[(6-(3-dimethylaminocarbonylphenoxy)-4-(carboxymethyl)(methyl)aminocarbonylpyridin-2-yl)oxy]benzamidine, trifluoroacetic acid salt;

4-hydroxy-3-[(3,5-difluoro-6-(3-(guanidino)phenoxy)-4-(4-carboxy-methylpiperazin-1-yl)pyridin-2-yl)oxy]benzamidine, trifluoroacetic acid salt;

4-hydroxy-3-[(6-(3-dimethylaminophenoxy)-4-(4-carboxymethylpiperazin-1-oyl)pyridin-2-yl)oxy]benzamidine; and 4-hydroxy-3-[(3,5-difluoro-6-(3-(1-methylimidazolin-2-yl)phenoxy)-4-(3-aminocarbonyl-5-carboxyphenoxy)pyridin-2-yl)oxy]benzamidine, trifluoroacetic acid salt.

C. In a similar manner, the following compounds are made:

4-hydroxy-3-[(3,5-difluoro-6-(3-dimethylaminocarbonyl)phenoxy)-4-(2-methoxy-5-carboxyphenoxy)pyridin-2-yl)oxy]benzamidine;

4-hydroxy-3-[(3,5-difluoro-6-(3-dimethylaminocarbonylphenoxy)-4-(2,3-dimethoxy-5-carboxyphenoxy)pyridin-2-yl)oxy]benzamidine;

4-hydroxy-3-[(3,5-difluoro-6-(3-dimethylaminocarbonylphenoxy)-4-(4-carboxyphenoxy)pyridin-2-yl)oxy]benzamidine;

4-hydroxy-3-[(3,5-difluoro-6-(3-dimethylaminocarbonylphenoxy)-4-(3-carboxyphenoxy)pyridin-2-yl)oxy]benzamidine;

4-hydroxy-3-[(3,5-difluoro-6-(3-dimethylaminocarbonylphenoxy)-4-(3,5-dicarboxyphenoxy)pyridin-2-yl)oxy]benzamidine;

4-hydroxy-3-[(3,5-difluoro-6-(3-dimethylaminocarbonylphenoxy)-4-(2,6-dimethoxy-4-carboxyphenoxy)pyridin-2-yl)oxy]benzamidine;

4-hydroxy-3-[(3,5-difluoro-6-(3-dimethylaminocarbonylphenoxy)-4-(2-chloro-4-carboxyphenoxy)pyridin-2-yl)oxy]benzamidine;

4-hydroxy-3-[(3,5-difluoro-6-(3-dimethylaminocarbonylphenoxy)-4-(2,6-dimethyl-4-carboxyphenoxy)pyridin-2-yl)oxy]benzamidine;

4-hydroxy-3-[(3,5-difluoro-6-(3-dimethylaminocarbonylphenoxy)-4-((1-carboxymethylpiperidin-4-yl)(methyl)amino)pyridin-2-yl)oxy]benzamidine;

4-hydroxy-3-[(3,5-difluoro-6-(3-dimethylaminocarbonylphenoxy)-4-((1-carboxymethylpiperidin-4-yl)amino)pyridin-2-yl)oxy]benzamidine; 4-hydroxy-3-[(3,5-difluoro-6-(3-dimethylaminocarbonylphenoxy)-4-( 2-methoxy-4-carboxymethylphenoxy)pyridin-2-yl)oxy]benzamidine;

4-hydroxy-3-[(3,5-difluoro-6-(3-dimethylaminocarbonylphenoxy)-4-(2,6-dimethoxy-4-(2-carboxyethenyl)phenoxy)pyridin-2-yl)oxy]benzamidine;

4-hydroxy-3-[(3,5-difluoro-6-(3-dimethylaminocarbonylphenoxy)-4-(3-(2-carboxyethenyl)phenoxy)pyridin-2-yl)oxy]benzamidine;

4-hydroxy-3-[(3,5-difluoro-6-(3-dimethylaminocarbonylphenoxy)-4-(4-(2-carboxyethenyl)phenoxy)pyridin-2-yl)oxy]benzamidine;

4-hydroxy-3-[(3,5-difluoro-6-(3-dimethylaminocarbonylphenoxy)-4-(2,6-dimethoxy-4-(2-carboxyethyl)phenoxy)pyridin-2-yl)oxy]benzamidine;

4-hydroxy-3-[(3,5-difluoro-6-(3-dimethylaminocarbonylphenoxy)-4-(3-(2-carboxyethyl)phenoxy)pyridin-2-yl)oxy]benzamidine;

4-hydroxy-3-[(3,5-difluoro-6-(3-dimethylaminocarbonylphenoxy)-4-(1-carboxymethylpiperidin-4-yloxy)pyridin-2-yl)oxy]benzamidine;

4-hydroxy-3-[(3,5-difluoro-6-(3-(1-methylimidazol-2-yl)phenoxy)-4-(1-carboxymethylpiperidin-4-yloxy)pyridin-2-yl)oxy]benzamidine;

4-hydroxy-3-[(3,5-difluoro-6-(3-(1-methylimidazol-2-yl)phenoxy)-4-(2-hydroxy-4-carboxyphenoxy)pyridin-2-yl)oxy]benzamidine;

4-hydroxy-3-[(3,5-difluoro-6-(3-dimethylaminocarbonylphenoxy)-4-(2-hydroxy-4-carboxyphenoxy)pyridin-2-yl)oxy]benzamidine;

4-hydroxy-3-[(3,5-difluoro-6-(3-(guanidino)phenoxy)-4-(2-hydroxy-4-carboxyphenoxy)pyridin-2-yl)oxy]benzamidine;

4-hydroxy-3-[(3,5-difluoro-6-(3-(guanidino)phenoxy)-4-(3-carboxypiperidin-1-yl)pyridin-2-yl)oxy]benzamidine;

4-hydroxy-3-[(3,5-difluoro-6-(3-(1-methylimidazol-2-yl)phenoxy)-4-(3-carboxypiperidin-1-yl)pyridin-2-yl)oxy]benzamidine;

4-hydroxy-3-[(3,5-difluoro-6-(3-(guanidinolphenoxy)-4-(4-carboxypiperidin-1-yl)pyridin-2-yl)oxy]benzamidine;

4-hydroxy-3-[(3,5-difluoro-6-(3-(1 1-methylimidazol-2-yl)phenoxy)-4-(4-carboxypiperidin-1-yl)pyridin-2-yl)oxy]benzamidine;

4-hydroxy-3-[(3,5-difluoro-6-(3-(1-methylimidazol-2-yl)phenoxy)-4-(5-carboxypent-1-oxy)pyridin-2-yl)oxy]benzamidine;

4-hydroxy-3-[(3,5-difluoro-6-(3-dimethylaminocarbonylphenoxy)-4-(5-carboxypent-1-oxy)pyridin-2-yl)oxy]benzamidine;

4-hydroxy-3-[(3,5-difluoro-6-(3-(guanidino)phenoxy)-4-(5-carboxypent-1-oxy)pyridin-2-yl)oxy]benzamidihe;

4-hydroxy-3-[(3,5-difluoro-6(3-(1-methylimidazol-2-yl)phenoxy)-4-(4-carboxymethylpiperazin-1-yl)pyridin-2-yl)oxy]benzamidine;

4-hydroxy-3-[(3,5-difluoro-6-(3-dimethylaminocarbonylphenoxy)- 4-(3-aminocarbonyl-5-carboxyphenoxy)pyridin-2-yl)oxy]benzamidine;

4-hydroxy-3-[(3,5-difluoro-6-(3-(guanidinolphenoxy)-4 (3-aminocarbonyl-5-carboxyphenoxy)pyridin-2-yl)oxy]benzamidine;

4-hydroxy-3-[(3,5-difluoro-6-(3-(1-methylimidazol-2-yl)phenoxy)-4-(3-aminocarbonyl-5-carboxyphenoxy)pyridin-2-yl)oxy]benzamidine;

4-hydroxy-3-[(3,5-difluoro-6-(3-dimethylaminocarbonylphenoxy)-4-(5-carboxypyrrolidin-3-yloxy)pyridin-2-yl)oxy]benzamidine;

4-hydroxy-3-[(3,5-difluoro-6-(3-(guanidino)phenoxy)-4-(5-carboxypyrrolidin-3-yloxy)pyridin-2-yl)oxy]benzamidine;

4-hydroxy-3-[(3,5-difluoro-6-(3-(1-methylimidazol-2-yl)phenoxy)-4-(5-carboxypyrrolidin-3-yloxy)pyridin-2-yl)oxy]benzamidine;

EXAMPLE 13

3-[(3,5-Difluoro-6-(3-((phenyl)hydroxymethyl)phenoxy)-4-methylpyridin-2-yl)oxy]-benzamidine, Trifluoroacetic Acid Salt A. To 3-[(3,5-difluoro-4-methyl-6-(3-((phenyl)oxomethyl)phenoxy)-pyridin-2-yl)oxy]benzamidine, acetic acid salt, (0.10 g, 0.19 mmol) in methanol was added Pd-C (75 mg). After stirring under hydrogen for 2.5 hours, the reaction was filtered, concentrated in vacuo, and purified by HPLC as described above in Example 5 to give 3-[(3,5- difluoro-6-(3-((phenyl(hydroxymethyl)phenoxy)-4-methyl-pyridin-2-yl)oxy]benzamidine, trifluoroacetic, acid salt; NMR (DMSO-d$_6$) 9.45 (s,2), 9.35 (s,2), 7.55 (m,4), 7.1–7.4 (m,8), 6.95 (m,1), 5.64 (s,1), 2.4 (s,3) ppm.

EXAMPLE 14

4-Hydroxy-3-[(3,5-dichloro-6-(3-dimethylaminocarbonylphenoxy)-4-(1-(1-iminoethyl)pyrrolidin-3-yloxy)pyridin-2-yl)oxy] benzamidine, Trifluoroacetic Acid Salt A. To ethanol (8 mL) was added 4-hydroxy-3-[(3,5-dichloro-6-(3-dimethylaminocarbonylphenoxy3-4-(pyrrolidin-3-yloxy)pyridin-2-yl)oxy]benzamidine (0.16 9, 0.20 mmoll, ethylacetimidate hydrochloride (74 mg, 0.6 mmol), and triethylamine (0.10 g, 1.0 mmol). After stirring for 2 hours, the reaction mixture was concentrated and purified by HPLC as described above in Example 5 to give 4-hydroxy-3-[(3,5-dichloro-6-(3-dimethylaminocarbonyl-phenoxy)-4-(1-(1-iminoethyl)pyrrolidin-3-yloxy)pyridin-2-yl)oxy]benzamidine, trifluoroacetic acid salt.

B. In a similar manner, the following compounds were made:

4-hydroxy-3-[(3,5-difluoro-6-(3-dimethylaminophenoxy)-4-(1-(1-iminoethyl) pyrrolidin-3-yloxy)pyridin-2-yl)oxy]benzamidine, triluoroacetic acid salt;

4-hydroxy-3-[(3,5-difluoro-6-(3-dimethylaminocarbonylphenoxy)-4-(1-(1-iminoethyl) pyrrolidin-3-yloxy)pyridin-2-yl)oxy]benzamidine, trifluoroacetic acid salt; and 4-hydroxy-3-[(3,5-difluoro-6-(3-dimethylaminocarbonylphenoxy)-4-(1-(1-iminoethyl)-pyrrolidin-3-yloxy)pyridin-2-yl)oxy]benzamidine, trifluoroacetic acid salt 6922.

C. In a similar manner, the following compounds are made:

4-hydroxy-3-[(3,5-difluoro-6-(3-(1-methylimidazolin-2-yl)phenoxy)-4-(1-(1-pyrrolidin-3-yloxy)pyridin-2-yl) oxy]benzamidine, trifluoroacetic acid salt;

4-hydroxy-3-[(3,5-difluoro-6-(3-(guanidino)phenoxy)-4-(1-(1-iminoethyl)-pyrrolidin-3-yloxy)pyridin-2-yl) oxy]benzamidine, trifluoroacetic acid salt; and 4-hydroxy-3-[(3,5-difluoro-6-(3-(1-methylimidazol-2-yl) phenoxy)-4-(1-(1-pyrrolidin-3-yloxy)pyridin-2-yl) oxy]benzamidine, trifluoroacetic acid salt.

EXAMPLE 15

This example illustrates the preparation of representative pharmaceutical compositions for oral administration containing a compound of the invention, or a pharmaceutically acceptable salt thereof, e.g., 4-hydroxy-3-[(3,5-difluoro-6-(3-(1-methylimidazolin-2-yl)phenoxy)-4-(2,3-dimethoxy-5-carboxyphenoxy)pyridin-2-yl)oxy]benzamidine:

| A. | Ingredients | % wt./wt. |
|---|---|---|
| | Compound of the invention | 20.0% |
| | Lactose | 79.5% |
| | Magnesium stearate | 0.5% |

The above ingredients are mixed and dispensed into hard-shell gelatin capsules containing 100 mg each.

| B. | Ingredients | % wt./wt. |
|---|---|---|
| | Compound of the invention | 20.0% |
| | Magnesium stearate | 0.9% |
| | Starch | 8.6% |
| | Lactose | 79.6% |
| | PVP (polyvinylpyrrolidine) | 0.9% |

The above ingredients with the exception of the magnesium stearate are combined arid granulated using water as a granulating liquid. The formulation is then dried, mixed with the magnesium stearate and formed into tablets with an appropriate tableting machine.

| C. | Ingredients | |
|---|---|---|
| | Compound of the invention | 0.1 g |
| | Propylene glycol | 20.0 g |
| | Polyethylene glycol 400 | 20.0 g |
| | Polysorbate 80 | 1.0 g |
| | Water | q.s. 100 mL |

The compound of the invention is dissolved in propylene glycol, polyethylene glycol 400 acid polysorbate 80. A sufficient quantity of water is then added with stirring to provide 100 mL of the solution which is filtered and bottled.

| A. | Ingredients | % wt./wt. |
|---|---|---|
| | Compound of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Compound of the invention | 1.0% |
| | Methyl or carboxymethyl cellulose | 2.0% |
| | 0.9% saline | q.s. 100 mL |

The compound of the invention is dissolved in the cellulose/saline solution, filtered and bottled for use.

EXAMPLE 16

This example illustrates the preparation of a representative pharmaceutical formulation for parenteral administration containing a compound of the invention, or a pharmaceutically acceptable salt thereof, e.g., 4-hydroxy-3-[(3,5-difluoro-6-(3-(1-methylimidazolin-2-yl)phenoxy)-4-(1-carboxymethylpiperidin-4-yloxy)pyridin-2-yl)oxy]-benzamidine:

| Ingredients | |
|---|---|
| Compound of the invention | 0.02 g |
| Propylene glycol | 20.0 g |

-continued

| Ingredients | |
|---|---|
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2, membrane filter and packaged under sterile conditions.

EXAMPLE 17

This example illustrates the preparation of a representative pharmaceutical composition in suppository form containing a compound of the invention, or a pharmaceutically acceptable salt thereof, e.g., 4-hydroxy-3-[(3,5-difluoro-6-(3-(1-methyl-imidazolin-2-yl)phenoxy)-4-(4-ethoxycarbonylmethylpiperazin-1-yl)pyridin-2-yl)oxy]benzamidine:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 18

This example illustrates the preparation of a representative pharmaceutical formulation for insufflation containing a compound of the invention, or a pharmaceutically acceptable salt thereof, e.g., 4-hydroxy-3-[(3,5-difluoro-6-(3-(guanidino)phenoxy)-4-(2-methoxy-4-carboxyphenoxy)pyridin-2-yl)oxy]benzamidine:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 19

This example illustrates the preparation of a representative pharmaceutical formulation in nebulized form containing a compound of the invention, or a pharmaceutically acceptable salt thereof, e.g., 4-hydroxy-3-[(3,5-difluoro-6-(3-(1-methylimidazolin-2-yl)phenoxy)-4-(2-methoxy-4carboxyphenoxy)pyridin-2-yl)-oxy]benzamidine:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 20

This example illustrates the preparation of a representative pharmaceutical formulation in aerosol form containing a compound of the invention, or a pharmaceutically acceptable salt thereof, e.g., 4-hydroxy-3-[(3,5-difluoro-6-(3-(1-methylimidazolin-2-yl)phenoxy)-4-(2-methoxy-5-ethoxycarbonylphenoxy)pyridin-2-yl)oxy]benzamidine:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 21

In vitro assay for Factor Xa, Thrombin and Tissue Plasminogen Activator

This assay demonstrates the activity of the compounds of the invention towards factor Xa, thrombin and tissue plasminogen activator. The activities were determined as an initial rate of cleavage of the peptide p-nitroanilide by the enzyme. The cleavage product, p-nitroaniline, absorbs at 405 nm with a molar extinction coefficient of 9920 $M^{-1}cm^{-1}$.

Reagents and Solutions:
Dimethyl sulfoxide (DMSO) (Baker analyzed grade).
Assay Buffer:
50 mM TrisHCl, 150 mM NaCl, 2.5 mM $CaCl_2$, and 0.1% polyethylene glycol 6000, pH 7.5.
Enzymes (Enzyme Research Lab.):
1. Human factor Xa stock solution: 0.281 mg/mL in assay buffer, stored at −80° C. (working solution (2x): 106 ng/mL or 2 nM in assay buffer, prepare prior to use).
2. Human thrombin stock solution: Stored at −80° C. (working solution (2x): 1200 ng/mL or 40 nM in assay buffer, prepare prior to used).
3. Human tissue plasminogen activator (tPA) (Two chains, Sigma) stock solution: 1 mg/mL, stored at −80° C. (working solution (2x): 1361 ng/mL in assay buffer, prepare prior to use).
Chromogenic substrates (Pharmacia Hepar Inc.):
1. S2222 (FXa assay) stock solution: 6 mM in $dH_2O$, store at 4° C. (working solution (4x): 656 μM in assay buffer).
2. S2302 (Thrombin assay) stock solution: 10 mM in $dH_20$, stored at 4° C. (working solution (4x): 1200 μM in assay buffer).
3. S2288 (tPA assay) stock solution: 10 mM in $dH_2O$, stored at 4° C. (working solution (4x): 1484 μM in assay buffer).

(All substrate working solutions were prepared on assay day 5.)

Standard inhibitor compound stock solution:
5 mM in DMSO, stored at −20° C.
Test compounds (compounds of the invention) stock solutions:
10 mM in DMSO, stored at −20° C.
Assay Procedure:
Assays were performed in 96-well microtiter plates in a total volume of 200 μl. Assay components were in final concentration of 50 mM TrisHCl, 150 mM NaCl, 2.5 mM CaCl$_2$, 0.19% polyethylene glycol 6000, pH 7.5, in the absence or presence of the standard inhibitor or the test compounds and enzyme and substrate at following concentrations: (1) 1 nM factor Xa and 164 μM S2222; (2) 20 nM thrombin and 300 μM S2302; and (3) 10 nM tPA and 371 μM S2288. Concentrations of the standard inhibitor compound in the assay were from 5 μM to 0.021 μM in 1 to 3 dilution. Concentration of the test compounds in the assay typically were from 10 μM to 0.041 μM in 1 to 3 dilution. For potent test compounds, the concentrations used in the factor Xa assay. were further diluted 100 fold (100 nM to 0.41 nM) or 1000 fold (10 nM to 0.041 nM). All substrate concentrations used are equal to their Km values under the present assay conditions. Assays were performed at ambient temperature.

The first step in the assay was the preparation of 10 mM test compound stock solutions in DMSO (for potent test compounds, 10 mM stock solutions were further diluted to 0.1 or 0.01 mM for the factor Xa assay), followed by the preparation of test compound working solutions (4×) by ; 3 serial dilutions of 10 mM stock solutions with Biomek 1000 (or Multiprobe 204) in 96 deep well plates as follows:
(a) Prepare a 40 μM working solution by diluting the 10 mM stock 1 to 250 in assay buffer in 2 steps: 1 to 100, and 1 to 2.5.
(b) Make another five serial dilutions (1:3) of the 40 μM solution (600 μl for each concentration). A total of six diluted test compound solutions were used in the assay.
Standard inhibitor compound (5 mM stock) or DMSO (control) went through the same dilution step; as those described above for test compounds.

The next step in the assay was to dispense 50 μl of the test compound working solutions (4×) (from 40 M to 0.164 M) in duplicate to microtiter plates with Biomek or MP204. To this was added 100 μl of enzyme working solution (2×) with Biomek or MP204. The resulting solutions were incubated at ambient temperature for 10 minutes.

To the solutions was added 50 pl of substrate working solution (4×) with Biomek or MP204.

The enzyme kinetics were measured at 405 nm at 10 seconds intervals for five minutes in a THERMOmax plate reader at ambient temperature.

Calculation of K$_i$ of the Test Compounds:

Enzyme rates were calculated as mOD/min based on the first two minutes readings. The IC$_{50}$ values were determined by fitting the data to the log-logit equation (linear) or the Morrison equation (non-linear) with an EXCEL spreadsheet. Ki values were then obtained by dividing the IC$_{50}$ by 2. Routinely, Ki(factor Xa) values less than 3 nM were calculated from the Morrison equation.

Compounds of the invention, when tested in this assay, demonstrated the selective ability to inhibit human factor Xa and human thrombin.

EXAMPLE 22

In vtiro Assay for Human Prothrombinase

This assay demonstrates the ability of the compounds of the invention to inhibit prothrombinase. Prothrombinase (PTase) catalyzes the activation of prothrombin to yield fragment 1.2 plus thrombin with meizothrombin as the intermediate. This assay is an end point assay. Activity of the prothrombinase is measured by activity of thrombin (one of the reaction products) or by the amount of thrombin formed/time based on a thrombin standard curve (nM vs mOD/min). For determination of IC$_{50}$ (PTase) of the compounds of the invention, PTase activity was expressed by thrombin activity (mOD/min).

Materials:

Enzymes:
1. Human factor Va (Haematologic Technologies Inc., Cat# HCVA-0110) working solution: 1.0 mg/mL in 50% glycerol, 2 mM CaCl$_2$, stored at −20° C.
2. Human factor Xa (Enzyme Res. Lab. cat# HFXa1011) working solution: 0.281 mg/mL in assay buffer (without BSA), stored at −80° C.
3. Human prothrombin (FII) (Enzyme Res. Lab., Cat# HP1002) working solution:
Diluted FII to 4.85 mg/mL in assay buffer (without BSA), stored at −80° C.

Phospholipid (PCPS) vesicles:
PCPS vesicles (80% PC, 20% PS) were prepared by modification of the method reported by
Barenholz et al., *Biochemistry* (1977), Vol. 16, pp. 2806–2810.

Phosphatidyl serine (Avanti Polar Upids, Inc., Cat#840032):
10 mg/mL in chloroform, purified from brain, stored −20° C. under nitrogen or argor.

Phosphatidyl Choline (Avanti Polar Lipids, Inc., Cat# 850457):
50 mg/ml in chloroform, synthetic 16:0–18:1 Palmitoyl-Oleoyl, stored at −20° C. under nitrogen or argon.

Spectrozyme-TH (American Diagnostica Inc., Cat# 238L, 50 μmoles, stored at room temperature) working solution:
Dissolved 50 prmoles in 10 mL dH$_2$O.

BSA (Sigma Chem Co., Cat# A-7888, FractionV, RIA grade).

Assay buffer: 50 mM TrisHCl, pH 7.5, 150 mM NaCl, 2.5 mM CaCl$_2$, 0.1% PEG 6000 (BDH), 0.05% BSA (Sigma, Fr.V, RIA grade).

For one plate assay. prepare the following working solutions:
1. Prothrombinase complex:
   (a) 100 μM PCPS (27.5 μl of PCPS stock (4.36 mM) diluted to final 1200 μl with assay buffer.
   (b) 25 nM Human factor Va: 5.08 μl of Va stock(1 mg/mL) was diluted to final 1200 μl with assay buffer.
   (c) 5 μM Human factor Xa: Dilute Xa stock (0.281 mglmL) 1:1,220,000 with assay buffer. Prepare at least 1200 μl.
   Combine equal volumes (1100 μl) of each component in the order of PCPS, Va and Xa. Let stand at ambient temperature for 5 to 10 minutes and use immediately or store in ice (brini to ambient temperature before use).
2. 6 μM Human prothrombin (FII): dilute 124 μL of FII stock (4.85 mg/mL) to final 1400 μL with assay buffer.
3. 20 mM EDTAlAssay buffer: 0.8 mL of 0.5 M EDTA (pH 8.5) plus 19.2 mL assay buffer.
4. 0.2 mM Spectrozyme-TH/EDTA buffer: 0.44 mL of SPTH stock (5 mM) plus 10.56 mL of 20 mM EDTA/assay buffer.

5. Test compounds (compounds of the invention):
   Prepare a working solution (5X) from 10 mM stock (DMSO) and make a series of 1:3 dilution.
   Compounds were assayed at 6 concentrations in duplicate.

Assay Conditions and Procedure:
Prothrombinase reaction was performed in final 50 μL of mixture containing PTase (20 M PCPS, 5 nM hFVa, and 1 μM hFXa), 1.2 M human factor II and varied concentration of the test compounds (5 μM to 0.021 μM or lower concentration range). Reaction was started by addition of PTase and incubated for 6 minutes at room temperature. Reaction was stopped by addition of EDTA/buffer to final 10 mM. Activity of thrombin (product) was then measured in the presence of 0.1 mM of Spectrozyme-TH as substrate at 405 nm for 5 minutes (10 seconds intervals) at ambient temperature in a THEROmax microplate reader. Reactions were performed in 96-well microtiter plates.

In the first step of the assay, 10 μl of diluted test compound (5X) or buffer was added to the lates in duplicate. Then 10 μl of prothombin (hFII) (5X) was added to each well. Next 30 μl PTase was added to each well, mix for about 30 seconds. The plates were then incubated at ambient temperature for 6 minutes.

In the next step, 50 μl of 20 mM EDTA tin assay buffer) was added to each well to stop the reaction. The resulting solutions were then mixed for about 10 seconds. Then 100 μl of 0.2 mW spectrozyme was added to each well. The thrombin reaction rate was then measured at 405 nm for 5 minutes at 10 seconds intervals in a Molecular Devices microplate reader.

Calculations:
Thrombin reaction rate was expressed as mOD/miri. using OD readings from the five minute reaction. $IC_{50}$ values were calculated with the log-logit curve fit program.

The compounds of the invention demonstrated the ability to inhibit pro-thrombinase when tested in this assay.

EXAMPLE 23

In vivo Assay

The following assay demonstrates the ability of the compounds to act as anti-coagulants.

Male rats (250–330 g) were anesthetized with sodium pentobarbital (90 mg/kg, i.p.) and prepared for surgery. The left carotid artery was cannulated for the measurement of blood pressure as well as for taking blood samples to monitor clotting variables (prothrombin time (PT) and activated partial thromboplastin time (aPTT)). The tail vein was cannulated for the purpose of administering the test compounds (ie., the compounds of the invention and standards) and the thromboplastin infusion. The abdomen was opened via a mid-line incision and the abdominal vena cava was isolated for 2–3 cm distal to the renal vein. All venous branches in this 2–3 cm segment of the abdominal vena cava were ligated. Following all surgery, the animals were allowed to stabilize prior to beginning the experiment. Test compounds were administered as an intravenous bolus (t=0). Three minutes, later (t=3), a 5-minute infusion of thromboplastin was begun. Two minutes into the infusion (t=5), the abdominal vena cava was ligated at both the proximal and distal ends. The vessel was left in place for 60 minutes, after which it was excised from the animal, slit open, the clot (if any) carefully removed, and weighed. Statistical analysis on the results was performed using a Wilcoxin-matched-pairs signed rank test.

The compounds of the invention, when tested in this assay, demonstrated the ability and to inhibit the clotting of the blood.

While the present invention has been described with reference to the specific embodiments thereof, it should be understood by those skilled in the art that various changes may be made and equivalents may be substituted without departing from the true spirit and scope of the invention. Ir addition, many modifications may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A compound of selected from the group consisting of the following formulae:

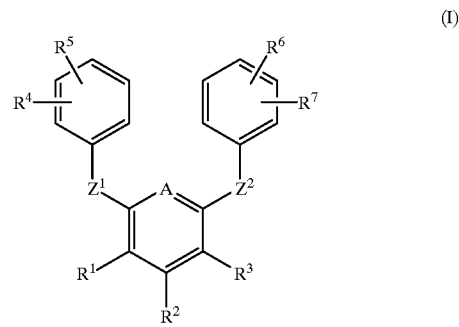

(I)

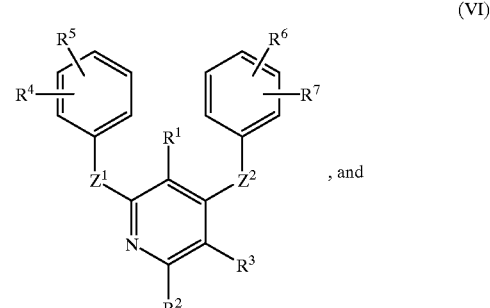

(VI)

, and

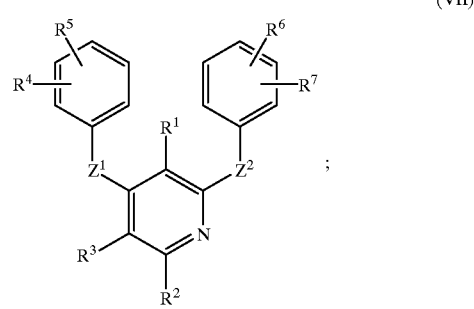

(VII)

;

wherein
  A is —N═;
  $Z^1$ and $Z^2$ are independently —N($R^8$)— or —S—;
  $R^1$ and $R^3$ are independently hydrogen, halo, alkyl, haloalkyl, alkoxy, haloalkoxy, nitro, —N($R^8$)$R^9$, —C(O)O$R^8$, —C(O)N($R^8$)$R^9$, —C(O)N(W)CH$_2$C(O)N($R^8$)$R^9$, —N($R^8$)C(O)N($R^8$)$R^9$, —N($R^8$)C(O)$R^8$, —N($R^8$)S(O)$_2R^{12}$, or —N($R^8$)C(O)N($R^8$)CH$_2$C(O)N($R^8$)$R^9$;
  $R^2$ is hydrogen; halo; alkyl; haloalkoxy; —O$R^8$; —C(O)O$R^8$; —C(O)N($R^8$)$R^9$; —N($R^8$)$R^9$; —C(O)N($R^8$)

$(CH_2)_mC(O)OR^8$ (where m is 0 to 3); —$N(R^8)(CH_2)_nC(O)OR^8$ (where n is 1 to 3); —$N((CH_2)_nN(R^8)R^9)(CH_2)_nC(O)OR^8$ (where each n is 1 to 3); —$O(CH_2)_nC(O)N(R^8)R^9$ (where n is 1 to 3); —$O(CH_2)_pC(O)OR^8$ (where p is 1 to 6); —$N(R^8)(CH_2)_nC(O)N(R^8)(CH_2)_nC(O)OR^8$ (where each n is independently 1 to 3); morpholin-4-yl; 3-tetrahydrofuranoxy;

or $R^2$ is aryloxy (optionally substituted by one or more substituents independently selected from the group consisting of —$OR^8$, —$C(O)N(R^8)R^9$, halo, alkyl, carboxy, alkoxycarbonyl, haloalkoxy, haloalkoxycarbonyl, alkoxycarbonylalkyl, carboxyalkyl, aminocarbonylalkyl, (alkylamino) carbonylalkyl, (dialkylamino)carbonylalkyl, (arylamino)carbonylalkyl, (aralkylamino) carbonylalkyl, alkoxycarbonylalkenyl, carboxyalkenyl, aminocarbonylalkenyl, (alkylamino)carbonylalkenyl, (dialkylamino)carbonylalkenyl, (arylamino) carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy) alkoxycarbonyl, tetrazolyl, morpholin-4-ylalkyl, and (1,2)-imidazolinyl (optionally substituted by alkyl));

or $R^2$ is piperazin-1-yl (optionally substituted by one or more substituents independently selected from the group consisting of alkyl, carboxy, —$C(O)N(R^8)R^9$, carboxyalkyl, alkoxycarbonyl, and alkoxycarbonylalkyl);

or $R^2$ is 1-piperazinoyl (optionally substituted by one or more substituents selected from the group consisting of alkyl, carboxy, —$C(O)N(R^8)R^9$, carboxyalkyl, alkoxycarbonyl, and alkoxycarbonylalkyl);

or $R^2$ is piperidin-1-yl (optionally substituted by one or more substituents selected from the group consisting of carboxy, —$C(O)N(R^8)R^9$, carboxyalkyl, alkoxycarbonyl, and alkoxycarbonylalkyl);

or $R^2$ is (3,4)-piperidinyloxy (optionally substituted by one or more substituents selected from the group consisting of alkylcarbonyl, carboxy, —$C(O)N(R^8)R^9$, alkoxycarbonyl, carboxyalkyl, alkoxycarbonylalkyl, and tetrazolylalkyl);

or $R^2$ is piperidin-4-ylamino (wherein the amino is optionally substituted by alkyl and the piperidinyl group is optionally substituted by one or more substituents selected from the group consisting of alkyl, alkoxycarbonyl, carboxyalkyl, —$C(O)N(R^8)R^9$, alkoxycarbonylalkyl and aralklyl);

or $R^2$ is 3-pyrrolidinyloxy (optionally substituted by one or more substituents selected from the group consisting of alkyl, aralkyl, amidino, 1-iminoethyl, carboxy, carboxyalkyl, —$C(O)N(R^8)R^9$, alkoxycarbonyl and alkoxycarbonylalkyl);

$R^4$ and $R^7$ are independently hydrogen, halo, alkyl, nitro, —$OR^8$, —$C(O)OR^8$, —$C(O)N(R^8)R^9$, —$N(R^8)R^9$, —$N(H)C(O)R^8$, or —$N(H)S(O)_2R^{12}$;

$R^5$ is —$C(NH)NH_2$, —$C(NH)N(H)OR^8$, —$C(NH)N(H)C(O)OR^{12}$, —$C(NH)N(H)S(O)_2R^{12}$, —$C(NH)N(H)C(O)N(R^8)R^9$, or —$C(NH)N(H)C(O)R^8$;

$R^6$ is halo, alkyl, haloalkyl, haloalkoxy, nitro, amino, ureido, guanidino, —$OR^8$, —$C(NH)NH_2$, —$C(NH)NHOH$, —$C(O)R^{10}$, —$(CH_2)_mC(O)N(R^8)R^9$ (where m is 0 to 3), —$CH(OH)C(O)N(R^8)R^9$, —$(CH_2)_mN(R^8)R^9$ (where m is 0 to 3), —$(CH_2)_mC(O)OR^8$ (where m is 0 to 3), —$N(H)C(O)R^8$, (1,2)-tetrahydropyrimidinyl (optionally substituted by alkyl), (1,2)-imidazolyl (optionally substituted by alkyl), or (1,2)-imidazolinyl (optionally substituted by alkyl);

each $R^8$ and $R^9$ is independently hydrogen, alkyl, aryl, or aralkyl;

$R^{10}$ is hydrogen, alkyl, aryl, aralkyl, 1-pyrrolidinyl, 4-morpolinyl, 4-piperazinyl, 4-(N-methyl)piperazinyl, or piperidin-1-yl; and $R^{12}$ is alkyl, aryl or aralkyl;

or a pharmaceutically acceptable salt thereof.

2. The compound of claim 1 selected from formula (I):

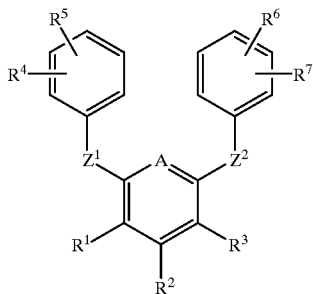

(I)

A is —N═;

$Z^1$ and $Z^2$ are both —$N(R^8)$—;

$R^1$ and $R^3$ are independently hydrogen, fluoro, chloro, haloalkyl, —$N(R^8)R^9$, —$C(O)OR^8$, —$C(O)N(R^8)R^9$, —$N(R^8)C(O)N(R^8)R^9$, —$N(R^8)C(O)R^8$, or —$N(R^8)S(O)_2R^{12}$;

$R^2$ is hydrogen; halo; alkyl; haloalkoxy; —$OR^8$; —$C(O)OR^8$; —$C(O)N(R^8)R^9$; —$N(R^8)R^9$; $C(O)N(R^8)(CH_2)_mC(O)OR^8$ (where m is 0 to 3); —$N(R^8)(CH_2)_nC(O)OR^8$ (where is 1 to 3); —$N((CH_2)_nN(R^8)R^9)(CH_2)_nC(O)OR^8$ (where each n is 1 to 3); —$O(CH_2)_nC(O)N(R^8)R^9$ (where n is 1 to 3); —$O(CH_2)_pC(O)OR^8$ (where p is 1 to 6); —$N(R^8)(CH_2)_nC(O)N(R^8)(CH_2)_nC(O)OR^8$ (where each n is independently 1 to 3); morpholin-4-yl; 3-tetrahydrofuranoxy;

or $R^2$ is aryloxy (optionally substituted by one or more substituents independently selected from the group consisting of —$OR^8$, —$C(O)N(R^8)R^9$, halo, alkyl, carboxy, alkoxycarbonyl, haloalkoxy, haloalkoxycarbonyl, alkoxycarbonylalkyl, carboxyalkyl, aminocarbonylalkyl, (alkylamino) carbonylalkyl, (dialkylamino)carbonylalkyl, (arylamino)carbonylalkyl, (aralkylamino) carbonylalkyl, alkoxycarbonylalkenyl, carboxyalkenyl, aminocarbonylalkenyl, (alkylamino)carbonylalkenyl, (dialkylamino)carbonylalkenyl, (arylamino) carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy) alkoxycarbonyl, tetrazolyl, morpholin-4-ylalkyl, and (1,2)-imidazolinyl (optionally substituted by alkyl));

or $R^2$ is piperazin-1-yl (optionally substituted by one or more substituents independently selected from the group consisting of alkyl, carboxy, —$C(O)N(R^8)R^9$, carboxyalkyl, alkoxycarbonyl, and alkoxycarbonylalkyl);

or $R^2$ is 1-piperazinoyl (optionally substituted by one or more substituents selected from the group consisting of alkyl, carboxy, —$C(O)N(R^8)R^9$, carboxyalkyl, alkoxycarbonyl, and alkoxycarbonylalkyl);

or $R^2$ is piperidin-1-yl (optionally substituted by one or more substituents selected from the group consisting of carboxy, —C(O)N(R⁸)R⁹, carboxyalkyl, alkoxycarbonyl, and alkoxycarbonylalkyl);

or R² is (3,4)-piperidinyloxy (optionally substituted by one or more substituents selected from the group consisting of alkylcarbonyl, carboxy, —C(O)N(R⁸)R⁹, alkoxycarbonyl, carboxyalkyl, alkoxycarbonylalkyl, and tetrazolylalkyl);

or R² is piperidin-4-ylamino (wherein the amino is optionally substituted by alkyl and the piperidinyl group is optionally substituted by one or more substituents selected from the group consisting of alkyl, alkoxycarbonyl, carboxyalkyl, —C(O)N(R⁸)R⁹, alkoxycarbonylalkyl and aralklyl);

or R² is 3-pyrrolidinyloxy (optionally substituted by one or more substituents selected from the group consisting of alkyl, aralkyl, amidino, 1-iminoethyl, carboxy, carboxyalkyl, —C(O)N(R⁸)R⁹, alkoxycarbonyl and alkoxycarbonylalkyl);

R⁴ is hydrogen, —OR⁸ or —N(R⁸)R⁹;

R⁵ is —C(NH)NH₂;

R⁶ is guanidino, —C(NH)NH₂, —C(O)N(R⁸)R⁹, —CH(OH)C(O)N(R⁸)R⁹, —(CH₂)ₘN(R⁸)R⁹ (where m is 0 to 3), 1-piperidinoyl, 1-pyrrolidinoyl, (1,2)-imidazolyl (optionally substituted by alkyl), or (1,2)-imidazolinyl (optionally substituted by alkyl);

R⁷ is hydrogen, halo, alkyl, —OR⁸, or —C(O)N(R⁸)R⁹;

each R⁸ and R⁹ is independently hydrogen, methyl, ethyl or phenyl; and

R¹² is methyl, ethyl, phenyl or benzyl.

3. The compound of claim 2 wherein:

$Z^1$ and $Z^2$ are both —N(CH₃)—;

R¹ and R³ are independently hydrogen, fluoro, chloro, trifluoromethyl, amino, —C(O)N(R⁸)R⁹, or —NHC(O)NHR⁹;

R² is hydrogen; halo; alkyl; haloalkoxy; —OR⁸; —C(O)OR⁸; —N(R⁸)R⁹; —N(R⁸)(CH₂)ₙC(O)OR⁸ (where n is 1 to 3); —N((CH₂)ₙN(R⁸)R)(CH₂)ₙC(O)OR⁸ (where each n is 1 to 3); —O(CH₂)ₙC(O)N(R⁸)R⁹ (where n is 1 to 3); —O(CH₂)ₚC(O)OR_e (where p is 1 to 6); —N(RW)(CH₂)ₙC(O)N(R⁸)(CH₂)ₙC(O)OR⁸ (where each n is independently 1 to 3); morpholin; or 3-tetrahydrofuranoxy;

or R² is aryloxy (optionally substituted by one or more substituents independently selected from the group consisting of —OR⁸, —C(O)N(R⁸)R⁹, halo, alkyl, carboxy, alkoxycarbonyl, alkoxycarbonylalkyl, carboxyalkyl, alkoxycarbonylalkenyl, carboxyalkenyl, tetrazolyl, morpholin-4-ylalkyl, and (1,2)imidazolinyl (optionally substituted by alkyl));

or R² is piperazin-1-yl (optionally substituted by one or more substituents independently selected from the group consisting of alkyl, —C(O)N(R⁸)R⁹, carboxyalkyl, and alkoxycarbonylalkyl);

or R² is piperidin-1-yl (optionally substituted by one or more substituents selected from the group consisting of —C(O)N(R⁸)R⁹, carboxy and alkoxycarbonyl);

or R² is (3,4)-piperidinyloxy (optionally substituted by one or more substituents selected from the group consisting of —C(O)N(R⁸)R⁹, carboxyalkyl and alkoxycarbonylalkyl);

or R² is piperidin-4-ylamino (wherein the amino is optionally substituted by alkyl and the piperidinyl group is optionally substituted by one or more substituents selected from the group consisting of —C(O)N(R⁸)R⁹, carboxyalkyl, alkoxycarbonylalkyl and aralklyl);

or R² is 3-pyrrolidinyloxy (optionally substituted by one or more substituents selected from the group consisting of —C(O)N(R⁸)R⁹, 1-iminoethyl, carboxy, carboxyalkyl, alkoxycarbonyl and alkoxycarbonylalkyl);

R⁴ is hydrogen, amino, hydroxy, or methoxy;

R⁵ is —C(NH)NH₂;

R⁶ is guanidino, —C(NH)NH₂, —C(O)N(R⁸)R⁹, —(CH₂)ₘN(R⁸)R⁹ (where m is 0 to 1), (1,2)-imidazolyl substituted by alkyl, or (1,2)-imidazolinyl substituted by alkyl;

R⁷ is hydrogen, methoxy or hydroxy; and each R⁸ and R⁹ is independently hydrogen, methyl, ethyl or phenyl.

4. A compound selected from the group consisting of the following formulae:

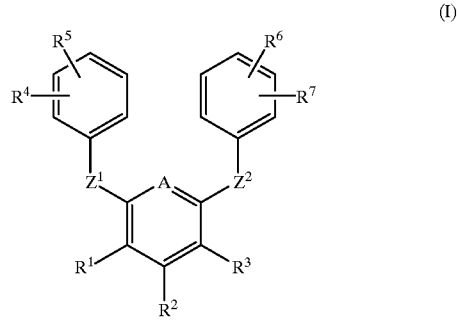

(I)

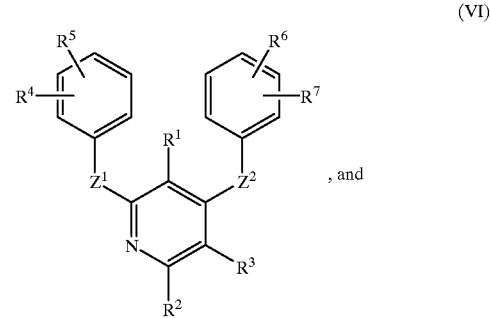

(VI)

, and

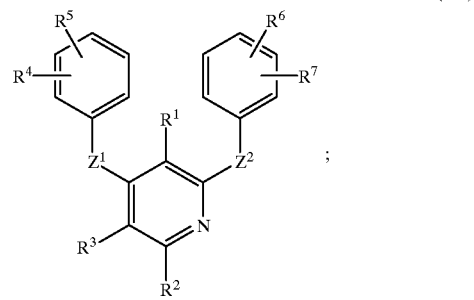

(VII)

;

wherein

A is —N═;

$Z^1$ and $Z^2$ are independently —O —N(R) or —S;

R¹ and R³ are independently hydrogen, halo, alkyl, haloalkyl, alkoxy, haloalkoxy, nitro, —N(R⁸)R⁹, —C(O)ORW, —C(O)N(R⁸)R⁹, —C(O)N(R⁸)CH₂C(O)N(R⁸)R⁹, —N(R⁸)C(O)N(R⁸)R⁹, —N(R⁸)C(O)R⁸, —N(R⁸)S(O)₂R¹², or —N(R⁸)G(O)N(R⁸)OH₂C(O)N(R⁸)R⁹;

R² is hydrogen; halo; alkyl; haloalkoxy; —OR⁸; —C(O)ORI; —C(O)N(R⁸)R⁹; —N(R⁸)R⁹; —C(O)N(R⁸)

$(CH_2)_mC(O)OR^8$ (where m is 0 to 3); —$N(R^8)(CH_2)_nC(O)OR^8$ (where n is 1 to 3); —$N((CH_2)_nN(R^8)R^9)(CH_2)_nC(O)OR^8$ (where each n is 1 to 3); —$O(CH_2)_nC(O)N(R^8)R^9$ (where n is 1 to 3); —$O(CH_2)_pC(O)OR^8$ (where p is 1 to 6); —$N(R^8)(CH_2)_nC(O)N(R^8)(CH_2)_nC(O)OR^8$ (where each n is independently 1 to 3); morpholin-4-yl; 3tetrahydrofuranoxy;

or $R^2$ is aryloxy (optionally substituted by one or more substituents independently selected from the group consisting of —$OR^8$, —$C(O)N(R^8)R^9$, halo, alkyl, carboxy, alkoxycarbonyl, haloalkoxy, haloalkoxycarbonyl, alkoxycarbonylalkyl, carboxyalkyl, aminocarbonylalkyl, (alkylamino)carbonylalkyl, (dialkylamino)carbonylalkyl, (arylamino)carbonylalkyl, (aralkylamino)carbonylalkyl, alkoxycarbonylalkenyl, carboxyalkenyl, aminocarbonylalkenyl, (alkylamino)carbonylalkenyl, (dialkylamino)carbonylalkenyl, (arylamino)carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy)alkoxycarbonyl, tetrazolyl, morpholin-4-ylalkyl, and (1,2)-imidazolinyl (optionally substituted by alkyl));

or $R^2$ is piperazin-1-yl (optionally substituted by one or more substituents independently selected from the group consisting of alkyl, carboxy, —$C(O)N(R^8)R^9$, carboxyalkyl, alkoxycarbonyl, and alkoxycarbonylalkyl);

or $R^2$ is 1-piperazinoyl (optionally substituted by one or more substituents selected from the group consisting of alkyl, carboxy, —$C(O)N(R^8)R^9$, carboxyalkyl, alkoxycarbonyl, and alkoxycarbonylalkyl);

or $R^2$ is piperidin-1-yl (optionally substituted by one or more substituents selected from the group consisting of carboxy, —$C(O)N(R^8)R^9$, carboxyalkyl, alkoxycarbonyl, and alkoxycarbonylalkyl);

or $R^2$ is piperidin-4-ylamino (wherein the amino is optionally substituted by alkyl and the piperidinyl group is optionally substituted by one or more substituents selected from the group consisting of alkyl, alkoxycarbonyl, carboxyalkyl, —$C(O)N(R^8)R^9$, alkoxycarbonylalkyl and aralklyl);

$R^4$ and $R^7$ are independently hydrogen, halo, alkyl, nitro, $R^8$, —$C(O)OR^8$, —$C(O)N(R^8)R^9$, —$N(RW)R^9$, —$N(H)C(O)R^8$, or —$N(H)S(O)_2R^{12}$;

$R^5$ is —$C(NH)NH_2$, —$C(NH)N(H)OR^8$, —$C(NH)N(H)C(O)OR^{12}$, —$C(NH)N(H)S(O)_2R^{12}$, —$C(NH)N(H)C(O)N(R^8)R^9$, or —$C(NH)N(H)C(O)R^8$;

$R^6$ is halo, alkyl, haloalkyl, haloalkoxy, nitro, amino, ureido, guanidino, —$OR^8$, —$C(NH)NH_2$, —$C(NH)NHOH$, —$C(O)R^{10}$, —$(CH_2)_mC(O)N(R^8)R^9$ (where m is 0 to 3), —$CH(OH)C(O)N(R^8)R^9$, —$(CH_2)_mN(R^8)R^9$ (where m is 0 to 3), —$(CH_2)_mC(O)OR^8$ (where m is 0 to 3), —$N(H)C(O)R^8$, (1,2)-tetrahydropyrimidinyl (optionally substituted by alkyl), (1,2)-imidazolyl (optionally substituted by alkyl), or (1,2)-imidazolinyl (optionally substituted by alkyl);

each $R^8$ and $R^9$ is independently hydrogen, alkyl, aryl, or aralkyl;

$R^{10}$ is hydrogen, alkyl, aryl, aralkyl, 1-pyrrolidinyl, 4-morpholinyl, 4-piperazinyl, 4-(Nmethyl)piperazinyl, or piperidin-1-yl; and $R^{12}$ is alkyl, aryl or aralkyl;

or a pharmaceutically acceptable salt thereof.

5. The compound of claim 4 selected from formula (I):

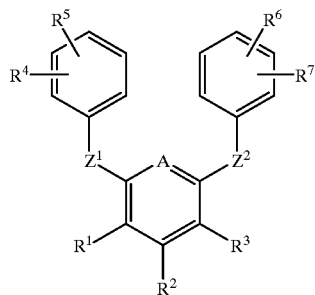

(I)

wherein:

A is —N=;

$Z^1$ and $Z^2$ are independently —O— or —$N(R^8)$—;

$R^1$ and $R^3$ are independently hydrogen, fluoro, chloro, haloalkyl, —$N(R^8)R^9$, —$C(O)OR^8$, —$C(O)N(R^8)R^9$, —$N(R^8)C(O)N(R^8)R^9$, —$N(R^8)C(O)R^8$, or —$N(R^8)S(O)_2R^{12}$;

$R^2$ is hydrogen; halo; alkyl; haloalkoxy; —$OR^8$; —$C(O)OR^8$; —$C(O)N(R^8)R^9$; —$N(R^8)R^9$; —$C(O)N(R^8)(CH_2)_mC(O)OR^8$ (where m is 0 to 3); —$N(R^8)(CH_2)_nC(O)ORR^8$ (where n is 1 to 3); —$N((CH_2)_nN(R^8)R^9)(CH_2)_nC(O)OR^8$ (where each n is 1 to 3); —$O(CH_2)_nC(O)N(R^8)R^9$ (where n is 1 to 3); —$O(CH_2)_pC(O)OR^8$ (where p is 1 to 6); —$N(R^8)(CH_2)_nC(O)N(R^8)(CH_2)_nC(O)OR^8$ (where each n is independently 1 to 3); morpholin-4-yl; 3-tetrahydrofuranoxy;

or $R^2$ is aryloxy (optionally substituted by one or more substituents independently selected from the group consisting of —$OR^8$, —$C(O)N(R^8)R^9$, halo, alkyl, carboxy, alkoxycarbonyl, haloalkoxy, haloalkoxycarbonyl, alkoxycarbonylalkyl, carboxyalkyl, aminocarbonylalkyl, (alkylamino)carbonylalkyl, (dialkylamino)carbonylalkyl, (arylamino)carbonylalkyl, (aralkylamino)carbonylalkyl, alkoxycarbonylalkenyl, carboxyalkenyl, aminocarbonylalkenyl, (alkylamino)carbonylalkenyl, (dialkylamino)carbonylalkenyl, (arylamino)carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy)alkoxycarbonyl, tetrazolyl, morpholin-4-ylalkyl, and (1,2)-imidazolinyl (optionally substituted by alkyl));

or $R^2$ is piperazin-1-yl (optionally substituted by one or more substituents independently selected from the group consisting of alkyl, carboxy, —$C(O)N(R^8)R^9$, carboxyalkyl, alkoxycarbonyl, and alkoxycarbonylalkyl);

or $R^2$ is 1-piperazinoyl (optionally substituted by one or more substituents selected from the group consisting of alkyl, carboxy, —$C(O)N(R^8)R^9$, carboxyalkyl, alkoxycarbonyl, and alkoxycarbonylalkyl);

or $R^2$ is piperidin-1-yl (optionally substituted by one or more substituents selected from the group consisting of carboxy, —$C(O)N(R^8)R^9$, carboxyalkyl, alkoxycarbonyl, and alkoxycarbonylalkyl);

or $R^2$ is piperidin-4-ylamino (wherein the amino is optionally substituted by alkyl and the piperidinyl group is optionally substituted by one or more substituents selected from the group consisting of alkyl, alkoxycarbonyl, carboxyalkyl, —$C(O)N(R^8)R^9$, alkoxycarbonylalkyl and aralklyl);

$R^4$ is hydrogen, $OR^8$ or —$N(R^8)R^9$;

$R^5$ is —$C(NH)NH_2$;

$R^6$ is guanidino, —$C(NH)NH_2$, —$C(O)N(R^8)R^9$, —$CH(OH)C(O)N(R^8)R^9$, —$(CH_2)_mN(R^8)R^9$ (where m is 0 to 3), 1-piperidinoyl, 1-pyrrolidinoyl, (1,2)-imidazolyl (optionally substituted by alkyl), or (1,2)-imidazolinyl (optionally substituted by alkyl);

$R^7$ is hydrogen, halo, alkyl, —$OR^8$, or —$C(O)N(R^8)R^9$;

each $R^8$ and $R^9$ is independently hydrogen, methyl, ethyl or phenyl; and $R^{12}$ is methyl, ethyl, phenyl or benzyl.

6. The compound of claim 5 wherein:

$Z^1$ and $Z^2$ are independently or —$N(CH_3)$—;

$R^1$ and $R^3$ are independently hydrogen, fluoro, chloro, trifluoromethyl, amino, —$C(O)N(R^8)R^9$, or —$NHC(O)NHR^9$;

$R^2$ is hydrogen; halo; alkyl; haloalkoxy; —$OR^8$; —$C(O)OR^8$; —$N(R^8)R^9$; —$N(R^8)(CH_2)_nC(O)OR^8$ (where n is 1 to 3); —$N((CH_2)_nN(R^8)R)(CH_2)_nC(O)OR^8$ (where each n is 1 to 3); —$O(CH_2)_nC(O)N(R^8)R^9$ (where n is 1 to 3); —$O(CH_2)_nC(O)OR^8$ (where p is 1 to 6); —$N(R^8)(CH_2)_nC(O)N(R^8)(CH_2)_nC(O)OR^8$ (where each n is independently 1 to 3); morpholin-4-yl; or 3-tetrahydrofuranoxy;

or $R^2$ is aryloxy (optionally substituted by one or more substituents independently selected from the group consisting of —$OR^8$, —$C(O)N(R^8)R^9$, halo, alkyl, carboxy, alkoxycarbonyl, alkoxycarbonylalkyl, carboxyalkyl, alkoxycarbonylalkenyl, carboxyalkenyl, tetrazolyl, morpholin-4-ylalkyl, and (1,2)-imidazolinyl (optionally substituted by alkyl));

or $R^2$ is piperazin-1-yl (optionally substituted by one or more substituents independently selected from the group consisting of —$C(O)N(R^8)R^9$, alkyl, carboxyalkyl, and alkoxycarbonylalkyl);

or $R^2$ is piperidin-1-yl (optionally substituted by one or more substituents selected from the group consisting of —$C(O)N(R^8)R^9$, carboxy and alkoxycarbonyl);

or $R^2$ is piperidin-4-ylamino (wherein the amino is optionally substituted by alkyl and the piperidinyl group is optionally substituted by one or more substituents selected from the group consisting of —$C(O)N(R^8)R^9$, carboxyalkyl, alkoxycarbonylalkyl and aralklyl);

$R^4$ is hydrogen, amino, hydroxy, or methoxy;

$R^5$ is —$C(NH)NH_2$;

$R^6$ is guanidino, —$C(NH)NH_2$, $C(O)N(R^8)R^9$, —$(CH_2)_mN(R^8)R^9$ (where m is 0 to 1), (1,2)-imidazolyl substituted by alkyl, or (1,2)-imidazolinyl substituted by alkyl;

$R^7$ is hydrogen, methoxy or hydroxy; and each $R^8$ and $R^9$ is independently hydrogen, methyl, ethyl or phenyl.

7. The compound of claim 6 wherein:

$Z^1$ and $Z^2$ are both —O—;

$R^1$ and $R^3$ are independently hydrogen, fluoro, or chloro;

$R^4$ is hydrogen, amino, hydroxy, or methoxy;

$R^5$ is —$C(NH)NH_2$;

$R^6$ is guanidino, —$C(NH)NH_2$, —$C(O)N(R^8)R^9$, —$(CH_2)_mN(R^8)R^9$ (where m is 0 to 1), (1,2)-imidazolyl substituted by alkyl, or (1,2)-imidazolinyl substituted by alkyl;

$R^7$ is hydrogen or hydroxy; and each $R^8$ and $R^9$ is independently hydrogen, methyl, ethyl or phenyl.

8. The compound of claim 7 wherein:

$R^4$ is hydroxy;

$R^6$ is dimethylamino or dimethylaminocarbonyl; and $R^7$ is hydrogen.

9. The compound of claim 7 wherein:

$R^4$ is hydroxy;

$R^6$ is (1,2)-imidazolyl substituted by methyl or 2-imidazolinyl substituted by methyl; and $R^7$ is hydrogen.

10. The compound of claim 7 wherein:

$R^4$ is hydroxy;

$R^6$ is guanidino; and $R^7$ is hydrogen.

11. A pharmaceutical composition useful in treating a human having a disease-state characterized by thrombotic activity, which composition comprises a therapeutically effective amount of a compound selected from the group consisting of the following formulae:

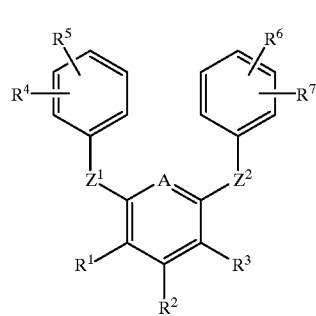
(I)

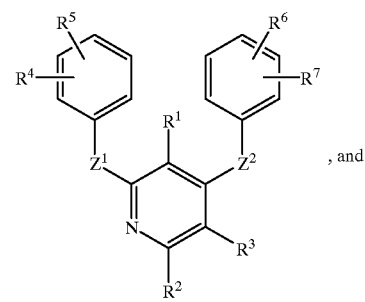
(VI)
, and

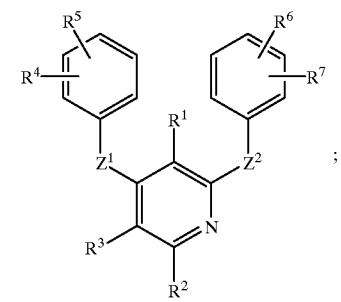
(VII)
;

wherein

A is —N=;

$Z^1$ and $Z^2$ are independently —$N(R^8)$— or —S—;

$R^1$ and $R^3$ are independently hydrogen, halo, alkyl, haloalkyl, alkoxy, haloalkoxy, nitro, —$N(R^8)R^9$, —$C(O)OR^8$, —$C(O)N(R^8)R^9$, —$C(O)N(R^8)CH_2C(O)$ N(R$^8$)R$^9$, —N(R$^8$)C(O)N(R$^8$)R$^9$, —N(R$^8$)C(O)R$^8$, —N(R$^8$)S(O)$_2$R$^{12}$ or —N(R$^8$)C(O)N(R$^8$)CH$_2$C(O)N(R$^8$)R$^9$;

R$^2$ is hydrogen; halo; alkyl; haloalkoxy; —OR$^8$; —C(O)OR$^8$; —C(O)N(R$^8$)R$^9$; —N(R$^8$)R$^9$; C(O)N(R$^8$)(CH$_2$)$_m$C(O)OR$^8$ (where m is 0 to 3); —N(R$^8$)(CH$_2$)$_n$C(O)OR$^8$ (where n is 1 to 3); —N((CH$_2$)$_n$N(R$^8$)R)(CH$_2$)$_n$C(O)OR$^8$ (where each n is 1 to 3); —O(CH$_2$)$_n$C(O)N(R$^8$)R$^9$ (where n is 1 to 3); —O(CH$_2$)$_p$C(O)OR$^8$ (where p is 1 to 6); —N(R$^8$)(CH$_2$)$_n$C(O)N(R$^8$)(CH$_2$)$_n$C(O)OR$^8$ (where each n is independently 1 to 3); morpholin-4-yl; 3-tetrahydrofuranoxy;

or R$^2$ is aryloxy (optionally substituted by one or more substuents independently selected from the group consisting of —OR$^8$, —C(O)N(R$^8$)R$^9$, halo, alkyl, carboxy, alkoxycarbonyl, haloalkoxy, haloalkoxycarbonyl, alkoxycarbonylalkyl, carboxyalkyl, aminocarbonylalkyl, (alkylamino)carbonylalkyl, (dialkylamino)carbonylalkyl, (arylamino)carbonylalkyl, (aralkylamino)carbonylalkyl, alkoxycarbonylalkenyl, carboxyalkenyl, aminocarbonylalkenyl, (alkylamino)carbonylalkenyl, (dialkylamino)carbonylalkenyl, (arylamino)carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy)alkoxycarbonyl, tetrazolyl, morpholin-4-ylalkyl, and (1,2)imidazolinyl (optionally substituted by alkyl));

or R$^2$ is piperazin-1-yl (optionally substituted by one or more substituents independently selected from the group consisting of alkyl, carboxy, —C(O)N(R$^8$)R$^9$, carboxyalkyl, alkoxycarbonyl, and alkoxycarbonylalkyl);

or R$^2$ is 1-piperazinoyl (optionally substituted by one or more substituents selected from the group consisting of alkyl, carboxy, —C(O)N(R$^8$)R$^9$, carboxyalkyl, alkoxycarbonyl, and alkoxycarbonylalkyl);

or R$^2$ is piperidin-1-yl (optionally substituted by one or more substituents selected from the group consisting of carboxy, —C(O)N(R$^8$)R$^9$, carboxyalkyl, alkoxycarbonyl, and alkoxycarbonylalkyl);

or R$^2$ is (3,4)-piperidinyloxy (optionally substituted by one or more substituents selected from the group consisting of alkylcarbonyl, carboxy, —C(O)N(R$^8$)R$^9$, alkoxycarbonyl, carboxyalkyl, alkoxycarbonylalkyl, and tetrazolylalkyl);

or R$^2$ is piperidin-4-ylamino (wherein the amino is optionally substituted by alkyl and the piperidinyl group is optionally substituted by one or more substituents selected from the group consisting of alkyl, alkoxycarbonyl, carboxyalkyl, —C(O)N(R$^8$)R$^9$, alkoxycarbonylalkyl and aralklyl);

or R$^2$ is 3-pyrrolidinyloxy (optionally substituted by one or more substituents selected from the group consisting of alkyl, aralkyl, amidino, 1-iminoethyl, carboxy, carboxyalkyl, —C(O)N(R$^8$)R$^9$, alkoxycarbonyl and alkoxycarbonylalkyl);

R$^4$ and R$^7$ are independently hydrogen, halo, alkyl, nitro, —OR$^8$, —C(O)OR$^8$, —C(O)N(R$^8$)R$^9$, —N(R$^8$)R$^9$, —N(H)C(O)R$^8$, or —N(H)S(O)$_2$R$^{12}$;

R$^5$ is —C(NH)NH$_2$, —C(NH)N(H)OR$^8$, —C(NH)N(H)C(O)OR$^2$, —C(NH)N(H)S(O)$_2$R$^{12}$, —C(NH)N(H)C(O)N(R$^8$)R$^9$, or —C(NH)N(H)C(O)R$^8$;

R$^6$ is halo, alkyl, haloalkyl, haloalkoxy, nitro, amino, ureido, guanidino, —OR$^8$, —C(NH)NH$_2$, —C(NH)NHOH, —C(O)Rlo, —(CH$_2$)$_m$C(O)N(R$^8$)R$^9$ (where m is 0 to 3), —CH(OH)C(O)N(R$^8$)R$^9$, —(CH$_2$)$_m$N(R$^8$)R$^9$ (where m is 0 to 3), —(CH$_2$)$_m$C(O)OR$^8$ (where m is 0 to 3), —N(H)C(O)R$^8$, (1,2)-tetrahydropyrimidinyl (optionally substituted by alkyl), (1,2)-imidazolyl (optionally substituted by alkyl), or (1,2)-imidazolinyl (optionally substituted by alkyl);

each R$^8$ and R$^9$ is independently hydrogen, alkyl, aryl, or aralkyl;

R$^{10}$ is hydrogen, alkyl, aryl, aralkyl, 1-pyrrolidinyl, 4-morpolinyl, 4-piperazinyl, 4-(N-methyl)piperazinyl, or piperidin-1-yl; and R$^{12}$ is alkyl, aryl or aralkyl;

or a pharmaceutically acceptable salt thereof;

and a pharmaceutically acceptable excipient.

12. A method of treating a human having a disease state characterized by thrombotic activity, which method comprises administering to a human in need thereof a therapeutically effective amount of a compound selected from the group consisting of the following formulae:

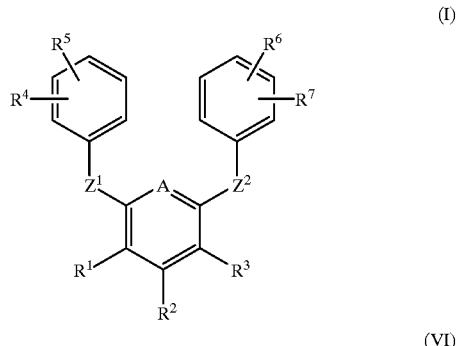
(I)

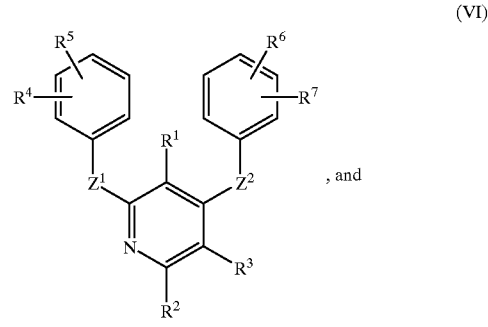
, and
(VI)

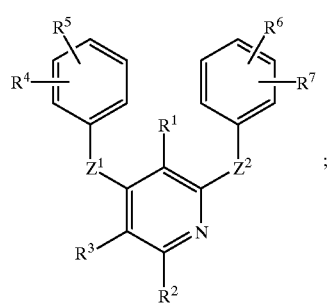
;
(VII)

wherein

A is or —N=;

Z$^1$ and Z$^2$ are independently —N(R$^8$)— or —S—:

R$^1$ and R$^3$ are independently hydrogen, halo, alkyl, haloalkyl, alkoxy, haloalkoxy, nitro, —N(R$^8$)R$^9$, —C(O)OR$^8$, —C(O)N(R$^8$)R$^9$, —C(O)N(R$^8$)CH$_2$C(O)N(R$^8$)R$^9$, —N(R$^8$)C(O)N(R$^8$)R$^9$, —N(R$^8$)C(O)R$^8$, —N(R⁸)ˢ⁽ᴼ⁾₂R¹², or —N(R⁸)C(O)N(R⁸)CH₂C(O)N(R⁸)R⁹; —N(R⁸)C(O)R⁸, —N(R⁸)S(O)₂R¹², or R² is hydrogen; halo; alkyl; haloalkoxy; —OR⁸; —C(O)OR⁶; —C(O)N(R⁸)R⁹; —N(R⁸)R⁹; —C(O)N(R⁸)(CH₂)ₘC(O)OR⁸ (where m is 0 to 3); —N(R⁸)(CH₂)ₙC(O)OR⁸ (where n is 1 to 3); —N((CH₂)ₙN(R⁸)R)(CH₂)ₙC(O)OR⁸ (where each n is 1 to 3); —O(CH₂)ₙC(O)N(R⁸)R⁹ (where n is 1 to 3); —O(CH₂)ₚC(O)OR⁸ (where p is 1 to 6); —N(R⁸)(CH₂)ₙC(O)N(R⁸)(CH₂)ₙC(O)OR⁸ (where each n is independently 1 to 3); morpholin-4-yl; 3-tetrahydrofuranoxy;

or R² is aryloxy (optionally substituted by one or more substituents independently selected from the group consisting of —OR⁸, —C(O)N(R⁸)R⁹, halo, alkyl, carboxy, alkoxycarbonyl, haloalkoxy, haloalkoxycarbonyl, alkoxycarbonylalkyl, carboxyalkyl, aminocarbonylalkyl, (alkylamino)carbonylalkyl, (dialkylamino)carbonylalkyl, (arylamino)carbonylalkyl, (aralkylamino)carbonylalkyl, alkoxycarbonylalkenyl, carboxyalkenyl, aminocarbonylalkenyl, (alkylamino)carbonylalkenyl, (dialkylamino)carbonylalkenyl, (arylamino)carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy)alkoxycarbonyl, tetrazolyl, morpholin-4-ylalkyl, and (1,2)-imidazolinyl (optionally substituted by alkyl));

or R² is piperazin-1-yl (optionally substituted by one or more substituents independently selected from the group consisting of alkyl, carboxy, —C(O)N(R⁸)R⁹, carboxyalkyl, alkoxycarbonyl, and alkoxycarbonylalkyl);

or R² is 1-piperazinoyl (optionally substituted by one or more substituents selected from the group consisting of alkyl, carboxy, C(O)N(R⁸)R⁹, carboxyalkyl, alkoxycarbonyl, and alkoxycarbonylalkyl);

or R² is piperidin-1-yl (optionally substituted by one or more substituents selected from the group consisting of carboxy, —C(O)N(R⁸)R⁹, carboxyalkyl, alkoxycarbonyl, and alkoxycarbonylalkyl);

or R² is (3,4)-piperidinyloxy (optionally substituted by one or more substituents selected from the group consisting of alkylcarbonyl, carboxy, —C(O)N(R⁸)R⁹, alkoxycarbonyl, carboxyalkyl, alkoxycarbonylalkyl, and tetrazolylalkyl);

or R² is piperidin-4-ylamino (wherein the amino is optionally substituted by alkyl and the piperidinyl group is optionally substituted by one or more substituents selected from the group consisting of alkyl, alkoxycarbonyl, carboxyalkyl, —C(O)N(R⁸)R⁹, alkoxycarbonylalkyl and aralklyl);

or R² is 3-pyrrolidinyloxy (optionally substituted by one or more substituents selected from the group consisting of alkyd, aralkyl, amidino, 1-iminoethyl, carboxy, carboxyalkyl, —C(O)N(R⁸)R⁹, alkoxycarbonyl and alkoxycarbonylalkyl);

R⁴ and R⁷ are independently hydrogen, halo, alkyl, nitro, —OR⁸, —C(O)OR⁸, —C(O)N(R⁸)R⁸, —N(R⁸)R⁹, —N(H)C(O)R⁸, or —N(H)S(O)₂R¹²;

R⁵ is —C(NH)NH₂, —C(NH)N(H)OR⁸, —C(NH)N(H)C(O)OR¹², —C(NH)N(H)C(O)₂R¹², —C(NH)N(H)C(O)N(R⁸)R⁹, or C(NH)N(H)C(O)R⁸;

R⁶ is halo, alkyl, haloalkyl, haloalkoxy, nitro, amino, ureido, guanidino, —OR⁸, —C(NH)NH₂, —C(NH)NHOH, —C(O)R¹⁰, —(CH₂)ₘC(O)N(R⁸)R⁹ (where m is 0 to 3), —CH(OH)C(O)N(R⁸)R⁹, (CH₂)ₘN(R⁸)R⁹ (where m is 0 to 3), —(CH₂)ₘC(O)OR⁸ (where m is 0 to 3), —N(H)C(O)R⁸, (1,2)-tetrahydropyrimidinyl (optionally substituted by alkyl), (1,2)-imidazolyl (optionally substituted by alkyl), or (1,2)-imidazolinyl (optionally substituted by alkyl);

each R⁸ and R⁹ is independently hydrogen, alkyl, aryl, or aralkyl;

R¹⁰ is hydrogen, alkyl, aryl, aralkyl, 1-pyrrolidinyl, 4-morpolinyl, 4-piperazinyl, 4-(NVmethyl)piperazinyl, or piperidin-1-yl; and R¹² is alkyl, aryl or aralkyl;

or a pharmaceutically acceptable salt thereof.

13. A pharmaceutical composition useful in treating a human having a disease-state characterized by thrombotic activity, which composition comprises a therapeutically effective amount of a compound selected from the group consisting of the following formulae:

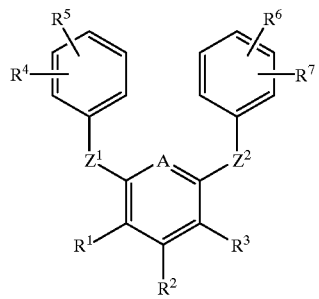

(I)

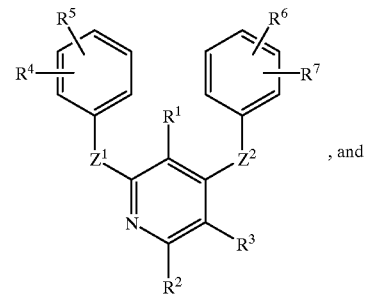

(VI), and

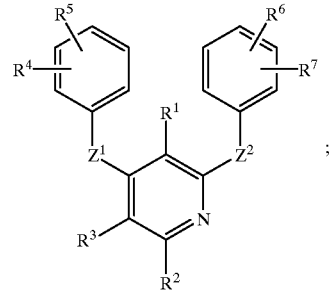

(VII);

wherein

A is —N=;

Z¹ and Z² are independently —O—, —N(R⁸) or —S—;

R¹ and R 3 are independently hydrogen, halo, alkyl, haloalkl, alkoxy, haloalkoxy, nitro, —N(R⁸)R⁹, —C(O)OR⁸, —C(O)N(R⁸)R⁹, —C(O)N(R⁸)CH₂C(O)N(R⁸)R⁹, —N(R⁸)C(O)N(R⁸)R⁹, —N(R⁸)ᶜ⁽ᴼ⁾ᴿ⁸, —N(R⁸)C(O)₂R¹², or —N(R⁸)C(O)N(R⁸)CH₂C(O)N(R)R⁹;

R² is hydrogen; halo; alkyl; haloalkoxy; —OR⁸; —C(O)OR⁸; —C(O)N(R⁸)R⁹; —N(R 8)R⁹; —C(O)N(R⁸)

(CH₂)C(O)OR⁸ (where m is 0 to 3); —N(R⁸)(CH₂)ₙC(O)OR⁸ (where n is 1 to 3); —N((CH₂)ₙN(R⁸)R⁹)(CH₂)ₙC(O)OR⁸ (where each n is 1 to 3); —O(CH₂)ₙC(O)N(R⁸)R⁹ (where n is 1 to 3); —O(CH₂)ₚC(O)OR⁸ (where p is 1 to 6); —N(R⁸)(CH₂)ₙC(O)N(R⁸)(CH₂)ₙC(O)OR⁸ (where each n is independently 1 to 3); morpholin-4-yl; 3tetrahydrofuranoxy;

or R² is aryloxy (optionally substituted by one or more substituents independently selected from the group consisting of —OR⁸, —C(O)N(R³)R⁹, halo, alkyl, carboxy, alkoxycarbonyl, haloalkoxy, haloalkoxycarbonyl, alkoxy,arbonylalkyl, carboxyalkyl, aminocarbonylalkyl, (alkylamino)carbonylalkyl, (dialkylamino)carbonylalkyl, (arylamino)carbonylalkyl, (aralkylamino)carbonylalkyl, alkoxycarbonylalkenyl, carboxyalkenyl, aminocarbonylalkenyl, (alkylamino)carbonylalkenyl, (dialkylamino)carbonylalkenyl, (arylamino)carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy)alkoxycarbonyl, tetrazolyl, morpholin-4-ylalkyl, and (1,2)-imidazolinyl (optionally substituted by alkyl));

or R² is piperazin-1-yl (optionally substituted by one or more substituents independently selected from the group consisting of alkyl, carboxy, —C(O)N(R⁸)R⁹, carboxyalkyl, alkoxycarbonyl, and alkoxycarbonylalkyl);

or R² is 1-piperazinoyl (optionally substituted by one or more substituents selected from the group consisting of alkyl, carboxy, —C(O)N(R⁸)R⁹, carboxyalkyl, alkoxycarbonyl, and alkoxycarbonylalkyl);

or R² is piperidin-1-yl (optionally substituted by one or more substituents selected from the group consisting of carboxy, —C(O)N(R⁸)R⁹, carboxyalkyl, alkoxycarbonyl, and alkoxycarbonylalkyl);

or R² is piperidin-4-ylamino (wherein the amino is optionally substituted by alkyl and the piperidinyl group is optionally substituted by one or more substituents selected from the group consisting of alkyl, alkoxycarbonyl, carboxyalkyl, C(O)N(R⁸)R⁹, alkoxycarbonylalkyl and aralklyl);

R⁴ and R⁷ are independently hydrogen, halo, alkyl, nitro, —OR⁸, —C(O)OR⁸, —C(O)N(R⁸)R⁹, —N(R⁸)R⁹, —N(H)C(O)R⁸, or —N(H)C(O)₂R¹²;

R⁵ is —C(NH)NH₂, —C(NH)N(H)OR⁸, —C(NH)N(H)C(O)OR¹², —C(NH)N(H)S(O)₂R¹², —C(NH)N(H)C(O)N(R⁸)R⁹, or —C(NH)N(H)C(O)R⁸;

R⁶ is halo, alkyl, haloalkyl, haloalkoxy, nitro, amino, ureido, guanidino, —OR⁸, C(NH)NH₂, —C(NH)NHOH, —C(O)R¹⁰, —(CH₂)ₘC(O)N(R⁸)R⁹ (where m is 0 to 3), —CH(OH)C(O)N(R⁸)R⁹, —(CH₂)ₘN(R⁸)R⁹ (where m is 0 to 3), —(CH₂)ₘC(O)OR⁸ (where m is 0 to 3), —N(H)C(O)R⁸, (1,2)-tetrahydropyrimidinyl (optionally substituted by alkyl), (1,2)-imidazolyl (optionally substituted by alkyl), or (1,2)-imidazolinyl (optionally substituted by alkyl);

each R⁸ and R⁹ is independently hydrogen, alkyl, aryl, or aralkyl;

R¹⁰ is hydrogen, alkyl, aryl, aralkyl, 1-pyrrolidinyl, 4-morpholinyl, 4-piperazinyl, 4-(N-methyl)piperazinyl, or piperidin-1-yl; and R¹² is alkyl, aryl or aralkyl;

or a pharmaceutically acceptable salt thereof;

and a pharmaceutically acceptable excipient.

14. A method of treating a human having a disease-state characterized by thrombotic activity, which method comprises administering to a human in need thereof a therapeutically effective amount of a compound selected from the group consisting of the following formulae:

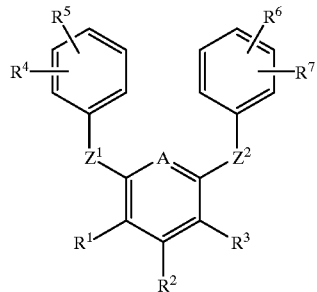

(I)

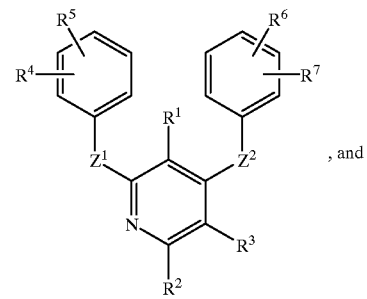

(VI)

, and

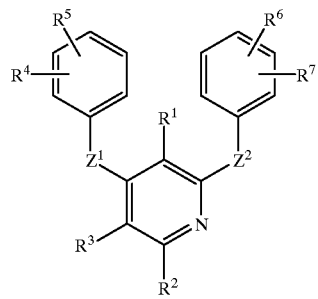

(VII)

;

wherein
A is —N═;
Z¹ and Z² are independently —O—, —N(R⁸) or —S—;
R¹ and R³ are independently hydrogen, halo, alkyl, haloalkyl, alkoxy, haloalkoxy, nitro, —N(R⁸)R, —C(O)OR⁸, —C(O)N(R⁸)R⁹, —C(O)N(R⁸)CH₂C(O)N(R⁸)R⁹, —N(R⁸)C(O)N(R⁸)R⁹, —N(R⁸)G(O)R⁸, —N(R⁸)C(O)₂R¹², or —N(R⁸)C(O)N(R⁸)CH₂C(O)N(R⁸)R⁹;

R² is hydrogen; halo; alkyl; haloalkoxy; —OR⁸; —C(O)OR⁸; —C(O)N(R⁸)R⁹; —N(R⁸)R⁹; —C(O)N(R⁸)(CH₂)ₙC(O)OR⁸ (where m is 0 to 3); —N(R⁸)(CH₂)ₙC(O)OR⁸ (where n is 1 to 3); —N((CH₂)ₙN(R⁸)R⁹)(CH₂)ₙC(O)OR⁸ (where each n is 1 to 3); —O(CH₂)ₙC(O)N(R⁸)R⁹ (where n is 1 to 3); —O(CH₂)ₚC(O)OR⁸ (where p is 1 to 6); —N(R⁸)(CH₂)ₙC(O)N(R⁸)(CH₂)ₙC(O)OR⁸ (where each n is independently 1 to 3); morpholin-4-yl; 3-tetrahydrofuranoxy;

or R² is aryloxy (optionally substituted by one or more substituents independently selected from the group consisting of —OR⁸, —C(O)N(R⁸)R⁹, halo, alkyl, carboxy, alkoxycarbonyl, haloalkoxy, haloalkoxycarbonyl, alkoxycarbonylalkyl, carboxyalkyl, aminocarbonylalkyl, (alkylamino)carbonylalkyl, (dialkylamino)carbonylalkyl, (arylamino)carbonylalkyl, (aralkylamino)carbonylalkyl, alkoxycarbonylalkenyl, carboxyalkenyl, aminocarbonylalkenyl, (alkylamino)carbonylalkenyl, (dialkylamino)carbonylalkenyl, (arylamino)carbonylalkenyl, (aralkylamino)carbonylalkenyl, (hydroxyalkoxy)carbonyl, (alkoxy)alkoxycarbonyl, (hydroxyalkoxy)alkoxycarbonyl, ((alkoxy)alkoxy)alkoxycarbonyl, tetrazolyl, morpholin-4-ylalkyl, and (1,2)-imidazolinyl (optionally substituted by alkyl));

or $R^2$ is piperazin-1-yl (optionally substittted by one or more substituents independently selected from the group consisting of alkyl, carboxy, —C(O)N($R^8$)$R^9$, carboxyalkyl, alkoxycarbonyl, and alkoxycarbonylalkyl);

or $R^2$ is 1-piperazinoyl (optionally substituted by one or more substituents selected from the group consisting of alkyl, carboxy, —C(O)N($R^8$)$R^9$, carboxyalkyl, alkoxycarbonyl, and alkoxycarbonylalkyl);

or $R^2$ is piperidin-1-yl (optionally substituted by one or more substituents selected from the group consisting of carboxy, —C(O)N($R^8$)$R^9$, carboxyalkyl, alkoxycarbonyl, and alkoxycarbonylalkyl);

or $R^2$ is piperidin-4-ylamino (wherein the amino is optionally substituted by alkyl and the piperidinyl group is optionally substituted by one or more substituents selected from the group consisting of alkyl, alkoxycarbonyl, carboxyalkyl, —C(O)N($R^8$)$R^9$, alkoxycarbonylalkyl and aralklyl);

$R^4$ and $R^7$ are independently hydrogen, halo, alkyl, nitro, —O$R^8$, —C(O)O$R^8$, —C(O)N($R^8$)$R^9$, —N($R^8$)$R^9$, —N(H)C(O)$R^8$, or —N(H)S(O)$_2R^{12}$;

$R^5$ is —C(NH)NH$_2$, —C(NH)N(H)O$R^8$, —C(NH)N(H)C(O)O$R^{12}$, —C(NH)N(H)C(O)$_2R^{12}$, —C(NH)N(H)C(O)N($R^8$)$R^9$, or —C(NH)N(H)C(O)$R^8$;

$R^6$ is halo, alkyl, haloalkyl, haloalkoxy, nitro, amino, ureido, guanidino, —O$R^8$, —C(NH)NH$_2$, —C(NH)NHOH, —C(O)$R^{10}$, —(CH$_2$)$_m$C(O)N($R^8$)$R^9$ (where m is 0 to 3), —CH(OH)C(O)N($R^8$)$R^9$, —(CH$_2$)$_m$N(RF)$R^9$ (where m is 0 to 3), —(CH$_2$)$_m$C(O)O$R^8$ (where m is 0 to 3), —N(H)C(O)$R^8$, (1,2)-tetrahydropyrimidinyl (optionally substituted by alkyl), (1,2)-imidazolyl (optionally substituted by alkyl), or (1,2)-imidazolinyl (optionally substituted by alkyl);

each $R^8$ and $R^9$ is independently hydrogen, alkyl, aryl, or aralkyl;

$R^{10}$ is hydrogen, alkyl, aryl, aralkyl, 1-pyrrolidinyl, 4-morpolinyl, 4-piperazinyl, 4-(AVmethyl)piperazinyl, or piperidin-1-yl; and $R^{12}$ is alkyl, aryl or aralkyl;

or a pharmaceutically acceptable salt thereof.

* * * * *